US011975054B2

(12) United States Patent
Herber

(10) Patent No.: US 11,975,054 B2

(45) Date of Patent: *May 7, 2024

(54) NUCLEIC ACID MOLECULES ENCODING CLOSTRIDIUM HISTOLYTICUM COLLAGENASE I AND METHODS OF PRODUCING THE SAME

(71) Applicant: ENDO GLOBAL VENTURES, Hamilton (GB)

(72) Inventor: Wayne K. Herber, Coopersburg, PA (US)

(73) Assignee: ENDO GLOBAL VENTURES, Hamilton (BM)

( * ) Notice: Subject to any disclaimer, the term of this patent is extended or adjusted under 35 U.S.C. 154(b) by 1093 days.

This patent is subject to a terminal disclaimer.

(21) Appl. No.: 16/816,097

(22) Filed: Mar. 11, 2020

(65) Prior Publication Data

US 2020/0206326 A1 Jul. 2, 2020

Related U.S. Application Data

(60) Continuation of application No. 15/669,286, filed on Aug. 4, 2017, now Pat. No. 10,603,365, which is a division of application No. 14/328,772, filed on Jul. 11, 2014, now Pat. No. 9,757,435, which is a continuation of application No. PCT/US2013/020940, filed on Jan. 10, 2013.

(60) Provisional application No. 61/585,909, filed on Jan. 12, 2012.

(51) Int. Cl.

| | |
|---|---|
| ***C12N 9/52*** | (2006.01) |
| ***A61K 38/48*** | (2006.01) |
| ***C12N 9/50*** | (2006.01) |
| ***C12Q 1/37*** | (2006.01) |
| ***G01N 33/50*** | (2006.01) |
| ***G01N 33/569*** | (2006.01) |

(52) U.S. Cl.

CPC ............ *A61K 38/4886* (2013.01); *C12N 9/50* (2013.01); *C12N 9/52* (2013.01); *C12Q 1/37* (2013.01); *C12Y 304/24003* (2013.01); *G01N 33/5044* (2013.01); *G01N 33/56911* (2013.01); *G01N 2333/96419* (2013.01); *Y02A 50/30* (2018.01)

(58) Field of Classification Search

CPC .............. C12N 9/52; C12Y 304/24003; A61K 38/4886

See application file for complete search history.

(56) References Cited

U.S. PATENT DOCUMENTS

| | | | |
|---|---|---|---|
| 3,821,364 | A | 6/1974 | Chiulli et al. |
| 4,338,000 | A | 7/1982 | Kamimori et al. |
| 4,338,300 | A | 7/1982 | Gelbard |
| 4,524,065 | A | 6/1985 | Pinnell |
| 4,542,065 | A | 9/1985 | Gaa |
| 4,645,668 | A | 2/1987 | Pinnell |
| 4,732,758 | A | 3/1988 | Hurion et al. |
| 5,252,461 | A | 10/1993 | Weisbart |
| 5,252,481 | A | 10/1993 | Holjevac et al. |
| 5,256,140 | A | 10/1993 | Fallick |
| 5,332,503 | A | 7/1994 | Lee et al. |
| 5,393,792 | A | 2/1995 | Stern et al. |
| 5,422,103 | A | 6/1995 | Stern et al. |
| 5,462,739 | A | 10/1995 | Dan et al. |
| 5,514,340 | A | 5/1996 | Lansdorp et al. |
| 5,514,370 | A | 5/1996 | Stern et al. |
| 5,589,171 | A | 12/1996 | Wegman |
| 5,705,170 | A | 1/1998 | Kong et al. |
| 5,753,485 | A | 5/1998 | Dwulet et al. |
| 5,753,785 | A | 5/1998 | Reddy et al. |
| 5,830,741 | A | 11/1998 | Dwulet et al. |
| 5,952,215 | A | 9/1999 | Dwulet et al. |
| 5,989,888 | A | 11/1999 | Dwulet et al. |
| 6,022,539 | A | 2/2000 | Wegman |
| 6,086,872 | A | 7/2000 | Wegman |
| 6,086,877 | A | 7/2000 | Nishioka et al. |
| 6,086,887 | A | 7/2000 | Parrott |
| 6,146,626 | A | 11/2000 | Markert et al. |
| 6,280,993 | B1 | 8/2001 | Yamato et al. |
| 6,335,388 | B1 | 1/2002 | Fotinos |
| 6,358,539 | B1 | 3/2002 | Murad |
| 6,475,764 | B1 | 11/2002 | Burtscher et al. |
| 6,953,583 | B1 | 10/2005 | Ghisalberti |
| 6,958,150 | B2 | 10/2005 | Wegman et al. |
| 7,083,964 | B2 | 8/2006 | Kurfuerst et al. |
| RE39,941 | E | 12/2007 | Wegman |
| 7,355,027 | B2 | 4/2008 | Brehm et al. |
| 7,358,067 | B2 | 4/2008 | Vrang et al. |

(Continued)

FOREIGN PATENT DOCUMENTS

| | | | |
|---|---|---|---|
| AU | 2006206393 | A1 | 7/2006 |
| BR | PI0607280-1 | A2 | 8/2009 |

(Continued)

OTHER PUBLICATIONS

Jung, Chang-Min et al., "Identification of Metal Ligands in the Clostridium histolyticum ColH Collagenase," J. of Bacteriology, 181(9):2816-2822 (1999).

(Continued)

*Primary Examiner* — Zachary C Howard

(74) *Attorney, Agent, or Firm* — BakerHostetler

(57) ABSTRACT

The invention relates to recombinant nucleic acid and polypeptides encoding collagenase I and collagenase II, methods for the preparation thereof and methods for the use thereof. The invention also encompasses methods related to releasing a composition comprising collagenase prior to therapeutic administration.

10 Claims, 28 Drawing Sheets

Specification includes a Sequence Listing.

(56) References Cited

U.S. PATENT DOCUMENTS

| | | | |
|---|---|---|---|
| 7,622,130 B2 | 11/2009 | Kolodney et al. |
| 7,811,560 B2 | 10/2010 | Sabatino et al. |
| 7,824,673 B2 | 11/2010 | Wegman et al. |
| 7,842,673 B2 | 11/2010 | Brink et al. |
| 7,854,929 B2 | 12/2010 | Badalemente et al. |
| 8,323,643 B2 | 12/2012 | Badalamente et al. |
| 8,380,531 B2 | 2/2013 | Paty et al. |
| 9,757,435 B2 | 9/2017 | Herber |
| 10,119,131 B2 | 11/2018 | Wegman et al. |
| 10,123,959 B2 | 11/2018 | Badalamente et al. |
| 10,603,365 B2 | 3/2020 | Herber |
| 2002/0036328 A1 | 3/2002 | Richards, Jr. et al. |
| 2003/0022856 A1 | 1/2003 | Richardson et al. |
| 2003/0026844 A1 | 2/2003 | Lee et al. |
| 2003/0129178 A1 | 7/2003 | Wegman et al. |
| 2004/0137596 A1 | 7/2004 | Kurfuerst et al. |
| 2005/0227910 A1 | 10/2005 | Yang et al. |
| 2005/0261584 A1 | 11/2005 | Eshel et al. |
| 2005/0267080 A1 | 12/2005 | Kolodney et al. |
| 2006/0020448 A1 | 1/2006 | Chelba et al. |
| 2006/0204488 A1 | 9/2006 | Badalamente |
| 2006/0241673 A1 | 10/2006 | Zadini et al. |
| 2006/0251581 A1 | 11/2006 | McIntyre et al. |
| 2007/0003541 A1 | 1/2007 | Faudoa et al. |
| 2007/0031482 A1 | 2/2007 | Castro et al. |
| 2007/0224183 A1 | 9/2007 | Sabatino et al. |
| 2007/0224184 A1 | 9/2007 | Badalemente et al. |
| 2008/0020001 A1 | 1/2008 | Brehm et al. |
| 2008/0206228 A1 | 8/2008 | Vaccaro et al. |
| 2008/0233614 A1 | 9/2008 | Cranenburgh et al. |
| 2008/0279900 A1 | 11/2008 | Longo et al. |
| 2008/0300429 A1 | 12/2008 | Sakanishi et al. |
| 2009/0053276 A1 | 2/2009 | Richard |
| 2010/0015262 A1 | 1/2010 | Goralczyk et al. |
| 2010/0021416 A1 | 1/2010 | Lichter et al. |
| 2010/0035868 A1 | 2/2010 | Jabbour |
| 2010/0086971 A1 | 4/2010 | Suppmann et al. |
| 2010/0137747 A1 | 6/2010 | Thomas et al. |
| 2010/0159564 A1 | 6/2010 | Dwulet et al. |
| 2010/0233150 A1 | 9/2010 | Wegman et al. |
| 2010/0233151 A1 | 9/2010 | Sabatino et al. |
| 2010/0330065 A1 | 12/2010 | Sabatino et al. |
| 2011/0070622 A1 | 3/2011 | Hoelke et al. |
| 2011/0158972 A1 | 6/2011 | Sabatino et al. |
| 2011/0160617 A9 | 6/2011 | Thomas et al. |
| 2011/0189153 A1 | 8/2011 | Sabatino et al. |
| 2011/0189163 A1 | 8/2011 | Sabatino et al. |
| 2011/0217252 A1 | 9/2011 | Koverech |
| 2011/0243908 A1 | 10/2011 | Sabatino et al. |
| 2011/0243909 A1 | 10/2011 | Sabatino et al. |
| 2011/0243919 A1 | 10/2011 | Sabatino et al. |
| 2011/0243920 A1 | 10/2011 | Sabatino et al. |
| 2011/0262508 A1 | 10/2011 | Watt et al. |
| 2011/0294192 A1 | 12/2011 | Fukushima et al. |
| 2012/0164131 A1 | 6/2012 | Huang et al. |
| 2012/0237492 A1 | 9/2012 | Walker |
| 2012/0237497 A1 | 9/2012 | Wegman et al. |
| 2012/0315265 A1 | 12/2012 | Lai et al. |
| 2013/0096596 A1 | 4/2013 | Schafer |
| 2013/0129663 A1 | 5/2013 | Friberg et al. |
| 2013/0195828 A1 | 8/2013 | Kibbe et al. |
| 2013/0217789 A1 | 8/2013 | Taylor et al. |
| 2013/0287759 A1 | 10/2013 | Munoz Montano |
| 2014/0004094 A1 | 1/2014 | Sabatino et al. |
| 2014/0271508 A1 | 9/2014 | Florence et al. |
| 2014/0271612 A1 | 9/2014 | Leppert et al. |
| 2014/0335072 A1 | 11/2014 | Hart |
| 2015/0010532 A1 | 1/2015 | Herber |
| 2015/0301064 A1 | 10/2015 | Yoshida et al. |
| 2016/0000890 A1 | 1/2016 | Yu et al. |
| 2016/0279046 A1 | 9/2016 | Badalamente et al. |
| 2017/0136039 A1 | 5/2017 | Jung et al. |
| 2017/0209201 A1 | 7/2017 | Slayton et al. |
| 2017/0228517 A1 | 8/2017 | Saliman et al. |
| 2017/0290848 A1 | 10/2017 | Walker |
| 2017/0319601 A1 | 11/2017 | Walker |
| 2019/0240253 A1 | 8/2019 | Abst et al. |
| 2022/0119791 A1 | 4/2022 | Sheaffer et al. |

FOREIGN PATENT DOCUMENTS

| | | | |
|---|---|---|---|
| CA | 2308842 A1 | 12/2000 |
| CA | 2643171 A1 | 9/2007 |
| CN | 1529751 A | 9/2004 |
| CN | 101684461 A | 3/2010 |
| EP | 0468411 A2 | 1/1992 |
| EP | 1433845 A1 | 6/2004 |
| EP | 2130551 | 12/2009 |
| EP | 2133415 A1 | 12/2009 |
| EP | 2180002 A1 | 4/2010 |
| EP | 2363461 A1 | 9/2011 |
| FR | 2788682 A1 | 7/2000 |
| IL | 192878 A | 3/2013 |
| JP | 61-289885 A | 12/1986 |
| JP | 03-091478 A | 4/1991 |
| JP | 05-219942 A | 8/1993 |
| JP | 06-237764 A | 8/1994 |
| JP | 08-500970 A | 2/1996 |
| JP | 09-508026 A | 8/1997 |
| JP | 10-262658 A | 10/1998 |
| JP | 11-501517 A | 2/1999 |
| JP | 11-504225 A | 4/1999 |
| JP | 2002-530873 A | 9/2002 |
| JP | 2003-284553 A | 10/2003 |
| JP | 2004-535197 A | 11/2004 |
| JP | 2005-006552 A | 1/2005 |
| JP | 2006-254876 A | 9/2006 |
| JP | 2008-500970 A | 1/2008 |
| JP | 2009-525283 A | 7/2009 |
| JP | 2009-291195 A | 12/2009 |
| JP | 2010-262658 A | 11/2010 |
| JP | 2011-504225 A | 2/2011 |
| JP | 2011-528716 A | 11/2011 |
| JP | 5309289 B2 | 10/2013 |
| JP | 2014-530873 A | 11/2014 |
| JP | 6496386 B2 | 4/2019 |
| KR | 10-2008-0093142 A | 10/2008 |
| KR | 10-2009-0125705 A | 12/2009 |
| KR | 10-2011-0046537 A | 5/2011 |
| RU | 2180002 C2 | 2/2002 |
| WO | 94/00580 A1 | 1/1994 |
| WO | 94/16086 A1 | 7/1994 |
| WO | 96/00283 A1 | 1/1996 |
| WO | 96/28543 A1 | 9/1996 |
| WO | 98/10079 A1 | 3/1998 |
| WO | 98/24889 A1 | 6/1998 |
| WO | 00/30182 A2 | 5/2000 |
| WO | 01/21574 A1 | 3/2001 |
| WO | 03/04628 A2 | 1/2003 |
| WO | 2004/085643 A1 | 10/2004 |
| WO | 2005/073367 A1 | 8/2005 |
| WO | 2005/123764 A1 | 12/2005 |
| WO | 2006/002646 A2 | 1/2006 |
| WO | 2006/010057 A2 | 1/2006 |
| WO | 2006/025226 A1 | 3/2006 |
| WO | 2006/078870 A2 | 7/2006 |
| WO | 2006/121968 A2 | 11/2006 |
| WO | 2007/089851 A2 | 8/2007 |
| WO | 2007/100590 A2 | 9/2007 |
| WO | 2007/100675 A2 | 9/2007 |
| WO | 2008/101406 A1 | 8/2008 |
| WO | 2010/011605 A2 | 1/2010 |
| WO | 2011/073925 A2 | 6/2011 |
| WO | 2011/130537 A2 | 10/2011 |
| WO | 2012/031245 A1 | 3/2012 |
| WO | 2012/041512 A1 | 4/2012 |
| WO | 2013/059619 A1 | 4/2013 |
| WO | 2015/108901 A1 | 7/2015 |

(56) References Cited

FOREIGN PATENT DOCUMENTS

| | | |
|---|---|---|
| WO | 2018/160905 A1 | 9/2018 |
| WO | 2018/183582 A2 | 10/2018 |

OTHER PUBLICATIONS

Keil et al., "Some Newly Characterized Collagenases from Procaryotes and Lower Eucaryotes," Entrez Pubmed Abstract (1979).

Kembhavi et al. ("Clostripain: characterization of the active site," FEBS, 1991, 277-280).

Khan et al., "Treatment of cellulite: Part I. Pathophysiology," J. Am. Acad. Dermatol., 2010, 62(3), 2010: 361-370.

Kikuchi, T. et al. 1998. Intra-articular injection of collagenase induces experimental osteoarthritis in mature rabbits. Osteoarthritis and Cartilage 6: 177-186. specif. pp. 177, 178.

Kilian 0 et al: "[The frozen shoulder. 1-10 Arthroscopy, histological findings and transmission electron micrgscopy imaging]" Der Chirurg; Zeitschrift Fur Alle Gebiete Der Operativen Medizen Nov. 2001, vol. 72, No. 11, Nov. 2001, pp. 1303-1308.

Kooi, et al., "Differentiation of Thermolysins and Serralysins by Monoclonal Antibodies," J. Med. Microbiol., vol. 45, pp. 219-225 (1996).

Kooi, et al., "Identification of Neutralizing Epitopes on Pseudomonas aeruginosa Elastase and Effects of Cross-Reactions on Other Thermolysin-Like Proteases," Infection and Immunity, vol. 65, No. 2, pp. 472-477 (1997).

Krishna et al., Immunogenicity to Biotherapeutics—The Role 0f Anti-Drug Immune Complexes, Frontiers in Immunology, 7: Article 21, pp. 1-13, 1, 6 (2016).

Kurnick et al. ("Buffer Exchange Using Size Exclusion Chromatography, Countercurrent Dialysis, and Tangential Flow Filtration: Models, Development and Industrial Application," Biotechnology and Bioengineering, 1995, 45, 149-157).

Kuwayama; Cell Interaction; Chapter 9, Enhancement of Homologous Recombination Efficiency by Homologous Oligonucleotides; published Oct. 10, 2012, pp. 233-244.

Labrou, et al., "The Structure-Function Relationship in the Clostripain Family of Peptidase," Eur. J. Biochem, vol. 271, pp. 983-992 (2004).

Lecroisey et al.; "Purification, Stability and Inhibition of the Collagenase from Achromobacter lophagus;" Febs Letters; Nov. 1975, vol. 59, No. 2, pp. 167-172—Exhibit B10 filed by defendant before KPC in connection with the Korean Appeal Suit case for Korean Patent Application No. 10-2011-7006197.

Leppert MD, PhD, P.C. et al., "Comparative ultrastructure of coiianen fibrils in uterine leiomyomas and normal myometrium," Fertil Steril, 82(0 3), pp. 1182-1187 (Oct. 2004).

Leppert, P.C., et al., "The Extracellular Matrix Contributes to Mechanotransduction in Uterine Fibroids," Hindawi Publishing Corporation, vol. 2014, Article ID 783289, pp. 1-12 (Jul. 3, 2014).

Lola K. Smalls et al., "Quantitative model of cellulite: Three-dimensional skin surface topography, biophysical characterization, and relationship to human perception"J. Cosmet. Set., 56, 105-120 (Mar./Apr. 2005) (Year: 2005).

Lukac et al; "The Metalloenzymic Nature of Collagenase-Like Peptidase of the Rat Testis;" J Reprod. Fert.; (1977) 49 pp. 95-99—Exhibit B9 filed by defendant before KPC in connection with the Korean Appeal Suit case for Korean Patent Application No. 10-2011-7006197.

MacLennan, "The Histotoxic Clostridial Infections of Man," Bacteriol. Rev., vol. 26, pp. 177-274 (1962).

Madan, M., et al., "In situ forming polymeric drug delivery systems," Indian Journal of Pharmaceutical Sciences, vol. 71(3), May-Jun. 2009, pp. 242-251.

Mandl, et al., "Multiplicity of Clostridium histolyticum Collagenases," Multiplicity of Collagenases, 3(11):1737-1741 (1964).

Matsushita, O., et al., "Gene Duplication and Multiplicity of Collagenases in Clostridium Histolyticum," Journal of Bacteriology 181(3): pp. 923-933 (Feb. 1999).

Matsushita, O., et al., "Substrate Recognition by the Collagen-binding Domain of Clostridium Histolyticum Class I Collagenase, The Journal of Biological Chemistry," 276(12): pp. 8761-8770 (2001).

Maui Derm 2018: Sadick NS, Young VL, Liu G, McLane MP, Hurley D, Goldman MP. Comparisons of Clinical Reported and Patient Reported Cellulite Severity Scales With Existing Scales for Measurement of Cellulite Severity.

Maui Derm 2018: Sadick NS, Young VL, Liu G, Shusterman NH, McLane MP, Hurley D, Goldman MP. Efficacy and Safety Evaluation of Collagenase Clostridium Histolyticum for the Treatment of Edematous Fibrosclerotic Panniculopathy. Poster presented at the Maui Derm for Dermatologist 2018; Jan. 28-Feb. 1, 2018; Maui, HI.

McMahon, C. G., et al., "Pharmacokinetics, Clinical Efficacy, Safety Profile, and Patient-Reported Outcomes in Patients Receiving Subcutaneous Testosterone Pellets 900 mg for Treatment of Symptoms Associated With Androgen Deficiency", J Sex Med. Jul. 2017;14(7):883-890.

MedlinePlus "Cellulite," http://www.nlm.nih.gov/medlineplus/encv/article/002033.htm, 2 pages, updated Oct. 10, 2010.

Melton-Witt, et al., "Identification of Functional Domains of Clostridium septicum Alpha Toxin," Biochem., vol. 45, No. 48, pp. 14347-14354 (2006).

Muppavarapu RC, et al., "Clinical outcomes following collagenase injections compared to fasciectomy in the treatment of Dupuytren's contracture," Hand, 2015;10(2):260-265.

Naam NH. Functional outcome of collagenase injections compared with fasciectomy in treatment of Dupuytren's contracture. Hand (N Y). 2013;8(4):410-416.

Narins RS, Brandt F, Leyden J, Lorenc ZP, Rubin M, Smith S. A randomized, double-blind, multicenter comparison of the efficacy and tolerability of restylane versus zyplast for the correction of nasolabial folds. Dermatol Surg. 2003;29(6):588-595.

National Library of Medicine "MeSH Descriptor Data—Hyaluronoglucosaminidase," http://www.nlm.nih.gov/cgi/mesh/2008/MB_cgi?mode=&term=hyaluronidase, 1 page, 2008.

NESPS 2017: Young VL, Sadick NS, Liu G, Shusterman NH, McLane M, Hurley D, Goldman MP. Comparisons of Clinician-Reported and Patient-Reported Cellulite Severity Scales with existing scales for measurement of cellulite severity. Podium presented at the 34th Annual Meeting of the Northeastern Society of Plastic Surgeons (NESPS); Sep. 8-10, 2017; Newport, RI.

Newsday Article—"Promising New Treatments for Stiff-Shoulder Condition", published on Oct. 2, 2001, p. 1.

Nguyen, M. K., & Leed. S., "Injectable biodegradable hydrogels," Macromol. Biosci., vol. 10, 2010, pp. 563-579.

Nielsen, et al., "Prediction of Signal Peptides and Signal Anchors by a Hidden Markov Model," AAAI Press, pp. 122-130 (1998).

Norian, J.M., et al., "Characterization of tissue biomechanics and mechanical signaling in uterine leiomyoma, " Matrix Biol., 31(1): 57-65, 12 pages. (Jan. 9, 2011).

Notice of Acceptance for Australian patent application No. 2015261743 dated Aug. 21, 2017, 3 pages.

Nydick JA, et al. "A comparison of percutaneous needle fasciotomy and collagenase injection for dupuytren disease,"J Hand Surg Am. 2013;38(12):2377-2380.

O'Donohue, et al., "Cloning and Expression in Bacillus subtilis of the NPR Gene from Bacillus thermoproteolyticus Rokko Coding for the Thermostable Metalloprotease Thermolysin," Biochem. J., vol. 300, pp. 599-603 (1994).

O'Donohue, et al., "The Roles of the Prosequence of Thermolysin in Enzyme Inhibition and Folding in Vitro," J. Biol. Chem., vol. 271, No. 43, pp. 26477-26481 (1996).

obgyn.net Headline News, Successful phase II results lead to phase III approval—Dupuytren disease. Posted at the web on Oct. 8, 2001, (at the web: http://www.obgyn.net/newsrx/general_h ealth-dupuytren_ d isease-20011008-21.asp), especially p. 2, last paragraph.

Omi et al., "Ultrastructural Assessment of Cellulite Morphology: Clues to a Therapeutic Strategy?" Laser Therapy, 2013, 22.2: 131-136.

Oppenheim et al., "A modified procedure for the purification of clostridial collagenase," Entrez Pubmed Abstract (1978).

(56) References Cited

OTHER PUBLICATIONS

Pall BioPharmaceuticals ("Mustang Q Capsule: The Only Disposable Process Chromatography Column for Pharmaceutical Manufacturing" Nov. 21, 2000).
Peavey, MD, M., et al., "Collagen-Binding all Integrin Expression in Human Myometrium and Fibroids Utilizing a Novel RNA In Situ Probe," Reproductive Sciences vol. 21(9) pp. 1139-1144, (2014).
Peimer CA, Blazar P, Coleman S, Kaplan FT, Smith T, Lindau T. Dupuytren contracture recurrence following treatment with collagenase clostridium histolyticum (CORDLESS [Collagenase Option for Reduction of Dupuytren Long-Term Evaluation of Safety Study]): 5-year data. J Hand Surg Am. 2015;40(8):1597-1605.
Povlsen B, Povlsen SD. "What is the better treatment for single digit dupuytren's contracture: surgical release or collagenase clostridium histolyticum (Xiapex) injection?," Hand Surg. 2014;19(3):389-392.
Priestley T, Chappa AK, Mould DR, Upton RN, Shusterman N, Passik S, Tormo VJ, Camper S. Converting from Transdermal to Buccal Formulations of Buprenorphine: A Pharmacokinetic Meta-Model Simulation in Healthy Volunteers. Pain Med. Oct. 1, 2018;19(10):1988-1996.
Protein I—Separation, Purification, and Property-, edited by Japan Biochemical Society, 1st Edition, 1st Issue, published by Tokyo Kagaku Dojin, Feb. 26, 1990, pp. 161-169.
PS 2018: Kirby MT, Lenderking WR, Bender RH, Chen J, Hurley D, Knoble NB, Liu G, Davidson JA, McLane MP. Assessing Cellulite Severity: Test-Retest Reliability of and Concordanance Between New Clinician Reported and Patient Reported Photonumeric Scales.
Eschbach et al., "Improved Erythrocyte Lysis Assay in Microtitre Plates for Sensitive Detection and Efficient Measurements of Hemolytic Compounds from Ichthyotoxic Algae", Journal of Applied Toxicology, 2001, vol. 21, pp. 513-519.
GenBank Under Accession No. CAA54291; Retrieved from: https://www.ncbi.nlm.nih.gov/protein/CAA54291; Retrieved on: May 19, 2023.
VCS 2018: Sadick NS. Collagenase Clostridium Histolyticum for the Treatment of Edematous Fibrosclerotic Panniculopathy.
VCS 2018: Sadick NS. New measurement and treatment options for edematous fibrosclerotic panniculopathy (cellulite): results from a randomized, double-blind, placebo-controlled trial of CCH. Podium presented by Dr. John Joseph at the Vegas Cosemetic Surgery (VCS); Jun. 6-10, 2018; Las Vegas, NV.
Vos-Scheperkeuter, et al: Histochemical Analysis of the Role of Class I and Class II Clostridium Histolyticum Collagenase in the Degradation of Rat Pancreatic Extracellular Matrix for Islet Isolation, Cell Transplantation, vol. 6, No. 4, pp. 403-412, 1997.
Wanner M et al., "An Evidence-Based Assessment of Treatments for Cellulite," J. Drugs Dermatol. Apr.; 7(4):341-5 (2008).
Waters MJ, et al. Am J Orthop (Belle Mead NJ). 2015;44(11):518-521.
Welton et al., "Collagenase Production by Achromobacter lophagus," Entrez Pubmed Abstract (1975).
Wetmore, et al., "The Efficiency of Processing and Secretion of the Thermolysin-like Neutral Protease from Bacillus cereus Does Not Require the Whole Prosequence, But Does Depend on the Nature of the Amino Acid Sequence in the Region of the Cleavage Site," Mol. Microbiol., vol. 12, No. 5, pp. 747-759 (1994).
Why Choose Recombinant Enzymes; 11 pages.
Wikipedia.org "Cellulite," http://en.wikipedia.org/wiki/cellulite, 5 pages, Dec. 15, 2012.
Wolters et al., Different Roles of Class I and Class II Clostridium Histolyticum Collagenase In Rat Pancreatic Islet solation, Diabetes 44: 227-233 (1995).
Xiaflex(Registered) (collagenase clostridium histolyticum) [Prescribing Information, Revised Nov. 2019]. Malvern, PA: Endo Pharmaceuticals Inc.
Yoshihara, K., et al., "Cloning and Nucleotide Sequence Analysis of the colH Gene from Clostridium Histolyticum Encoding a Collagenase and a Gelatinase," Journal of Bacteriology 176(21): pp. 6489-6496 (Nov. 1994).
Zhou C, et al., "Collagenase Clostridium Histolyticum versus Limited Fasciectomy for Dupuytren's Contracture," Plast Reconstr Surg 2015;136(1):87-97.
"Basic Biochemistry Experiment, Department of Biology, Beijing Normal University, Higher Education Press", pp. 38-39, Feb. 1984.
BD Bionutrients Technical Manual: Advanced Processing, 3rd edition, Oct. 2006.
Kagedal et al.; "Chemical, physical and chromatographic properties of Superdex 75 prep grade and Superdex 200 prep grade gel filtration media;" Journal of Chromatography; vol. 537, 1991, pp. 17-32.
Liberase Research Grade Purified Enzyme Blends, Reference material A10, Roche Diagnostics GmbH, Aug. 2013, Version 06, pp. 1-18.
Protein Purification Handbook, Amersham Biosciences; 2001, 1-98.
Rhodes et al, "Determination of Protein Purity," Methods in Enzymology, vol. 463, 2009, pp. 677-689.
Sigma-Aldrich, "Product Information on Collagenase, High Purity", dated Sep. 13, 2018, pp. 1-6.
U.S. Appl. No. 15/669,286, filed Aug. 4, 2017.
U.S. Appl. No. 14/328,772, filed Jul. 11, 2014.
Frigerio, et al., "Model Building of a Thermolysin-Like Protease by Mutagenesis," Protein Eng., vol. 10, No. 3, pp. 223-230 (1997).
Galardy et al..(Biochemistry, vol. 22, pp. 4556-4561, 1983.
Gaston, R.G., Larsen, S.E., Pess GM, et al., "The Efficacy and Safety of Concurrent Collagenase Clostridium Histolyticum Injections for 2 Dupuytren Contractures in the Same Hand: a Prospective, Multicenter study". J Hand Surg Am. 2015;40(10):1963-1971.
Gelbard et al.; "Collagenase Versus Placebo in the Treatment of Peyronie's Disease: A Double-Blind Study," The Journal of Urology, 1993, vol. 1489, pp. 56-58.
Gelbard et al.; "The Use of Collagenase in the Treatment of Peyronie's Disease," The Journal of Urology, 1985, vol. 134, pp. 280-283.
GenBank Database accession No. D29981 (https://www.ncbi.nlm.nih.gov/nuccore/D29981).
GenBank Database accession No. D87125 (https://www.ncbi.nlm.nih.gov/nuccore/D87125).
GenBank Database accession No. D87215 (https://www.ncbi.nlm.nih.gov/nuccore/D87215).
GenBank Database accession No. D87215.1 (https://www.ncbi.nlm.nih.gov/nuccore/D87215.I).
GenBank Database accession No. X63673 (https://www.ncbi.nlm.nih.gov/nuccore/X63673).
Gill et al., Journal of Diabetes Science and Technology, 2007, vol. 1, Issue 5, p. 725-729.
Gill, H. S., & Prausnitz, M. R., "Does needle size matter?," Journal of Diabetes Science and Technology, vol. 1(5), Sep. 2007, pp. 725-729.
Gilpin D, et al., "Injectable collagenase clostridium histolyticum: a new nonsurgical treatment for Dupuytren's disease, "J Hand Surg Am, 2010, 35(12), pp. 2027-2038.
Giudicelli et al. "Influence of trypsin on lipolysis in human fat cells comparison with rat adipocytes," Biochimica et Biophysica Acta, vol. 450, Issue 3, pp. 358-366, 1976.
Goldman et al. (Cellulite: A New Treatment Approach Combining Subdermal Nd: YAG Laser Lipolysis and Autologous Fat Transplantation. (Aesthetic Surg J 2008;28:656-662).
Goldstein, I., et al., "Changes in the Effects of Peyronie's Disease After Treatment With Collagenase Clostridium histolyticum: Male Patients and Their Female Partners", Sex Med. Jun. 2017;5(2):e124-e130.
Gordon, et al., "Clostridium septicum Alpha Toxin is Proteolytically Activated by Furin," Infection and Immunity, vol. 65, No. 10, pp. 4130-4134 (1997).
Green et al., "Cellfina Observations: Pearls and Pitfalls," Seminars in Cutaneous Medicine and Surgery; vol. 34: 144-46 (Sep. 2015).
Hale, M., et al., "Long-term safety and analgesic efficacy of buprenorphine buccal film in patients with moderate-to-severe chronic pain requiring around-the-clock opioids", J Pain Res. 2017; 10: 233-240.

(56) References Cited

OTHER PUBLICATIONS

Hannafin, et al., "Adhesive capsulitis, A treatment approach", Clinical Orthopaedics and Related Research, No. 372, pp. 95-109 2000.
Harmon "Is Cellulite Forever?," Scientific American, http://www.scientificamerican.com/article.cfm?id=is-cellulite-forever, 4 pages, May 4, 2009.
Hatheway, "Toxigenic Clostridia," Clin. Microbiol. Rev., vol. 3, No. 1, pp. 66-98 (1990).
Hay DC, et al. "Surgical findings in the treatment of Dupuytren's disease after initial treatment with clostridial collagenase (Xiaflex)," J Hand Surg Eur vol. 2014;39(5):463-465.
Health News, WebMD, pp. 1-2 (2006).
Hellstrom, Wayne J.G., et al., "Safety Profile of Collagenase Clostridium Histolyticum Stratified by Degree of Penile Curvature in Patients With Peyronie Disease", Urology (106), Aug. 2017, pp. 237.e9-237.e14.
Hesse et al., "Recombinant enzymes for islet isolation: purification of a collagenase from clostridium histolyticum and cloning/expression of the gene," Transplantation Proceedings, 27(6):3287-3289 (1995).
Heuck, et al., "Conformational Changes That Effect Oligomerization and Initiate Pore Formation are Triggered Throughout Perfringolysin O Upon Binding to Cholesterol," J. Biol. Chem., vol. 282, No. 31, pp. 22629-22637 (2007).
Hexsel DM, Dal'Forno T, Hexsel CL. A validated photonumeric cellulite severity scale. JEADV 2009; 23: 523-528.
Hexsel et al., "A validated photonumeric cellulite severity scale", Journal compilation 2009 European Academy of Dermatology and Venereology (Year: 2009).
Hexsel et al., "Side-By-Side Comparison of Areas with and without Cellulite Depressions Using Magnetic Resonance Imaging," Dermatol. Surg. 2009, 35: 1471-1477.
Hexsel, et al., JEADV; A validated photonumeric cellulite severity scale; DOI: 10.1111/j.1468-3083.2009.03101.x; 2009; pp. 1-6.
High Performance Liquid Chromatography (HPLC) Tutorial; 7 pages.
Hiroshi et al., "Cloning a neutral protease of Clostridium histolyticum, determining its substrate specificity, and designing a specific substrate", Applied Microbiology and Biotechnology, Springer, DE, vol. 99, No. 24, Aug. 26, 2015, pp. 10489-10499.
Hulstyn, et al., "Adhesive capsulitis of the shoulder", Orthopaedic Review, pp. 425-433, Apr. 1993.
Hurst, L. C., et al., "Injectable Collagenase Clostridium Histolyticum for Dupuytren's Contracture" N Engl J Med. 2009; 361(10), pp. 968-979.
Hurst, L.C., et al., "Injectable clostridial collagenase: striving toward nonoperative treatment options for fibroproliferative disorders," available at http://www.aaos.org/research/committee/research/Kappa/KD2009.sub.-Hurst.pdf.
Hutchinson, J.W., et al., "Dupuytren's Disease and Frozen Shoulder Induced by Treatment with a Matrix Metalloproteinase Inhibitor," The Journal of Bone and Joint Surgery 80B(5): pp. 907-908 (1998).
Ibrahim-Grant et al; "Expression of PZ-Peptidases by Cultures of Several Pathogenic Fungi. Purification and Characterization of a Collagenase from Trichophyton Schoenleinii;" Journal of Medical & Veterinary Mycology; 1996, 34, pp. 83-90—Reference material B5 filed by defendant before KPC in connection with the Korean Appeal Suit case for Korean Patent Application No. 10-2011-7006197.
Imhof M, Kuhne, "A Phase III Study of IncobotulinumtoxinA in the Treatment of Glabellar Frown Lines", J Clin Aesthet Dermatol. 2011;4(10):28-34.
International Preliminary Report issued on Mar. 20, 2018, for corresponding application PCT/US2016/051670, 8 pages.
International Search Report and Written Opinion of PCT/US2018/020551 mailed on May 28, 2018 (22 pages).
Ippolito, E., et al.; "Experimental Study on the Use of Collagenase in Localized Connective Tissue Fibrosis", Database EMBASE on STN. 1976, Acc. No. 1976196184, Abstract.
ISPOR 2018: Kirby MT, McLane MP, Lenderking WR, Bender R, Chen J, Hurley D, Knoble N, Liu G, Davidson JA. Assessing cellulite severity: method for assessing reliability of a new clinician-reported and a new patient-reported photonumeric scale. Poster presented at the International Society of Pharmacoeconomics and Outcomes Research (ISPOR); May 19-23, 2018; Baltimore, MD.
Iwahashi, M., et al., "Immunohistochemical analysis of collagen expression in uterine leiomyornata during the menstrual cycle," Experimental and Therapeutic Medicine 2011, 2:287-290.
Jang et al.; "The Anti-Wrinkle and Whitening Effect of Extracts of Castanea crenata Inner Shell;" Journal of Life Science; 2011; vol. 21; No. 5; pp. 734-738—Exhibit B11 filed by defendant before KPC in connection with the Korean Appeal Suit case for Korean Patent Application No. 10-2011-7006197.
Jayes, DVM, PhD, F.L, et al., "Loss of stiffness in collangen-rich uterine fibroids after digestion with purified collagenase Clostridium histolyticum," American Journal of Obstetrics & Gynecology, 1.e1, 8 pages (2016).
Jayes, F. L., et al., "Treatment of Uterine Fibroids with Highly Purified Clostridal Collagenase," Fertility and Sterility, vol. 98, No. 3, p. S232, XP055127058, Oct. 24, 2012.
Jin, B., et al.; "Reversibility of Experimental Rabbit Liver Cirrhosis by Portal Collagenase Administration", Laboratory Investigation (2005) 85, pp. 992-1002.
Joanna Bauer "Non-contact thermal imaging as potential tool for personalized diagnosis and prevention of cellulite" (Year: 2017).
Jung et al., "Expression of the colH gene encoding clostridium histolyticum collagenase in bacillus subtilis and its application to enzyme purification," Microbial. Immunol., 40(12):923-929 (1996).
"Citation of Prior Art and Statements Under 35 U.S.C. 301" dated Dec. 23, 2019; (Attached Exhibits 1-3); 17 page document.
The Declaration of Thomas Wegman and Bo Yu Dated Mar. 13, 2013 and Filed in U.S. Appl. No. 13/713,019.
AAD 2017: Goldman MP, Sadick NS, Liu G, Shusterman NH, McLane MP, Young VL. Efficacy and safety of collagenase clostridium histolyticum for the treatment of edematous fibrosclerotic panniculopathy.
AAHS 2018: Divino V, Camper SB, DeKoven M, Hurley D. Total cost of care associated with collagenase clostridium histolyticum versus fasciectomy for the treatment of Dupuytren's contracture: a retrospective cohort analysis.
AAPS 2018: McLane MP, Goldman MP, Sadick NS, Liu G, Hurley D, Young VL. Analysis of potential impact of healthcare provider gender on rating cellulite severity.
Akers, "Excipient-drug interactions in parenteral formulations," J. Pharm. Sci., 91:2283-2300, 2002.
Almeida et al., "Intra- and inter-observer reliability of the application of the cellulite severity scale to a Spanish female population : CSS reliability in a Spanish female population", Jeadv. Journal of the european academy of dermatology and venereology., vol. 27, No. 6, Apr. 6, 2012, pp. 694-698.
AMCP Nexus 2017: Camper SB, Divino V, Hurley D, DeKoven. Cost per episode of care with collagenase clostridium histolyticum versus fasciectomy for Dupuytren's contracture: a real-world claims database analysis. Poster presented at the Annual Academy of Managed Care Pharmacy Nexus (AMCP Nexus); Oct. 16-19, 2017; Grapevine, TX.
Angleton et al., "Preparation and Reconstitution with Divalent Metal Ions of Class I and Class II Clostridium Histolyticum Apocollagenases," Biochemistry, 1988, vol. 27, pp. 7406-7412.
Anonymous: "Stony Brook Announces New Clinical Trial with BioSpecifics Injectable Collagenase for Adhesive Capsulitis," (Oct. 2000); Retrieved from the Internet Oct. 12, 2015.
Apostol et al., "Uncertainty Estimates of Purity Measurements Based on Current Information: Toward a "Live Validation" of Purity Methods," Pharm Res, 2012, 16 pages.
ASDS 2017: Sadick NS, Goldman MP, Liu G, Shusterman NH, McLane MP, Hurley D, Young VL. Comparisons of Clinician Reported and Patient Reported Cellulite Severity Scales With Existing Scales for Measurement of Cellulite Severity. Poster presented at the 2017 American Society for Dermatologic Surgery Annual Meeting (ASDS); Oct. 5-8, 2017; Chicago, IL.

(56) References Cited

OTHER PUBLICATIONS

ASDS 2017: Sadick NS, Young VL, Liu G, Shusterman NH, McLane MP, Hurley D, Goldman MP. Efficacy and Safety Evaluation of Collagenase Clostridium Histolyticum for the Treatment of Edematous Fibrosclerotic Panniculopathy (Cellulite). Poster presented at the 2017 American Society for Dermatologic Surgery Annual Meeting (ASDS); Oct. 5-8, 2017; Chicago, IL.

ASHT 2016: Kaplan FTD, Curtin C, Kaufman GJ. Predictors of recurrence for joints successfully treated with collagenase clostridium histolyticum injections. Podium presented at the 39th Annual Meeting of the American Society for Hand Therapists (ASHT); Sep. 15-18, 2016; Washington, DC.

ASPS 2017 (Aesthetica): Young VL, Sadick Ns, Liu G, Shusterman NH, McLane MP, Goldman MP. Efficacy and safety of collagenase clostridium histolyticum for the treatment of edematous fibrosclerotic panniculopathy (cellulite). Podium presented at the American Society of Plastic Surgeons Aesthetica 2017 Super Symposium; Mar. 2-4, 2017; New Orleans, LA.

ASPS 2018: McLane MP, Goldman MP, Sadick NS, Liu G, Hurley D, Young VL. Analysis of Potential Impact of Healthcare Provider Gender on Rating Cellulite Severity.

ASPS 2018: McLane MP, Lenderking WR, Bender RH, Chen J, Hurley D, Knoble NB, Liu G, Davidson JA. Assessing Cellulite Severity: Test-Retest Reliability of and Concordanance Between New Clinician Reported and Patient Reported Photonumeric Scales.

Assessment Report, Xiapex, Common name: Collagenase clostridium histolyticum, Procedure No. EMEA/H/C/2048, 2011, 71 pages.

ASSH 2016: Costas B, Coleman S, Kaufman G, James R, Gaston RG. A randomized phase 2A, double-blind, placebo-controlled, dose-ranging study to evaluate the safety and effectiveness of collagenase clostridium histolyticum (cch) in the treatment of Dupuytren disease nodules. Podium presented at the 71st Annual Meeting of the American Society for Surgery of the Hand (ASSH); Sep. 29-Oct. 1, 2016; Austin, TX.

Atroshi I, et al., "Costs for collagenase injections compared with fasciectomy in the treatment of Dupuytren's contracture: a retrospective cohort study," BMJ Open. 2014;4(1):e004166 (7 pages).

AUA 2017: Ralph DJ, Raheem AA, Liu G. The safety and efficacy of collagenase clostridium histolyticum in combination with vacuum therapy for the treatment of Peyronie's disease. Podium presented at the 112th Annual Meeting of the American Urological Association (AUA); May 12-16, 2017; Boston, MA.

AUA 2018: Goldstein I, Liu G, McLane M, Hurley D. Baseline severity of Peyronie's Disease Symptoms Predicts Improved Female Partner Burden Scores After Treatment with Collagenase Clostridium Histolyticum. Podium presented at the American Urological Association (AUA); May 21, 2018; San Francisco, CA.

AUA 2018: Goldstein I, Liu G, McLane M, Hurley D. Impact of Collagenase Clostridium Histolyticum Treatment of Men With Peyronie's Disease on Improvement of Female Partner Sexual Function.

Australian Public Assessment Report for Collagenase clostridium histolyticum, Australian Government, Department of Health, Therapeutic Goods Administration, Proprietary Product Name: Xiaflex, Aug. 2016, 58 pages.

Australian Public Assessment Report for Collagenase clostridium histolyticum, Australian Government, Department of Health, Therapeutic Goods Administration, Proprietary Product Name: Xiaflex, Sponsor: Actelion Pharmaceuticals Australia Pty Ltd, Nov. 2013, 83 pages.

Auxilium et al. (Auxilium Pharmaceuticals, Inc. Announces First Patients Dosed in Xiaflex Phase Ib Cellulite Study. Jan. 26, 2011, pp. 1-7).

Badalamente et al., "Enzyme injection as a nonoperative treatment for Dupuytren's disease", Drug Delivery, 1996, vol. 3, pp. 35-40.

Badalamente et al., "Enzyme Injection as Nonsurgical Treatment of Dupuytren's Disease," The Journal of Hand Surgery, 2000, 25A(4), pp. 629-636.

Badalamente et al: "Collagen as a clinical target: Nonoperative treatment of dupuytren's disease" The Journal of Hand Surgery, W.B. Saunders, vol. 27, No. 5, Sep. 1, 2002, pp. 788-798.

Badalamente, Marie A., et al. "Efficacy and Safety of Injectable Mixed Collagenase Subtypes in the Treatment of Dupuytren's Contracture," The J. of Hand Surgery, 32A(6):767-774 (2007).

Bains, et al., "Primary frozen shoulder, The untold story!", Journal of Bone and Joint Surgery—British Volume vol. 90-B. Supp.sub.--II, 352 (abstract), 2006.

Balci, N., et al., "Shoulder Adhesive Capsulitis and Shoulder Range of Motion in Type II Diabetes Mellitus: Associations with Diabetic Complications," Journal of Diabetes Complications, 13(3): pp. 135-140 (1999), Abstract Only.

Ballard, et al., "Purification and Characterization of the Lethal Toxin (Alpha-Toxin) of Clostridium septicum," Infection and Immunity, vol. 60, No. 3 pp. 784-790 (1990).

BD BioPharmaceutical Production ("Bionutrient Technical Manual", Mar. 2004).

Bear, B. J., et al., "Treatment of Recurrent Dupuytren Contracture in Joints Previously Effectively Treated with Collagenase Clostridium Histolyticum", J Hand Surg Am. 2017; vol. 42(5): pp. 391.e1-391.e8.

Behera, MD, M.A., et al., "Thrombospondin-1 and Thrombospondin-2 mRNA and TSP-1 and TSP-2 Protein Expression in Uterine Fibroids and Correlation to the Genes COL1A1 and COL3A1 and to the Collagen Cross-link Hydroxyproline," Reproductive Sciences, vol. 14, No. 8S, pp. 63-76 (Dec. 2007).

Bielfeldt et al., "Non-invasive evaluation techniques to quantify the efficacy of cosmetic anti-cellulite products", Skin Research and Technology 2008; 14: p. 336-346 (Year: 2008).

Billington, et al., "Thiol-Activated Cytolysins: Structure, Function and Role in Pathogenesis," FEMS Microbiol. Lett., vol. 182, No. 2, pp. 197-205 (2000).

Bio-Rad; "Chromatography Column Performance and Data Analysis Success Guide;" 17 pages.

Bond et al., "Purification and separation of individual collagenases of clostridium histolyticum using red dye ligand chromatography," Biochemistry 23:3077-3085, 1984.

Bond, et al., "Characterization of the Individual Collagenases from Clostridium Histolyticum," Biochemistry, 1984, vol. 23, pp. 3085-3091.

Bonnerjea J. et al.; "Protein purification: the right step at the right time;" Bio/technology, Nov. 1986, v4, pp. 954-958.

Bowen, "A Comparison of the Lethal and Hemolytic Toxins of Clostridium Histolyticum," Yale J. Biol. Med., vol. 25, No. 2, pp. 124-138 (1952).

Brandhorst et al., "Ajustment of the radio between collagenase class II and I improves islet isolation outcome," Transplantation Proceedings, 37:3450-3451, 2005.

Brandhorst, H. et al. 2008. The ratio between collagenase class I and class II influences the efficient islet release from the rat pancreas. Transplantation 85: 456-461. specif. pp. 456, 457.

Brandt F, Bassichis B, Bassichis M, O'Connell C, Lin X. "Safety and Effectiveness of Small and Large Gel-Particle Hyaluronic Acid in the Correction of Perioral Wrinkles", J Drugs Dermatol. 2011;10(9):982-987.

Brunengraber, MD, L.N. et al., "Injectable Clostridium Histolyticum Collagenase as a Potential Treatment for Uterine Fibroids," Reproductive Sciences, vol. 21(12), pp. 1452-1459 (2014).

Buhren et al., "Hyaluronidase: From Clinical Applications to Molecular and Cellular Mechanisms," Eur. J. Med. Res. vol. 21:5 (2016).

Bunker T 0 et al: "The pathology of 1-10 frozen shoulder. A Dupuytren-like disease." The Journal of Bone and Joint Surgery British vol. Sep. 1995, vol. 77, No. 5, Sep. 1995, pp. 677-683.

Bunker, T.D., "Frozen shoulder: unravelling the enigma", Ann R Coll Surg Engl 79, pp. 210-213, 1997.

Callaghan III, MD, et al.: Seminars in Cutaneous Medicine and Surgery, vol. 36, Dec. 2017, Cellulite: a review of pathogenesis-directed therapy, pp. 179-184.

Casabona et al., "Microfocused Ultrasound with Visualization and Calcium Hydroxlapatite for Improving Skin Laxity and Cellulite Appearance," PRS Global Open 2017.

(56) References Cited

OTHER PUBLICATIONS

Center for Drug Evaluation and Research; Application No. 20633Orig1s000; Other Review(s); PMR/PMC Development Template; https://www.accessdata.fda.gov/drugsatfda_docs/nda/2015/206333Orig1s000OtherR.pdf; Last Updated Apr. 27, 2015.
Center Watch Staff "BioSpecifics Technologies announces positivedata from phase lib cellulite study" Nov. 21, 2016. (Year:2016).
Chen, H.R., et al., "Clinicopathological Study on Submucosal Injection of Collagenase in the Treatment of Submucous Fibrosis in the Oral Cavity", The Kaohsiung Journal of Medical Sciences, 1986, 2(3), pp. 212-219.
Collagenase—Worthington Enzyme Manual available at http://www.worthington-biochem.com/cls/default.html; downloaded from internet on Dec. 1, 2020; 4 pages.
Collagenase P, From Clostridium histolyticum; Roche Diagnostics GmbH, Jul. 2005, 2 pages.
Collagenase P; Jul. 2005—Exhibit A5 filed by Plaintiff before KPC in connection with the Korean Appeal Suit case for Korean Patent Application No. 10-2011-7006197.
Communication from European Patent Office in application serial No. EP 16770624.1 dated Apr. 20, 2018, 3 pages.
Coons S, Gwaltney C, Hays R, Lundy J, Sloan J, Revicki D, Lenderking W, Cella D, Basch E. Recommendations on Evidence Needed to Support Measurement Equivalence between Electronic and Paper-Based Patient-Reported Outcome (PRO) Measures: ISPOR ePRO Good Research Practices Task Force Report. Value in Health. 2009; 12:419-429.
Costas, B., et al., "Efficacy and safety of collagenase clostridium histolyticum for Dupuytren disease nodules: a randomized controlled trial", BMC Musculoskelet Disord. Aug. 3, 20170;18(1):374.
Court Decision dated Aug. 11, 2017 in Korean Appeal Suit case for Korean Patent Application No. 10-2011-7006197.
Cuggino, J.C., et al., "Synthesis, characterization and slow drug delivery of hydrogels based in N-acryloyl-tris-(hydroxymethyl) aminomethane and N-isopropyl acrylamide," Reactive & Functional Polymers, vol. 71, 2011, pp. 440-446.
Dargatz, et al., "The Heterodimeric Protease Clostripain from Clostridium Histolyticum is Encoded by a Single Gene," Mol. Gen. Genet., vol. 240, pp. 140-145 (1993).
Declaration of inventor Benjamin Del Tito, Jr. dated Feb. 7, 2010 and filed in U.S. Appl. No. 11/699,302.
Declaration of inventors Thomas Wegman and Bo Yu dated Mar. 13, 2013 filed in U.S. Appl. No. 13/713,019.
Del Carlo, et al. "Comparative Analysis of Collagen Degradation in Peyronie's Disease Plaque and Dupuytren's Contracture Cord Tissues Injected with Mixed Collagenase Subtypes." The Journal of urology 181.4 (2009): 279.
Demidyuk, et al., "Structural Organization of Precursors of Thermolysin-like Proteinases," Protein J., vol. 27, pp. 343-354 (2008).
Denkler et al., "Evidence-Based Medicine: Options for Dupuytren's Contracture: Incise, Excise, and Dissolve," Plastic and Reconstructive Surgery 139(1): 240e-255e (2016).
Dhaneshwar, S.S. et al. 2006. Dextran: a promising macromolecular drug carrier. Indian Journal of Pharmaceutical Sciences. Nov.-Dee., pp. 705-714. specif, p. 706.
Difeo and BBL Manual, 2003, 458-460.
Dimarcantonio, T., "Multiple Collagenase Injections Effective, Safe for Treating 'Frozen Shoulder'," ORTHOSuper Site, Retrieved from the Internet: http://www.orthosupersite.com/view.aspx?rid=16738#jump [retrieved on Nov. 8, 2011] (May 2008).
Doris Hexsel et al., "Noninvasive treatment of cellulite utilizing an expedited treatment protocol with a dual wavelength laser-suction and massage device"Journal of Cosmetic and Laser Therapy, 2013; 15: 65-69 (Year: 2013).
Ducka et al., "A universal strategy for high-yield production of soluble and functional clostridial collagenases in *E. coli*," Appl. Microbiol Biotechnol 83:1055-1065 (2009).
Eckhard et al., "Structural Basis for Activity Regulation and Substrate Preference of Clostridial Collagenases G, H, and T", J. Biol. Chem., vol. 288, No. 28, Jul. 12, 2013, pp. 20184-20194.
Edkins et al., Assessment of Potential Cross-Reactivity of Human Endogenous Matrix Metalloproteinases With Collagenase Clostridium Histolyticum Antibodies In Human Sera Obtained From Patients With Dupuytren's Contracture, Clinical and Vaccine Immunology, 19(4) 562-569 (2012).
EMBL (Protein Expression and Purification Core Facility. Cloning Choice of Expression Systems. 2002).
Endo Pharmaceuticals, "News Release: Endo Announces Positive Data From Phase 2b Study of Collagenase Clostridium Histolyticum (CCH) in Patients with Celluite," Nov. 17, 2016.
Eoanna Bauer "Endo International plc,"Endo Announces Positive Data from Phase 2b Study of Collagenase Clostridium Histolyticum (CCH) in Patients with Cellulite, Nov. 17, 2016, 08:30 ET (Year: 2016).
European Search Opinion received in EP 12155228 on Jun. 11, 2012.
Evans (1985). The lanthanide-enhanced affinity chromatography of clostridial collagenase. Biochem J 225(2): 553-556.
Exhibit 1 of the Declaration of Dr. Dagum dated Sep. 4, 2017: "Curriculum Vitae of Alexander B. Dagum, M.D."
Exhibit 1 of the Declaration of Dr. Michael Mclane: "Auxilium Press Release; "Auxilium Pharmaceuticals, Inc. Announces First Patients Dosed in Xiaflex Phase Ib Cellulite Study;" Jan. 26, 2011; 4 pages; downloaded from: https://www.sec.gov/Archives/edgar/data/1182129/000119312512024205/d290313dex991.htm".
Exhibit 1 of the Declaration of Dr. Susan G. Emeigh Hart: "Assignment Recorded with the USPTO on Aug. 17, 2016 at Reel 039466 Frame 0337".
Exhibit 1: U.S. Pat. No. 4,542,065; Issued Jun. 18, 1985; Inventor: Sheldon R. Pinnell; 5 pages.
Exhibit 2—Information Related to ClinicalTrials.gov Identifier: NCT01518907; "The Safety, Effectiveness, and Pharmacokinetics of AA4500 for the Treatment of Edematous Fibrosclerotic Panniculopathy (Commonly Known as Cellulite);" 9 pages; first Posted: Jan. 26, 2012; downloaded on Oct. 24, 2017 from: https://clinicaltrials.gov/ct2/show/NCT01518907.
Exhibit 2: Press Releases: Endo Announces Positive Results from Phase 3 Studies of Collagenase Clostridium Histolyticum (CCH) in Patients with Cellulite; Nov. 7, 2018; 3 pages.
Exhibit 3—Eddie Staley; "Auxilium Pharmaceuticals Announces First Patients Dosed in Xiaflex Phase Ib Cellulite Study;" Jan. 26, 2012; 1 page; downloaded from: https://www.benzinga.com/news/12/01/2291202/auxilium-pharmaceuticals-announces-first-patients-dosed-in-xiaflex-hase-ib-cellu.
Exhibit 3 of the Declaration of Dr. Michael Mclane: "Auxilium Drug Shipment Request Form for Domestic Studies regarding Protocol No. AUX-CC-830".
Exhibit 3: Draelos, Zoe Diana: The disease of cellulite; Journal of Cosmetic Dermatology, vol. 4, Issue 4, First Published Dec. 5, 2005; 3 pages.
Exhibit 4—Press Release "Auxilium Pharmaceuticals, Inc. Announces First Patients Dosed in Xiaflex Phase Ib Cellulite Study;" Jan. 26, 2012; 1 page; downloaded from: http://phx.corporate-ir.net/phoenix.zhtml?c=142125&p=irol-newsArchiveArticle&ID=1653001.
Exhibit 4 of the Declaration of Dr. Michael Mclane: "Auxilium Shipment Authorization Request regarding Investigational Study AUX-CC-830".
Exhibit 5—Press Release; PRNewswire; "Auxilium Pharmaceuticals, Inc. Announces First Patients Dosed in Xiaflex Phase IB Cellulite Study;" Jan. 26, 2012; 7 pages; downloaded from: https://www.pmewswire.com/news-releases/auxilium-pharmaceuticals-inc-announces-first-patients-dosed-in-xiaflex-phase-ib-cellulite-study-138113223.html.
Exhibit 5 of the Declaration of Dr. Michael Mclane: "Eddie Staley; "Auxilium Pharmaceuticals Announces First Patients Dosed in Xiaflex Phase Ib Cellulite Study;" Jan. 26, 2012; 1 page; downloaded from: https://www.benzinga.com/news/12/01/2291202/auxilium-pharmaceuticalsannounces-first-patients-dosed-in-xiaflex-phase-ib-cellu".
Exhibit 6 of the Declaration of Dr. Michael Mclane: "Auxilium Pharmaceuticals, Inc. Announces First Patients Dosed in Xiaflex Phase Ib Cellulite Study;" Jan. 26, 2012; 1 page; downloaded from:

(56) References Cited

OTHER PUBLICATIONS http://phx.corporate-ir.net/phoenix.zhtml?c=142125&p=irolnewsArchiveArticle&ID=1653001.
Exhibit 7 of the Declaration of Dr. Michael Mclane: "Press Release; PRNewswire; "Auxilium Pharmaceuticals, Inc. Announces First Patients Dosed in Xiaflex Phase IB Cellulite Study;" Jan. 26, 2012; 7 pages; downloaded from: https://www.pmewswire.com/news-releases/auxilium-pharmaceuticals-incannounces-first-patients-dosed-in-xiaflex-phase-ib-cellulile-sludy-138113223.html".
Food and Drug Administration, "Guidance for Industry on Patient-Reported Outcome Measures: Use in Medical Product Development to Support Labeling Claims", Availability Use in Medical Product Development to Support Labeling claims. Federal Register. 2009;74(235):65132-65133.
Friedman et al. "Degradation of porcine dermal connective tissue by collagenase and hyaluronidase," British Journal of Dermatology, vol. 115, pp. 403-408, 1986.
Friedmann et al., "Cellulite: a Review with a Focus on Subcision," Clin Cosmet Investig Dermatol, 2017, 10: 17-23.
Sigma Aldrich (Collagenase Guide, pp. 1-4; Feb. 10, 2005).
International Search Report of PCT/US13/20940 mailed on Jul. 19, 2013.
Written Opinion of PCT/US13/20940 competed on Jul. 8, 2013.
Specific Activity—https://terms.naver.com/entry.nhn?docId=1913800&cid=50314&categoryId=50314, dated Jun. 10, 2017, pp. 1-3.
PS 2018: Young VL, Goldman MP, Sadick NS, Liu G, Hurley D, McLane MP: Analysis of Potential Impact of Healthcare Provider Gender on Rating Cellulite Severity.
Q6A Specifications: Test procedures and acceptance guidance criteria for new drug substances and new drug products: Chemical Substances; 2000; 16 pages.
Queiroz et al. ("Hydrophobic interaction chromatography of proteins," J. Biotechnology, 2001, 87, 143-159).
Querleux et al., "Anatomy and Physiology of Subcutaneous Adipose Tissue by in vivo Magnetic Resonance Imaging and Spectroscopy: Relationships with Sex and Presence of Cellulite," Skin Res. and Technology 8:118-124 (2002).
Ralph, D.J., et al., "Treatment of Peyronie's Disease With Collagenase Clostridium histolyticum and Vacuum Therapy: A Randomized, Open-Label Pilot Study", J Sex Med. Nov. 2017; 14(11):1430-1437.
Rhodes et al, "Determination of Protein Purity," Methods in Enzymology, vol. 463, Elsevier Inc.; 2009; pp. 677-689.
Roche Applied Science ("The Complete Guide for Protease Inhibition" 2004).
Rogers, BS. R., et al., "Mechanical homeostasis is altered in uterine leiomyoma," Am. J. Obstet. Gynecol., 198(4):474.e1-474.11, 22 pages (Apr. 2008).
Rotunda, Adam, M. et al., "Mesotherapy and phosphatidycholine injections: historical clarification and review," Dematologic Surgery: Official Publication for American Society for Dermatologic Surgery [et al.] 32(4):465-480 (2006).
Sasaki, Gordon H., "Single Treatment of Grades II and III Cellulite Using a Minimally Invasive 1,440-nm Pulsed Nd:YAG Laser and Side-Firing Fiber: An Institutional Review Board-Approved Study witha 24-Month Follow-Up Period" published on Oct. 11, 2013, 37, 1073-1089.
Scherman, P. et al., "One-year results of needle fasciotomy and collagenase injection in treatment of Dupuytren's contracture: A two-centre prospective randomized clinical trial, "J Hand Surg Eur vol. 2016;41(6):577-582.
Serefoglu, E. C., et.al., "Factors Associated With Erectile Dysfunction and the Peyronie's Disease Questionnaire in Patients With Peyronie Disease", Urology Sep. 2017; 107:155-160.
Shimada, et al., "C-terminal Amino Acid Residues are Required for the Folding and Cholesterol Binding Property of Perfringolysin O, a Pore-forming Cytolysin," The Journal of Biological Chemistry, vol. 274, No. 26, pp. 18536-18542 (1999).
Siegel, L.B., et al., "Adhesive Capsulitis: A Sticky Issue", American Family Physician 59(7), pp. 1843-1852, available at http://www.aafp.org/ afp/990401ap/1843.html, Apr. 1, 1999.
Sigma-Aldrich Product Information on Collagenase, High Purity—Exhibit A9 filed by Plaintiff before KPC in connection with the Korean Appeal Suit case for Korean Patent Application No. 10-2011-7006197.
Skov, S.T., et al., J Hand Surg Am. 2017;42(5):321-328.
Smalls; "Development of Quantitative Modes for the Investigation of Gynoid Lipodystrophy (Cellulite);" Ph.D. Thesis; University of Cincinnati; Apr. 21, 2005 (210 pages).
Smalls; "Effect of Weight Loss on Cellulite: Gynoid Lypodystrophy;" Plast. Reconstr. Surg.; 2006; vol. 118, No. 2; pp. 510-516.
Smalls; "Quantitative Model of Cellulite: Three-Dimensional Skin Surface Topography, Biophysical Characterization, and Relationship to Human Perception;" J. Cosmet. Sci., Mar./Apr. 2005; pp. 105-120.
Smith SR, Munavalli G, Weiss R, Maslowski JM, Hennegan KP, Novak JM. A multicenter, double-blind, placebo-controlled trial of autologous fibroblast therapy (Azficel-T) for the treatment of nasolabial fold wrinkles. Dermatol Surg. 2012;38(7):1234-1243.
SMSNA 2016: Ralph DJ, Raheem AA, Liu G. Collagenase clostridium histolyticum in combination with vacuum therapy in patients with Peyronie's disease. Podium presented at the 22nd Annual Fall Scientific Meeting of the Sexual Medicine Society of North America (SMSNA); Nov. 3-6, 2016; Scottsdale, AZ.
SMSNA 2016: Ralph DJ, Raheem AA, Liu G. The safety and efficacy of collagenase clostridium histolyticum (CCH) in combination with vacuum therapy for the treatment of Peyronie's disease.
SMSNA 2017: Goldstein I, Liu G, McLane M, Hurley D. Baseline severity of Peyronie's Disease Symptoms Predicts Improved Female Partner Burden Scores After Treatment with Collagenase Clostridium Histolyticum. Moderated poster presented at the Sexual Medicine Society of North America (SMSNA): Oct. 26-29, 2017: San Antonio, TX.
SMSNA 2017: Goldstein I, Liu G, McLane MP, Hurley D. Extent of female partner sexual function improvement in female partners of men with Peyronie's disease who received collagenase clostridium histolyticum.
Soledad, MD, J., et al., "Mechanical Signaling in Reproductive Tissues: Mechanisms and Importance," Reproductive Sciences, vol. 21(9), pp. 1093-1107 (2014).
Staby et al. ("Comparison of chromatographic ion-exchange resins. II. More strong anion-exchange resins," J. Chromatogr. A, 2001, 908, 149-161, Abstract).
Steinbrink et al., "Substrate Specificity of Beta-Collagenase from Clostridium histolyticum," The Journal of Biological Chemistry, 1985, vol. 260, pp. 2771-2776.
Stewart, E.A. Jan. 27, 2001.Uterine fibroids. The Lancet 357: 293-298. specif. p. 293.
Strömberg, J., et al., "Percutaneous Needle Fasciotomy Versus Collagenase Treatment for Dupuytren Contracture, A Randomized Controlled Trial with a Two-Year Follow-up", J Bone Joint Surg Am. 2018; 100:1079-1086.
Strömberg, J., et al., J Hand Surg Am. 2016;41(9):873-880.
Successful Phase II Results Lead to Phase III Approval—Dupuytren's Disease, Internet Citation, retrieved Aug. 20, 2010, pp. 1-2 (2001).
Sugasawara et al., "Purification and Characterization of Three Forms of Collagenase from Clostridium histolytium," Entrez Pubmed abstract; 1984; 5175-5181.
surgerynews.net, pp. 1-3 (Apr. 2005).
Takahashi et al., "New culture conditions for clostridium histolyticum leading to production of collagenase of high specific activity," J. Appl. Bact. 35:641-657, 1972.
Takahashi, et al., "Elastolytic Activities of Clostridium histolyticum," Biochem. Biophys Res. Commun., vol. 39, No. 6, pp. 1058-1064 (1970).
Tay TK, et al. "Comparison between Collagenase Injection and Partial Fasciectomy in the Treatment of Dupuytren's Contracture," Hand Surg. 2015;20(3):386-390.
Taylor et al. , Drug Discov Today Ther Strateg., 2012, vol. 9, No. 1, p. e41-e49.

(56) References Cited

OTHER PUBLICATIONS

Taylor, D. K., et al., 2011. "Temperature-responsive biocompatible copolymers incorporating hyperbranched polyglycerols for adjustable functionality." Journal of Functional Biomaterials 2:173-194, specif. pp. 173, 174.
Taylor, D., et al., "Putting the Moose on the Table: Understanding the Molecular Biology of Uterine Fibroids and Development of Non-invasion Treatment," XP055257658, 64 pages, Oct. 28, 2012.
Taylor, D., et al., "Recent scientific advances in leiomyoma (uterine fibroids) research facilitates better understanding and management," F1000Research, XP055257667, 11 pages, Jul. 6, 2015.
Taylor, D., et al., "Treatment for Uterine Fibroids: Searching for Effective Drug Therapies," Drug Discovery Today Therapeutic Strategies, vol. 9, No. 1, pp. e41-e49, 2012.
TeensHealth "Cellulite," TeensHealth.org, 2 pages, reviewed, May 2009.
Thomas, A. et al., "The Emerging Role of Clostridium histolyticum Collagenase in the Treatment of Dupuytren Disease", Ther Clin Risk Manag. 2010;6: p. 557-572.
Thorne, J.T., et al., "Dynamic Reciprocity Between Cells and Their Microenvironment in Reproduction," Biology of Reproduction, 92(1), Article 25, pp. 1-10, online before print Nov. 19, 2014. DOI 10.1095/bioreprod.114.121368.
Tonkin, Michael A., J Hand Surg Am. 2015;40(2):415-416 (Classification of Congenital Anomalies of the Hand and Upper Limb).
U.S. Appl. No. 12/759,065 (Continuation of U.S. Appl. No. 11/699,302), filed Apr. 13, 2010 in the names of Sabatino, Del Tito, Bassett, Tharia, Hitchcock, Wegman and Yu, entitled "Compositions and Methods of Treating Collagen-Mediated Diseases" and all papers filed in connection therewith.
U.S. Department of Health and Human Services, Food and Drug Administration, Center for Drug Evaluation and Research (CDER), Center for Biologics Evaluation and Research (CBER), Center for Devices and Radiological Health (CDRH), Guidance for Industry, Patient-Reported Outcome Measures: Use in Medical Product Development to Support Labeling Claims, Clinical/Medical, Dec. 2009, 43 pages.
U.S. Patent Application filed Dec. 15, 1994;, U.S. Appl. No. 08/356,112.
U.S. Patent Application filed Nov. 27, 1995;, U.S. Appl. No. 08/757,904.

```
                         10          20          30          40          50
                         |           |           |           |           |
C. septicum α S75954 → 001 NSKKSFAKKVICTSHIAIQCAAVVPHVQAYAINEEGKANHNNASSIK  SEQ ID NO:7
CLH_2834 & 2835      → 001 MLKKSFEKKAICASLVVLQCLILVSPAQTLASTDLPTKG----K-TSIE  SEQ ID NO:8
                         051 IFGYEDNEDLKAKIIQDPEFIRNWANVAHSLGFGWGGTANPNVGQGEF
                             :|:.|:   |:                      :||||  | ||:|
                         045 LFNYEDH--M------------------AHCLGFGWFGTASKEIGEDEF
                                *
                         101 KREVGAGGKVSYLLSARKNPNDPYASG-KRAKDRLSMKISNVRFVIDNDS
                             || .|:  ||:|:|||| | | |||.  :|| ||  ::..|| |:|||:
                         076 KR-AEEEGKTVYYLSARKNQNEPYAKGYKRAHDRIVMKVSNARFFIDHDS
                                                    *
                         150 IKLGTPKVKKLAPLNSASFDLINESKTESKLSKTFNYTTSKTVSKTDNFK
                             :|||| .:: | ||:|:  ::::.||::.|:  ::  |:. |::||:|:
                         125 LTLGKAKVISLDPLASSTLQVVNKSNSEARTSLSFQYETTESTSKTDHVK
                         200 FGEKIGVKTSFKVGLEAIADSKVETSFEFNAEQGWSNTNSTTETKQESTT
                             |||||| ||: ||   :  . ::|. ||||:||||||.:.|:.::: ::
                         175 FGEKIGIKSSFNVKVPFIGEKSIETNLEFNSEQGWSNTKTNSVTTKHTIS
                               *
                         250 YTATVSPQTKKRLFLDVLGSQIDIPYEGKIYHEYDIELMCEIRYIGNAKE
                             :| : |  :|:|: :|:  .:|||||||||:||||:||CEIRYIGNAKK
                         225 HTTTTPAKSRKKVRLNVLNKKSDIPYEGKIYMEYDIEFFCEIRYIGNARK
                               **
                         300 CHEILHETVKLKF-GKNGMSAEEHLKDLYSHKNINGKSEQDKWVDEKFG
                             ||:.|.:|  ||  ||| . |.   :|:||::||:||||KSE.D.WI:ENFY
                         275 CHPTIREPSVSVKFGGKNNMSAVDHIIDLYKHKDINGKSEDDNWIEENFY
                                                                       *******
                         349 YLFKNSYDALTSRKLGGIIKGSFTNINGTKIVREGKEIPLPDKKERCKK
                             |::|| | :: : ||||: |||:||:|||:|| |||| |:.:|:: . :
                         325 DRFSEYSSNVASQYFGGIISGVFTNVGGTDVKVEEGRERPLKNISST-EQ
                         399 SVDSLDAR-LQNEGIRIENIETQDVPGFRLNSITYND-KKLILINN-I
                             .|: :    ||:||  . :.|   |  |::|::| :  :.::.||:
                         374 NVEVQNEKSKSKEFRVGSL-TYTTENGE-QTIYPEDVSSLNANNNEN
```

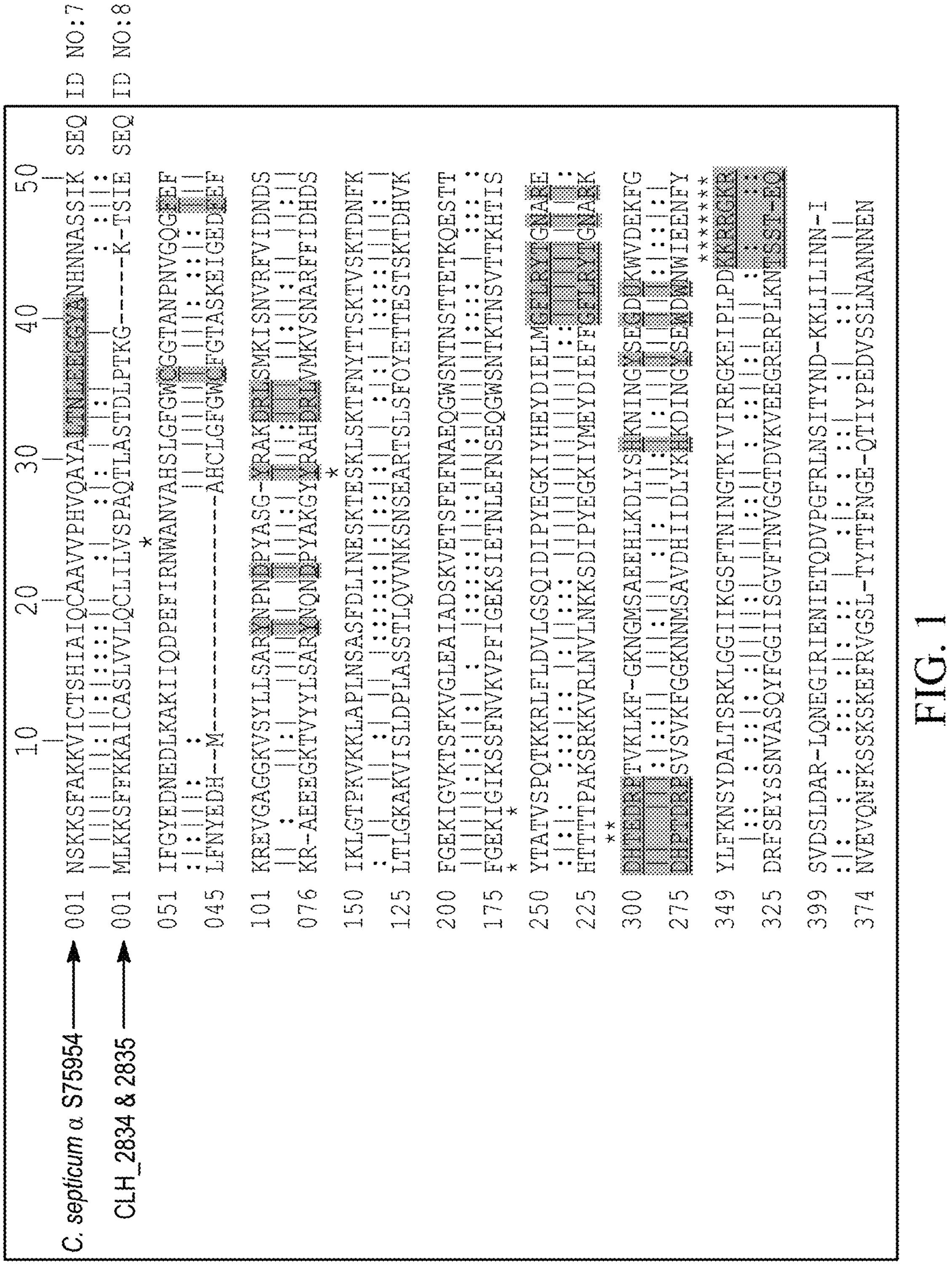

FIG. 1

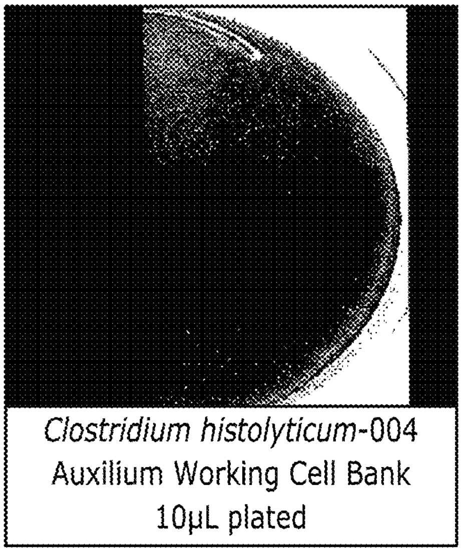
*Clostridium histolyticum*-004
Auxilium Working Cell Bank
10µL plated
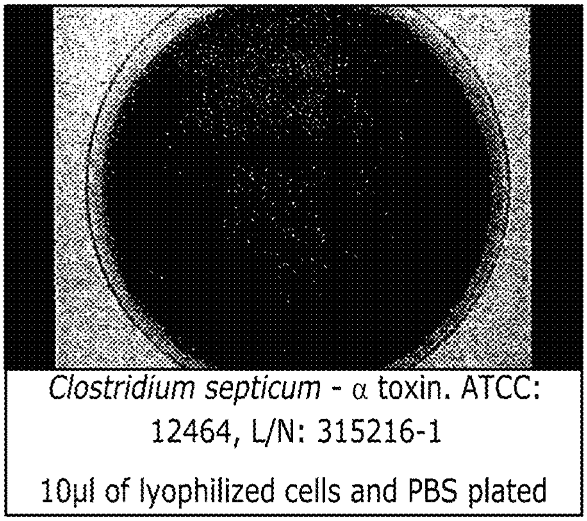
*Clostridium septicum* - α toxin. ATCC: 12464, L/N: 315216-1
10µl of lyophilized cells and PBS plated
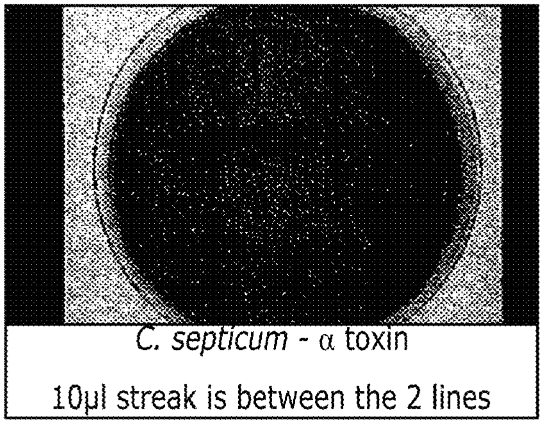
*C. septicum* - α toxin
10µl streak is between the 2 lines
Blood Agar Plating of *C. septicum* Arrows Indicate Beta Hemolytic Activity
FIG. 2

```
                            10        20        30        40        50
                            |         |         |         |         |
          → 001 HKHKHKLASFGLAAGLAAQV-FLPYNALASTKNVTWNQQFQTPQFISGDL      SEQ ID NO: 9
                || |  |:  ||   : ::::  ::  :  :|  :::::    :: :     :: ||
Thermolysin
  CLH_2576 → 001 HK-K-KFLSFIIISAISLNISSHTVGA-ROVKEJKPPEDRESISVLKTDL      SEQ ID NO: 10

            050 KVNGTSPEELVYQYVEK-NENKEKFHENAEDTIQLKEKUNINLGEIPMR
                |:::  :  ::    :|   ||  ::|  :|   |  :::  :|::|   |    :|
            048 EKTKNIKSNNKEGDDVTKVVKSALKEEGNLGD-FKVDNKETDVKGKKHLR

            099 KQQTIKGIPUFGAVYSHY-KDGTITALSGTIIPNLDTKGSLESGKKISE
                |:   |||||:|  |   |:  |||  :::|   : :     |:|:  ::::
            097 SOUFIDGIPVYGSQVIIHTNKDGQVYSVNGK-VDKQPKAQSFKNRVRTKD

            148 KGARDIAEKDLVANVTKEVPEYEGGKDTEFVYINGDEASLAYVNLNFL
                 :|   |||  :|   ::  :|    :|   :::: :: ||| :    : |:|:::
            146 DKAIKIAEDSLGKEIKKN-KNY-RSESKLYLYKVUGDLQPV-YLVKISST

            198 PPEPSNULTIDAVDGKILNETNOLDAAKIGDVKSITGTSTVGVGRGVLG
                 || : |  ::::|  :|||::|:| |  : :   ::   :|::: |   : :|:
            193 EPEASFVHHFVSAENGKIVDKYNAL-SCOATHAQ-VRGUNSSGEHK-ILN

            248 DOKNINTTYSTYYYLQDNTR-GNG-IFTYDAKYRT-TLPGSLWADADNOF
                 : : |    :  |:|  |:||  :||  |:||||:  :  :|||:|::   : |
            240 GHFE-N---G-RYFLADSTRPENGYILTYDANNORYGFPGSLFSNLTGIF

            295 FASYDAPAVDAMYYAGUTYDYYENVHNRLSYDGMNAAIRSSVHYSQGYNN
                 ::  :  :||||:       :|||||||| || |:||::|:|  |||| ::: ||
            285 DSDROKAGUDAHHNLTQVYDYYINVLNADSFDGKGASIISSVKVGNALNN

            345 AFUNGSQUVYGDGDGQTFIPLSGGIDVVAHELTHAVTDYTAGLIYONESG
                 |||||  |:::|||||  ||   |:    ::::|||:|||||:  ||||  |:  :||
            335 AFUNGRQILFGDGDGVTFSNLAKCLEVTAHEFTHAVTOSTAGLEYRFOSG

            395 AINEAISDIFGTLVEFYANKNPDWEIGEDVYTPGISGDSLRSHSDPAKYG
                 |:|||:|||:|    :   :::  |  ||||||||:|||::::|:||||:|   |
            385 ALNEAFSDILG--IAVHSDPN-DUEIGEDIYTPNVAGDALASHSNPRLYR

            445 DPDUYSKR-Y-TGTQDNGGVHINSGIINKAAYLISQGGTHYGVSVVGIGR
                 :|||::    |    ::::|||||  ||||   ||||||      |  :       |  |:
            432 QPDHUKDYLYHDYSMDKGGVHYNSGIPNKAAYLM---G-K---E-V--GK

            493 DKLGKIFYRALTQYLTPTSNFSQLRAAAVQSATDLYGSTSQE-VASVKQA
                 |:::|||:||:||:::|||  |:|  : |  |:::|  ||:| ||:| :|:|       ::|:
            472 DSHAKIYYHALVNYLTPOSTFEDARNAVVSSAIDLHGENSKERKLAIKSW

            542 FD-AVG---VK
                 | :||    |:
            522 ADVGVGEEAVR
```

FIG. 3

```
                          10        20        30        40        50
                           |         |         |         |         |
Thermolysin Pro --> 001 STEHVTHNQQFQTPQFISGDLLKINGTSPEELVYQYVEKNENKFKFHENA SEQ ID NO: 11
                        :  :   : :    :: :   :| |:   :: | : | |  : :| : |
CLH_2576 Pro -->    001 KPPKDKESISVLKTDLEKTKNIKSNNKEGDD-VTKVV-K--SALREEGNL SEQ ID NO: 12

                    051 KDTLQLKEKKNDNLGFTFHRFQQTYKGIPVFGAVVTSHV-KDGTLTALSG
                         | ::: :|::|  |   :| |:   ||||:|: |  |: ||| : :::|
                    047 GD~FKVDNKETDUKOKKHLRSONFIDGIPVYGSQVIIHTNKDGQVYSVNG

                    100 TLIPNLDTKGSLKSGKKLSEKQARDIAEKDLVANVTKEVPEYEQGKDTEF
                          : :     |:|:  :::: :|  ||| :|  :: |:  :| ::::  :
                    096 K-VDKOPKAQSFKNRVRIKDDKAIKIAEDSLGKEIKKN-KNY-HSESKLY
                                                      **          ****
                    150 VVYVNGDEASLAYVVNLNFLTPEPGNWLYIIDAVDGKILNKFNQLDAAKP
                        :  ||||   : |:|:::   || : | ::::| :|||::|:| | : :
                    143 LYKVHGDLQPV-YLVKISSTEPEASFUHMFVSAENGKIVDKYNAL-SCQA
                        *****
                    200 GDVKS
                          ::
                    191 THAQ-
```

FIG. 4

```
                                  10        20        30        40        50
                                   |         |         |         |         |
Thermolysin Mature ---> 001 ITGTSTVGVGRGVLGDQKNINTTYSTYYYLQDNTR-GNG-IFTYDAKYRT SEQ ID NO: 13
                            : |::: |  : :|: : : |   :  |:| |:|| :|| |:||||: :
CLH_2576 Mature    ---> 001 VROVNSSGEEK-ILNGHFE-N---G-RYFLADSTRPSNGYILTYDANNQE SEQ ID NO: 14

049 -TLPGSLUADADNQFFASYDAPAVDAHYYAGVTYDYYKWVHNRLSYDGNN
      :||||:::  : | :: :  :||||:    :||||||| || |:||::
045 YGFPGSLFSNLTGIFDSDRQKAGVDAHHNLTQVYDYYKNVLNRDSFDGKG

                                           **   *
098 AAXRSSVHYSQGYNNAFWNGSOHVYGDGDGQTFIPLSGGIDVVAHELTHA
    |:| |||| ::: |||||| |:::|||| ||  |:  ::|:||||:|||
095 ASIISSVEVGINLNNAFWNGRQILFGDGDGVTFSNLAKCLEVTAHEFTHA

                   *
148 VTDYTAGLIYONESGAINEAISDIFGTLVEFYANKNPDVEIGEDVYTPGI
    ||: |||| |: :|||:||:||:|  :  ::: | |||||||:|||::
145 VTQSTAGLEYRFOSGALNEAFSDILG--IAVESDPN-DUEIGEDIYTPNV

198 SGDSLRSHSDPAKYGDPDHYSKA-Y-TOTODNGGVHINSGIINKAAYLIS
    :||:||||:|  | :||::    |    ::|:|||| |||| ||||||:
192 AGDALRSHSNPRLYRQPDHMKDYLYUDYSMDKGGVHYNSGIPNKAAYLH-

246 QGGTHYGVSVVGIGRDKLGKIFYRALTOYLTPTSNFSOLRAAAVOSATDL
     | :     |  |:|:::||:|:||::|||| |:| : | |:|:|| ||
241 --G-K---E-V--GKDSHAKIYYHALVNYLTPOSTFEDARNAVUSSAIDL

296 YGSTSQE-VASVKQAFD-AVG---VK
    :| :|:|   ::|:  | :||   |:
282 HGENSKERKLAIKSVADUGUGEEAVR
```

FIG. 5

Perfringolysin

CLH_1920

```
              10        20        30        40        50
               |         |         |         | *       |
001 H-I--R-FKK-TK--LIASI-AMALC--L---FS-QPVISFSKDI-TD--  SEQ ID NO: 15
    | |  : ::: ::  ||: | :::    |   |: : |:  : :  ||
001 NKITKKGLRSLSRLHLITHITGLTYNYHLGSSENGNRVVLANPNTKTING  SEQ ID NO: 16

034 -KNOS--IDSGISSLSYNRNEVLASNGDKIESFVPKEGKKTGNKFIVVER
     ||:|  ||  | :|||:  ::|: ||:|:|:||| | :::::|| |::|
051 IKNNSDEIDEKIYGLSYDPYKILSYNGEKVENFVPAECSENSGKFTVIKR

081 OKRSLTTSPVDISIIDSVNDRTYPGALQLADKAFVENRPTILEVKRKPIN
    :|:::: | :||||:||:|||||||||:|||:: ::||:|:::  :||||:
101 EKKNISDSTTDISINDSINDRTYPGAIOLANRDLIENKPNLISCERKPIT

131 INIDLPGLKGENSIK-VDDPTYGKVSGAIDELVSKUNEKYSSTHTLPART
    |::||||: ||:: | |::|||::|::||: |:: || |||| :|:|:|
151 ISVDLPGH-GEDGKKVVNSPTYSSVNSAINYLLDTUNSKYSSKYTIPTRN

180 QYSESHVYSKSQISSALNVNAKVLENSLGVDFNAVANNEKKVNILAYKOI
    :||::|||||||:|: :: | ||:| :||::||::: ::|||:|||:||||
200 NYSDTHVYSKSQLSTHFSCNFKTLSKSLNIDFDSIFKGEKKANILSYKQI

230 FYTVSADLPKNPSDLFDDSVTFNDLKQKGVSNEAPPLAVSNVAYGRTIYV
    |||||:| |: |||||   ||| ::|  |||:|: || :|||||||||:||
250 FYTVSVDGPNRPSDLFGYSVTSKSLALKGVNNDNPPAYVSNVAYGRTVYV

280 KLETTSSSKDVQAAFKALIKNTDIKNSQQYKDIYENSSFTAVVLGGDAQE
    ||||||:|: |:||||||::| ||::: :|||| ::|||||:|||| ||:
300 KLETTSKSSKVKAAFKALVENODISSNAEYKDIINQSSFTATVLGGGAQK

330 HNKVVTKDFDEIRKVIKDNATFSTKNPAYPISYTSVFLKDNSVAAVHNKT
    |||||||||| ||::||:|:::| :||:||||||||:||||||::|:|:|:|
350 HNKVVTKDFDVIRNIIKNNSVYSPONPGYPISYTSTFLKDNKIATVNNRT

380 DYIETTSTEYSKGKINLDHSGAYVAQFEVAWDEVSYDKEGNEVLTHKTHD
    :||||||:||||::||| |||||:||||||||:|||||||||:||||:: ||:|:
400 EYIETTATEYDSGKIMLDHSGVYVAQFEVTWDEVSYDKQGNEIIEHKSUS

430 GNYQDKTAHYSTVIPLEANARNIRIKARECTGLAWEWWRDVISEYDVPLT
    || :|:|||::| : |::||||| |||:||||||||||| |::  ::||:
450 GNNSDKTAHENTELYLKGNARNISIKAKECTGLAWEWWRTVVLAKNLPLV
                                   ****
480 NNINVSINGTTLYPOSSITYN
    :: ::|||||||||  |:  :
500 KERKLSIUGTTLYPRYSHEEK
```

FIG. 6

*Tetanolysin*

10μg of 100μg/ml

```
                          10        20        30        40   *    50
SEQ ID NO: 17              |         |         |         |         |
              001 HLRRKVSTLLHTALITTSFLNSKPVYANPVTKSKDNNLKEVQQVTSKSNK
(SEQ ID NO: 18)   ||||||||||||||||||||||||||||||||||||||||||||| ||||
              001 HLRRKVSTLLMTALITTSFLNSKPVYANPVTKSKDNNLKEVQQVISKSNK

              051 NINQKVTIMYYCDADNNLEGSLLNDIEENKTGYKDSPNLNLYALVORSPR
                  ||||||||||||||||||||||||||||||||||||||||||||||||||
              051 NINORVTINYYCDADNNLEGSLLNDTEENKTGYKOSPNLNLLALVDRSPR
                                          *
              101 YSSDEKVLGEDFSDTRLYKIEHNZANRLDGKNEFPEISTTSKYEANEGDP
                  ||||||||||||||||||||| ||||||||||||||||||||||||||||
              101 YSSDEKVLGEDFSDTRLYKIELNKANRLDGKNEFPEISTTSKYEANMGDP

              151 EVLKKFIDYCKSNYEADKYVLIHANHGGGAREKSNPRLNRAICUDDSNLD
                  ||||||||||||||||||||||||||||||||||||||||||||||||||
              151 EVLKKFIDYCKSNYEADRYVIIMANHGGGAREKENPRUNRAICUDDSNLD

              201 INGEADCLYNGEISDELTEROSVDLLAFDACLMGTAEVAYQYRPGNGGES
                  ||||||||||||||||||||||||||||||||||||||||||||||||||
              201 KNGEADCLYAGETSDHLTEKOBVDLLAFDACLMGTAZVAYQYRPGNGOFS

              251 ADTLVASSPVVUGFGFKYDKIFDRIKAGGGINNEDDLTLGGKEQNFOPAT
                  ||||||||||||||||||||||||||||||||||||||||||||||||||
              251 ADTLVASSPVVNGFGFKYDKIFDRIKAGGGINNEDDLTLOGKEONFDPAT

              301 ITNEQLGALFVEEQRDSTHANGRYDOHLSFYDLKKAESVKRAIDHLAVNL
                  ||||||||||||||||||||||||||||||||||||||||||||||||||
              301 ITNEOLGALFVEEORDSTHANGRYDQHLSFYDLKKAZSVKRAIDWLAVNL

              351 SHENEKSEIEKLRGEGINTDLHHTEDEYSEGEUVEYPYFDVYDLCEKINK
                  ||||||||||||||||||||||||||||||||||||||||||||||||||
              351 SHENKESEIEKLRGSGIKTDLAHYFDEYSEGEWVEYPYFDVYDLCEKINK

              401 SINFSSKTKDLASNARNKLNENIVYSFGDPSNNFKEGKNGLSIFLPHGDK
                  ||||||||||||||||||||||||||||||||||||||||||||||||||
              401 SENFSSKTKDLASNAMNKLNEMIVYSFGDPSNNFKEGKNGLSIFLPNGDK

              451 KYSTYTTSTKIPHUTHOSWYNSIDTVKYGUNFYGKLEWCKDGQDPEINKV
                  ||||||||||||||||||||||||||||||||||||||||||||||||||
              451 KYSTYYTSTEIPHUTHOSVYNSIDTVKYGLNPYGKLSUCKOGQDPEINKV

              501 GNUPELLSUFDKINDVTGGVWHYQW
                  |||||||||||||||||||||||||
              501 GUUFELLDEFDKINDVTGGVNHYQW
```

Clostripain Locus X63673

CLH_1861

FIG. 8

```
                  Identities = 1113/1118 (100%), Positives = 1118/1118 (100%)
SEQ ID NO:3    0001 MKKNILKILMDSYSKESKIQTVRRVTSVSLLAAYLTANTSSLVLARPIENTNDTSIKNVEKLAN
                    ||||||||||||||||||||||||||||||||:|||||||||||||||||||||||||||||||
SEQ ID NO: 19  0001 MKKNILKILMDSYSKESKIQTVRRVTSVSLLAVYLTMNTSSLVIARPIENTNDTSIKNVEKLRN
                                                      N-terminus of mature protein Ile 111

               0065 APNEENSKKVEDSKNDKVEHVENIEZAKVEQVAPEVKSKSTLRSASTANTNSEKYDFEYLNGLS
                    ||||||||||||||||||:|||||||||||||||||||||||||||||||||||||||||||||
               0065 APNEENSKKVEDSKNDKVEHVKNIEEAKVEQVAPEVKSKSTLRSASIANTNSEKYDFEYLNGLS

               0129 YTELTNLIKNIKUNQINGLFNYSTG3QKFFGDKNRVQATINALQESGRTYTANDNKGIETFTEV
                    ||||||||||||||||||||||||||||||||||||||||||||||||||||||||||||||||
               0129 YTELTNLIKNIKUNQINGLINYSTGSQKFFGDKNRVOAIINALQESGRTYTANDMKGIETFTEV

               0193 LRAGFYLGYYNDGLSYLNDRNFQDKCIPAMIAIQKNPNFELGTAVQDEVITSLGKLIGNASANA
                    ||||||||||||||||||||||||||||||||||||||||||||||||||||||||||||||||
               0193 LRAGFYLGYYNDGLSYLNDRNFQDKCIPAMIAIQKNPNFKLGTAVODEVITSLGKLIGNASANA

               0257 EVVNNCVPVLKOFRENLNQYAPDYVKGTAVNELIKGIEFDFSGAAYEKDVKTHPWYGKIDPFIN
                    ||||||||||||||||||||||||||||||||||||||||||||:|||||||||||||||||||
               0257 EVVNNCVPVLKOFRENLNQYAPDYUKOTAVNELIKGIEFDFSGAAYEKDVKTHPWYGKIDPFIN

               0321 ELKALGLYGNITSATEWASDVGIYYLSKFGLYSTNRNDIVQSLEKAVDNYKYGKIAFVAMERIT
                    ||||||||||||||||||||||||||||||||||||||||||||||||||||||||||||||||
               0321 ELKALGLYGNITSATEWASDVGIYYLSKFGLYSTNRNDIVQSLEKAVDMYKYGKIAYVANERIT

               0385 UDYDGIGSNGKKVDHDKFLDDAEKHYLPKTYTFDNGTFLIRAGEKUSEEKIKRLYVASREVKSQ
                    ||||||||||||||||:||||||||||||||||||||||||||:||||||||||||||||||||
               0385 UDYDGIGSNGKKVDHDKFLDDAEKHYLPKTYTFDNGTFITRAGDKVSEEKIKRLYVASREVKSO

               0449 FHRVVGNDKALEVGNADDVLTEKIFNSPEEYKENTNINGVSTDNGGLYIEPRGTFYTYERTPQQ
                    ||||||||||||||||||||||||||||||||||||||||||||||||||||||||||||||||
               0449 FHRVVGNDKALEVGNADDVLTMKIFNSPEEYKYNININGVSTDNGGLYIEPRGTFYTYERTPQQ

               0513 SIFSLEELFRHEYTHYLQARYLVDGLUGQGPFYEKNRLTWFDEGTAEFFAGSTRTSGVLFRKSI
                    ||||||||||||||||||||||||||||||||||||||||||||||||||||||||||||||||
               0513 SIFSLEELFRHEYTHYLQARYLVDGLWGQGPFYEKNRLTUFDEGTAEFFAGSTRTSGVLPRKSI
```

FIG. 9A

```
0577 LGYLAKDRVDHRYSLKKTLNSGYDDSDUMFYNYGFAVAHYLYEKDMPTFIKANKAILNTDVKSY
     ||||||||||||||||||||||||||||||||||||||||||||||||||||||||||||||||
0577 LGYLAKDKVDHRYSLKKTLNSGYDDSDUMFYNYGFAVAHYLYEKDMPTFIKMNKAILNTDVKSY

0641 DEIIKKLSDDANKNTEYONHIQELADRYQGAGIPLVSDDYLEDHGYKKASEVYSEISKAASLTN
     ||||||||||||||||||||||||||||||||||||||||||||||||||||||||||||||||
0641 DEIIKKLSDDANKNTEYONHIQELADKYQGAGIPLVSDDYLKDHGYKKASEVYSEISKAASITN

0705 TSVTAEKSQYFNTFTLRGTYTGETSKGEFKDUDEMSKKLDGTLESLAKNSWSGYKTLTAYFINY
     ||||||||||||||||||||||||||||||||||||||||||||||||||||||||||||||||
0705 TSVTAEKSQYFNTFTLRGTYTGETSKGEFKDEDEMSKKLDGTLESLAKNSUSGYKTLTAYFTNY

0769 RUTSDNKVQYDVVFHGVLTDNADISNNKAPIAKVTGPSTGAVERNIEFSGKDSKDEDGKIVSYD
     ||||||||||||||||||||||||||||||||||||||||||||||||||||||||||||||||
0769 RVTSDNKVQYDVVFHGVLTINADISNNKAPIAKVTGPSTGAVGRNIEFSGKDSKDEDGKIVSYD

0833 WDFGDGATSRGKNSVHAYKXTGTYNVTLKVTDDKGATATESFTIEIKNEDTITPITKEMEPNDD
     ||||||||||||||:||||||||||||||||||||||||:||||||||||||||||||||||||
0833 EDFGDGATSRGKNSVHAYKKAGTYNVTLKVTDDKGATATESFTIEIKNEDTTTPITKEMEPNDD

0897 IKEANGPIVEGVTVKGDLNGSDDADTFYFDVKEDGDVTIELPYSGSSNFTULVYKEGDDONHIA
     |||||||||||||||||||||||||||||||||||||||:||||||||||||||||||||||||
0897 IKEANGPIVEGVTVKGDLNGSDDADTFYFDVKEDGDVTIELFYSGSSNFTELVYKEGDDONHIA

0961 SGIDKNNSKVGTFKATKGRHYVFIYXHDSASNISYSLNIKGLGNEKLKEKENNDSSDKATVIPN
     ||||||||||||||:||||||||||||||||||||||||:||||||||||||||||||||||||
0961 SGIDKNNSKVGTFKSTKGRHYVFTYKHDSASNISYSLNIKGLGNEKLREKENNDSSDKATVIPN

1025 FNTTHQGSLLGDDSRDYYSFEVKEEGEVNIELDKKDEFGUTUTLHPESNINDRITYGOVDGNKV
     ||||||||||||||||||||||||||||||||||||||||||||||||||||||||||||||||
1025 FNTTHQGSLLGDDSRDYYSFEVKEEGEVNIELDKKDEFGVTYTLHPESNINDRITYGQVDGNKV

1089 SNKVKLRFOKYYLLVYKYSGSGNYELRUNK
     ||||||||||||||||||||||||||||||
1089 SNKVKLRPGKYYLLVYKYSGSGNYELRVNK
```

FIG. 9B

```
                                Identities = 1013/1021 (99%), Positives = 1021/1021 (100%)
(SEQ ID NO:20)    colH --> 0001 KRRKCLSKALILAITHATIFTUNSTLPIYAAVDKINATAAVONESKRYTVSYLKTLNYYDLVUL
                                ||||||||||||||||||||||||||||||||||||||||||||||||||||||||||||||||
             SEQ ID      --> 0001 HERKCLSKALILAITHATIFTUNSTLPIYAAVDKOIATAAVONESKRYTUSYLKTLNYYDLVPL
             NO:4
Alignment Assessment       0065 LVKZEIENLPOLFQTSSDAKEFYGHKTRISFINDEIGRRAPOTTEIDERGIFTLVEVVRAGFYL
                                ||||||||||||||||||||||||||||||||||||||||||||||||||||||||||||||||
                           0065 LVITEIEMLPDLFOVSSDAKEFYGNETRUSFINDEIGRRAPGYTEIDUNGIPTLVEVVRAGFYL

Collagenase II             0129 GFHNKELNEINKRSYKERVIPSILATOKNPNFRLOTEVODKIVSATGLLAGNETAPPEVVNIFT
Green shading of                ||||||||||||||||||||||||||||||||||||||||||||||||||||||||||||||||
N-termini of mature        0129 GFHNKELNEINKRSFKERVIPSILAIQKNPNFKLGTEVQDKIVSATGLLAGNETAPPEVVNNPT
protein A31 in AVDK
stretch
                           0193 PIEQDCIKNEDRYALDDLESKALENULAAPTYDITEYLRATKERPENTPHYGKIDGEINELEKL
Green shading-single ep         ||:||||||:||||||||||||||||||||||||||||||||||||||||||||||||||||||
B amino acid               0193 PIIQDCIKNHDRYALDDLESKALFNVLAAPTYDITEYLRATKERPENTPAYOKIDOFINELKKL
differences in entire
molecule                   0257 ALYGKINDNNSUIIDNGIYHIAPLGKLHSNNKIGIETLTEVHKYYPYLSBOHLOTADQIKASYD
                                |||||||||||||||||||||||||||||||||||||||||||:|||||||||||||||:||||
                           0257 ALYGKINDNNSWIIDNGIYHIAPLGKLHSNNKIGIETLTEVMKIYPYLSHQHLQSADQIERHYD

                           0321 SRDAEGNKIPLDKFKKEGKEKYCFKTYTFDDGKVIIKAGARVESEKVEELYVASKEVUSOFFRV
                                ||||||||||||||||||||||||||||||||||||||||||||||||||||||||||||||||
                           0321 SEBAEGNETPLDEFEKEGKEKYCPKTYTFDDOKVIIKAGARVEEEKVEELYRASREVNSQFFRV

                           0385 YOIDEPLEEGNPDDILTHVIYNSPEEYKINSVLYGYDTNNGONYIEPEGTFFTYZREAQESTYT
                                |||||||||||||||||||||||||||||||||||||||||||||||:||||||||:|:|||||
                           0385 YGIDKPLEEGIPODILTHVIYNSPEETELNSULYOYDTHIGGRYIEPDGTEFTYERKAEESTYT

                           0449 LEELFRHEYTHYLQGRYAVPGQHGRTKLYDNDRLTWYEEGGAELFAGSTRTSGILPAKSIVSNI
                                ||||||||||||||||||||||||||||||||||||||||||||||||||||||||||||||||
                           0449 LEELFAHEYTHYLQORYAVPOQUERTELYDIDELTWYEEGGAELFAGSTATSGILPRESIVENI

                           0513 HNTTANNRYKLSDTVISKYGASFEFYNYACHENDYBYNKDNGILNKINDLAKHNDVIGYDNVIR
                                ||||||||||||||||||||||||||||||||||||||||||||||||||||||||||||||||
                           0513 HNTTRNNRYKLSDTVHSKYGASFEFYNYACHFHDYHYNKDHGILNKLNDLAKNNDVDGYDNYIR
```

FIG. 10A

```
colH ──► 0577 DLSSNYALNDKYQOHNQERIDNYENLTVPFVADDYLVRHAYKNPHELYSEISEVAKLKDAKSEV
              |||||:||||||||||||||||||||||||||||||||||||||||||||||||||||||||||
SEQ ID NO: 4 ──► 0577 DLSSNHALNDKYQDHHQERIDNYENLTVPFVADDYLVANAYKNPNELYSEISEVAKLKDAKSEV

0641 KKSQYYSTFTLRGSYTOGASKOKLEDOKANNKFIODSLKKLDTYSESGYKTLTAYFINYKVDSS
     ||||||||||||||||||||||||||||||||||||||||||||||||||||||||||||||||
0641 KKBQYFBTFTLROSYTGGASKOKLEDOKAHNKYIDDSLKKLDTYSUSGYKTLTATETNYKUDSS

0705 NRVTYDVVFHGYLPHEGDSKNSLPYGKINGTYKOTEKEKIKFSSEGSFDPDGKIVSYEUDFGDG
     ||||||||||||||||||||||||||||||||||||||||||||||||||||||||||||||||
0705 NRVTYDVVFBGYLFNEGDSKNSLPYGKINGTYKGTEKEKIRFSSEGSFDPDGKIVSYEHDFGDG

0769 NKSNEENPEHSYDEVGTYTVKLKVTDDEGESSVSTITAEIKOLSENKLPVIYNHVPKSGALNOK
     ||||||||||||||||||||||||||||||||||||||||||||||||||||||||||||||||
0769 NRSNEENPEHSYDKVGTYTVKLKVTDDKGESSVSTITAEIKDLSENKLPVIYNEVPESGALNOK

0833 VVFYGKGTYDPDGSIAGYOWDFGDGSDFSSEQNFSHVYTKKGEYIVTLAVMDSSCONSEKTIKI
     ||||||||||||||||||||||||||||||||||||||||||||||||||||||||||||||||
0833 VVFYGKGTYDPDGSIAGYQWDFGDGSDFSSEQNPSHVYTKKGEYTVTLRVMDSSGQHSEKTHKI

0897 KITDPVYPIGTEKEPINSKETASOPIVPGIPVSGTIENTSDODYFYFDVITPGEVKIDINKLGY
     ||||||||||||||||||||||||||||||||||||||||||||||||||||||||||||||||
0897 KITDPVYPIGTEKEPNNSKETASGPIVPGIPVSGTIENTEDODYFYFDVITPGEVKIDINKLGY

0961 GGATIVVYDENNNAVSYATODGQNLSORYKADEFGRYYINLYHFNGSYMPYRINIEGSVGR
     ||||||||||||||||||||||||||||||||||||||||||||||||||||||||||||
0961 GGATHUVYPENNNAVSYATDDGONLSGKEKADKPGRYYIHLYHINGSYMPYRINIEGSVOR
```

FIG. 10B

SEQ ID NO: 1

ATGAAAAAAAATATTTTAAAGATTCTTATGGATAGTTATTCTAAAGAATC
TAAAATTCAAACTGTACGTAGGGTTACGAGTGTATCACTTTTAGCGGCAT
ATCTTACTATGAATACTTCAAGTTTAGTTTTAGCAAAACCAATAGAAAAT
ACTAATGATACTAGTATAAAAAATGTGGAGAAATTAAGAAATGCTCCAAA
TGAAGAGAATAGTAAAAAGGTAGAAGATAGTAAAAATGATAAGGTAGAAC
ATGTGGAAAATATAGAAGAGGCAAAAGTTGAGCAAGTTGCACCCGAAGTA
AAATCTAAATCAACTTTAAGAAGTGCTTCTATAGCGAATACTAATTCTGA
GAAATATGATTTTGAGTATTTAAATGGTTTGAGCTATACTGAACTTACAA
ATTTAATTAAAAATATAAAGTGGAATCAAATTAATGGTTTATTTAATTAT
AGTACAGGTTCTCAAAAGTTCTTTGGAGATAAAAATCGTGTACAAGCTAT
AATTAATGCTTTACAAGAAAGTGGAAGAACTTACACTGCAAATGATATGA
AGGGTATAGAAACTTTCACTGAGGTTTTAAGAGCTGGTTTTTATTTAGGG
TACTATAATGATGGTTTATCTTATTTAAATGATAGAAACTTCCAAGATAA
ATGTATACCTGCAATGATTGCAATTCAAAAAAATCCTAACTTTAAGCTAG
GAACTGCAGTTCAAGATGAAGTTATAACTTCTTTAGGAAAACTAATAGGA
AATGCTTCTGCTAATGCTGAAGTAGTTAATAATTGTGTACCAGTTCTAAA
ACAATTTAGAGAAAACTTAAATCAATATGCTCCTGATTACGTTAAAGGAA
CAGCTGTAAATGAATTAATTAAAGGTATTGAATTCGATTTTTCTGGTGCT
GCATATGAAAAAGATGTTAAGACAATGCCTTGGTATGGAAAAATTGATCC
ATTTATAAATGAACTTAAGGCCTTAGGTCTATATGGAAATATAACAAGTG
CAACTGAGTGGGCATCTGATGTTGGAATATACTATTTAAGTAAATTCGGT
CTTTACTCAACTAACCGAAATGACATAGTACAGTCACTTGAAAAGGCTGT
AGATATGTATAAGTATGGTAAAATAGCCTTTGTAGCAATGGAGAGAATAA
CTTGGGATTATGATGGGATTGGTTCTAATGGTAAAAAGGTGGATCACGAT
AAGTTCTTAGATGATGCTGAAAAACATTATCTGCCAAAGACATATACTTT
TGATAATGGAACCTTTATTATAAGAGCAGGGGAGAAGGTATCCGAAGAAA
AAATAAAAAGGCTATATTGGGCATCAAGAGAAGTGAAGTCTCAATTCCAT
AGAGTAGTTGGCAATGATAAAGCTTTAGAGGTGGGAAATGCCGATGATGT
TTTAACTATGAAAATATTTAATAGCCCAGAAGAATATAAATTTAATACCA
ATATAAATGGTGTAAGCACTGATAATGGTGGTCTATATATAGAACCAAGA
GGGACTTTCTACACTTATGAGAGAACACCTCAACAAAGTATATTTAGTCT
TGAAGAATTGTTTAGACATGAATATACTCACTATTTACAAGCGAGATATC
TTGTAGATGGTTTATGGGGACAAGGTCCATTTTATGAAAAAAATAGATTA
ACTTGGTTTGATGAAGGTACAGCTGAATTCTTTGCAGGATCTACCCGTAC
ATCTGGTGTTTTACCAAGAAAATCAATATTAGGATATTTGGCTAAGGATA
AAGTAGATCATAGATACTCATTAAAGAAGACTCTTAATTCAGGGTATGAT
GACAGTGATTGGATGTTCTATAATTATGGATTTGCAGTTGCACATTATCT
ATATGAAAAAGATATGCCTACATTTATTAAGATGAATAAAGCTATATTGA
ATACAGATGTGAAATCTTATGATGAAATAATAAAAAAATTAAGTGATGAT
GCAAATAAAAATACAGAATATCAAAACCATATTCAAGAGTTAGCAGATAA
ATATCAAGGAGCAGGCATACCTCTAGTATCAGATGATTACTTAAAAGATC
ATGGATATAAGAAAGCATCTGAAGTATATTCTGAAATTTCAAAAGCTGCT
TCTCTTACAAACACTAGTGTAACAGCAGAAAAATCTCAATATTTTAACAC
ATTCACTTTAAGAGGAACTTATACAGGTGAAACTTCTAAAGGTGAATTTA
AAGATTGGGATGAAATGAGTAAAAAATTAGATGGAACTTTGGAGTCCCTT
GCTAAAAATTCTTGGAGTGGATACAAAACTTTAACAGCATACTTTACGAA
TTATAGAGTTACAAGCGATAATAAAGTTCAATATGATGTAGTTTTCCATG
GGGTTTTAACAGATAATGCGGATATTAGTAACAATAAGGCTCCAATAGCA
AAGGTAACTGGACCAAGCACTGGTGCTGTAGGAAGAAATATTGAATTTAG
TGGAAAAGATAGTAAAGATGAAGATGGTAAAATAGTATCATATGATTGGG

FIG. 11 A

ATTTTGGCGATGGTGCAACTAGTAGAGGCAAAAATTCAGTACATGCTTAC
AAAAAAACAGGAACATATAATGTTACATTAAAAGTAACTGACGATAAGGG
TGCAACAGCTACAGAAAGCTTTACTATAGAAATAAAGAACGAAGATACAA
CAACACCTATAACTAAAGAAATGGAACCTAATGATGATATAAAAGAGGCT
AATGGTCCAATAGTTGAAGGTGTTACTGTAAAAGGTGATTTAAATGGTTC
TGATGATGCTGATACCTTCTATTTTGATGTAAAAGAAGATGGTGATGTTA
CAATTGAACTTCCTTATTCAGGGTCATCTAATTTCACATGGTTAGTTTAT
AAAGAGGGAGACGATCAAAACCATATTGCAAGTGGTATAGATAAGAATAA
CTCAAAAGTTGGAACATTTAAAGCTACAAAAGGAAGACATTATGTGTTTA
TATATAAACACGATTCTGCTTCAAATATATCCTATTCTTTAAACATAAAA
GGATTAGGTAACGAGAAATTGAAGGAAAAAGAAAATAATGATTCTTCTGA
TAAAGCTACAGTTATACCAAATTTCAATACCACTATGCAAGGTTCACTTT
TAGGTGATGATTCAAGAGATTATTATTCTTTTGAGGTTAAGGAAGAAGGC
GAAGTTAATATAGAACTAGATAAAAAGGATGAATTTGGTGTAACATGGAC
ACTACATCCAGAGTCAAATATTAATGACAGAATAACTTACGGACAAGTTG
ATGGTAATAAGGTATCTAATAAAGTTAAATTAAGACCAGGAAAATATTAT
CTACTTGTTTATAAATACTCAGGATCAGGAAACTATGAGTTAAGGGTAAA
TAAATAA

FIG. 11 B

SEQ ID NO: 2

ATGAAAAGGAAATGTTTATCTAAAAGGCTTATGTTAGCTATAACAATGGC
TACAATATTTACAGTGAACAGTACATTACCAATTTATGCAGCTGTAGATA
AAAATAATGCAACAGCAGCTGTACAAAATGAAAGTAAGAGGTATACAGTA
TCATATTTAAAGACTTTAAATTATTATGACTTAGTAGATTTGCTTGTTAA
GACTGAAATTGAGAATTTACCAGACCTTTTTCAGTATAGTTCAGATGCAA
AAGAGTTCTATGGAAATAAAACTCGTATGAGCTTTATCATGGATGAAATT
GGTAGAAGGGCACCACAGTATACAGAGATAGATCATAAAGGTATTCCTAC
TTTAGTAGAAGTTGTAAGAGCTGGATTTTACTTAGGATTCCATAACAAGG
AATTGAATGAAATAAATAAGAGGTCTTTTAAAGAAAGGGTAATACCTTCT
ATATTGGCAATTCAAAAAAATCCTAATTTTAAACTAGGTACTGAAGTTCA
AGATAAAATAGTATCTGCAACAGGACTTTTAGCTGGTAATGAAACAGCGC
CTCCAGAAGTTGTAAATAATTTTACACCAATAATTCAAGACTGTATCAAA
AATATGGACAGATATGCTCTTGATGATTTAAAGTCAAAAGCATTATTTAA
TGTTTTAGCTGCACCTACCTATGATATAACTGAGTATTTAAGAGCTACTA
AAGAAAAACCAGAAAACACTCCTTGGTATGGTAAAATAGATGGGTTTATA
AATGAACTTAAAAAGTTAGCTCTTTATGGAAAAATAAATGATAATAACTC
TTGGATAATAGATAATGGTATATATCATATAGCACCTTTAGGGAAGTTAC
ATAGCAATAATAAAATAGGAATAGAAACTTTAACAGAGGTTATGAAGATA
TATCCTTATTTAAGTATGCAACATTTACAATCAGCAGATCAAATTGAGCG
TCATTATGATTCAAAAGATGCTGAAGGAAATAAAATACCTTTAGATAAGT
TTAAAAAGGAAGGAAAAGAGAAATACTGTCCAAAAACTTATACATTTGAT
GATGGAAAAGTAATAATAAAAGCTGGTGCTAGGGTAGAAGAAGAAAAAGT
TAAAAGACTATACTGGGCATCAAAGGAAGTTAACTCTCAATTCTTTAGGG
TATATGGAATAGACAAACCATTAGAAGAAGGTAATCCAGATGATATATTA
ACAATGGTTATCTACAACAGTCCTGAAGAATATAAACTTAATAGTGTTCT
ATACGGATATGATACTAATAATGGTGGTATGTATATAGAGCCAGATGGAA
CTTTCTTCACATATGAAAGAAAAGCTGAAGAAAGCACATACACATTAGAA
GAATTATTTAGACATGAATATACACACTATTTACAAGGAAGATATGCAGT
TCCTGGTCAATGGGGAAGAACAAAACTTTATGACAATGATAGATTAACTT
GGTATGAAGAAGGTGGAGCAGAATTATTTGCAGGTTCTACTAGAACTTCT
GGAATATTACCAAGAAAGAGTATAGTATCAAATATTCATAATACAACAAG
AAATAATAGATATAAGCTTTCAGACACTGTACATTCTAAATATGGTGCTA
GTTTTGAATTCTATAATTATGCATGTATGTTTATGGATTATATGTATAAT
AAAGATATGGGTATATTAAATAAACTAAATGATCTTGCAAAAAATAATGA
TGTTGATGGATATGATAATTATATTAGAGATTTAAGTTCTAATCATGCTT
TAAATGATAAATATCAAGATCATATGCAGGAGCGCATAGATAATTATGAA
AATTTAACAGTGCCTTTTGTAGCTGATGATTATTTAGTAAGACATGCTTA
TAAGAACCCTAATGAAATTTATTCTGAAATATCTGAAGTAGCAAAATTAA
AGGATGCTAAGAGTGAAGTTAAGAAATCACAATATTTTAGTACCTTTACT
TTGAGAGGTAGTTACACAGGTGGAGCATCTAAGGGGAAATTAGAAGATCA
AAAAGCAATGAATAAGTTTATAGATGATTCACTTAAGAAATTAGATACGT
ATTCTTGGAGTGGGTATAAAACTTTAACTGCTTATTTCACTAATTATAAA
GTTGACTCTTCAAATAGAGTTACTTATGATGTAGTATTCCACGGATATTT
ACCAAACGAAGGTGATTCCAAAAATTCATTACCTTATGGCAAGATCAATG
GAACTTACAAGGGAACAGAGAAAGAAAAAATCAAATTCTCTAGTGAAGGC
TCTTTCGATCCAGATGGTAAAATAGTTTCTTATGAATGGGATTTCGGAGA
TGGTAATAAGAGTAATGAGGAAAATCCAGAGCATTCATATGACAAGGTAG
GAACTTATACAGTGAAATTAAAAGTTACTGATGACAAGGGAGAATCTTCA
GTATCTACTACTACTGCAGAAATAAAGGATCTTTCAGAAAATAAACTTCC
AGTTATATATATGCATGTACCTAAATCCGGAGCCTTAAATCAAAAAGTTG
TTTTCTATGGAAAAGGAACATATGACCCAGATGGATCTATCGCAGGATAT
CAATGGGACTTTGGTGATGGAAGTGATTTTAGCAGTGAACAAAACCCAAG

FIG. 12A

CCATGTATATACTAAAAAAGGTGAATATACTGTAACATTAAGAGTAATGG
ACAGTAGTGGACAAATGAGTGAAAAAACTATGAAGATTAAGATTACAGAT
CCGGTATATCCAATAGGCACTGAAAAAGAACCAAATAACAGTAAAGAAAC
TGCAAGTGGTCCAATAGTACCAGGTATACCTGTTAGTGGAACCATAGAAA
ATACAAGTGATCAAGATTATTTCTATTTTGATGTTATAACACCAGGAGAA
GTAAAAATAGATATAAATAAATTAGGGTACGGAGGAGCTACTTGGGTAGT
ATATGATGAAAATAATAATGCAGTATCTTATGCCACTGATGATGGGCAAA
ATTTAAGTGGAAAGTTTAAGGCAGATAAACCAGGTAGATATTACATCCAT
CTTTACATGTTTAATGGTAGTTATATGCCATATAGAATTAATATAGAAGG
TTCAGTAGGAAGATAA

FIG. 12B

CLH_2835 and CLH_2834 (SEQ ID NO: 8)

MLKKSFFKKAICASLVVLQCLILVSPAQTLASTDLPTKGKTSIELFNYEDHMAHCLGF
GWCFGTASKEIGEDFEFKRAEEEGKTVYYLSARYNQNDPYAKGYYRAHDRLVMKV
SNARFFIDHDSLTLGKAKVISLDPLASSTLQVVNKSNSEAKTSLSFGYETTESTSKTDH
VKFGEKIGIKSSFNVKVPFIGEKSIETNLEFNSEQGWSNTKTNSVTTKHTISHTTTTPA
KSRKKVRLNVLNKKSDIPYEGKIYMEYDIEFFGFLRYTGNARKDHPTDRPSVSVKFG
GKNNMSAVDHIIDLYKHKDINGYSEWDWNWIEENFYDRFSEYSSNVASQYFGGIISG
VFTNVGGTDVKVEEGRERPLKNTSSTEQNVEVQNFKSSKSKEFRVGSLTYTTPNGEQ
TIYPEDVSSLNANNNEN

FIG. 13A

CLH_2834&2835 (SEQ ID NO: 21)

ATGTTAAAAAAATCTTTTTTTAAAAAGGCAATTTGCGCATCTTTGGTGGT
GCTACAATGTTTGATATTAGTGTCACCAGCTCAAACATTGGCATCAACAG
ATTTGCCGACAAAAGGAAAAACTTCAATTGAACTATTTAACTATGAAGAT
CATTAAATGGCTCATTGTTTGGGATTTGGATGGTGCTTCGGTACAGCATC
AAAAGAAATAGGGGAAGATTTTGAATTTAAAAGAGCAGAAGAAGAAGGAA
AAACAGTATATTATTTATCAGCTAGATACAATCAAAATGATCCTTACGCT
AAAGGCTATTATCGCGCGCATGATAGGCTTGTTATGAAGGTTAGTAATGC
TAGGTTTTTTATCGATCATGATTCATTAACTTTAGGAAAAGCTAAAGTTA
TAAGTCTAGATCCACTGGCATCATCAACTCTTCAAGTAGTAAATAAAAGT
AATTCTGAAGCTAAAACATCATTATCTTTTGGATATGAAACTACTGAAAG
TACTTCCAAAACGGATCACGTTAAATTCGGAGAAAAAATTGGAATTAAGT
CATCATTTAATGTTAAAGTTCCATTTATAGGAGAAAAATCAATTGAAACA
AATCTTGAATTCAATTCAGAGCAGGGTTGGTCCAATACGAAAACTAACTC
TGTAACTACTAAACATACAATTTCTCATACAACAACAACACCTGCAAAGA
GCAGGAAAAAGGTACGATTAAATGTTCTTAATAAAAAGTCCGACATACCA
TATGAGGGTAAGATATATATGGAATATGATATAGAGTTTTTTGGTTTTTT
AAGATATACTGGAAATGCGCGTAAAGATCATCCTACAGATAGACCTAGTG
TATCAGTAAAATTTGGGGGAAAAAATAATATGAGTGCGGTAGATCATATT
ATAGATTTGTACAAGCATAAAGATATTAATGGCTATTCAGAATGGGATTG
GAATTGGATTGAAGAAAATTTTTATGATAGATTTAGTGAATATTCATCTA
ATGTTGCTAGTCAATATTTTGGGGGCATTATTTCTGGTGTATTTACTAAT
GTGGGTGGAACAGATGTAAAAGTTGAAGAAGGTAGAGAAAGGCCACTTAA
AAATACAAGTTCTACAGAACAAAATGTCGAAGTACAGAATTTTAAAAGCT
CTAAATCTAAAGAGTTTAGAGTGGGTAGTTTAACATATACTACTCCTAAT
GGAGAACAGACCATATATCCTGAAGACGTATCATCTCTTAACGCTAACAA
CAATGAGAATTAA

FIG. 13B

CLH_2576 (SEQ ID NO: 10)

MKKKFLSFIIISAISLNISSMTVGAKQVKEIKPPKDKESISVLKTDLEKTKNIKSNNKEG
DDVTKVVKSALKEEGNLGDFKVDNKETDVKGKKHLRSQMFIDGIPVYGSQVIIHTN
KDGQVYSVNGKVDKQPKAQSFKNRVRIKDDKAIKIAEDSLGKEIKKNKNYHSESKL
YLYKVNGDLQPVYLVKISSTEPEASFWHMFVSAENGKIVDKYNALSCQATHAQVRG
VNSSGEHKILNGMFENGRYFLADSTRPSNGYILTYDANNQEYGFPGSLFSNLTGIFDS
DRQKAGVDAHHNLTQVYDYYKNVLNRDSFDGKGASIISSVHVGNNLNNAFWNGRQ
ILFGDGDGVTFSNLAKCLEVTAHEFTHAVTQSTAGLEYRFQSGALNEAFSDILGIAVH
SDPNDWEIGEDIYTPNVAGDALRSMSNPRLYRQPDHMKDYLYWDYSMDKGGVHY
NSGIPNKAAYLMGKEVGKDSMAKIYYHALVNYLTPQSTFEDARNAVVSSAIDLHGE
NSKEHKLAIKSWADVGVGEEAVR

FIG. 14A

CLH_2576 (SEQ ID NO: 22)

ATGAAAAAAAAATTTTTAAGTTTTATTATTATTTCTGCCATATCACTTAA
CATTTCTTCTATGACTGTGGGGGCAAAGCAAGTGAAAGAAATCAAACCTC
CAAAAGATAAAGAATCTATTTCTGTATTAAAAACAGATTTAGAAAAAACC
AAGAATATAAAATCTAATAATAAGGAGGGGGATGATGTAACAAAAGTAGT
TAAGAGTGCTTTAAAAGAAGAAGGCAATTTAGGAGATTTTAAGGTTGATA
ATAAAGAAACTGATGTAAAAGGTAAAAAGCACTTGCGTTCACAAATGTTT
ATAGATGGTATTCCTGTATATGGTAGTCAAGTTATAATTCATACTAATAA
AGATGGACAAGTATATAGCGTAAATGGAAAAGTAGATAAACAGCCTAAAG
CTCAATCTTTTAAGAACCGTGTAAGGATTAAGGACGATAAAGCTATTAAA
ATAGCAGAAGACAGTTTAGGTAAGGAAATAAAGAAAAACAAAAATTATCA
TTCTGAAAGTAAGTTGTACCTATACAAGGTTAATGGAGATTTACAACCTG
TGTATTTGGTAAAGATATCATCTACAGAACCAGAAGCTTCATTTTGGCAT
ATGTTTGTAAGTGCTGAAAATGGAAAGATAGTTGATAAGTATAATGCTTT
ATCATGCCAAGCTACACATGCTCAAGTAAGAGGAGTTAATAGCAGTGGAG
AGCATAAAATCTTAAATGGTATGTTTGAAAATGGAAGATATTTTTTAGCA
GATTCAACAAGACCTTCAAATGGATATATATTAACATATGATGCTAATAA
CCAAGAGTATGGTTTCCCAGGTAGCTTATTTAGTAATTTAACAGGCATTT
TTGATAGTGATAGACAAAAGGCAGGAGTAGATGCTCACCATAATCTAACT
CAAGTATATGATTATTATAAAAATGTTTTAAATAGAGATAGTTTTGATGG
AAAAGGTGCTAGTATAATATCTTCTGTGCATGTAGGAAATAATTTAAATA
ATGCTTTCTGGAATGGTAGACAAATACTTTTTGGTGATGGAGACGGAGTT
ACATTTAGTAACCTAGCAAAATGTTTAGAAGTTACTGCCCATGAATTTAC
ACATGCAGTTACTCAAAGTACTGCAGGTCTAGAATATAGATTTCAATCTG
GTGCTCTAAATGAAGCTTTTTCTGATATTTTAGGTATAGCTGTTCACAGT
GATCCAAATGATTGGGAAATTGGAGAAGATATATACACTCCTAATGTAGC
AGGAGATGCTTTAAGAAGTATGTCAAATCCTAGATTATATAGACAACCAG
ACCATATGAAGGACTATTTATATTGGGATTATTCAATGGATAAAGGTGGA
GTTCATTATAATTCAGGTATTCCAAATAAAGCAGCTTATTTGATGGGAAA
AGAAGTTGGAAAAGATTCAATGGCTAAAATTTATTATCATGCTTTAGTGA
ATTATTTAACTCCTCAAAGTACATTTGAAGATGCTAGAAATGCAGTAGTA
TCATCTGCAATAGATTTACATGGTGAGAATAGTAAAGAACATAAACTTGC
TATAAAATCTTGGGCAGATGTAGGCGTTGGAGAAGAGGCAGTAAGATAA

FIG. 14B

CLH_1920 (SEQ ID NO: 16)

MKITKKGLRSLSRLMLITMITGLTYNYHLGSSFNGNRVVLANPNTKTDNLIKNNSDEI
DEKIYGLSYDPYKILSYNGEKVENFVPAECSENSGKFTVIKREKKNISDSTTDISIMDSI
NDRTYPGAIQLANRDLIENKPNLISCERKPITISVDLPGMGEDGKKVVNSPTYSSVNS
AINYLLDTWNSKYSSKYTIPTRMNYSDTMVYSKSQLSTMFGCNFKTLSKSLNIDFDSI
FKGEKKAMILSYKQIFYTVSVDGPNRPSDLFGYSVTSKSLALKGVNNDNPPAYVSNV
AYGRTVYVKLETTSKSSKVKAAFKALVENQDISSNAEYKDIINQSSFTATVLGGGAQ
KHNKVVTKDFDVIRNIIKNNSVYSPQNPGYPISYTSTFLKDNKIATVNNRTEYIETTAT
EYDSGKIMLDHSGVYVAQFEVTWDEVSYDKQGNEIIEHKSWSGNNSDRTAHFNTEL
YLKGNARNISIKAKECTGLAWEWWRTVVDAKNLPLVKERKLSIWGTTLYPRYSMEE
K

FIG. 15A

CLH_1920 (SEQ ID NO: 23)

ATGAAGATTACAAAGAAAGGCTTAAGATCATTATCACGCTTAATGTTAAT
TACTATGATAACAGGATTAACATACAATTATCACCTAGGTAGTAGCTTTA
ATGGGAATCGAGTAGTACTTGCAAATCCAAATACAAAAACAGATAATTTA
ATTAAGAATAATAGTGATGAAATAGACGAAAAGATTTATGGATTGTCTTA
TGATCCATATAAAATATTATCTTATAATGGAGAAAAGGTTGAAAACTTTG
TTCCAGCTGAATGTTCCGAGAATTCCGGAAAATTTACTGTAATAAAACGT
GAAAAGAAAAATATTTCAGATTCAACTACAGATATTTCAATAATGGATTC
AATAAATGATAGAACTTATCCTGGTGCTATACAACTAGCAAATAGGGATC
TTATAGAAAATAAGCCTAATTTAATTTCATGCGAGAGAAAACCTATTACT
ATAAGTGTTGATTTACCTGGTATGGGTGAGGATGGGAAAAAGGTTGTTAA
TTCTCCAACATACTCTTCAGTTAATTCAGCAATAAATTATTTGCTAGATA
CATGGAATTCAAAATATTCATCTAAATATACTATACCTACAAGGATGAAT
TATTCTGATACTATGGTGTATAGTAAATCACAGTTATCTACAATGTTTGG
ATGTAACTTTAAAACTTTAAGTAAATCCTTAAATATAGATTTTGATTCTA
TATTTAAAGGCGAAAAAAAGGCTATGATTCTATCATATAAACAAATTTTC
TACACAGTGAGTGTAGATGGACCTAATCGCCCATCAGATTTATTTGGTTA
CAGTGTAACTTCTAAGAGCTTAGCTTTAAAAGGAGTAAATAATGATAATC
CTCCAGCATACGTTTCCAATGTTGCATATGGTAGAACTGTTTATGTAAAA
CTAGAGACAACATCTAAGAGTTCAAAGGTTAAAGCAGCATTTAAGGCATT
AGTAGAGAATCAAGATATAAGTAGTAATGCAGAATATAAAGACATAATAA
ATCAAAGTTCATTTACAGCTACTGTTCTAGGTGGAGGAGCACAAAAACAC
AATAAAGTAGTTACTAAAGATTTCGATGTAATAAGAAATATTATTAAAAA
TAATTCAGTATATAGCCCACAAAATCCTGGATATCCTATTTCATATACAA
GTACATTTTTAAAAGACAATAAAATAGCAACTGTAAACAATAGAACAGAA
TATATAGAAACAACTGCAACAGAATACGATAGCGGCAAAATAATGCTTGA
CCATAGTGGAGTTTATGTTGCTCAATTTGAAGTAACCTGGGATGAAGTTA
GTTATGACAAACAAGGAAATGAAATAATTGAGCATAAATCTTGGTCTGGA
AACAATAGTGATAGAACAGCTCACTTTAATACAGAACTATATTTAAAAGG
AAATGCAAGAAACATTTCTATAAAAGCAAAAGAATGTACAGGCCTTGCTT
GGGAATGGTGGAGAACTGTTGTAGATGCTAAAAATTTACCACTTGTAAAA
GAAAGAAAGTTATCAATATGGGGTACAACATTATATCCTAGATATTCTAT
GGAAGAGAAATAA

FIG. 15B

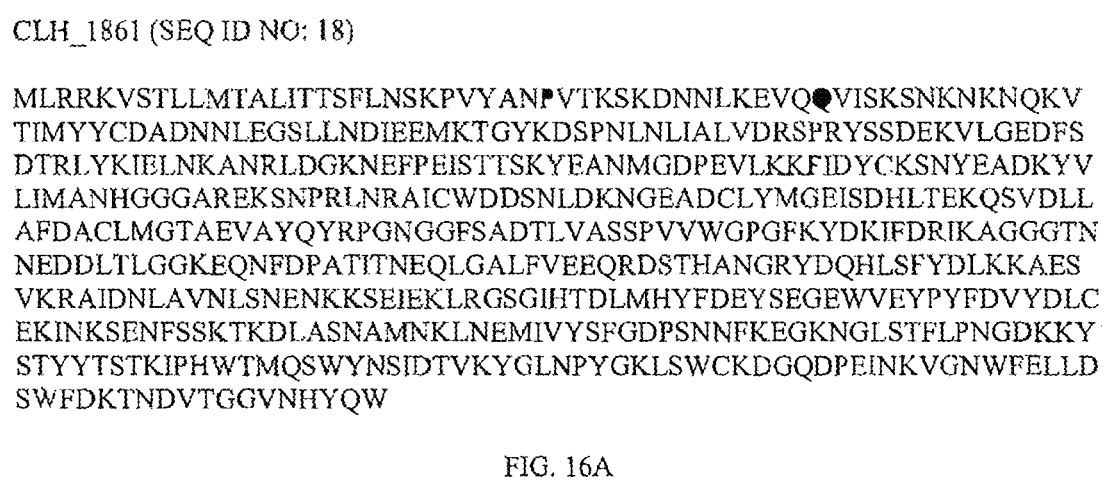

CLH_1861 (SEQ ID NO: 18)

MLRRKVSTLLMTALITTSFLNSKPVYANPVTKSKDNNLKEVQ[illegible]VISKSNKNKNQKV
TIMYYCDADNNLEGSLLNDIEEMKTGYKDSPNLNLIALVDRSPRYSSDEKVLGEDFS
DTRLYKIELNKANRLDGKNEFPEISTTSKYEANMGDPEVLKKFIDYCKSNYEADKYV
LIMANHGGGAREKSNPRLNRAICWDDSNLDKNGEADCLYMGEISDHLTEKQSVDLL
AFDACLMGTAEVAYQYRPGNGGFSADTLVASSPVVWGPGFKYDKIFDRIKAGGGTN
NEDDLTLGGKEQNFDPATITNEQLGALFVEEQRDSTHANGRYDQHLSFYDLKKAES
VKRAIDNLAVNLSNENKKSEIEKLRGSGIHTDLMHYFDEYSEGEWVEYPYFDVYDLC
EKINKSENFSSKTKDLASNAMNKLNEMIVYSFGDPSNNFKEGKNGLSTFLPNGDKKY
STYYTSTKIPHWTMQSWYNSIDTVKYGLNPYGKLSWCKDGQDPEINKVGNWFELLD
SWFDKTNDVTGGVNHYQW

FIG. 16A

CLH_1861 (SEQ ID NO: 24)

ATGttaagaagaaaagtatcaacactattaatgacagctttgataactacttcatttttaaat
tccaaacccgtatatgcaaatccagtaactaaatccaaggataataacttaaaagaagtac
aacaagttataagcaagagtaataaaaacaaaaatcaaaaagtaactattatgtactattgc
gacgcagataataacttggaaggaagtctattaaatgatatcgaggaaatgaaaacagga
tataaggatagtcctaatttaaatttaattgctcttgtagacagatccccaagatatagcagtg
acgaaaaagttttaggtgaagattttagtgatacacgtctttataagattgaactcaataagg
caaatagattagacggtaaaaatgaatttccagaaataagtactactagtaaatatgaagct
aacatgggggatcctgaagttcttaaaaaatttattgattattgtaaatctaattatgaggctg
ataaatatgtgcttataatggctaatcatggtggtggtgcaagggaaaaatcaaatccaag
attaaatagagcaatttgctgggatgatagtaaccttgataaaaatggtgaagcagactgc
ctttatatgggtgaaatttcagatcatttaacagaaaaacaatcagttgatttacttgcctttga
tgcatgccttatgggaactgcagaagtagcgtatcagtatagaccaggtaatggaggattt
tctgccgatactttagttgcttcaagcccagtagtttggggtcctggattcaaatatgataag
attttcgataggataaaagctggtggaggaactaataatgaggatgatttaactttaggtgg
taaagaacaaaactttgatcctgcaaccattaccaatgagcaattaggtgcattatttgtaga
agagcaaagagactcaacacatgccaatggtcgctatgatcaacacttaagcttttatgatt
taaagaaagctgaatcagtaaaaagagccatagataatttagctgttaatctaagtaatgaa
aacaaaaaatctgaaattgaaaaattaagaggaagtggaattcatacagatttaatgcatta
cttcgatgaatattctgaaggagaatgggttgaatatccttattttgacgtgtatgatttatgtg
aaaaaataaataaaagtgaaaattttagtagtaaaactaaagatttagcttcaaatgctatga
ataaattaaatgaaatgatagtttattcttttggagaccctagtaataattttaaagaaggaaa
aaatggattgagtacattcttacctaatggagataaaaaatattcaacttattatacatcaacc
aagatacctcattggactatgcaaagttggtataattcaatagatacagttaaatatggattg
aatccttacggaaaattaagttggtgtaaagatggacaagatcctgaaataaataaagttg
gaaattggtttgaacttctagattcttggtttgataaaactaatgatgtaactggaggagttaa
tcattaccaatggTAA

FIG. 16B

SEQ ID NO: 3 (colG)

MKKNILKILMDSYSKESKIQTVRRVTSVSLLAAYLTMNTSSLVLAKPIENTNDTSIKN
VEKLRNAPNEENSKKVEDSKNDKVEHVENIEEAKVEQVAPEVKSKSTLRSASIANTN
SEKYDFEYLNGLSYTELTNLIKNIKWNQINGLFNYSTGSQKFFGDKNRVQAIINALQE
SGRTYTANDMKGIETFTEVLRAGFYLGYYNDGLSYLNDRNFQDKCIPAMIAIQKNPN
FKLGTAVQDEVITSLGKLIGNASANAEVVNNCVPVLKQFRENLNQYAPDYVKGTAV
NELIKGIEFDFSGAAYEKDVKTMPWYGKIDPFINELKALGLYGNITSATEWASDVGIY
YLSKFGLYSTNRNDIVQSLEKAVDMYKYGKIAFVAMERITWDYDGIGSNGKKVDHD
KFLDDAEKHYLPKTYTFDNGTFIIRAGEKVSEEKIKRLYWASREVKSQFHRVVGNDK
ALEVGNADDVLTMKIFNSPEEYKFNTNINGVSTDNGGLYIEPRGTFYTYERTPQQSIF
SLEELFRHEYTHYLQARYLVDGLWGQGPFYEKNRLTWFDEGTAEFFAGSTRTSGVL
PRKSILGYLAKDKVDHRYSLKKTLNSGYDDSDWMFYNYGFAVAHYLYEKDMPTFI
KMNKAILNTDVKSYDEIIKKLSDDANKNTEYQNHIQELADKYQGAGIPLVSDDYLKD
HGYKKASEVYSEISKAASLTNTSVTAEKSQYFNTFTLRGTYTGETSKGEFKDWDEMS
KKLDGTLESLAKNSWSGYKTLTAYFTNYRVTSDNKVQYDVVFHGVLTDNADISNN
KAPIAKVTGPSTGAVGRNIEFSGKDSKDEDGKIVSYDWDFGDGATSRGKNSVHAYK
KTGTYNVTLKVTDDKGATATESFTIEIKNEDTTTPITKEMEPNDDIKEANGPIVEGVT
VKGDLNGSDDADTFYFDVKEDGDVTIELPYSGSSNFTWLVYKEGDDQNHIASGIDK
NNSKVGTFKATKGRHYVFIYKHDSASNISYSLNIKGLGNEKLKEKENNDSSDKATVIP
NFNTTMQGSLLGDDSRDYYSFEVKEEGEVNIELDKKDEFGVTWTLHPESNINDRITY
GQVDGNKVSNKVKLRPGKYYLLVYKYSGSGNYELRVNK

FIG. 17A

SEQ ID NO: 5

IANTNSEKYDFEYLNGLSYTELTNLIKNIKWNQINGLFNYSTGSQKFFGDKNRVQAII
NALQESGRTYTANDMKGIETFTEVLRAGFYLGYYNDGLSYLNDRNFQDKCIPAMIAI
QKNPNFKLGTAVQDEVITSLGKLIGNASANAEVVNNCVPVLKQFRENLNQYAPDYV
KGTAVNELIKGIEFDFSGAAYEKDVKTMPWYGKIDPFINELKALGLYGNITSATEWA
SDVGIYYLSKFGLYSTNRNDIVQSLEKAVDMYKYGKIAFVAMERITWDYDGIGSNG
KKVDHDKFLDDAEKHYLPKTYTFDNGTFIIRAGEKVSEEKIKRLYWASREVKSQFHR
VVGNDKALEVGNADDVLTMKIFNSPEEYKFNTNINGVSTDNGGLYIEPRGTFYTYER
TPQQSIFSLEELFRHEYTHYLQARYLVDGLWGQGPFYEKNRLTWFDEGTAEFFAGST
RTSGVLPRKSILGYLAKDKVDHRYSLKKTLNSGYDDSDWMFYNYGFAVAHYLYEK
DMPTFIKMNKAILNTDVKSYDEIIKKLSDDANKNTEYQNHIQELADKYQGAGIPLVS
DDYLKDHGYKKASEVYSEISKAASLTNTSVTAEKSQYFNTFTLRGTYTGETSKGEFK
DWDEMSKKLDGTLESLAKNSWSGYKTLTAYFTNYRVTSDNKVQYDVVFHGVLTD
NADISNNKAPIAKVTGPSTGAVGRNIEFSGKDSKDEDGKIVSYDWDFGDGATSRGKN
SVHAYKKTGTYNVTLKVTDDKGATATESFTIEIKNEDTTTPITKEMEPNDDIKEANGP
IVEGVTVKGDLNGSDDADTFYFDVKEDGDVTIELPYSGSSNFTWLVYKEGDDQNHI
ASGIDKNNSKVGTFKATKGRHYVFIYKHDSASNISYSLNIKGLGNEKLKEKENNDSS
DKATVIPNFNTTMQGSLLGDDSRDYYSFEVKEEGEVNIELDKKDEFGVTWTLHPESN
INDRITYGQVDGNKVSNKVKLRPGKYYLLVYKYSGSGNYELRVNK

FIG. 17B

SEQ ID NO: 4 (colH)

MKRKCLSKRLMLAITMATIFTVNSTLPIYAAVDKNNATAAVQNESKRYTVSYLKTL
NYYDLVDLLVKTEIENLPDLFQYSSDAKEFYGNKTRMSFIMDEIGRRAPQYTEIDHK
GIPTLVEVVRAGFYLGFHNKELNEINKRSFKERVIPSILAIQKNPNFKLGTEVQDKIVS
ATGLLAGNETAPPEVVNNFTPIIQDCIKNMDRYALDDLKSKALFNVLAAPTYDITEYL
RATKEKPENTPWYGKIDGFINELKKLALYGKINDNNSWIIDNGIYHIAPLGKLHSNNK
IGIETLTEVMKIYPYLSMQHLQSADQIERHYDSKDAEGNKIPLDKFKKEGKEKYCPKT
YTFDDGKVIIKAGARVEEEKVKRLYWASKEVNSQFFRVYGIDKPLEEGNPDDILTMV
IYNSPEEYKLNSVLYGYDTNNGGMYIEPDGTFFTYERKAEESTYTLEELFRHEYTHYL
QGRYAVPGQWGRTKLYDNDRLTWYEEGGAELFAGSTRTSGILPRKSIVSNIHNTTRN
NRYKLSDTVHSKYGASFEFYNYACMFMDYMYNKDMGILNKLNDLAKNNDVDGYD
NYIRDLSSNHALNDKYQDHMQERIDNYENLTVPFVADDYLVRHAYKNPNEIYSEISE
VAKLKDAKSEVKKSQYFSTFTLRGSYTGGASKGKLEDQKAMNKFIDDSLKKLDTYS
WSGYKTLTAYFTNYKVDSSNRVTYDVVFHGYLPNEGDSKNSLPYGKINGTYKGTEK
EKIKFSSEGSFDPDGKIVSYEWDFGDGNKSNEENPEHSYDKVGTYTVKLKVTDDKGE
SSVSTTTAEIKDLSENKLPVIYMHVPKSGALNQKVVFYGKGTYDPDGSIAGYQWDFG
DGSDFSSEQNPSHVYTKKGEYTVTLRVMDSSGQMSEKTMKIKITDPVYPIGTEKEPN
NSKETASGPIVPGIPVSGTIENTSDQDYFYFDVITPGEVKIDINKLGYGGATWVVYDE
NNNAVSYATDDGQNLSGKFKADKPGRYYIHLYMFNGSYMPYRINIEGSVGR

FIG. 18A

SEQ ID NO: 6

AVDKNNATAAVQNESKRYTVSYLKTLNYYDLVDLLVKTEIENLPDLFQYSSDAKEF
YGNKTRMSFIMDEIGRRAPQYTEIDHKGIPTLVEVVRAGFYLGFHNKELNEINKRSFK
ERVIPSILAIQKNPNFKLGTEVQDKIVSATGLLAGNETAPPEVVNNFTPIIQDCIKNMD
RYALDDLKSKALFNVLAAPTYDITEYLRATKEKPENTPWYGKIDGFINELKKLALYG
KINDNNSWIIDNGIYHIAPLGKLHSNNKIGIETLTEVMKIYPYLSMQHLQSADQIERHY
DSKDAEGNKIPLDKFKKEGKEKYCPKTYTFDDGKVIIKAGARVEEEKVKRLYWASK
EVNSQFFRVYGIDKPLEEGNPDDILTMVIYNSPEEYKLNSVLYGYDTNNGGMYIEPD
GTFFTYERKAEESTYTLEELFRHEYTHYLQGRYAVPGQWGRTKLYDNDRLTWYEEG
GAELFAGSTRTSGILPRKSIVSNIHNTTRNNRYKLSDTVHSKYGASFEFYNYACMFM
DYMYNKDMGILNKLNDLAKNNDVDGYDNYIRDLSSNHALNDKYQDHMQERIDNY
ENLTVPFVADDYLVRHAYKNPNEIYSEISEVAKLKDAKSEVKKSQYFSTFTLRGSYT
GGASKGKLEDQKAMNKFIDDSLKKLDTYSWSGYKTLTAYFTNYKVDSSNRVTYDV
VFHGYLPNEGDSKNSLPYGKINGTYKGTEKEKIKFSSEGSFDPDGKIVSYEWDFGDG
NKSNEENPEHSYDKVGTYTVKLKVTDDKGESSVSTTTAEIKDLSENKLPVIYMHVPK
SGALNQKVVFYGKGTYDPDGSIAGYQWDFGDGSDFSSEQNPSHVYTKKGEYTVTLR
VMDSSGQMSEKTMKIKITDPVYPIGTEKEPNNSKETASGPIVPGIPVSGTIENTSDQDY
FYFDVITPGEVKIDINKLGYGGATWVVYDENNNAVSYATDDGQNLSGKFKADKPGR
YYIHLYMFNGSYMPYRINIEGSVGR

FIG. 18B

NUCLEIC ACID MOLECULES ENCODING CLOSTRIDIUM HISTOLYTICUM COLLAGENASE I AND METHODS OF PRODUCING THE SAME

RELATED APPLICATIONS

This application is a continuation of U.S. patent application Ser. No. 15/669,286 filed on Aug. 4, 2017, which is a divisional of U.S. patent application Ser. No. 14/328,772 filed on Jul. 11, 2014, which is a continuation application of International Application No. PCT/US13/020940, which designated the United States and was filed on Jan. 10, 2013, published in English which claims the benefit of U.S. Provisional Application No. 61/585,909 filed Jan. 12, 2012. The entire contents of the above-referenced applications are incorporated by reference herein.

SEQUENCE LISTING

The contents of the electronic sequence listing (15669286-Substitute-Seq.txt; Size: 116,711 bytes; and Date of Creation: Mar. 11, 2020) is herein incorporated by reference in its entirety.

BACKGROUND OF THE INVENTION

Collagen is the major structural constituent of mammalian organisms and makes up a large portion of the total protein content of skin and other parts of the animal body. In humans, it is particularly important in the processes of wound healing process and natural aging. Various skin traumas, including burns, surgery, and infection, are characterized by the accumulation of fibrous tissue rich in collagen and having increased proteoglycan content. In addition to the replacement of the normal tissue which has been damaged or destroyed, excessive and disfiguring deposits of new tissue sometimes form during the healing process. The excess collagen deposition has been attributed to a disturbance in the balance between collagen synthesis and collagen degradation.

Diseases and conditions associated with excess collagen deposition and the erratic accumulation of fibrous tissue rich in collagen can be referred to as "collagen-mediated diseases." Collagenase, an enzyme that has the specific ability to digest collagen, has been used to treat a variety of collagen-mediated diseases, including, for example, Dupuytren's contracture, Peyronie's disease, lipoma and adhesive capsulitis. U.S. Pat. Nos. 6,086,872 and 5,589,171, incorporated herein by reference, disclose the use of collagenase preparations in the treatment of Dupuytren's disease. U.S. Pat. No. 6,022,539, incorporated herein by reference, discloses the use of collagenase preparations in the treatment of Peyronie's disease. U.S. Pat. Nos. 6,958,150 and 7,842,673, incorporated herein by reference, disclose the use of collagenase for the treatment of lipoma. U.S. Patent Application Publication No. 2006/020448A1, incorporated herein by reference, discloses the use of collagenase in the treatment of adhesive capsulitis. Collagenase for use in therapy may be obtained from a variety of sources including mammalian, fungal, and bacterial sources. One common source of crude collagenase is from a bacterial fermentation process, specifically the fermentation of *Clostridium histolyticum* (*C. histolyticum*). The crude collagenase obtained from *C. histolyticum* may be purified using any of a number of chromatographic techniques.

One drawback of the fermentation of bacteria is that various toxins will be produced, that if present in the therapeutic composition, would be detrimental to the health of the patient. For example, *C. histolyticum* fermentation results in the synthesis of the hemolytic toxins alpha and epsilon, which can cause lysis of red blood cells (hemolysis), potentially leading to hemolytic crisis and hemolytic anemia. Hemolytic crisis occurs when there is a rapid destruction of large numbers of red blood cells in conjunction with the body's inability to replenish the red blood cells quickly enough to reestablish normal red blood cell levels. A hemolytic crisis causes acute (and often severe) hemolytic anemia, and can result in fatigue, shortness of breath, dizziness, headache, coldness in the hands and feet, pale skin, chest pain, jaundice, pain in the upper abdomen, leg ulcers and pain, severe reactions to a blood transfusion, arrhythmias, an enlarged heart, and heart failure. In order to ensure that the therapeutic collagenase preparation does not contain hemolytic toxins that might be expressed during *C. histolyticum* fermentation, a method for releasing a drug product prior to administration to a patient is presented.

As discussed above, collagenase for use in therapy can be obtained from a variety of sources such as bacterial sources (e.g. from the fermentation of *C. histolyticum*). It would be useful to develop additional sources of collagenase such as recombinant forms of collagenase enzymes.

SUMMARY OF THE INVENTION

In some aspects, the present invention is based on the discovery of mutated polynucleotide sequences that encode functional collagenase I and collagenase II. The invention thus encompasses recombinant nucleic acid and polypeptides comprising the novel polynucleotide or polypeptide sequences and methods for the use thereof. The present invention also provides a method for detecting the secretion of a hemolytic toxin by a bacterial production strain, wherein the production strain produces a collagenase, prior to therapeutic administration of said collagenase to a patient and methods for detecting the presence of a hemolytic toxin in a collagenase composition.

In one embodiment, the invention is directed to a recombinant nucleic acid molecule comprising a polynucleotide having the sequence of SEQ ID NO: 1 (collagenase I nucleotide sequence) or the complement of SEQ ID NO: 1. In certain aspects, the recombinant nucleic acid further comprises a heterologous regulatory sequence operably linked to the polynucleotide. In certain additional embodiments, the invention is a recombinant nucleic acid molecule consisting of a polynucleotide of SEQ ID NO: 1. In yet additional aspects, the invention relates to a recombinant nucleic acid molecule consisting of a polynucleotide of SEQ ID NO: 1 and a heterologous regulator sequence operably linked to the polynucleotide.

In another embodiment, the invention is a recombinant nucleic acid molecule comprising a polynucleotide having the sequence of SEQ ID NO: 2 (collagenase II nucleotide sequence) or the complement of SEQ ID NO: 2. In certain aspects, the recombinant nucleic acid further comprises a heterologous promoter operatively linked to the polynucleotide. In certain additional embodiments, the invention is a recombinant nucleic acid molecule consisting of a polynucleotide of SEQ ID NO: 2. In yet additional aspects, the invention relates to a recombinant nucleic acid molecule consisting of a polynucleotide of SEQ ID NO: 2 and a heterologous regulator sequence operably linked to the polynucleotide.

The invention also includes recombinant polypeptides encoded by a recombinant nucleic acid comprising a polynucleotide having the sequence of SEQ ID NO: 1 or SEQ ID NO: 2.

In certain additional embodiments, the invention is directed to an expression cassette comprising a recombinant nucleic acid, wherein the nucleic acid comprises a polynucleotide having the sequence of SEQ ID NO: 1 or SEQ ID NO: 2.

In yet an additional embodiment, the invention is directed to a vector comprising a recombinant nucleic acid, wherein the nucleic acid comprises a polynucleotide having the sequence of SEQ ID NO: 1 or SEQ ID NO: 2. In some embodiments, the vector is a plasmid.

In a further aspect, the invention is directed to a recombinant host cell comprising the vector or plasmid comprising a polynucleotide having the sequence of SEQ ID NO: 1 or SEQ ID NO: 2. The invention also encompasses a method of producing collagenase I or collagenase II comprising culturing the host cell under conditions suitable for expression of the nucleic acid and recovering the collagenase I or collagenase II. The invention also includes a collagenase enzyme produced by culturing the recombinant host cell.

In some embodiments, the invention is directed to a recombinantly produced collagenase I comprising the amino acid sequence of SEQ ID NO: 3, a recombinantly produced collagenase II comprising the amino acid sequence SEQ ID NO: 4, a recombinantly produced collagenase I comprising the amino acid sequence of SEQ ID NO: 5, or a recombinantly produced collagenase II comprising the amino acid sequence of SEQ ID NO: 6.

Also included in the present invention are pharmaceutical compositions comprising collagenase I as described herein, collagenase II as described herein, or a combination thereof. In certain aspects, the present invention is directed to a pharmaceutical composition comprising a pharmaceutically acceptable carrier and a polypeptide comprising the amino sequence of SEQ ID NO: 3, a polypeptide comprising the amino acid sequence of SEQ ID NO: 4, or a combination thereof. In certain additional aspects, the present invention is directed to a pharmaceutical composition comprising a pharmaceutically acceptable carrier and a polypeptide comprising the amino sequence of SEQ ID NO: 5, a polypeptide comprising the amino acid sequence of SEQ ID NO: 6, or a combination thereof. The invention additionally includes methods of treating a collagen-mediated disease comprising administering an effective amount of collagenase I, collagenase II, or a combination thereof.

As discussed above, the invention encompasses methods for detecting the secretion of a hemolytic toxin by a bacterial production strain and methods for detecting the presence of a hemolytic toxin in a collagenase composition.

In one embodiment of the invention, a bacterial strain that produces collagenase is tested for the production of hemolytic toxins using a hemolysis assay. In one aspect, the hemolysis assay is performed using a blood agar substrate.

In another embodiment, a collagenase product is tested for the presence of hemolytic toxins using a hemolysis assay. In certain aspects, the hemolysis assay is performed using a blood agar substrate. In additional aspects, the hemolysis assay is performed using photometric detection of released hemoglobin. The absence of hemolytic toxins, as determined by a hemolysis assay or photometric detection, would support the release of the drug product for therapeutic administration.

Various strains of collagenase-producing bacteria can be assayed for hemolytic activity according to a method of the invention, in support of the release of a collagenase drug product for therapeutic administration. For example, members of the genera *Actinobacillus, Actinomadura, Bacillus, Bacteroides, Bifidobacterium, Brucella, Capnocytophaga, Clostridium, Enterococcus, Escherichia, Eubacterium, Flavobacterium, Fusobacterium, Peptococcus, Peptostreptococcus, Porphyromonas, Prevotella, Proteus, Pseudomonas, Serratia, Staphylococcus, Streptomyces, Streptococcus, Treponema*, and *Vibrio* can be assayed for hemolytic activity according to a method of the invention, in support of the release of a collagenase drug product for therapeutic administration.

In another embodiment, a collagenase product produced by, and purified from, a strain of collagenase-producing bacteria is assayed for hemolytic activity according to a method of the invention, in support of the release of a collagenase drug product for therapeutic administration.

In some embodiments, the production strain is selected from, but not limited to, the above-listed genera. In another aspect of the invention, the production strain is an *Escherichia coli* (*E. coli*) strain, including forms of *E. coli* that have been transformed with recombinant forms of collagenase I and collagenase II. In certain aspects of the invention, the production strain is a *Clostridium perfringens* (*C. prefrigens*) strain. In additional aspects, the production strain is a *C. histolyticum* strain.

In yet another embodiment of the invention, the collagenase composition is assayed for hemolytic activity according to a method of the invention, wherein the collagenase composition comprises a combination of purified *C. histolyticum* collagenase I and collagenase II. In an additional embodiment, the invention is a method of producing a drug product consisting of *C. histolyticum* collagenase I and II, wherein said method comprises testing a bacterial production strain for the absence of a functional, secreted hemolytic toxin according to a method of the invention.

In yet another embodiment, the invention is a method of purifying a crude collagenase composition, wherein said method comprises purifying the composition by filtration and column chromatography, followed by confirming the absence of a hemolytic toxin according to a method described herein.

In a further embodiment, the invention is a method of treating a collagen-mediated condition in a patient in need thereof, wherein said method comprises administering to said patient an effective amount of a drug product comprising collagenase, wherein the absence of a hemolytic toxin in said drug product or in a bacterial production strain producing said collagenase is confirmed according to a method of the invention prior to administration of said drug product to a patient, and/or formulation of the collagenase in a pharmaceutical composition.

Kits for testing for the presence or absence of hemolytic toxins in a sample are also described.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 shows protein alignment of *Clostridium septicum* (*C. septicum*) alpha toxin with the putative alpha toxin of *C.*

Figure 7:
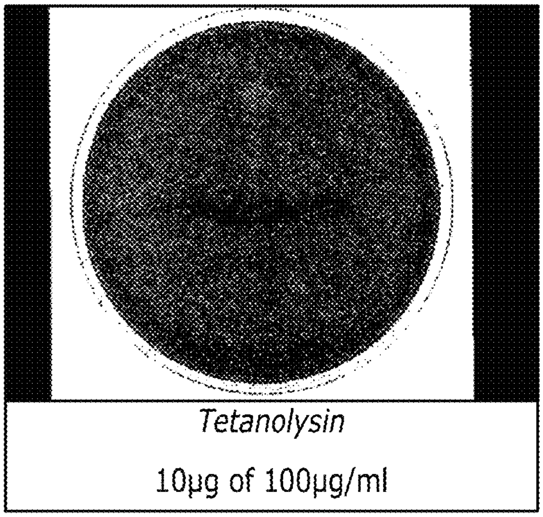

*histolyticum* CLH_2834 and 2835. The *C. septicum* alpha toxin amino acid sequence (SEQ ID NO: 7) is the upper sequence in each row. The *C. histolyticum* CLH_2834 & 2835 (SEQ ID NO: 8) is the lower sequence in each row. The underlined, shaded sequence is the N-terminus of the mature *C. septicum* alpha toxin. The asterisks above the amino acids shows non-conserved essential residues critical for functionality (identifies mismatch in sequence). The shading shows conserved essential residues (confirms identity). The sequence numbering is based on the *C. septicum* sequence.

FIG. 2 shows blood agar plating of *C. septicum*. The arrows indicate beta hemolytic activity.

FIG. 3 shows amino acid alignment of *Bacillus proteolyticus* thermolysin with the putative delta toxin of *C. histolyticum* CLH_2576. The upper sequence in each row shows the sequence of *Bacillus proteolyticus* (B. *proteolyticus*) thermolysin protein (SEQ ID NO: 9). The lower sequence in each row is the sequence of *C. histolyticum* CLH_2576 (SEQ ID NO: 10). The green shading shows the proprotein region. The numbering is based on the thermolysin sequence.

FIG. 4 shows the prosequence amino acid alignment of B. *proteolyticus* thermolysin with the putative delta toxin of *C. histolyticum* CLH_2576. The upper sequence in each row is the prosequence of B. *proteolyticus* thermolysin protein (SEQ ID NO: 11). The lower sequence in each row is the prosequence of *C. histolyticum* CLH_2576 (SEQ ID NO: 12). The asterisks above the amino acids show the non-conserved essential residues critical for functionality (identifies mismatch in sequence). The green shading shows the conserved essential residues (confirms identity). The numbering is based on the thermolysin sequence.

FIG. 5 shows the mature sequence protein alignment of B. *proteolyticus* thermolysin with the putative delta toxin of *C. histolyticum* CLH_2576. The upper sequence in each row is the mature sequence of B. *proteolyticus* thermolysin (SEQ ID NO: 13). The lower sequence in each row is *C. histolyticum* CLH_2576 (SEQ ID NO: 14). The asterisks above the amino acids show non-conserved essential residues critical for functionality (identifies mismatch in sequence). The green shading shows conserved essential residues (confirms identity). The numbering is based on thermolysin sequence.

FIG. 6 shows the protein alignment of *C. perfringens* perfringolysin with the putative epsilon toxin of *C. histolyticum* CLH_1920. The upper sequence in each row is *C. perfringens* perfringolysin amino acid sequence (SEQ ID NO: 15). The lower sequence in each row is the amino acid sequence of *C. histolyticum* CLH_1920 (SEQ ID NO: 16). The blue star shows the signal peptidase cleavage site of perfringolysin K43. The asterisks above the amino acids show non-conserved essential residues critical for functionality (identifies mismatch in sequence). The green shading shows conserved essential residues (confirms identity). The numbering is based on the perfringolysin sequence.

FIG. 7 shows the beta hemolytic phenotype of tetanolysin.

FIG. 8 shows the protein alignment of *C. histolyticum* clostripain with the putative gamma toxin of *C. histolyticum* CLH_1861. The upper sequence in each row is *C. histolyticum* clostripain amino acid sequence (SEQ ID NO: 17). The lower sequence in each row is *C. histolyticum* CLH_1920 amino acid sequence (SEQ ID NO: 18). The asterisks above the amino acids shows non-conserved essential residues critical for functionality (identifies mismatch in sequence). The green shading shows the conserved essential residues (confirms identity). The numbering based on clostripain X63673 sequence.

FIGS. 9A and 9B show an alignment comparison of the translated amino acid sequence from colG and the amino acid sequence of SEQ ID NO: 3 (the translated amino acid sequence from CLH_1768 and 1769; the upper sequence). As shown in FIGS. 9A and 9B, the mature protein encoded by the amino acid sequence of SEQ ID NO: 3 differs from the translated amino acid sequence from colG amino acid sequence by three amino acids. The N-terminus of the mature protein begins at Ile 119 of the sequence of SEQ ID NO: 3. The amino acid sequence of the mature protein beginning at Ile 119 of SEQ ID NO: 3 is SEQ ID NO: 5.

FIGS. 10A and 10B show an alignment comparison of the translated amino acid sequence from colH and SEQ ID NO: 4 (the translated amino acid sequence from CLH_2116; the bottom sequence). As shown in FIGS. 10A and 10B, the mature protein encoded by the amino acid sequence of SEQ ID NO: 4 differs from the translated colG amino acid sequence by eight amino acids. The N-terminus of the mature protein begins at Ala 31 in colG and in SEQ ID NO: 4. The amino acid sequence of the mature protein beginning at Ala 31 of SEQ ID NO: 4 is SEQ ID NO: 6.

FIGS. 11A and 11B show the nucleotide sequence of SEQ ID NO: 1 (CLH_1768 and 1769; collagenase I).

FIGS. 12A and 12B show the nucleotide sequence of SEQ ID NO: 2 (CLH_2116; collagenase II).

FIGS. 13A and 13B show the amino acid and nucleotide sequence of SEQ ID NO: 8 and SEQ ID NO: 21, respectively (CLH_2835 and CLH_2834; alpha toxin).

FIGS. 14A and 14B show the amino acid and nucleotide sequence of SEQ ID NO: 10 and SEQ ID NO: 22, respectively (CLH_2576; delta toxin).

FIGS. 15A and 15B show the amino acid and nucleotide sequence of SEQ ID NO: 16 and SEQ ID NO: 23, respectively (CLH_1920; epsilon toxin).

FIGS. 16A and 16B show the amino acid and nucleotide sequence of SEQ ID NO: 18 and SEQ ID NO: 24, respectively (CLH_1861; gamma toxin).

FIG. 17A shows the amino acid sequence of SEQ ID NO: 3 (colG).

FIG. 17B shows the amino acid sequence of SEQ ID NO: 5.

FIG. 18A shows the amino acid sequence of SEQ ID NO: 4 (colH).

FIG. 18B shows the amino acid sequence of SEQ ID NO: 6.

DETAILED DESCRIPTION OF THE INVENTION

A description of preferred embodiments of the invention follows.

The words "a" or "an" are meant to encompass one or more, unless otherwise specified. For example, "a hemoloytic toxin" refers to one or more hemolytic toxins.

The practice of the present invention will employ, unless otherwise indicated, conventional techniques of cell culture, molecular biology, microbiology, cell biology, and immunology, which are well within the skill of the art. Such techniques are fully explained in the literature. See, e.g., Sambrook et al., 1989, "Molecular Cloning: A Laboratory Manual", Cold Spring Harbor Laboratory Press; Ausubel et al. (1995), "Short Protocols in Molecular Biology", John Wiley and Sons; Methods in Enzymology (several volumes); Methods in Cell Biology (several volumes), and Methods in Molecular Biology (several volumes); the contents of each of which are expressly incorporated by reference herein.

A. Recombinant Nucleic Acids and Proteins

A major source of collagenase is from the fermentation of *C. histolyticum*. An injectable formulation comprising *C. histolyticum* collagenase I and collagenase II is sold under the trade name XIAFLEX® and is approved by the U.S. Food and Drug Administration for the treatment of Dupuytren's contracture. Amino acid sequences for collagenase I and collagenase II encoded by the colG and colH genes, respectively, have been described in the literature. For example, colG is described in GenBank Acc. No. D87215 and Matsushita et al. (1999), *Journal of Bacteriology* 181 (3): 923-933, and colH has been described in GenBank Acc. No. D29981 and Yoshihara et al. (1994), *Journal of Bacteriology* 176(21): 6489-6496, the contents of each of which are expressly incorporated by reference herein. The present invention is based partially on sequencing analysis of the genes encoding collagenase I and collagenase II in a *C. histolyticum* strain (Clone 004 described below in the Examples) which produces and secretes functional collagenase I and collagenase II. The nucleotide sequences of the genes encoding collagenase I and collagenase II were found to be different from the literature-described sequences for *C. histolyticum* (e.g., GenBank Acc. Nos. D87125 and D29981) (SEQ ID NO: 19 and 20) (FIGS. 9A, 9B, 10A, and 10B).

Collagenase I and collagenase II are metalloproteases and require tightly bound zinc and loosely bound calcium for their activity (Eddie L. Angleton and H. E. Van Wart, *Biochemistry* 1988, 27, 7406-7412). Collagenase I and collagenase II have broad specificity toward all types of collagen (Steinbrink, D; Bond, M and Van Wart, H; (1985), *JBC,* 260 p 2771-2776). Collagenase I and collagenase II digest collagen by hydrolyzing the triple-helical region of collagen under physiological conditions (Steinbrink, D; Bond, M and Van Wart, H; (1985), *JBC,* 260 p 2771-2776). Even though each collagenase shows different specificity (e.g., each has a different preferred amino sequence for cleavage), together, they have synergistic activity toward collagen (Mandl, I., (1964), *Biochemistry,* 3: p. 1737-1741; Vos-Scheperkeuter, GH, (1997), *Cell Transplantation,* 6: p. 403-412).

The invention encompasses a recombinant nucleic acid molecule comprising or consisting of a polynucleotide of SEQ ID NO: 1 or the complement of SEQ ID NO: 1. In certain aspects, the recombinant nucleic acid further comprises a heterologous regulatory sequence operably linked to the polynucleotide. The invention further encompasses a recombinant nucleic acid molecule comprising or consisting of a polynucleotide of SEQ ID NO: 2 or the complement of SEQ ID NO: 2. In certain aspects, the recombinant nucleic acid further comprises a heterologous promoter operatively linked to the polynucleotide.

The invention also encompasses recombinant polypeptides encoded by the recombinant nucleic acids described herein. In some aspects, the recombinant polypeptides are encoded by the recombinant nucleic acids comprising or consisting of a nucleotide sequence selected from the group consisting of SEQ ID NO: 1 and SEQ ID NO: 2. In some embodiments, the recombinant polypeptide comprises the amino acid sequence of SEQ ID NO: 3 or SEQ ID NO: 4. In additional embodiments, the recombinant polypeptide comprises the amino acid sequence of SEQ ID NO:5 (the mature collagenase I protein, beginning at Ile 119 of SEQ ID NO: 3 in FIGS. 9A and 9B) or SEQ ID NO:6 (the mature collagenase II protein, beginning at Ala 31 of SEQ ID NO: 4 in FIGS. 10A and 10B). In yet another embodiment, the recombinant polypeptide consists of the amino acid sequence of SEQ ID NO: 3, SEQ ID NO: 4, SEQ ID NO: 5 or SEQ ID NO: 6.

In yet another embodiment, the invention is directed to a recombinant nucleic acid that encodes a polypeptide which comprises or consists of the amino acid sequence of SEQ ID NO:3 or SEQ ID NO:4. In a further embodiment, the invention is directed to a recombinant nucleic acid that encodes a polypeptide which comprises or consists of the amino acid sequence of SEQ ID NO: 5 or SEQ ID NO: 6. In a further aspect, the recombinant nucleic acid comprises a nucleotide sequence that encodes a polypeptide of amino acid sequence SEQ ID NO: 3, SEQ ID NO: 4, SEQ ID NO: 5 or SEQ ID NO: 6.

A recombinant nucleic acid is a nucleic acid molecule that contains, in addition to a polynucleotide sequence described herein (for example, the polynucleotide sequence of SEQ ID NO: 1 or SEQ ID NO: 2), a further heterologous coding or non-coding nucleotide sequence. The term "heterologous" means that the polynucleotide originates from a different species or from the same species, however, from another location in the genome than said added nucleotide sequence. Recombinant polypeptides or proteins refer to polypeptides or proteins produced using recombinant techniques, for example, those proteins or polypeptides produced from cells transformed by an exogenous nucleic acid construct encoding the desired polypeptide or protein.

The invention also relates to nucleic acids comprising the polynucleotide sequence of SEQ ID NO: 1 or SEQ ID NO: 2, wherein said nucleic acid is operatively linked to a regulatory sequence. The invention further relates to nucleic acids comprising a polynucleotide that encodes a polypeptide comprising the amino acid sequence of SEQ ID NO: 3, SEQ ID NO: 4, SEQ ID NO: 5 or SEQ ID NO: 6, wherein said nucleic acid is operatively linked to a regulatory sequence. Regulatory sequences include those regulatory sequences which direct constitutive expression of a nucleotide sequence in many types of host cells and/or those which direct expression of the nucleotide sequence only in certain host cells (e.g., tissue-specific regulatory sequences). Non-limiting examples of regulatory sequences are promoters and enhancers. Regulatory sequences also include other expression control elements, for example, those described in Goeddei, Gene Expression Technology: Methods in Enzymology 185, Academic Press, San Diego, CA (1990), the contents of which are expressly incorporated by reference herein. A nucleic acid is "operably linked" to a regulatory sequence when the nucleic acid molecule is linked to the regulatory sequence in a manner which allows expression of the nucleic acid sequence.

A nucleic acid molecule described herein can additionally be fused to a marker sequence, for example, a sequence that encodes a polypeptide to assist in isolation or purification of the polypeptide. Such sequences include, but are not limited to, those which encode a glutathione-S-transferase (GST) fusion protein, those which encode a hemaglutin A (HA) polypeptide marker from influenza, and those which encode hexa-histidine peptide, such as the tag provided in a pQE vector (Qiagen, Inc.). In certain aspects, the invention is directed to a polypeptide comprising an amino acid sequence of SEQ ID NO: 3, SEQ ID NO: 4, SEQ ID NO: 5, or SEQ ID NO: 6, wherein said polypeptide is fused a marker amino acid sequence.

In a further aspect, the invention is directed to a nucleic acid that is a variant of the nucleotide sequence of SEQ ID NO: 1 or SEQ ID NO: 2. A variant nucleic acid is a nucleic acid that includes an nucleotide substitution, addition or deletion relative to nucleotide sequence of SEQ ID NO: 1 or SEQ ID NO: 2. In some aspects, the variant is a nucleic acid that encodes identical or substantially identical amino acid sequences as that of the nucleotide sequences of SEQ ID NO: 1 or SEQ ID NO: 2. As will be understood by the skilled artisan, because of the degeneracy of the genetic code, several different nucleic acid sequences can encode a given protein. For instance, the codons GCA, GCC, GCG and GCU each encode the amino acid alanine. Thus, for example, at every position where a specific amino acid is specified by one codon, the codon can be changed to any of the corresponding codons that encode the same amino acid without altering the amino acid sequence of the encoded polypeptide. One of ordinary skill in the art will understand that each codon in a nucleotide sequence (except AUG, which is the only codon for methionine, and TGG, which is usually the only codon for tryptophan) can be modified to yield a functionally identical molecule.

In certain embodiments, the invention is directed to polypeptide comprising or consisting of amino acid sequence of SEQ ID NO: 3, SEQ ID NO: 4, SEQ ID NO: 5 or SEQ ID NO: 6, wherein one or more amino acids have been deleted or added, wherein the polypeptide possesses the activity of degrading or lysing collagen. In yet an additional embodiment, the polypeptide comprises or consists of the amino acid sequence of SEQ ID NO: 3, SEQ ID NO: 4, SEQ ID NO: 5 or SEQ ID NO: 6, wherein one or more amino acid residues have been replaced with a different amino acid residue, wherein the polypeptide possesses the activity of degrading or lysing collagen and wherein the polypeptide comprises or consists of an amino acid sequence that is different from the amino acid sequences of GenBank Acc. Nos. D87125 (SEQ ID NO: 19) and D29981 (SEQ ID NO: 20). In certain aspects, when an amino acid is replaced, the replacement is a conservative amino acid change. A conservative amino acid change is, for example, substitution of a nonpolar amino acid for another nonpolar amino acid or substitution of a polar amino acid for another polar amino acid or substitution of a positively charged amino acid for another positively charged amino acid, and the like. For example, nonpolar (hydrophobic) amino acids include alanine, leucine, isoleucine, valine, proline, phenylalanine, tryptophan, and methionine; polar neutral amino acids include glycine, serine, threonine, cysteine, tyrosine, asparagine, and glutamine; positively charged (basic) amino acids include arginine, lysine, and histidine; and negatively charged (acidic) amino acids include aspartic acid and glutamic acid.

An isolated nucleic acid and an isolated polypeptide are not in the form or environment in which they exist in nature. For example, an isolated nucleic acid is one that is separated from the nucleotides which normally flanks the nucleic acid molecule in nature. Recombinant nucleic acids and recombinant nucleic acids within a vector are also an example of an isolated nucleic acid. Also, isolated nucleic acid molecules include recombinant nucleic acid molecules in heterologous host cells, as well as partially or substantially purified nucleic acid molecules in solution.

As described in more detail below, the invention also encompasses recombinant host cells, such as bacterial cells, fungal cells, plants cells, insect cells, avian cells, amphibian cells and mammalian cells, comprising the nucleic acid molecules described herein.

An expression cassette is a nucleotide sequence which is capable of affecting expression of a structural gene (i.e., a protein coding sequence, such as a collagenase of the invention) in a host compatible with such sequences. Expression cassettes can include a promoter operably linked with the polypeptide coding sequence; and, optionally, with other sequences, e.g., transcription termination signals. Additional factors necessary or helpful in effecting expression may also be used, e.g., enhancers.

The invention also relates to vectors comprising a nucleic acid of the invention. In one embodiment, the nucleic acid is SEQ ID NO: 1 or SEQ ID NO: 2, or a complement thereof. In another embodiment, the nucleic acid is a nucleic acid that encodes a polypeptide having the amino acid sequence of SEQ ID NO: 3, SEQ ID NO: 4, SEQ ID NO: 5 or SEQ ID NO: 6. A "vector" is a nucleic acid molecule capable of transporting another nucleic acid to which it has been linked. A non-limiting example of a vector is a plasmid which is a circular double stranded DNA into which an additional DNA segment can be ligated. Another example of a vector is a viral vector, wherein an additional DNA segment is ligated into the viral genome. Certain vectors are capable of autonomous replication in a host cell into which they are introduced (e.g., bacterial vectors having a bacterial origin of replication and episomal mammalian vectors). Other vectors (e.g., non-episomal mammalian vectors) are integrated into the genome of a host cell upon introduction into the host cell, and thereby are replicated along with the host genome. Expression vectors are capable of directing the expression of genes to which they are operably linked. Such expression vectors include, for example, plasmids. The invention encompasses other expression vectors, such as viral vectors (e.g., replication defective retroviruses, adenoviruses and adeno-associated viruses) that are capable of directing gene expression. As will be appreciated by the skilled artisan, the design of the expression vector depends on several factors, such as the choice of the host cell to be transformed, the level of expression of protein desired, and the like. Expression vectors include one or more regulatory sequences which are selected based on the host cell to be used for expression. As discussed above, the regulatory sequence is operably linked to the nucleic acid to be expressed, for example, a nucleic acid of the invention. In some embodiments, the regulatory sequence is a regulatory sequence native to the transformed host cell. An expression vector can comprise one or more selectable markers, including, but not limited to, the gene that encodes dihydrofolate reductase and the genes that confer resistance to neomycin, tetracycline, ampicillin, chloramphenicol, kanamycin and streptomycin resistance.

Prokaryotic and eukaryotic host cells can be transfected by the vectors described herein. Host cells which can be transfected with the vectors of the present invention include, but are not limited to, bacterial cells such as *E. coli* (e.g., *E. coli* K12 strains), *Streptomyces, Pseudomonas, Serratia marcescens* and *Salmonella typhimurium*, insect cells (baculovirus), including *Drosophila*, fungal cells, such as yeast cells, plant cells and mammalian cells, such as thymocytes, Chinese hamster ovary cells (CHO), COS cells, and *Lactococcus lactis* cells. In some embodiments, the host cell is a bacterial cell. In yet another embodiment, the host cell is an *E. coli* strain. In yet an additional embodiment, the host cell is *Lactococcus lactis* cell. Methods for the production of recombinant polypeptides in *Lactococcus lactis* bacteria have been described, for example, in U.S. Pat. No. 7,358,067, the contents of which are expressly incorporated by reference herein. In one embodiment, the host cell is *Lactococcus lactis* and the nucleic acid comprises the nucleotide sequence of SEQ ID NO: 1 or SEQ ID NO: 2 operably linked to pH regulatable promoter P170 and derivatives thereof. The P170 promoter and derivatives thereof have been described in detail in WO 94/16086 and WO 98/10079, the contents of which are incorporated by reference herein.

Ligating the nucleic acid molecule into a gene construct, such as an expression vector, and transforming or transfecting into hosts, either eukaryotic (yeast, avian, insect, plant or mammalian) or prokaryotic (bacterial cells), are standard procedures. A vector described herein can be introduced into prokaryotic or eukaryotic cells using conventional transformation or transfection techniques, including, but not limited to, calcium phosphate or calcium chloride co-precipitation, DEAE-dextran-mediated transfection, lipofection, or electroporation. The polypeptides of the present invention can be isolated or purified (e.g., to homogeneity) from recombinant cell culture by a variety of processes.

The invention encompasses methods of producing a functional collagenase I or collagenase II or a combination thereof comprising culturing a host cell transformed or transfected with a vector comprising a nucleic acid of the invention. The method additionally comprises isolating the polypeptide from the medium or the host cell. A functional collagenase is a polypeptide that has a biological activity of a naturally-occurring collagenase, for example, a collagenase that possesses the ability to degrade collagen.

The polypeptide can be isolated by methods including, but not limited to, anion or cation exchange chromatography, ethanol precipitation, affinity chromatography and high performance liquid chromatography (HPLC), or a combination of any of thereof. The particular method used will depend upon the properties of the polypeptide and the selection of the host cell; appropriate methods will be readily apparent to those skilled in the art.

In some embodiments, the invention is a method of producing collagenase I or collagenase II, said method comprising the steps of (i) constructing a recombinant bacterium comprising the nucleotide sequence of SEQ ID NO: 1 or SEQ ID NO:2, or the polynucleotide encoding the polypeptide sequence of SEQ ID NO: 3, 4, 5 or 6 operably linked to an appropriate regulatory sequence; (ii) cultivating said recombinant bacterium under suitable conditions to express the gene, and (iii) harvesting from the recombinant bacterium, the collagenase I or collagenase II. The collagenase I and collagenase II can be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and metal chelation chromatography. In some embodiments, the collagenase I and collagenase II are purified via filtration and column chromatography and the purified collagenase I and II are combined in a ratio of about 1 to 1 using methods described in U.S. Pat. No. 7,811,250, the contents of which are expressly incorporated by reference herein.

Examples of collagen mediated-diseases that can be treated by the compositions (comprising collagenase I, collagenase II, or a combination thereof encoded by the nucleic acids described herein and/or comprising the amino acid sequences of SEQ ID NO: 3 and/or SEQ ID NO: 4) and methods of the invention include, but are not limited to, Dupuytren's disease, Peyronie's disease, frozen shoulder (adhesive capsulitis), keloids, hypertrophic scars, depressed scars, such as those resulting from inflammatory acne; post-surgical adhesions, acne vulgaris, lipomas, and disfiguring conditions such as wrinkling, cellulite formation and neoplastic fibrosis. U.S. Pat. Nos. 6,086,872 and 5,589,171, incorporated herein by reference, disclose the use of collagenase preparations in the treatment of Dupuytren's disease. U.S. Pat. No. 6,022,539, incorporated herein by reference, discloses the use of collagenase preparations in the treatment of Peyronie's disease.

In addition to its use in treating collagen-mediated diseases, a composition comprising a recombinant polypeptide described herein is also useful for the dissociation of tissue into individual cells and cell clusters as is useful in a wide variety of laboratory, diagnostic and therapeutic applications. These applications involve the isolation of many types of cells for various uses, including microvascular endothelial cells for small diameter synthetic vascular graft seeding, hepatocytes for gene therapy, drug toxicology screening and extracorporeal liver assist devices, chondrocytes for cartilage regeneration, and islets of Langerhans for the treatment of insulin-dependent diabetes mellitus. Enzyme treatment works to fragment extracellular matrix proteins and proteins which maintain cell-to-cell contact. Since collagen is the principle protein component of tissue ultrastructure, the enzyme collagenase has been frequently used to accomplish the desired tissue disintegration. In general, the composition of the present invention is useful for any application where the removal of cells or the modification of an extracellular matrix, are desired.

The invention encompasses pharmaceutical compositions comprising a pharmaceutically acceptable carrier and collagenase I and/or collagenase II produced according to a method described herein. In yet another embodiment, the pharmaceutical compositions comprises collagenase I comprising or consisting of the amino acid sequence of SEQ ID NO: 3 or SEQ ID NO: 5. In a further embodiment, the pharmaceutical composition comprises collagenase II comprising or consisting of the amino acid sequence of SEQ ID NO: 4 or SEQ ID NO: 6. In yet another aspect, the pharmaceutical composition comprises a pharmaceutically acceptable carrier and a collagenase I and collagenase II as described herein. In a further aspect, the pharmaceutical composition comprises a pharmaceutically acceptable carrier and the collagenase I and collagenase II at 1:1 mass ratio. The pharmaceutical composition of the present invention comprises an effective amount of a collagenase the present invention formulated together with one or more pharmaceutically acceptable carriers or excipients.

B. Methods of Detecting the Presence of a Hemolytic Toxin

In some embodiments, the invention encompasses methods of detecting the presence of a hemolytic toxin in a bacterial fermentation, wherein the bacterial fermentation produces a collagenase. In certain aspects, the invention provides a method for releasing a collagenase drug product prior to the therapeutic administration of said collagenase drug substance to a patient comprising detecting the presence of a hemolytic toxin in the drug product production strain. The term "drug product production strain," "production strain," "collagenase production strain," and "bacterial production strain" are used interchangeably and refer to a bacterial strain from which a collagenase is obtained. In other aspects, the invention provides a method for releasing a collagenase drug product prior to the therapeutic administration of said collagenase drug product to a patient, comprising detecting the presence of a hemolytic toxin in the drug product.

As used herein, the phrase "releasing a collagenase drug product" means to confirm the absence of a hemolytic toxin in the collagenase drug product. It is understood that the terms "drug substance", "drug product" or "collagenase composition" can be used interchangeably. Also as used herein, the terms "hemolysin" and "hemolytic toxin" are used interchangeably, and refer to a toxin that is responsible for the lysis of a red blood cell.

It has been discovered that the collagenase production strain and drug product can be assayed for the presence or absence of hemolytic activity, ensuring that the collagenase drug substance provides a highly reproducible and optimal enzymatic activity and superior therapeutic effect, while lowering the potential for side effects. In accordance with the invention, methods are provided for assaying the production strain or drug product for the secretion or presence of a functional hemolytic toxin that may be co-present with collagenase in the drug product. The invention encompasses a method of assaying a test sample for the presence of a hemolytic toxin, wherein the test sample comprises a bacterial production strain or a collagenase composition, comprising incubating the test sample with red blood cells, followed by detection of lysis of red blood cells.

Specific methods for detecting lysis of red blood cells are described throughout the literature, including, for example, 1) Ryan K J and Ray C G. Principles of laboratory diagnosis. In *Sherris medical microbiology: an introduction to infectious diseases*. Ryan K J, Ray C G, and Sherris J C (eds.) McGraw-Hill Professional, 2004; 229-260; and 2) Eschbach E et al. Improved erythrocyte lysis assay in microtitre plates for sensitive detection and efficient measurement of hemolytic compounds from ichthyotoxic algae. *Journal of Applied Toxicology* 21, 513-519 (2001), the contents of each of which are expressly incorporated by reference herein.

In one embodiment of the invention, the method comprises incubating samples of a collagenase production strain, a partially purified collagenase isolated from a collagenase production strain, or a collagenase drug product on a blood agar substrate, and observing the blood agar for zones of clearance after the period of incubation, wherein a zone of clearance indicates the lysis of red blood cells. If the bacterial product strain was tested, the lysis of red blood cells indicates the secretion of a functional hemolytic toxin from the bacterial production strain. If a partially purified collagenase or a collagenase drug product was tested, the lysis of red blood cells indicates the presence of a functional hemolytic toxin in the partially purified collagenase or in collagenase drug product. In certain embodiments, the production strain is a strain of *C. histolyticum*. The absence of a zone of clearance indicates the absence of a hemolytic toxin. The observed absence of zones of clearance indicate or confirm the absence of hemolytic toxins in the collagenase production strain, in the partially purified collagenase, or in the collagenase drug product, and allow the drug product to be released for therapeutic administration.

In another embodiment, the method comprises incubating red blood cells with extracts taken from a collagenase production strain, or with a partially purified collagenase isolated from a collagenase production strain, or with a collagenase drug product, followed by photometrically analyzing the incubation mixture for the lysis of red cells as indicated by the appearance of hemoglobin in the incubation mixture. A hemolytic toxin will lyse the red blood cells, releasing hemoglobin into the incubated sample. The photometric detection of hemoglobin can provide a sensitive assay for the presence of hemolytic toxins. In one aspect, red blood cells are incubated with extracts taken from a collagenase production strain, or with a partially purified collagenase isolated from a collagenase production strain, or with a collagenase drug product, and then photometrically analyzing the extracts for the presence of hemoglobin at a wavelength of 540 nm. In another aspect, the photometric analysis is performed at a wavelength of 414 nm. In yet another aspect, incubation and photometric analysis can be performed using microtiter plates. The absence of hemoglobin, and thus the absence of hemolytic toxins, would allow the release of the drug product for therapeutic administration to a patient.

Hemolytic toxins as found in *C. histolyticum* belong to two different families of hemolysins: aerolysin-like hemolysins, and oxygen-labile hemolysins. The aerolysin-like hemolysins are synthesized by the bacterium as inactive preproteins that are secreted into the extracellular environment as inactive protoxins. The inactive protoxins will bind to receptors on a target cell membrane, for example, receptors on a red blood cell where the protoxins are cleaved into their active structures by proteases. Once activated, the toxins oligomerize on the cell surface into a prepore complex, followed by insertion of a beta-barrel into the target cell membrane. The beta-barrel forms a pore in the membrane, allowing the rapid influx of calcium ions into the cell, with toxic consequences to the cell. The alpha toxin of *C. histolyticum* is most likely an aerolysin-like hemolysin, as it has been discovered to share significant homology with *Clostridium septicum* alpha toxin, which is a member of the aerolysin-like family of toxins, and which possess hemolytic activity (see, for example, Example 1 below).

Epsilon toxin of *C. histolyticum*, and tetanolysin of *Clostridium tetani* (*C. tetani*), have been described as an oxygen-labile hemolysins [Hatheway C L. *Clin Microbiol Rev* 3(1): 66-98 (1990)]. Epsilon toxin of *C. histolyticum* has been discovered to share homology with tetanloysin, which is a member of thiol-activated, beta-barrel, pore-forming toxins with affinity for cholesterol. Such proteins are part of a family of Cholesterol Dependent Cytolysins (CDC). These proteins are secreted by the bacterium into the extracellular environment as water-soluble monomeric proteins where they bind to target cell membranes, mediated by cholesterol binding. The toxin then oligomerizes on the membrane surface to form arcs and ring-like structures that are responsible for cytolysis. The epsilon toxin of *C. histolyticum* is known to be an oxygen-labile hemolysin, and is similar serologically to those oxygen-labile hemolysins produced by other strains of *Clostridium*, such as *C. tetani, C. novyi*, and *C. septicum.*

In certain aspects, the invention is directed to a method of detecting the presence of *C. histolyticum* alpha toxin in a bacterial production strain using an assay described herein. In other aspects, the invention is directed to a method of detecting the presence of *C. histolyticum* alpha toxin in a drug product. In a further aspect, the invention is directed to a method of detecting the presence of *C. histolyticum* epsilon toxin in a bacterial production strain. In yet another aspect, the invention is directed to a method of detecting the presence of *C. histolyticum* epsilon toxin in a drug product. In a still further aspect, the invention is directed to a method of detecting the presence of *C. histolyticum* alpha toxin and epsilon toxin in a bacterial production strain. In an additional embodiment, the invention is directed to a method of detecting the presence of *C. histolyticum* alpha toxin and epsilon toxin in a drug product.

The invention also encompasses a method of producing a drug product consisting of collagenase I and collagenase II, wherein the collagenase I and II are obtained from *C. histolyticum*, and wherein the method comprises the steps of fermenting a strain of *C. histolyticum* in which the absence of a functional, secreted hemolytic toxin has been confirmed by incubating the production strain with red blood cells under conditions suitable for lysis of red blood cells by a hemolytic toxin, wherein lysis of red blood cells indicates secretion of a hemolytic toxin and wherein the absence of lysis of the red blood cells indicates the absence of a hemolytic toxin. In another aspect, the invention is directed to a method of producing a drug product consisting of collagenase I and collagenase II, wherein the collagenase I and II are obtained from *C. histolyticum*, and wherein the method comprises the steps of confirming the absence of a functional, secreted hemolytic toxin in the drug product by incubating the drug product with red blood cells under conditions suitable for lysis of red blood cells by a hemolytic toxin, wherein lysis of red blood cells indicates secretion of a hemolytic toxin and wherein the absence of lysis of the red blood cells indicates the absence of a hemolytic toxin.

Further aspects of the invention include methods of purifying a crude collagenase composition comprising purifying the composition by filtration and column chromatography followed by confirming the absence of a hemolytic toxin by incubating a sample of the purified composition with red blood cells under conditions suitable for lysis of red blood cells by a hemolytic toxin, wherein lysis of red blood cells indicates secretion of a hemolytic toxin and wherein the absence of lysis of the red blood cells indicates the absence of a hemolytic toxin.

As discussed above, several diseases and conditions are associated with excess collagen deposition and the erratic accumulation of fibrous tissue rich in collagen and can be treated with collagen drug products. Such diseases and conditions are collectively referred to herein as "collagen-mediated diseases". The invention also encompasses a method of treating a collagen-mediated disease in a patient in need thereof, wherein the composition comprising collagenase is administered to said patient and wherein, prior to said administration, said composition or bacterial production strain is assayed for the presence or absence of hemolytic toxins using a method described herein. Examples of collagen mediated-conditions that may be treated by the compositions and methods described herein include but are not limited to: Dupuytren's disease; Peyronie's disease; frozen shoulder (adhesive capsulitis), keloids; hypertrophic scars; depressed scars such as those resulting from inflammatory acne; post-surgical adhesions; acne vulgaris; lipomas, and disfiguring conditions such as wrinkling, cellulite formation and neoplastic fibrosis. In certain aspects, the assayed composition is administered to a patient to treat Peyronie's or Dupuytren's diseases or adhesive capsulitis.

With respect to the production strain that can be assayed according to a method of the invention, it is known, for example, that collagenase is expressed by bacteria that are members of the genera *Actinobacillus, Actinomadura, Bacillus, Bacteroides, Bifidobacterium, Brucella, Capnocytophaga, Clostridium, Enterococcus, Escherichia, Eubacterium, Flavobacterium, Fusobacterium, Peptococcus, Peptostreptococcus, Porphyromonas, Prevotella, Proteus, Pseudomonas, Serratia, Staphylococcus, Streptomyces, Streptococcus, Treponema*, and *Vibrio*. In one embodiment of the invention, the production strain is selected from the above listed genera. In another embodiment, the production strain is an *E. coli* strain, including forms of *E. coli* that have been transformed with recombinant forms of collagenase I and collagenase II. In a more preferred embodiment, the production strain is a *C. perfringens* strain. In a most preferred embodiment, the production strain is a *C. histolyticum* (*C. his*) strain.

In certain aspects, the production strain produces a collagenase composition comprising a mixture of collagenase I and collagenase II. In a further embodiment, the production strain used to produce a mixture of collagenase I and collagenase I is *C. histolyticum*. In another embodiment, the collagenase drug product comprises a mixture of highly purified *C. histolyticum* collagenase I and collagenase II in a mass ratio of about 1 to 1.

Kits for testing for the presence of hemolysins in a sample are also presented, wherein a hemolysin is a substance that causes lysis of red blood cells. The kits allow the identification of test substances that are hemolytic, or contain, hemolysins. Test substances include, but are not limited to, chemical, biological, and radiation-emitting substances. In one embodiment, the kit comprises materials for testing for the presence of hemolysins in a test sample including, for example, a kit comprising red blood cells and related test materials. In another embodiment, the kit comprises a petri dish comprised of blood agar, a positive control, and a negative control comprised of a bacterial strain wherein the hemolytic genes are mutated or knocked out, and wherein no functional hemolytic proteins are produced. In yet another embodiment, the kit comprises red blood cells, microtiter plates, a positive control, and a negative control comprised of the drug product.

As will be understood, the inventive kits and methods can be used to detect the presence or absence of hemolysins in collagenase compositions, wherein the collagenase is obtained from a bacteria.

The crude collagenase obtained from *C. histolyticum* can be purified by a variety of methods known to those skilled in the art, including dye ligand affinity chromatography, heparin affinity chromatography, ammonium sulfate precipitation, hydroxylapatite chromatography, size exclusion chromatography, ion exchange chromatography, and metal chelation chromatography. Crude and partially purified collagenase is commercially available from many sources including Advance Biofactures Corp., Lynbrook, New York. Methods of purification of crude collagenase obtained from *C. histolyticum* are also described in U.S. Pat. No. 7,811,560, the contents of which are expressly incorporated herein by reference. In certain embodiments, the purification procedure comprises the steps of: a) filtering the crude harvest through a MUSTANG Q anion-exchange capsule filter; b) adding ammonium sulphate; preferably to a final concentration of 1M; c) filtering the crude harvest; preferably through a 0.45 μm filter; d) subjecting the filtrate through a HIC column; preferably a phenyl sepharose 6FF (low sub); e) adding leupeptin to the filtrate; preferably to a final concentration of 0.2 μm to post HIC eluted product; f) removing the ammonium sulfate and maintaining leupeptin for correct binding of collagenase I and collagenase II with buffer exchange by TFF; preferably with buffer exchange by TFF; g) filtering the mixture of step; (f) preferably through a 0.45 μm filter; h) separating collagenase I and collagenase II using Q-Sepharose HP; i) preparing TFF concentration and formulation for collagenase I and collagenase II separately; wherein TFF is a tangential flow filtration using 10 and/or 30 K MWCO (molecular weight cut-off) PES or RC-polyethersulfone or regenerated cellulose filter membranes (TFF provides a means to retain and concentrate select protein and exchange the protein from one buffer solution into another); and j) filtering through a 0.2 μm filtration system.

C. *C. histolyticum* Alpha, Beta, Delta, Epsilon and Gamma Toxins

The amino acid sequences of the alpha, delta and epsilon toxins of *C. histolyticum* Clone 004 are shown in the Figures and are SEQ ID NO: 8, SEQ ID NO: 12 and SEQ ID NO: 16, respectively. The nucleotide sequences of the alpha, delta and epsilon toxins of *C. histolyticum* Clone 004 are also shown in the Figures and are SEQ ID NO: 21, SEQ ID NO: 22, and SEQ ID NO: 23, respectively. Each of the amino acid sequences of SEQ ID NO: 8, SEQ ID NO: 12, SEQ ID NO: 16 have sequence characteristics that render these proteins non-functional and/or unsecreted.

For the gamma toxin (clostripain), there are only three amino acid differences when compared to the model protein (see Examples section) and none of the amino acid residues which are found to differ in the *C. histolyticum* Clone 004 gamma toxin have been identified as essential for activity. Thus, it is predicted that the *C. histolyticum* Clone 004 gamma toxin (having the amino acid sequence of SEQ ID NO: 18) is secreted and functional. The nucleotide sequence of the *C. histolyticum* Clone 004 gamma toxin is SEQ ID NO: 24.

As discussed above, the beta toxins having amino acid sequences of SEQ ID NO: 3 and SEQ ID NO: 4 are fully functional.

As will be understood, one or more mutations (for example, deletion or addition of one or more amino acid residues or nucleic acid residues) can be introduced into the nucleotide and/or amino acid sequences of *C. histolyticum* alpha, beta, epsilon or gamma toxins (SEQ ID NO: 8, SEQ ID NO: 12, SEQ ID NO: 16 and SEQ ID NO: 18, SEQ ID NO: 21, SEQ ID NO: 22, SEQ ID NO: 23 and SEQ ID NO: 24). In certain aspects, one or mutations are introduced in order to improve or impair the activity, function, production and/or secretion of the toxin. In one embodiment, a mutation can be introduced that renders the alpha, beta, and/or epsilon toxins functional and/or secreted. In another embodiment, the sequence of the gamma toxin (SEQ ID NO: 18) can be mutated so as to render the protein non-functional and/or unsecreted.

Also encompassed by the present invention are methods of producing antibodies against *C. histolyticum* or a *C. histolyticum* toxin comprising administering to a subject an effective amount of a composition comprising a protein or peptide, wherein said protein or peptide comprises an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof, or a combination of any of thereof. In addition, the present invention includes methods of stimulating an immune response to a *C. histolyticum* toxin comprising administering to a subject an effective amount of a composition comprising a protein or peptide comprising an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof, or a combination of any of thereof. The invention also includes a vaccine comprising an effective amount of a protein or peptide comprising an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof, or a combination of any of thereof. The protein or peptide comprising an amino acid sequence selected from the group consisting of SEQ ID NO: 8, SEQ ID NO: 10, SEQ ID NO: 12, SEQ ID NO: 14, SEQ ID NO: 16, SEQ ID NO: 18, SEQ ID NO: 3, SEQ ID NO: 4, SEQ ID NO: 5 and SEQ ID NO: 6, or a fragment or variant thereof can be produced by a *C. histolyticum* strain or can be a recombinant protein or peptide.

D. Pharmaceutical Compositions Comprising Collagenase and Methods of Treatment

The invention described herein encompass pharmaceutical compositions comprising the protein sequences and recombinant proteins and also, pharmaceutical compositions comprising a collagenase drug product assayed according to methods described herein. As used herein, the term "pharmaceutically acceptable carrier or excipient" means a non-toxic, inert solid, semi-solid or liquid filler, diluent, encapsulating material or formulation auxiliary of any type. "Treating" or "treatment" includes the administration of the compositions, compounds or agents of aspects of the present invention to prevent or delay the onset of the symptoms, complications, or biochemical indicia of a disease, alleviating or ameliorating the symptoms or arresting or inhibiting further development of the disease, condition, or disorder. A "therapeutically effective amount" or an "effective amount" is an amount which, alone or in combination with one or more other active agents, can control, decrease, inhibit, ameliorate, prevent or otherwise affect one or more symptoms of a disease or condition to be treated. In the context of producing an immune response or in the preparation of a vaccine, an "effective amount" encompasses an amount effective to produce an immune response, including the generation of antibodies against an antigen.

Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, perfuming agents, preservatives and antioxidants can also be present in the composition, according to the judgment of the formulator.

Collagenase compositions can also be prepared by mixing either a specific number of activity units or specific masses of the preferably purified enzymes. Collagenase activity can be measured by the enzyme's ability to hydrolyze either synthetic peptide or collagen substrate. Those skilled in the art will recognize that enzyme assays other than those disclosed herein may also be used to define and prepare functionally equivalent enzyme compositions. Collagenase activity can be described, for example, in SRC units. One SRC unit will solubilize rat tail collagen into ninhydrin reaction material equivalent to 1 nanomole of leucine per minute, at 25° C. and pH 7.4. In certain embodiments of the present invention, collagenase activity is described in ABC units. This potency assay of collagenase is based on the digestion of undenatured collagen (from bovine tendon) at pH 7.2 and 37° C. for 20-24 hours. The number of peptide bonds cleaved is measured by reaction with ninhydrin. Amino groups released by a trypsin digestion control are subtracted. One net ABC unit of collagenase will solubilize ninhydrin reactive material equivalent to 1.09 nanomoles of leucine per minute. 1 SRC unit equals approximately 6.3 ABC units.

In certain aspects, the drug substance for injectable collagenase consists of two microbial collagenases, referred to as Collagenase AUX I and Collagenase ABC I and Collagenase AUX II and Collagenase ABC II. It is understood that the terms “Collagenase I”, “ABC I”, “AUX I”, “collagenase AUX I”, and “collagenase ABC I” mean the same and can be used interchangeably. Similarly, the terms “Collagenase II”, “ABC II”, “AUX II”, “collagenase AUX II”, and “collagenase ABC II” refer to the same enzyme and can also be used interchangeably. These collagenases are secreted by bacterial cells. They are isolated and purified from *C. histolyticum* culture supernatant by chromatographic methods. Both collagenases are special proteases and share the same EC number (E.C. 3.4.24.3).

Collagenase AUX I has a single polypeptide chain consisting of approximately 1000 amino acids with a molecular weight of 115 kDa. Collagenase AUX II has also a single polypeptide chain consisting of about 1000 amino acids with a molecular weight of 110 kDa.

In some embodiments, the drug substance (collagenase concentrate) has an approximately 1 to 1 mass ratio for collagenase AUX I and AUX II. In one embodiment, the collagenase concentrate has an extinction coefficient of 1.528.

The pharmaceutical compositions of this invention can be administered parenterally, topically, or via an implanted reservoir. The term “parenteral,” as used herein, includes subcutaneous, intracutaneous, intravenous, intramuscular, intraarticular, intraarterial, intrasynovial, intrasternal, intrathecal, intralesional and intracranial injection or infusion techniques. In a preferred embodiment, the composition is injected into the affected tissue. In the case of Peyronie’s or Duputyren’s diseases or adhesive capsulitis, the composition is injected into the cord of the hand or the Peyronies’ plaque. The term “local administration” is defined herein to embrace such direct injection into the affected tissue. In certain aspects, the pharmaceutical composition of the invention is an injectable formulation. In certain additional aspects, the pharmaceutical composition is a topical formulation.

Furthermore, depending on the treatment, improved results can, in some circumstances, be obtained by immobilizing the site of injection after administration of the pharmaceutical composition. For example, the site of administration (e.g., the hand), can be immobilized for 4 or more hours.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer’s solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids, such as oleic acid, are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use. The sterile solutions may also be lyophilized for later use.

In some embodiments, the composition comprising collagenase is a lyophilized, injectable composition formulated with sucrose, Tris at a pH level of about 8.0. Generally, a source of calcium is included in the formulation, such as calcium chloride.

Dosage forms for topical or transdermal administration of a pharmaceutical compositions of this invention include ointments, pastes, creams, lotions, gels, powders, solutions, sprays, inhalants or patches. The active component is admixed under sterile conditions with a pharmaceutically acceptable carrier and any needed preservatives or buffers as may be required.

The ointments, pastes, creams and gels may contain, in addition to a polypeptide of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the polypeptides of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of an active agent to the body. Such dosage forms can be made by dissolving or dispensing the active agent in the proper medium. Absorption enhancers can also be used to increase the flux of the polypeptide across the skin. The rate can be controlled by either providing a rate-controlling membrane or by dispersing the polypeptide of the invention in a polymer matrix or gel.

Therapeutic administration of the pharmaceutical may be parenterally, topically, or via an implanted reservoir. The term parenteral as used herein includes subcutaneous, intracutaneous, intravenous, intramuscular, intraarticular, intraarterial, intrasynovial, intrasternal, intrathecal, intralesional and intracranial injection or infusion techniques. The term “local administration” is defined herein to embrace such direct injection. In one embodiment, therapeutic administration of the pharmaceutical composition is by injection.

Therapeutic administration of the pharmaceutical in dosage forms for topical or transdermal administration include ointments, pastes, creams, lotions, gels, powders, solutions, sprays, inhalants or patches. The active component is admixed under sterile conditions with a pharmaceutically acceptable carrier and any needed preservatives or buffers as may be required.

The ointments, pastes, creams and gels may contain, in addition to an active compound of the drug product, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of the drug product, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

The invention will be better understood in connection with the following examples, which are intended as an illustration only and not limiting of the scope of the invention. Various changes and modifications to the disclosed embodiments will be apparent to those skilled in the art and such changes and modifications may be made without departing from the spirit of the invention and the scope of the appended claims.

EXAMPLES

Example 1: *C. histolyticum* Genome Sequencing and Toxin Sequence Analysis

A dearth of scientific studies related to the *C. histolyticum* alpha, delta and epsilon (α, δ, and ε toxins) has resulted in limited knowledge about the protein structure of these toxins. To address this knowledge deficit, a genome sequencing initiative was undertaken to more fully understand the production organism with particular focus on the identification of putative toxin genes. As a consequence of this effort, the complete genome of the Collagenase *Clostridium Histolyticum* production strain (Clone 004) (Auxilium Product Operation, Malvern, PA) has only recently been generated, representing apparently, the first time that the genome sequence of any *C. histolyticum* strain has been reported.

There were three fundamental steps involved in the genome sequence project. First, genomic DNA was extracted from a Clone 004 cultivation and forwarded to Creative Genomics for sequencing (Shirley, NY, USA). The genome sequence of *C. histolyticum* Clone 004 was obtained using industry standard methods. Second, the results obtained from the genome sequence were analyzed using standard bioinformatics methods (BLAST analysis) in order to query the sequence information against genome sequence databases. This second stage resulted in the assignment of protein information for each *C. histolyticum* gene that was identified. The use of two databases ensured a comprehensive evaluation but also served as a second source to verify the protein assignment. The third step in the project was a comparative analysis of the *C. histolyticum* putative toxin sequence with the protein assigned automatically by the BLAST analysis.

i. *C. histolyticum* Genome Sequencing and Identification of Model Proteins

Samples of genomic DNA isolated from an expansion of *C. histolyticum* (CLH) WCB derived from Clone 004 was forwarded to Creative Genomics (Shirley, NY, USA) for genome sequencing. Creative Genomics employed standard methods used for sequence determination of genomic DNA samples submitted by clients. The genome sequence was generated from Roche/454 GS-FLX system with titanium chemistry (fragment sequencing) accompanied with Illumina/Solexa Genome Analyzer. The ANI 3730x1 was employed to accomplish genome finishing by primer walking. The entire genome sequence of 2,842,906 base pairs with a 29.44% GC content was completed and these values were typical of the genome size and GC content obtained for other Clostridial genomes. Each of the 2,887 open reading frames (ORFs) identified was assigned a unique CLH number. Each of the putative 2,887 genes was further investigated using BLAST analysis of the GenBank and SwissProt databases resulted in the tentative assignment of the loci for beta, gamma, alpha, and epsilon toxins. The results of the initial assessment are presented in Table 1. Thus, the assignment of model proteins was completed as a result of an automated analysis via a comprehensive search of two databases. The model protein assignment was not influenced by operator interpretation.

TABLE 1

Assignments of Model Proteins for Putative CLH Toxins based upon Comparison with Two Sequence Databases

| Toxin | CLH Name | Common Name | Model Protein |
|---|---|---|---|
| alpha | CLH -2834 & 2835 | Lethal factor | Aerolysin/Hemolysin (*C. septicum* alpha toxin) |
| beta | CLH_1768 & 1769 | Collagenase I | Collagenase I from colG |
| beta | CLH_2116 | Collagenase II | Collagenase II from colH |
| epsilon | CLH_1920 | Oxygen labile hemolysin | *C. perfringens* perfringolysin *C. tetani* tetanolysin |
| gamma | CLH_1861 | Clostripain | *C. histolyticum* clostripain |

An inspection of the BLAST analysis results of the *C. histolyticum* genome did not reveal an ORF coding for an elastase. However, proteases have been classified by MEROPS (MEROPS.sanger.ac.uk/) based upon the criterion of the most prominent functional group in the active site of those proteases. Using this MEROPS based functional approach, an elastase falls into the M4 peptidase family of which thermolysin (EC 3.4.24.27) is the best studied member of the family and is the classical model for such proteases. Using this knowledge, a re-inspection of the BLAST analysis output suggested that *C. histolyticum* possesses a single ORF that shares significant homology with thermolysin. Therefore, the putative delta toxin gene within *C. histolyticum* has been assigned as a homolog of B. *proteolyticus* thermolysin.

The results of the initial assessment are presented in Table 2 below based upon comparison with two sequence databases.

TABLE 2

Assignments of Model Proteins for Putative CLH Toxins

| Toxin | CLH Name | Common Name | Model Protein |
|---|---|---|---|
| alpha | CLH 2834 & 2835 | Lethal factor | *C. septicum* alpha toxin |
| beta | CLH_1768 & 1769 | Collagenase I | Collagenase I from colG |
| beta | CLH_2116 | Collagenase II | Collagenase II from colH |
| delta | CLH_2576 | Elastase | *B. thermoproteolyticus* thermolysin |
| epsilon | CLH_1920 | Oxygen labile hemolysin | *C. perfringens* perfringolysin |
| gamma | CLH_1861 | Clostripain | *C. histolyticum* clostripain |

ii. Protein Sequence Alignments and Analysis

To identify the signal peptide, the sample and control sequences were analyzed in a program termed SignalP identify potential signal peptide sequences (Nielsen (2004), J. Glasgow et al., eds., Proc. Sixth Int. Conf. on Intelligent Systems for Molecular Biology, 122-130. AAAI Press, 1998). A signal peptide is usually located within the first seventy amino acids (or the N-terminus region) of the protein sequence and acts as a signal sequence for the enzyme to be secreted. The signal peptide is cleaved and the resulting protein sequence is the mature protein. Using SignalP, the user can identify the signal peptide cleavage site location in order to identify the N-terminus of the mature protein. For some sample sequences, in particular alpha toxin and beta toxin (AUX-I), however, only the mature protein was identified, not the entire protein sequence including the signal peptide sequence. Further examination revealed that the sequence fragmentation procedure employed separated the signal peptide sequence from the mature protein. The mature protein and signal sequences were reassembled and processed through the alignment tool.

Once all the protein sequences were collected, pair wise sequence alignments were constructed using MATLAB 7.0.10 (The MathWorks, Inc., 2010). Pair wise sequence alignments are direct comparisons of two sequences to determine the similarities and differences between two sequences. Both control and sample sequences were uploaded into MATLAB and an alignment was made using the Needleman-Wunsch algorithm and BLOSUM50 scoring matrix. The algorithm and scoring matrix assist in assembling the alignment as the algorithm dictates the value of each amino acid match or mismatch based off of the scoring matrix and incorporates gap values when necessary. Gaps can occur for multiple reasons, including, but not limited to, two sequences having varying lengths and to ensure that the appropriate amino acids are matching up to one another. The scoring matrix is based off of substitution rates observed frequently among sequences and serves to rate the similarity or dissimilarity between two sequences (National Center for Biotechnology Information).

The Hatheway (1990) review (Clin Microbiol Rev 3: 66-98) indicated that all five toxins were secreted proteins (exosubstances) and all five toxins had identifiable functionality. This information was used to conduct analysis of the putative CLH toxins. To analyze the protein function of the putative CLH toxins, a number of model proteins were selected based upon literature findings and BLAST results. The controls were downloaded from the National Center for Biotechnology Information (NCBI) in Fasta format.

1. Alpha (α) Toxin

Sparse information related to *C. histolyticum* alpha toxin following the work of Bowen (1952) (Yale *J Biol Med* 25:124-138) exists in the literature. Thus, the interrogation of the genome sequence for putative toxin genes was of interest. A preliminary analysis of the genome suggested that *C. histolyticum* possessed a single ORF that shares significant amino acid homology with *C. septicum* alpha toxin as determined by BLAST analysis of two databases. Therefore, the putative alpha toxin gene within *C. histolyticum* has been assigned as a homolog of *C. septicum* alpha toxin. Studied extensively by the Rodney K. Tweten laboratory, *C. septicum* alpha toxin was classified as a member of the aerolysin-like family of toxins. Notably, *C. septicum* alpha toxin does possess haemolytic activity (Ballard et al. (1992), *Infect Immun* 60: 784-790; Melton-Witt et al. (2006), *Biochem* 45: 14347-14354) and is distinct from oxygen labile hemolysins as described for *C. histolyticum* F toxin (Hatheway (1990), *Clin Microbiol Rev* 3:66-98).

The *C. septicum* alpha toxin is elaborated as an inactive preproprotein which is processed to the extracellular environment as an inactive protoxin. The protoxin then binds to receptors on the cell membrane where they are cleaved into their active structures by proteases (usually furin). A furin consensus site within the toxin is essential for activation by eukaryotic proteases. The activation involves the cleavage of 40-45 amino acids from the C-terminus. Absent the C-terminal cleavage the *C. septicum* alpha toxin is not functional. Full length *C. septicum* alpha toxin is haemolytic (Ballard et al. 1992). The active toxin is approximately 41.3 kDa (Gordon et al. 1997). Once activated, the toxins oligomerize on the cell surface into a prepore complex followed by insertion of a beta-barrel into the membrane.

The model *C. septicum* alpha toxin consists of three distinct domains termed: D1, D2, and D3. The D1 domain is involved with receptor binding and oligomerization, while the D2 domain contributes to amphipathic-hairpin structure. The D3 domain has a D3 propeptide region that includes a short carboxyl-terminal peptide cleaved at the known AT activation site (R398) and functions as an intramolecular chaperone that prevents premature oligomerization of the alpha toxin. Using saturation mutagenesis, single amino acid substitutions within each domain have allowed the determination of those residues essential for biological activity (Melton-Witt et al., 2006). Importantly, the functional assay utilized a cell viability assay to determine $LD_{50}$ doses. Thus, the relative effect of single amino acid substitutions within the entire coding region was assessed using a functional assay.

To further understand the primary structure of the CLH alpha toxin, the protein alignment, performed in MATLAB, of the model protein (*C. septicum* alpha toxin) was made with the CLH alpha toxin. The results are presented in FIG. 1.

The translated CLH putative alpha toxin has an identifiable signal sequence and has a very high probability of being a secreted protein. Thus, the first criterion of an exosubstance is achieved. There is a 75% positive homology between the *C. septicum* alpha toxin protein sequence and the CLH alpha toxin protein sequence. Multiple regions of high homology were identified between the model alpha toxin and the CLH putative alpha toxin. Such regions and essential amino acid residues are highlighted in green shading in FIG. 1.

Notably, the alignment shows multiple differences in essential amino acid residues that, based on the work of Melton-Witt et al. (2006) (Biochem 45:14347-14354), individually render the CLH_2834 & 2835 protein non-functional. Beginning with the N-terminal region of the mature protein, a 17 amino acid sequence region is missing in the CLH alpha toxin sequence which is located about 20 amino acids downstream from the putative signal peptide cleavage site. Within this 17 amino acid stretch, a W74 residue on *C. septicum* alpha toxin has been identified as a critical residue in loop 1 (L1). The lack of 17 amino acids from the D1 domain in the CLH sequence version suggests an altered structure for this domain relative to a wild type and a disruption of the receptor binding functionality.

Within the C-terminal region of the protein, several amino acid residue changes also render the CLH protein non-functional. The amino acid T302 in the *C. septicum* alpha toxin was replaced by Proline in the CLH alpha toxin. Residue E303 in the *C. septicum* alpha toxin is replaced by Threonine in the CLH alpha toxin. The studies of Melton-Witt et al. (2006) (Biochem 45: 14347-14354) indicated that each of these modifications will individually result in 0% lethality. Of note is the comparison of the activation site, or furin cleavage site, between the two sequences. The *C. septicum* alpha toxin exhibits a furin consensus cleavage site beginning with K391 and terminating at R398. This region fits the consensus furin cleavage sequence Arg-X-Lys/Arg-Arg (SEQ ID NO: 31), although the minimal cleavage sequence is Arg-X-X-Arg (SEQ ID NO: 32). The CLH putative alpha toxin has a Glutamine residue instead of Arginine in the analogous R398 position. Thus, the *C. septicum* activation site possesses the amino acid sequence, DKKRRGKRSVDS (SEQ ID NO: 26), with R398 identified as a critical residue. The CLH alpha toxin homologous sequence in the D3 peptide is NTSST-EQNVEV (SEQ ID NO: 27); beginning with N367 of SEQ ID. NO. 8. Therefore, the putative *C. histolyticum* alpha toxin furin cleavage site appears to be non-functional, and this protein, even if expressed, could not be processed by contact with eukaryotic cells furin protease to generate a functional toxin. The findings of the comparative amino acid sequence analysis are summarized in Table 3.

TABLE 3

Summary of Amino Acid Sequence Alignment Comparison for Putative CLH alpha toxin

| Protein | | |
|---|---|---|
| *C. septicum* α toxin Essential Amino Acid Residue | CLH 2834 & 2835 | Effect on Function |
| W 74 | Missing | Receptor binding disrupted |
| T302 | P | Lack of lethality |
| E303 | T | Lack of lethality |
| K391-R398 | T --- Q | Incapable of activation |

The summary of the sequence alignment analysis suggests that the putative CLH alpha toxin possess a significant number of amino acid residues differences that would make the mature protein non-functional. The phenotypic linkage to functionality for alpha toxin is the demonstration of haemolytic activity. Importantly, the Collagenase *Clostridium Histolyticum* production strain does not exhibit haemolytic activity when plated on blood agar. The results of a Blood agar hemolytic assessment are illustrated in FIG. 2.

Panel A of FIG. 2 shows the results obtained when a sample of *C. histolyticum* Clone 004 cell expansion is cultivated on Blood agar. There is no evidence of any beta hemolytic phenotype. In contrast, panel B of FIG. 2 shows the results obtained when a sample of *C. septicum* is cultivated on Blood agar. There is clear evidence of beta hemolysis that extends well beyond the area of sample application as indicated in Panel C. The images presented do not adequately represent the qualitative difference observed when one views the test articles. The appearance of beta hemolysis is easily discernable and the complete lack of any hemolysis in the *C. histolyticum* plate stands in stark contrast to the broad zone of hemolysis noted when the *C. septicum* culture (producer of a toxin) is inspected.

2. Delta (δ) Toxin

Hatheway et al. (1990) (*Clin Microbiol Rev* 3: 66-98) has defined the δ toxin of *C. histolyticum* as an elastase, primarily based on the initial research communication by Takahashi, et al. (1970) (*BBRC* 39: 1058-1064). No further substantial studies on this toxin have apparently been published since then. Four fractions demonstrating elastase activity were isolated from *C. histolyticum* by Takahashi et al. using differential ultrafiltration. The primary focus was on a fraction which passed through membranes of nominal 50 kDa cut-off membranes but was retained by membranes with a nominal 10 kDa cut-off.

Thermolysin is a zinc metalloprotease with a mature enzyme molecular weight of 34.6 kDa. Importantly, thermolysin is a model protein for a class of proteins that contain a presequence employed in secretion (signal peptide) but also a lengthy prosequence of approximately 200 amino acid residues that is two thirds the size of the mature protein. Thermolysin-like enzymes are elaborated as inactive pre-proproteins with the prosequence serving a role as an inhibitor of the mature enzyme and also as a chaperone to ensure proper folding of the enzyme (O'Donohue et al. (1996), *JBC* 271:26477-26481). The prosequence is autocatalytically removed by the mature enzyme portion of the molecule in the extracellular environment. Thus, the maturation pathway for thermolysin-like enzymes includes: a secretion step, the presence of a pro-mature form in the extracellular matrix, the cleavage of the prosequence, and the presence of a mature, active enzyme.

The gene sequence alignment for thermolysin and CLH_2576, the putative *C. histolyticum* delta toxin, is illustrated in FIG. 3. This image displays the full length prepromature amino acid sequence as a single unit that is theoretically transcribed as a single polypeptide. The initial 28 amino acids at the N-terminus of thermolysin are shown juxtaposed to the green shaded prosequence which terminates at Ser232. The unshaded mature amino acid sequence begins with Ile233. Using the SignalP program, the thermolysin and the CLH_2576 polypeptides are predicted to be secreted. The translated putative *C. histolyticum* delta toxin has an identifiable signal sequence and a very high probability of being a secreted protein. There is a 65% positive homology between the thermolysin protein sequence and the CLH delta toxin protein sequence.

To understand the nature of the pro and mature forms of both proteins, the individual regions were analyzed as distinct sequences with regards to functionality. The prosequence alignment is depicted in FIG. 4. There is a 57% positive homology between the two prosequence forms. A recent review of the primary structural analysis of the prosequences of over 100 thermolysin-like proteases was conducted by Demidyuk et al. (2008) (*Protein J*27: 343-354). These investigators noted that considerable variability existed within the prosequences, alternatively termed precursors or propeptides. The prosequences were more tolerant to mutations compared to the corresponding mature enzymes. Nevertheless, regions exhibiting a high degree of conservation and substitutions in key residues were noted which may dramatically alter the function. The residues shaded green in FIG. 3 identify those amino acid residues that are critical for the prosequence to function. No differences are noted between the thermolysin and CLH_2756 sequences. Two residues corresponding to Ile183 and Arg184 in the thermolysin sequence are shaded yellow; however, the substitutions in the CLH_2756 sequence are similar amino acids that likely do not result in any alteration of function.

Importantly, there is a region of non-homology at the C-terminus of the prosequences as illustrated by the yellow shading of the CLH_2756 sequence beginning with Ser185. This region is the site of autocatalysis and suggests that the CLH_2756 sequence is not an acceptable substrate for cleavage by the active site of the mature enzyme. The criticality of the amino acid residues around the cleavage site was investigated by Wetmore et al. (1994) (*Mol Microbiol* 12:747-759), using *Bacillus cereus* thermolysin-like neutral protease as the model enzyme. These investigators determined that the processing was particularly sensitive to the nature of the amino acid three residues upstream from the cleavage site. A consensus sequence was identified for the sequence around the proprotein processing site and alterations in key residues resulted in the non-export or nonprocessing of the protein to a mature, functional enzyme. Key features of the consensus sequence were: the presence of a non-polar residue in position $P_3$ (Gly, Ala, Ile, Leu, or Val), a polar residue or Pro in position $P_1$ (Pro, Ser, His, Glu), and a non-polar residue in position $P_1'$. Additionally, the prothermolysin maturation has been shown to occur between a serine and isoleucine residue (O'Donohue et al.

(1994), *Biochem J.* 300: 599-603). To explore the sequence alignment around the cleavage site, a comparative sequence assessment of the proprotein processing sites for thermolysin and for CLH_2576 can be made by inspection. It is apparent that the CLH_2576 amino acid sequence in the proprotein processing area does not contain the appropriate amino acid arrangement to allow autocatalysis. When one conducts a theoretical exercise to interrogate the CLH_2576 amino sequence to determine if the proprotein processing site is reasonably close to the predicted site based on sequence alignment, it is clear that no adjustment allows the proper amino acid sequence to be identified. Shifting the proprotein processing site 2 residues to the C-terminal side allows for the proper arrangement of amino acids that do not violate the Wetmore et al. rules. However, the Ser-Ile rule of O'Donohue et al. (1994) (*Biochem J.* 300: 599-603) is not present. Thus, it is concluded that the proprotein form of the CLH_2576 polypeptide is not a suitable substrate for autocatalysis. The net effect is that the mature, active enzyme is not present in the cell broth of *C. histolyticum* (Clone 004).

To explore the mature forms of both proteins, the comparative sequence alignment is depicted in FIG. 5. An inspection of the sequence alignment in FIG. 5 suggests that many essential amino acids have been conserved. Notably, the AHELTHAVTD sequence (SEQ ID NO: 28) of the Mature Thermolysin, beginning with Ala140 of SEQ. ID. NO. 13 has been identified as a component of the active site for thermolysin and the high homology displayed by CLH_2576 of SEQ ID. NO. 14 suggests that CLH delta toxin is a member of the thermolysin class of proteases (Kooi et al. (1996), *J Med Microbiol* 45:219-225; Kooi, et al., (1997), *Infect Immun* 65:472-477). Multiple residues shaded in green have been identified as essential for binding or catalysis. One notable difference between the sequences of the two molecules is the GGI region beginning with G135 in thermolysin. This stretch of amino acid residues is highly conserved in thermolysin-like proteases with no defined function assigned (Frigerio et al. (1997), *Protein Eng* 10:223-230). The corresponding CLH_2576 region possesses several significant differences in this sequence. Nevertheless, the overall high degree of homology and the conservation of essential amino acid residues confirm the selection of CLH_2576 as delta toxin with predicted molecular mass of approximately 35 kDa. This assessment aligns with the information presented by Takahashi et al (1970) (*BBRC* 39: 1058-1064).

In summary, the putative CLH delta toxin has been identified using genome sequence analysis. However, the interrogation of this sequence suggests that the cleavage of the proprotein will not occur, rendering this molecule non-functional. Therefore, it is deduced that the 6 toxin, if expressed and secreted in the Clone 004 derivative of *C. histolyticum* ATCC 21000, is not functional.

3. Epsilon (ε) Toxin

MacLennan et al. (1962) (Bact Rev 26:176-274) and Hatheway described the F toxin of *C. histolyticum* as an oxygen-labile haemolysin serologically similar to those produced by other strains of *Clostridium*, such as *C. tetani, C. novyi*, and *C. septicum*. Bowen (1952) (Yale *J Biol Med* 25:124-138) demonstrated that the F toxin was expressed during the exponential phase and degraded during the stationary phase as observed for the a toxin activity, and was similarly degraded by proteinases in vitro.

An inspection of the BLAST analysis results of the *C. histolyticum* genome identified an ORF coding for a hemolysin that was in the same class as perfringolysin and tetanolysin, which are members of thiol-activated, pore forming proteins with affinity for cholesterol. Such proteins are part of a family of Cholesterol Dependent Cytolysins (CDC) and all exhibit distinctive protein sequences and unique structures. Over 25 CDC proteins have been identified with complete protein sequences available. The CDCs are a group of B-barrel pore-forming toxins secreted by various species of Gram positive bacteria all in the 50-60 kDa molecular weight range. The prototypical CDC is perfringolysin which serves as a model protein for all CDCs (Heuck et al. 2007, *JBC* 282: 22629-22637). The typical organization of a CDC includes a cleavable signal sequence to facilitate the exports to the extracellular environment as a water-soluble monomeric protein. Subsequently, the folded monomeric form binds to a target eukaryotic membrane, mediated by cholesterol binding, and then oligomerizes on the membrane surface to form arcs and ring-like structures that are responsible for the cytolysis. The CDCs are also known as thiol-activated cytolysins and were originally described as hemolysins (Billington et al., 2000).

The gene sequence alignment for perfringolysin and CLH_1920, the putative epsilon toxin, is illustrated in FIG. 6. This image displays the full length (pre plus mature) protein sequence as a single unit that is theoretically transcribed as a single polypeptide. The initial 29 amino acids at the N-terminus of perfringolysin are illustrated with a blue star above Lys 29 at the site of signal peptidase cleavage. The SignalP analysis of the CLH_1920 sequence did not identify a recognizable signal peptide cleavage site and was predicted to be a non-secreted protein. There is an 84% positive homology between the perfringolysin protein sequence and the CLH_1920 putative epsilon toxin protein sequence.

The amino acid residues shaded in green denote essential amino acids that are conserved between the two proteins. Importantly, the 11 amino acid sequence ECTGLAWEWWR (SEQ ID NO: 29), beginning with glutamine 458 of SEQ. ID. NO. 15, is an essential region that is termed the undecapeptide sequence. Along with the high degree of homology within the sequence designated as the mature protein region, this undecapeptide sequence serves to identify the CLH_1920 protein as a CDC. Therefore, the CLH_1920 protein, if elaborated as a secreted protein, would be expected to have haemolytic functionality. A single region of non-homology between the two proteins is highlighted in yellow shading. Importantly, the C-terminus of CDCs has been shown to be critical for cholesterol binding (Shimada et al., 1999, *JBC* 274: 18536-18542). The process of hemolysis by CDCs involves two critical steps prior to pore formation: binding and membrane insertion. Shimada, et al. (1999) (*JBC* 274: 18536-18542) demonstrated that modest changes to the C-terminus affected the binding step. An alteration of the 3' terminal amino acids severely reduces cholesterol binding as measured by an ELISA method. The corresponding haemolytic activity on red blood cells was coordinately reduced or eliminated depending upon the severity of the C-terminal amino acid change. An inspection of the C-terminus of the CLH_1920 sequence shows some significant differences compared to the perfringolysin sequence.

As summarized in Table 4, the haemolytic activity of the putative *C. histolyticum* epsilon toxin may be absent due to two features of the theoretical amino acid sequence. First, the molecule is predicted not be secreted; thus, the molecule would not be available for interaction with target cells. Second, the C-terminus of CLH_1920 protein does not possess a homologous region for cholesterol binding, which suggests that an important element associated with hemolysis may be defective.

TABLE 4

Summary of Amino Acid Sequence Alignment Comparison for Putative CLH epsilon toxin

| Protein | | |
|---|---|---|
| Perfringolysin Region | CLH 1920 Characteristic | Effect on Function |
| N-terminal | Missing signal peptidase cleavage sequence | Not secreted |
| C-terminal | Non-consensus | Lack of cholesterol binding/ no activation |

Non-clinical toxicity studies demonstrated no clinical and morphological indications of hemolysin effects in vivo. The data generated by local and IV bolus administration support the absence of haemolytic toxins such as F toxin.

The absence of haemolytic toxins can be verified by the plating of test material on blood agar which is routinely performed at the end of each *C. histolyticum* Clone 004 fermentation, which also confirms the absence of foreign growth. The expression of haemolytic toxins results in the lysis of the blood cells, and thereby resulting in the formation of distinct halos around colonies producing haemolysins. The Collagenase *C. histolyticum* production strain does not produce halos or zones of clearance (see FIG. 2) supporting the absence of F toxin and any other haemolytic entities in the production strain. To verify the hemolytic function of a CDC, commercially available tetanolysin was applied to Blood agar to mimic the routine plating test. The results are illustrated in FIG. 7 which shows the beta hemolytic phenotype observed when 10 μcL of a 10 μg/mL solution of tetanolysin in phosphate buffered saline is applied to the surface of Blood agar, then incubated for 24 hours at 37° C. Thus, if a functional CDC were present in the test material, the beta hemolytic phenotype should be observed.

4. Clostripain or Gamma (γ)-Toxin

The gamma toxin of *C. histolyticum* has been described as clostripain, a cysteine endopeptidase (EC 3.4.22.8). Dargatz, et al. (1993) (*Mol Gen Genet* 240:140-145) cloned and sequenced the *C. histolyticum* gene for clostripain and this information was deposited in GenBank under accession number X63673 (www.ncbi.nlm.nih.gov/nuccore/X63673.1). To understand the primary structure of the CLH_1861 gamma toxin, the protein sequence alignment from MATLAB of the model protein (*C. histolyticum* clostripain) was made with the CLH_1861 gamma toxin theoretical sequence. The results are presented in FIG. 8.

An inspection of FIG. 8 shows a very high degree of homology (99%) between the model clostripain and the sequence obtained from the genome analysis. In fact, there are only 3 amino acid differences, none of which are residues identified as essential for activity. Those critical amino acids identified in literature studies as essential for functionality are shown in green shading. SignalP analysis of both proteins indicated that high secretion score and the signal cleavage site depicted with a blue star (Labrou et al. (2004). *Eur J Biochem* 271:983-992). Thus, one would predict that the CLH_1861 molecule would be secreted and functional. A residual clostripain analysis was conducted as part of routine release.

The clostripain analysis supports the merits of the sequence alignment approach for the *C. histolyticum* toxins in general. One would predict that the presence of a functional toxin gene would necessarily translate into an amino acid sequence that shared a high degree of homology with a known model protein. Further, the conservation of essential amino acid residues would also be a characteristic of a functional toxin gene.

The information obtained from the genome sequence analysis provided evidence that loci for putative alpha, delta, and epsilon toxins were present. Further analysis of the theoretical primary structure of each toxin indicated that non-functional forms of each toxin were predicted as a consequence of key defects in the amino acid sequence of each toxin. Notably, the alpha and epsilon toxins can be assigned as homologues to two classes of pore-forming, hemolytic molecules. As the end of fermentation, samples from every batch are plated onto blood agar as part of a routine purity test. The lack of halos or zones of clearance around the colonies confirm the absence of haemolytic activity in the culture and fermentation. Consequently, the absence of haemolytic halos around the end of fermentation samples demonstrate the absence of both α and ε toxins on a continuing basis.

Table 5 shows the results from the sequence analysis and predicted functionality. The results confirm why Clone 004 has functionally shown the absences of toxicity and the lack haemolytic activity.

TABLE 5

Summary - Predicted Status of *C. histolyticum* Clone 4 Exosubstances

| Toxin | CLH Name | Sequence Result | Predicted Functionality |
|---|---|---|---|
| alpha | CLH_2834 & 2835 | Missing critical aa residues | Non functional; correlated through absence of haemolytic activity on blood agar plates |
| delta | CLH_2576 | Missing consensus proprotein cleavage sequence | Non-functional |
| epsilon | CLH_1920 | Signal peptidase cleavage site defective & non-consensus cholesterol binding sequence | Not secreted, non-functional correlated through absence of haemolytic activity on blood agar plates |
| gamma | CLH_1861 | Clostripain | Functional |

5. *C. histolyticum* Sequence Analysis of Beta Toxins (Collagenase I and Collagenase II)

The sequence analysis of the putative *C. histolyticum* beta toxin loci is presented in FIGS. 9A, 9B, 10A, and 10B. As shown in FIGS. 9A and 9B, the amino acid sequence of the mature collagenase I of clone 004 (CLH_1768 and 1769; SEQ ID NO: 3) differs from the translated colG sequence (SEQ ID NO: 19) by three amino acids. FIGS. 10A and 10B show that the amino acid sequence of the mature collagenase II of clone 004 (CLH_2116; SEQ ID NO: 4) differs from the translated colH sequence (SEQ ID NO: 20) by eight amino acids. Both collagenases are fully functional.

The patent and scientific literature referred to herein establishes the knowledge that is available to those with skill in the art. All United States patents and published or unpublished United States patent applications cited herein are incorporated by references. All published foreign patents and patent applications cited herein are hereby incorporated by reference. All other published references, documents, manuscripts and scientific literature cited herein are hereby incorporated by reference.

REFERENCES

1. Nielsen et al. (2004) In J. Glasgow et al., eds., Proc. Sixth Int. Conf. on Intelligent Systems for Molecular Biology, 122-130. AAAI Press, 1998.
2. Hatheway (1990) Clin Microbiol Rev 3:66-98.
3. Ballard et al. (1992) Infect Immun 60:784-790.
4. Melton-Witt et al. (2006) Biochem 45:14347-14354.
5. Gordon et al. (1997) Infect immun 65:4130-4134.
6. Takahashi et al. (1970) BBRC 39:1058-1064.
7. O'Donohue & Beaumont (1996) JBC 271:26477-26481.
8. Demidyuk et al. (2008) Protein J 27:343-354.
9. Wetmore et al. (1994) Mol Microbiol 12:747-759.
10. O'Donohue et al. (1994) Biochem J. 300:599-603.
11. Kooi & Sokol (1996) J Med Microbiol 45:219-225.
12. Kooi et al. (1997) Infect Immun 65:472-477.
13. Frigerio et al. (1997) Protein Eng 10:223-230.
14. MacLennan (1962) Bact Rev 26:176-274.
15. Bowen (1952) Yale J Biol Med 25:124-138.
16. Heuck et al. (2007) JBC 282:22629-22637.
17. Billington et al. (2000) FEMS Microbiol Lett 182:197-205.
18. Shimada et al. (1999) JBC 274:18536-18542
19. Dargatz et al. (1993) Mol Gen Genet 240:140-145.
20. Labrou & Rigden (2004) Eur J Biochem 271:983-992.

While this invention has been particularly shown and described with references to preferred embodiments thereof, it will be understood by those skilled in the art that various changes in form and details may be made therein without departing from the scope of the invention encompassed by the appended claims.

What is claimed is:

1. A recombinant nucleic acid molecule, comprising:

a polynucleotide encoding the amino acid sequence of SEQ ID NO: 5; and a heterologous regulatory sequence operably linked to the polynucleotide.

2. The recombinant nucleic acid molecule of claim 1, wherein the heterologous regulatory sequence is a promoter.

3. The recombinant nucleic acid molecule of claim 1, wherein the recombinant nucleic acid molecule is fused to a marker sequence.

4. The recombinant nucleic acid molecule of claim 3, wherein the marker sequence encodes a polypeptide selected from a glutathione-S-transferase (GST) fusion protein, a hemagglutinin A (HA) polypeptide from influenza, and a hexa-histidine peptide.

5. A vector comprising the recombinant nucleic acid molecule of claim 1.

6. The vector of claim 5, wherein the vector is a plasmid.

7. A recombinant host cell comprising the vector of claim 5.

8. The recombinant host cell of claim 7, wherein the host cell is selected from a bacterial cell, a fungal cell, an insect cell, a plant cell, and a mammalian cell.

9. The recombinant host cell of claim 8, wherein the host cell is *E. coli*, a *Streptomyces* species, a *Pseudomonas* species, *Serratia marcescens, Salmonella typhimurium*, a yeast cell, a plant cell, a thymocyte, a Chinese hamster ovary cell (CHO), a COS cell, or *Lactococcus lactis.*

10. A method of producing collagenase I, the method comprising culturing the recombinant host cell of claim 7 under conditions suitable for expression of the polynucleotide and recovering the collagenase I.

* * * * *

UNITED STATES PATENT AND TRADEMARK OFFICE

CERTIFICATE OF CORRECTION

PATENT NO. : 11,975,054 B2
APPLICATION NO. : 16/816097
DATED : May 7, 2024
INVENTOR(S) : Wayne K. Herber It is certified that error appears in the above-identified patent and that said Letters Patent is hereby corrected as shown below:

In the Drawings

Please replace FIGS. 1, 3, 4, 5, 6, 8, 9A, 9B, 10A and 10B with FIGS. 1, 3, 4, 5, 6, 8, 9A, 9B, 10A and 10B as shown on attached pages.

Signed and Sealed this
Third Day of June, 2025

Coke Morgan Stewart
*Acting Director of the United States Patent and Trademark Office*

```
                              10        20        30        40        50
C. septicum a. S75954 → 001  MSKKSFAKKVICTSMIAIQCAAVVPHVQAYALTNLEEGGYANHNNASSIK   SEQ ID NO: 7
                             |  ||||  ||:||:|:::||  :|  :|: | |:|    |    : :|||
CLH_2834 & 2835       → 001  MLKKSFFKKAICASLVVLQCLILVSPAQTLASTDLPTKG-----K-TSIE   SEQ ID NO: 8

                        051  IFGYEDNEDLKAKIIQDPEFIRNWANVAHSLGFGWCGGTANPNVGQGFEF
                             :|:|||:   :            ||  ||||||  |||:  ::|:  |||
                        045  LFNYEDH--M----------------AHCLGFGWCFGTASKEIGEDFEF

                        101  KREVGAGGKVSYLLSARYNPNDPYASG-YRAKDRLSMKISNVRFVIDNDS
                             || :    ||: |  ||||||  ||||:||  |||:|||  ||:||:||  ||:||
                        076  KR-AEEEGKTVYYLSARYNQNDPYAKGYYRAHDRLVMKVSNARFFIDHDS

                        150  IKLGTPKVKKLAPLNSASFDLINESKTESKLSKTFNYTTSKTVSKTDNFK
                             : ||    || :|  ||  |::::::|:::|::|  | :|:|  |:::::|:::|||
                        125  LTLGKAKVISLDPLASSTLQVVNKSNSEAKTSLSFGYETTESTSKTDHVK

                        200  FGEKIGVKTSFKVGLEAIADSKVETSFEFNAEQGWSNTNSTTETKQESTT
                             ||||||:|:||:|  :    |:::::|||::|:||||||||:::: | ::: :
                        175  FGEKIGIKSSFNVKVPFIGEKSIETNLEFNSEQGWSNTKTNSVTTKHTIS

                        250  YTATVSPQTKKRLFLDVLGSQIDIPYEGKIYMEYDIELMGFLRYTGNARE
                             :|:|:    ::::|::   |::||::: |:||||:: ||||||||||||||:  ||||||||:
                        225  HTTTTPAKSRKKVRLNVLNKKSDIPYEGKIYMEYDIEFFGFLRYTGNARK

                        300  DHTEDRPTVKLKF-GKNGMSAEEHLKDLYSHKNINGYSEWDWKWVDEKFG
                             ||  |||:|:::||   |||:|||  :|:  |||:|:|||||||||||:|::::|
                        275  DHPTDRPSVSVKFGGKNNMSAVDHIIDLYKHKDINGYSEWDWNWIEENFY

                        349  YLFKNSYDALTSRKLGGIIKGSFTNINGTKIVIREGKEIPLPDKKRRGKR
                             |:|   : ::|: :||||:|  |||:|:|   : ::||:|  :   ::
                        325  DRFSEYSSNVASQYFGGIISGVFTNVGGTDVKVEEGRERPLKNTSST-EQ

                        399  SVDSLDAR-LQNEGIRIENIETQDVPGFRLNSITYND-KKLILINN-I
                             :|:   : :   ::: :|:  :: |   :|:   ::|  :|  ::|     ||
                        374  NVEVQNFKSSKSEFRVGSL-TYTTPNGE-QTIYPEDVSSLNANNNEN
```

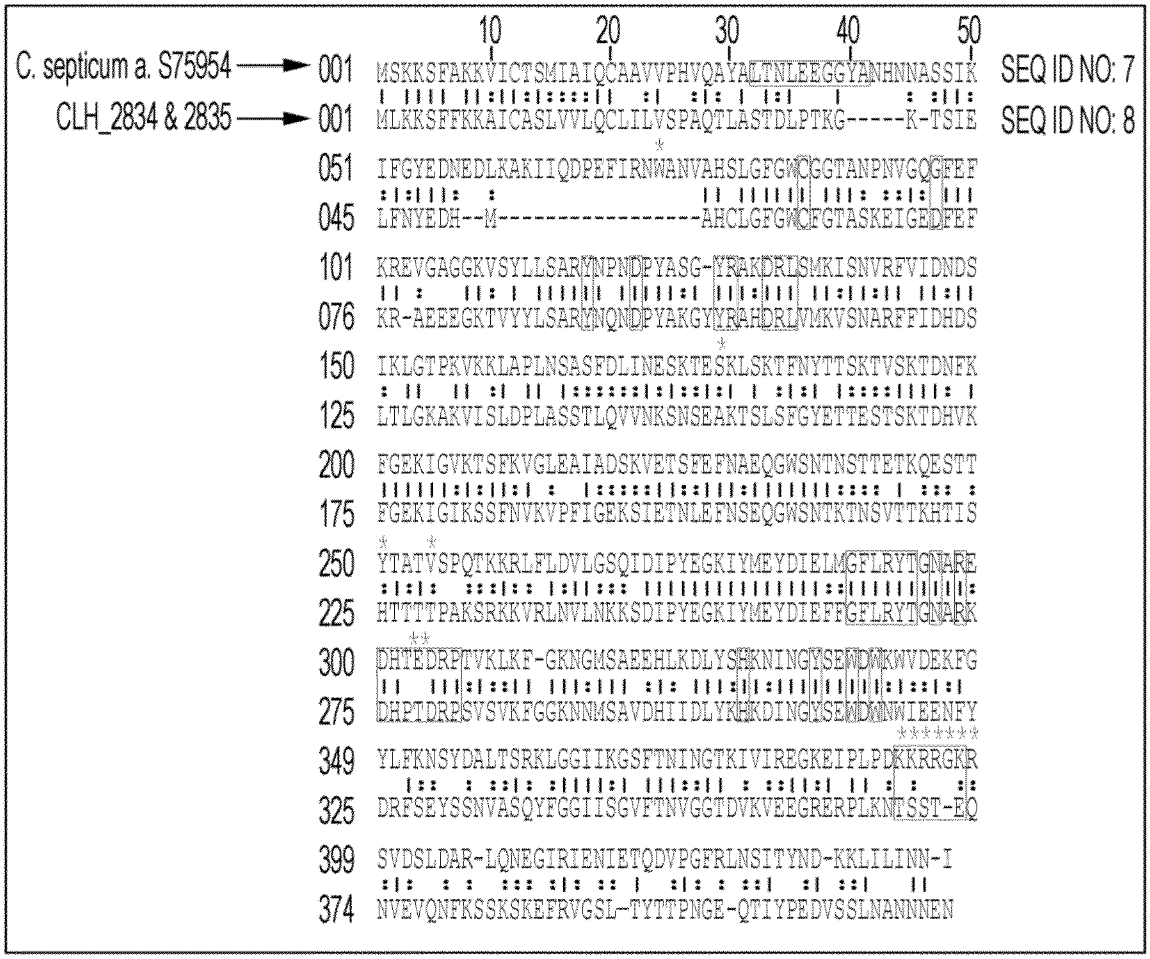

FIG. 1

```
                         10        20        30        40        50
                         |         |         |         |         |
Thermolysin ──▶  001 MKMKMKLASFGLAAGLAAQV-FLPYNALA STEHVTWNQQFQTPQFISGDL   SEQ ID NO: 9
                     ||  |  |: || : :::: ::  :|  :::::    :: ::  :: ||
CLH_2576 ──▶     001 MK-K-KFLSFIIISAISLNISSMTVGA-KQVKEIKPPKDKESISVLKTDL   SEQ ID NO: 10

                 050 LKVNGTSPEELVYQYVEK-NENKFKFHENAKDTLQLKEKKNDNLGFTFMR
                     ||::  : ::       :||   ::  :| : |  |::: ::::|   :|
                 048 EKTKNIKSNNKEGDDVTKVVKSALKEEGNLGD-FKVDNKETDVKGKKHLR

                 099 FQQTYKGIPVFGAVVTSHV-KDGTLTALSGTLIPNLDTKGSLKSGKKLSE
                     |:  ||||:|:  |  |: |||  : :::|   : :      |:|:  ::::
                 097 SQMFIDGIPVYGSQVIIHTNKDGQVYSVNGK-VDKQPKAQSFKNRVRIKD

                 148 KQARDIAEKDLVANVTKEVPEYEQGKDTEFVVYVNGDEASLAYVVNLNFL
                     :|  ||| :|  ::  |: :|  :::: ::   ||||  : |:|:::
                 146 DKAIKIAEDSLGKEIKKN-KNY-HSESKLYLYKVNGDLQPV-YLVKISST

                 198 TPEPGNWLYIIDAVDGKILNKFNQLDAAKPGDVKSITGTSTVGVGRGVLG
                     ||  : |  :::::  :||||:|||  ::|    :   :   |::   :  :|:
                 193 EPEASFWHMFVSAENGKIVDKYNAL-SCQATHAQ-VRGVNSSGEHK-ILN

                 248 DQKNINTTYSTYYYLQDNTR-GNG-IFTYDAKYRT-TLPGSLWADADNQF
                     :  :  |  : |:| |:||  :||    :|||||:  :    :||||:::   : |
                 240 GMFE-N---G-RYFLADSTRPSNGYILTYDANNQEYGFPGSLFSNLTGIF

                 295 FASYDAPAVDAHYYAGVTYDYYKNVHNRLSYDGNNAAIRSSVHYSQGYNN
                     ::  :  :|||||:      :||||||| || |:||::|:| ||||  :::  ||
                 285 DSDRQKAGVDAHHNLTQVYDYYKNVLNRDSFDGKGASIISSVHVGNNLNN

                 345 AFWNGSQMVYGDGDGQTFIPLSGGIDVVAHELTHAVTDYTAGLIYQNESG
                     ||||| |:::|||||| ||  |:     :::|:|||:|||||: ||||  |: :||
                 335 AFWNGRQILFGDGDGVTFSNLAKCLEVTAHEFTHAVTQSTAGLEYRFQSG

                 395 AINEAISDIFGTLVEFYANKNPDWEIGEDVYTPGISGDSLRSMSDPAKYG
                     |:|||:|||:|     :   ::  :|  |||||||||:::::||||||:|   |
                 385 ALNEAFSDILG--IAVHSDPN-DWEIGEDIYTPNVAGDALRSMSNPRLYR

                 445 DPDHYSKR-Y-TGTQDNGGVHINSGIINKAAYLISQGGTHYGVSVVGIGR
                     :||||::        |    ::|:|||| ||||  ||||||:   |   |   |:
                 432 QPDHMKDYLYWDYSMDKGGVHYNSGIPNKAAYLM---G-K---E-V--GK

                 493 DKLGKIFYRALTQYLTPTSNFSQLRAAAVQSATDLYGSTSQE-VASVKQA
                     |:::||:|:|| :|| ::||||  |:|  :   ||:|:||  ||:| :|:|   ::|:
                 472 DSMAKIYYHALVNYLTPQSTFEDARNAVVSSAIDLHGENSKEHKLAIKSW

                 542 FD-AVG---VK
                     |  :||   |:
                 522 ADVGVGEEAVR
```

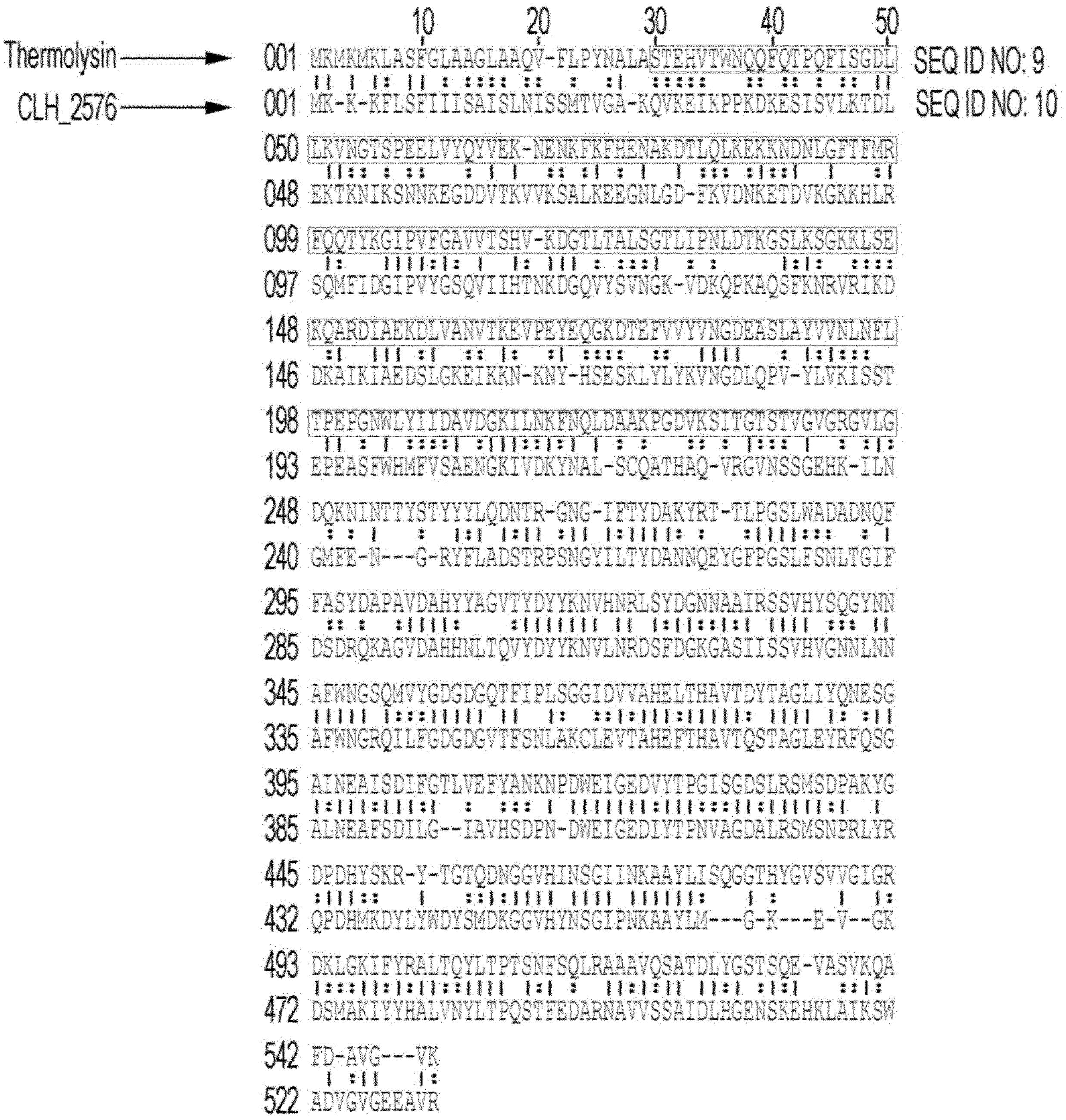

FIG. 3

```
                         10        20        30        40        50
                         |         |         |         |         |
Thermolysin Pro ──▶ 001 STEHVTWNQQFQTPQFISGDLLKVNGTSPEELVYQYVEKNENKFKFHENA SEQ ID NO: 11
                         :    :    : :       :| |:   :: | :  |  | ::| : |
CLH_2576 Pro    ──▶ 001 KPPKDKESISVLKTDLEKTKNIKSNNKEGDD-VTKVV-K--SALKEEGNL SEQ ID NO: 12

                    051 KDTLQLKEKKNDNLGFTFMRFQQTYKGIPVFGAVVTSHV-KDGTLTALSG
                         | ::: :|::|   |    :|| |: ||||||:|: |  |: ||| : :::||
                    047 GD-FKVDNKETDVKGKKHLRSQMFIDGIPVYGSQVIIHTNKDGQVYSVNG

                    100 TLIPNLDTKGSLKSGKKLSEKQARDIAEKDLVANVTKEVPEYEQGKDTEF
                         : :      |:|:  ::::  :|   ||| :|   ::  |:   :| :::: :
                    096 K-VDKQPKAQSFKNRVRIKDDKAIKIAEDSLGKEIKKN-KNY-HSESKLY
                                                       **                ****
                    150 VVYVNGDEASLAYVVNLNFLTPEPGNWLYIIDAVDGKILNKFNQLDAAKP
                         :  ||||    :  ||:|:::    || : |  ::|::| :|||::|:|  |  : :
                    143 LYKVNGDLQPV-YLVKISSTEPEASFWHMFVSAENGKIVDKYNAL-SCQA
                         *****
                    200 GDVKS
                         : :
                    191 THAQ-
```

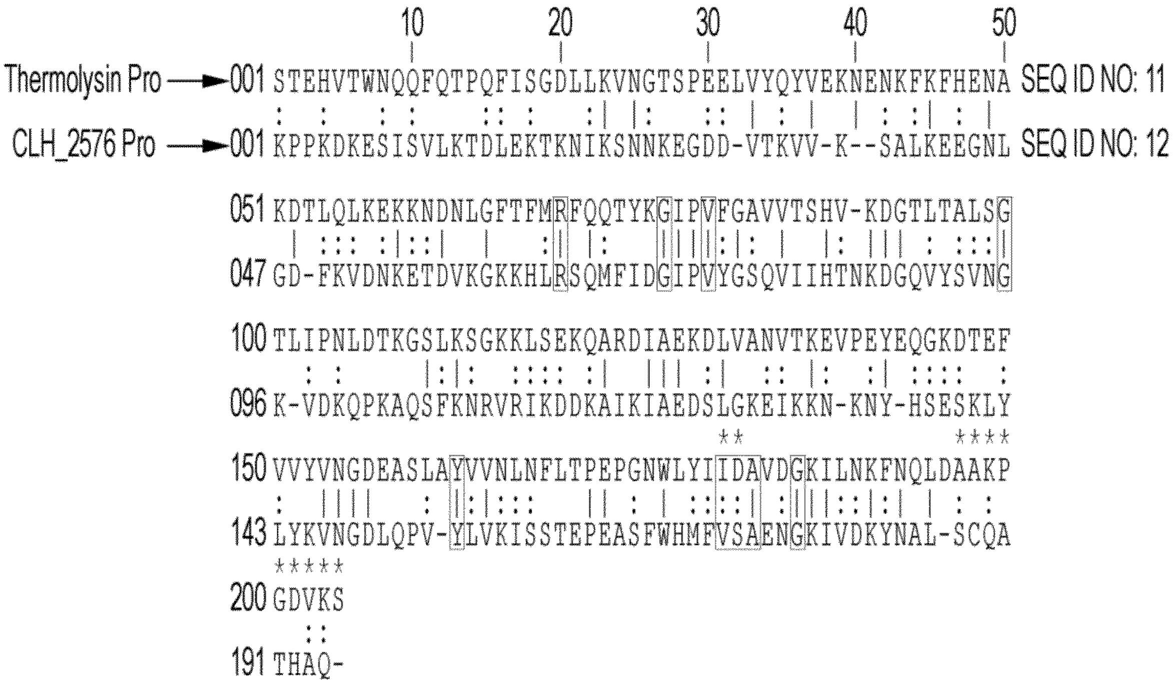

FIG. 4

```
                          10        20        30        40        50
                          |         |         |         |         |
Thermolysin Mature → 001  ITGTSTVGVGRGVLGDQKNINTTYSTYYYLQDNTR-GNG-IFTYDAKYRT SEQ ID NO: 13
                          : |::: |  : :|: : :I   :  |:| |:|| :|| |:||||: :
CLH_2576 Mature   → 001   VRGVNSSGEHK-ILNGMFE-N---G-RYFLADSTRPSNGYILTYDANNQE SEQ ID NO: 14

                     049  -TLPGSLWADADNQFFASYDAPAVDAHYYAGVTYDYYKNVHNRLSYDGNN
                          :||||::: : | :: :  :||||:    :|||||||| || |:||::
                     045  YGFPGSLFSNLTGIFDSDRQKAGVDAHHNLTQVYDYYKNVLNRDSFDGKG

                     098  AAIRSSVHYSQGYNNAFWNGSQMVYGDGDGQTFIPLSGGIDVVAHELTHA
                          |:| |||| ::: ||||||| |:::||||| ||  |:  ::|:|||:|||
                     095  ASIISSVHVGNNLNNAFWNGRQILFGDGDGVTFSNLAKCLEVTAHEFTHA

                     148  VTDYTAGLIYQNESGAINEAISDIFGTLVEFYANKNPDWEIGEDVYTPGI
                          ||: |||| |: :||||:|||:|||:|   :  ::: |  ||||||||:|||::
                     145  VTQSTAGLEYRFQSGALNEAFSDILG--IAVHSDPN-DWEIGEDIYTPNV

                     198  SGDSLRSMSDPAKYGDPDHYSKR-Y-TGTQDNGGVHINSGIINKAAYLIS
                          :||:|||||:|  | :|||::    |    ::|:|||| |||| ||||||:
                     192  AGDALRSMSNPRLYRQPDHMKDYLYWDYSMDKGGVHYNSGIPNKAAYLM-

                     246  QGGTHYGVSVVGIGRDKLGKIFYRALTQYLTPTSNFSQLRAAAVQSATDL
                            | :     |  |:|:::||:|:||::|||| |:| : | |:|:|| ||
                     241  --G-K---E-V--GKDSMAKIYYHALVNYLTPQSTFEDARNAVVSSAIDL

                     296  YGSTSQE-VASVKQAFD-AVG---VK
                          :| :|:|   ::|:  | :||   |:
                     282  HGENSKEHKLAIKSWADVGVGEEAVR
```

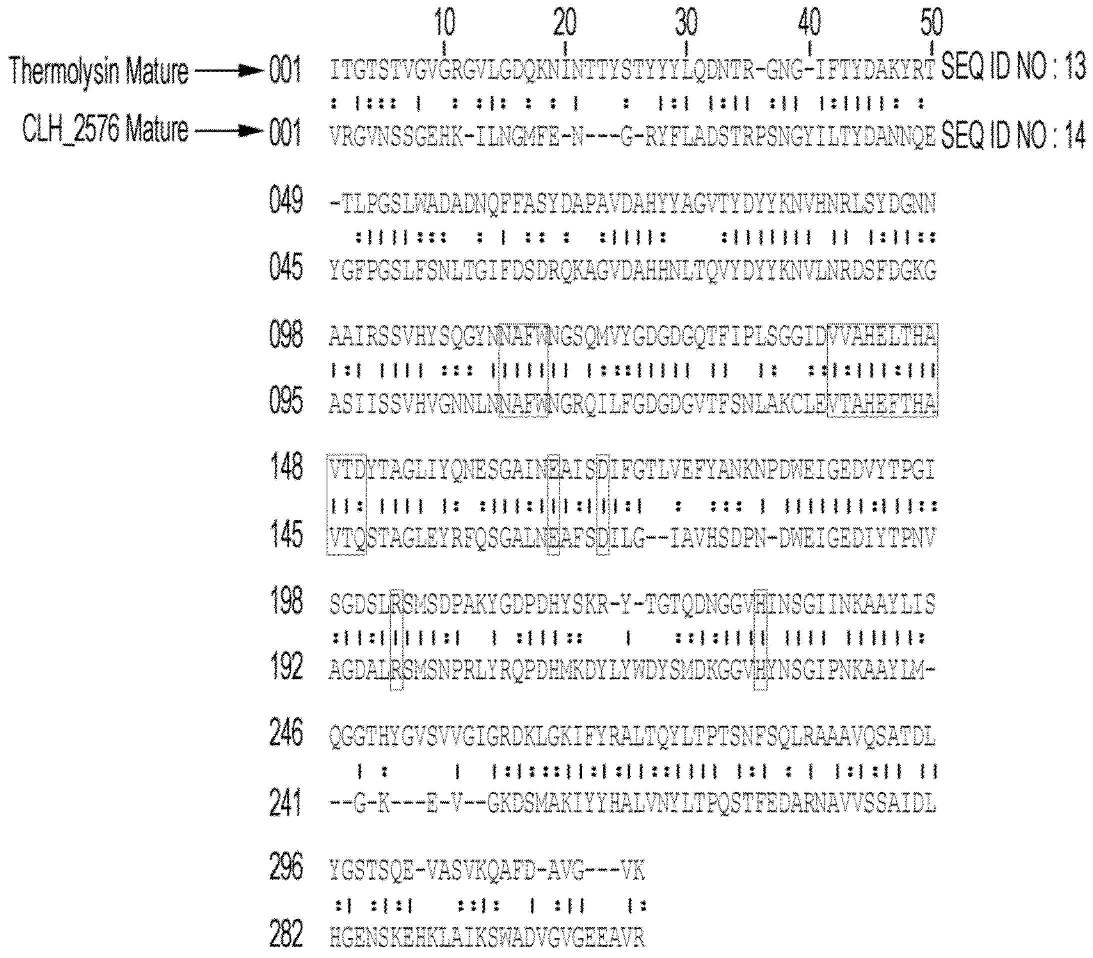

FIG. 5

```
Perfringolysin ──▶ 001  M-I--R-FKK-TK--LIASI-AMALC--L---FS-QPVISFSKDI-TD--     SEQ ID NO: 15
                        | |  : ::: ::  ||: | :::   |   |: : |:  : :  ||
CLH_1920     ──▶ 001  MKITKKGLRSLSRLMLITMITGLTYNYHLGSSFNGNRVVLANPNTKTDNL        SEQ ID NO: 16

              034  -KNQS--IDSGISSLSYNRNEVLASNGDKIESFVPKEGKKTGNKFIVVER
                    ||:|   ||   |  :||||:    ::|:  ||:|:|:|||  |  | :::::||  |::|
              051  IKNNSDEIDEKIYGLSYDPYKILSYNGEKVENFVPAECSENSGKFTVIKR

              081  QKRSLTTSPVDISIIDSVNDRTYPGALQLADKAFVENRPTILMVKRKPIN
                    :|::::  |  :|||||:||:|||||||:||:|||: ::|:|::  :|||||:
              101  EKKNISDSTTDISIMDSINDRTYPGAIQLANRDLIENKPNLISCERKPIT

              131  INIDLPGLKGENSIK-VDDPTYGKVSGAIDELVSKWNEKYSSTHTLPART
                    |::  |||:  ||::  |   |:::::|||:|:  ||:   ||  ||||  :|:|:|
              151  ISVDLPGM-GEDGKKVVNSPTYSSVNSAINYLLDTWNSKYSSKYTIPTRM

              180  QYSESMVYSKSQISSALNVNAKVLENSLGVDFNAVANNEKKVMILAYKQI
                    :||::||||||||:|:  ::  | |:|  :||::|:|:  ::||||:||||||:|||
              200  NYSDTMVYSKSQLSTMFGCNFKTLSKSLNIDFDSIFKGEKKAMILSYKQI

              230  FYTVSADLPKNPSDLFDDSVTFNDLKQKGVSNEAPPLMVSNVAYGRTIYV
                    |||||:|  |:  |||||  |||   ::|   |||:|   ||  |:|||||||||||:||
              250  FYTVSVDGPNRPSDLFGYSVTSKSLALKGVNNDNPPAYVSNVAYGRTVYV

              280  KLETTSSSKDVQAAFKALIKNTDIKNSQQYKDIYENSSFTAVVLGGDAQE
                    ||||||:|:  |:|||||||:|  ||:::  :||||  ::||||||:|||||  ||:
              300  KLETTSKSSKVKAAFKALVENQDISSNAEYKDIINQSSETATVLGGGAQK

              330  HNKVVTKDFDEIRKVIKDNATFSTKNPAYPISYTSVFLKDNSVAAVHNKT
                    ||||||||||| ||::||:::|::::|  :||||||||||:|||||||:|:|
              350  HNKVVTKDFDVIRNIIKNNSVYSPQNPGYPISYTSTFLKDNKIATVNNRT

              380  DYIETTSTEYSKGKINLDHSGAYVAQFEVAWDEVSYDKEGNEVLTHKTWD
                    :||||||:|||::|||  ||||||||:|||||||:|||||||||::  ||:|:
              400  EYIETTATEYDSGKIMLDHSGVYVAQFEVTWDEVSYDKQGNEIIEHKSWS

              430  GNYQDKTAHYSTVIPLEANARNIRIKARECTGLAWEWWRDVISEYDVPLT
                    ||  :|:||||::|  :  |::|||  |||  |||||||||||||  |::   ::||
              450  GNNSDRTAHFNTELYLKGNARNISIKAKECTGLAWEWWRTVVDAKNLPLV

              480  NNINVSIWGTTLYPGSSITYN
                    ::  ::|||||||||  |:   :
              500  KERKLSIWGTTLYPRYSMEEK
```

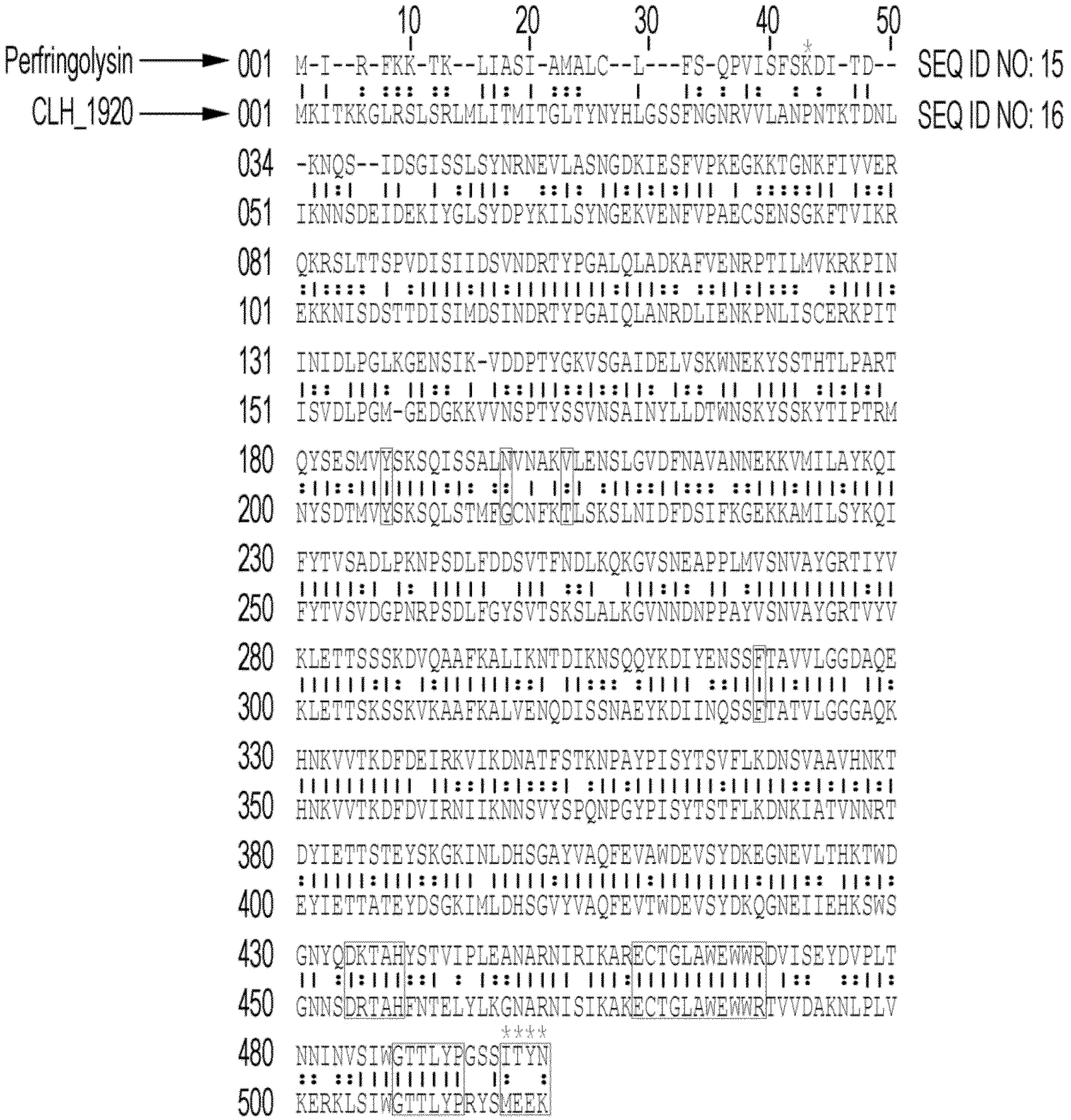

FIG. 6

Clostripain Locus X63673 — SEQ ID NO: 17
CLH_1861 — (SEQ ID NO: 18)

```
         10         20         30         40      *  50
001 MLRRKVSTLLMTALITTSFLNSKPVYANPVTKSKDNNLKEVQQVTSKSNK
    |||||||||||||||||||||||||||||||||||||||||| |||||
001 MLRRKVSTLLMTALITTSFLNSKPVYANPVTKSKDNNLKEVQQVISKSNK

051 NKNQKVTIMYYCDADNNLEGSLLNDIEEMKTGYKDSPNLNLIALVDRSPR
    |||||||||||||||||||||||||||||||||||||||||||||||||
051 NKNQKVTIMYYCDADNNLEGSLLNDIEEMKTGYKDSPNLNLIALVDRSPR

                          *
101 YSSDEKVLGEDFSDTRLYKIEHNKANRLDGKNEFPEISTTSKYEANMGDP
    |||||||||||||||||||| ||||||||||||||||||||||||||||
101 YSSDEKVLGEDFSDTRLYKIELNKANRLDGKNEFPEISTTSKYEANMGDP

151 EVLKKFIDYCKSNYEADKYVLIMANHGGGAREKSNPRLNRAICWDDSNLD
    |||||||||||||||||||||||||||||||||||||||||||||||||
151 EVLKKFIDYCKSNYEADKYVLIMANHGGGAREKSNPRLNRAICWDDSNLD

201 KNGEADCLYMGEISDHLTEKQSVDLLAFDACLMGTAEVAYQYRPGNGGFS
    |||||||||||||||||||||||||||||||||||||||||||||||||
201 KNGEADCLYMGEISDHLTEKQSVDLLAFDACLMGTAEVAYQYRPGNGGFS

251 ADTLVASSPVVWGPGFKYDKIFDRIKAGGGTNNEDDLTLGGKEQNFDPAT
    |||||||||||||||||||||||||||||||||||||||||||||||||
251 ADTLVASSPVVWGPGFKYDKIFDRIKAGGGTNNEDDLTLGGKEQNFDPAT

301 ITNEQLGALFVEEQRDSTHANGRYDQHLSFYDLKKAESVKRAIDNLAVNL
    |||||||||||||||||||||||||||||||||||||||||||||||||
301 ITNEQLGALFVEEQRDSTHANGRYDQHLSFYDLKKAESVKRAIDNLAVNL

351 SNENKKSEIEKLRGSGIHTDLMHYFDEYSEGEWVEYPYFDVYDLCEKINK
    |||||||||||||||||||||||||||||||||||||||||||||||||
351 SNENKKSEIEKLRGSGIHTDLMHYFDEYSEGEWVEYPYFDVYDLCEKINK

                                              *
401 SENFSSKTKDLASNAMNKLNEMIVYSFGDPSNNFKEGKNGLSIFLPNGDK
    |||||||||||||||||||||||||||||||||||||||||| ||||||
401 SENFSSKTKDLASNAMNKLNEMIVYSFGDPSNNFKEGKNGLSTFLPNGDK

451 KYSTYYTSTKIPHWTMQSWYNSIDTVKYGLNPYGKLSWCKDGQDPEINKV
    |||||||||||||||||||||||||||||||||||||||||||||||||
451 KYSTYYTSTKIPHWTMQSWYNSIDTVKYGLNPYGKLSWCKDGQDPEINKV

501 GNWFELLDSWFDKTNDVTGGVNHYQW
    ||||||||||||||||||||||||||
501 GNWFELLDSWFDKTNDVTGGVNHYQW
```

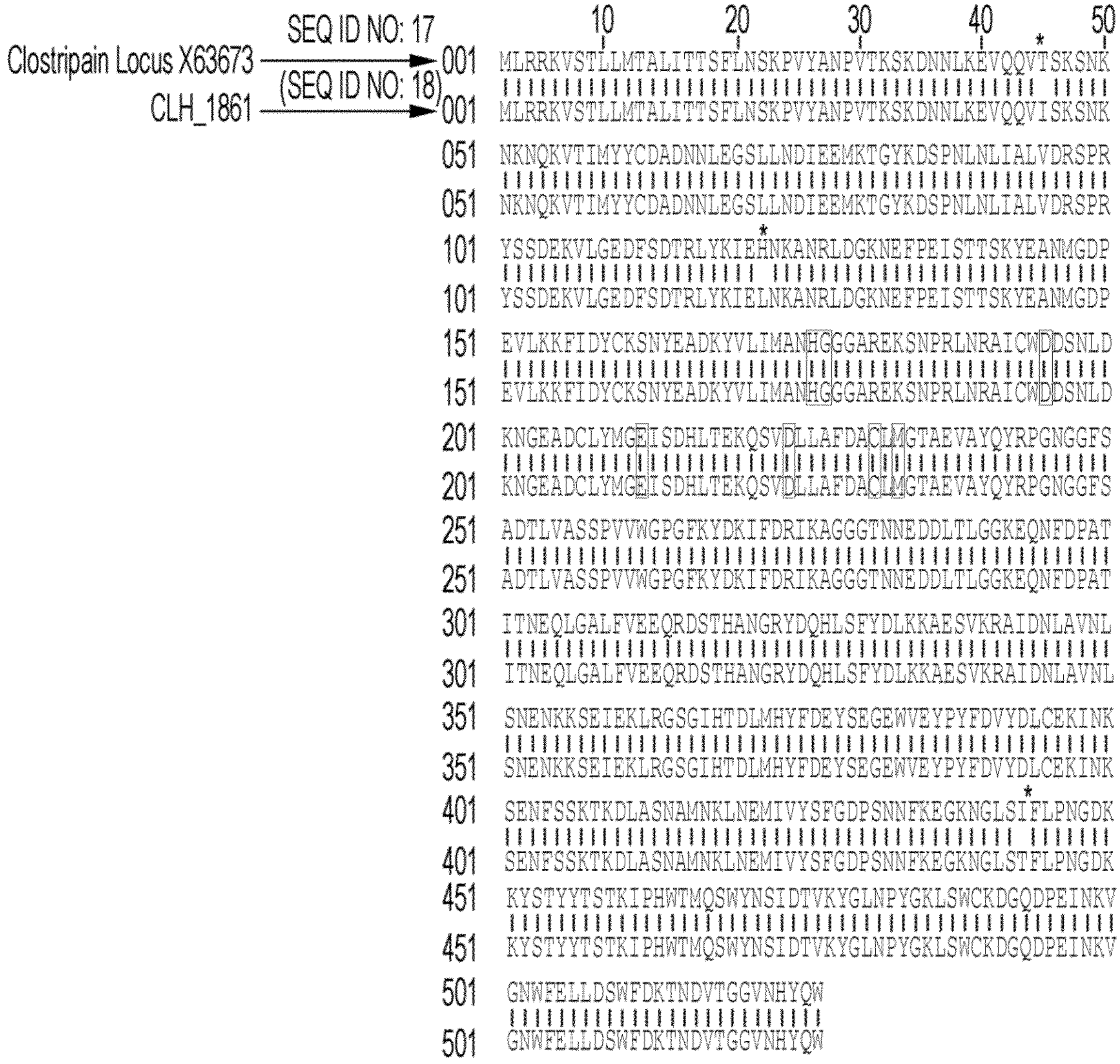

FIG. 8

```
                  Identities = 1113/1118 (100%), Positives = 1118/1118 (100%)
SEQ ID NO: 3  0001 MKKNILKILMDSYSKESKIQTVRRVTSVSLLAAYLTMNTSSLVLAKPIENTNDTSIKNVEKLRN
                   |||||||||||||||||||||||||||||||||:||||||||||||||||||||||||| |||||
SEQ ID NO: 19 0001 MKKNILKILMDSYSKESKIQTVRRVTSVSLLAVYLTMNTSSLVLAKPIENTNDTSIKNVEKLRN
                                                          N-terminus of mature protein Ile 111
              0065 APNEENSKKVEDSKNDKVEHVENIEEAKVEQVAPEVKSKSTLRSASIANTNSEKYDFEYLNGLS
                   |||||||||||||||||||||:||||||||||||||||||||||||||||||||||||||||||
              0065 APNEENSKKVEDSKNDKVEHVKNIEEAKVEQVAPEVKSKSTLRSASIANTNSEKYDFEYLNGLS

              0129 YTELTNLIKNIKWNQINGLFNYSTGSQKFFGDKNRVQAIINALQESGRTYTANDMKGIETFTEV
                   ||||||||||||||||||||||||||||||||||||||||||||||||||||||||||||||||
              0129 YTELTNLIKNIKWNQINGLFNYSTGSQKFFGDKNRVQAIINALQESGRTYTANDMKGIETFTEV

              0193 LRAGFYLGYYNDGLSYLNDRNFQDKCIPAMIAIQKNPNFKLGTAVQDEVITSLGKLIGNASANA
                   ||||||||||||||||||||||||||||||||||||||||||||||||||||||||||||||||
              0193 LRAGFYLGYYNDGLSYLNDRNFQDKCIPAMIAIQKNPNFKLGTAVQDEVITSLGKLIGNASANA

              0257 EVVNNCVPVLKQFRENLNQYAPDYVKGTAVNELIKGIEFDFSGAAYEKDVKTMPWYGKIDPFIN
                   ||||||||||||||||||||||||||||||||||||||||||||||||||||||||||||||||
              0257 EVVNNCVPVLKQFRENLNQYAPDYVKGTAVNELIKGIEFDFSGAAYEKDVKTMPWYGKIDPFIN

              0321 ELKALGLYGNITSATEWASDVGIYYLSKFGLYSTNRNDIVQSLEKAVDMYKYGKIAFVAMERIT
                   ||||||||||||||||||||||||||||||||||||||||||||||||||||||||||||||||
              0321 ELKALGLYGNITSATEWASDVGIYYLSKFGLYSTNRNDIVQSLEKAVDMYKYGKIAFVAMERIT

              0385 WDYDGIGSNGKKVDHDKFLDDAEKHYLPKTYTFDNGTFIIRAGEKVSEEKIKRLYWASREVKSQ
                   |||||||||||||||||||||||||||||||||||||||||||:||||||||||||||||||||
              0385 WDYDGIGSNGKKVDHDKFLDDAEKHYLPKTYTFDNGTFIIRAGDKVSEEKIKRLYWASREVKSQ

              0449 FHRVVGNDKALEVGNADDVLTMKIFNSPEEYKFNTNINGVSTDNGGLYIEPRGTFYTYERTPQQ
                   ||||||||||||||||||||||||||||||||||||||||||||||||||||||||||||||||
              0449 FHRVVGNDKALEVGNADDVLTMKIFNSPEEYKFNTNINGVSTDNGGLYIEPRGTFYTYERTPQQ

              0513 SIFSLEELFRHEYTHYLQARYLVDGLWGQGPFYEKNRLTWFDEGTAEFFAGSTRTSGVLPRKSI
                   ||||||||||||||||||||||||||||||||||||||||||||||||||||||||||||||||
              0513 SIFSLEELFRHEYTHYLQARYLVDGLWGQGPFYEKNRLTWFDEGTAEFFAGSTRTSGVLPRKSI
```

FIG. 9A

```
0577 LGYLAKDKVDHRYSLKKTLNSGYDDSDWMFYNYGFAVAHYLYEKDMPTFIKMNKAILNTDVKSY
     ||||||||||||||||||||||||||||||||||||||||||||||||||||||||||||||||
0577 LGYLAKDKVDHRYSLKKTLNSGYDDSDWMFYNYGFAVAHYLYEKDMPTFIKMNKAILNTDVKSY

0641 DEIIKKLSDDANKNTEYQNHIQELADKYQGAGIPLVSDDYLKDHGYKKASEVYSEISKAASLTN
     ||||||||||||||||||||||||||||||||||||||||||||||||||||||||||||||||
0641 DEIIKKLSDDANKNTEYQNHIQELADKYQGAGIPLVSDDYLKDHGYKKASEVYSEISKAASLTN

0705 TSVTAEKSQYFNTFTLRGTYTGETSKGEFKDWDEMSKKLDGTLESLAKNSWSGYKTLTAYFTNY
     ||||||||||||||||||||||||||||||||||||||||||||||||||||||||||||||||
0705 TSVTAEKSQYFNTFTLRGTYTGETSKGEFKDWDEMSKKLDGTLESLAKNSWSGYKTLTAYFTNY

0769 RVTSDNKVQYDVVFHGVLTDNADISNNKAPIAKVTGPSTGAVGRNIEFSGKDSKDEDGKIVSYD
     ||||||||||||||||||||||||||||||||||||||||||||||||||||||||||||||||
0769 RVTSDNKVQYDVVFHGVLTDNADISNNKAPIAKVTGPSTGAVGRNIEFSGKDSKDEDGKIVSYD

0833 WDFGDGATSRGKNSVHAYKKTGTYNVTLKVTDDKGATATESFTIEIKNEDTTTPITKEMEPNDD
     ||||||||||||||||||||:|||||||||||||||||||||||||||||||||||||||||||
0833 WDFGDGATSRGKNSVHAYKKAGTYNVTLKVTDDKGATATESFTIEIKNEDTTTPITKEMEPNDD

0897 IKEANGPIVEGVTVKGDLNGSDDADTFYFDVKEDGDVTIELPYSGSSNFTWLVYKEGDDQNHIA
     ||||||||||||||||||||||||||||||||||||||||||||||||||||||||||||||||
0897 IKEANGPIVEGVTVKGDLNGSDDADTFYFDVKEDGDVTIELPYSGSSNFTWLVYKEGDDQNHIA

0961 SGIDKNNSKVGTFKATKGRHYVFIYKHDSASNISYSLNIKGLGNEKLKEKENNDSSDKATVIPN
     ||||||||||||||:|||||||||||||||||||||||||||||||||||||||||||||||||
0961 SGIDKNNSKVGTFKSTKGRHYVFIYKHDSASNISYSLNIKGLGNEKLKEKENNDSSDKATVIPN

1025 FNTTMQGSLLGDDSRDYYSFEVKEEGEVNIELDKKDEFGVTWTLHPESNINDRITYGQVDGNKV
     ||||||||||||||||||||||||||||||||||||||||||||||||||||||||||||||||
1025 FNTTMQGSLLGDDSRDYYSFEVKEEGEVNIELDKKDEFGVTWTLHPESNINDRITYGQVDGNKV

1089 SNKVKLRPGKYYLLVYKYSGSGNYELRVNK
     ||||||||||||||||||||||||||||||
1089 SNKVKLRPGKYYLLVYKYSGSGNYELRVNK
```

FIG. 9B

Identities = 1013/1021 (99%), Positives = 1021/1021 (100%)

(SEQ ID NO: 20) colH → 0001 MKRKCLSKRLMLAITMATIFTVNSTLPIYAAVDKNNATAAVQNESKRYTVSYLKTLNYYDLVDL
SEQ ID NO: 4 → 0001 MKRKCLSKRLMLAITMATIFTVNSTLPIYAAVDKNNATAAVQNESKRYTVSYLKTLNYYDLVDL Alignment Assessment 0065 LVKTEIENLPDLFQYSSDAKEFYGNKTRMSFIMDEIGRRAPQYTEIDHKGIPTLVEVVRAGFYL
0065 LVKTEIENLPDLFQYSSDAKEFYGNKTRMSFIMDEIGRRAPQYTEIDHKGIPTLVEVVRAGFYL Collaijenose II
Green shading, N-terminal of
mature protein
A31 in AVDKinch 0129 GFHNKELNEINKRSFKERVIPSILAIQKNPNFKLGTEVQDKIVSATGLLAGNETAPPEVVNNFT
0129 GFHNKELNEINKRSFKERVIPSILAIQKNPNFKLGTEVQDKIVSATGLLAGNETAPPEVVNNFT 0193 PILQDCIKNTDRYALDDLKSKALFNVLAAPTYDITEYLRATKEKPENTPWYGKIDGFINELKKL
0193 PILQDCIKNMDRYALDDLKSKALFNVLAAPTYDITEYLRATKEKPENTPWYGKIDGFINELKKL Green shading - single on
B-amino acid differences in
ending molecule 0257 ALYGKINDNNSWIIDNGIYHIAPLGKLHSNNKIGIETLTEVMKWYPYLSMQHLQSADQIKRHYD
0257 ALYGKINDNNSWIIDNGIYHIAPLGKLHSNNKIGIETLTEVMKLYPYLSMQHLQSADQIERHYD 0321 SKDAEGNKIPLDKFKKEGKEKYCPKTYTFDDGKVIIKAGARVEEEKVKRLYWASKEVNSQFFRV
0321 SKDAEGNKIPLDKFKKEGKEKYCPKTYTFDDGKVIIKAGARVEEEKVKRLYWASKEVNSQFFRV 0385 YGIDKPLEEGNPDDILTMVIYNSPEEYKLNSVLYGYDTNNGGMYIEPEGTFFTYEREAQESTYT
0385 YGIDKPLEEGNPDDILTMVIYNSPEEYKLNSVLYGYDTNNGGMYIEPDGTFFTYERKAEESTYT 0449 LEELFRHEYTHYLQGRYAVPGQWGRTKLYDNDRLTWYEEGGAELFAGSTRTSGILPRKSIVSNI
0449 LEELFRHEYTHYLQGRYAVPGQWGRTKLYDNDRLTWYEEGGAELFAGSTRTSGILPRKSIVSNI 0513 HNTTRNNRYKLSDTVHSKYGASFEFYNYACMFMDYMYNKDMGILNKLNDLAKNNDVDGYDNYIR
0513 HNTTRNNRYKLSDTVHSKYGASFEFYNYACMFMDYMYNKDMGILNKLNDLAKNNDVDGYDNYIR

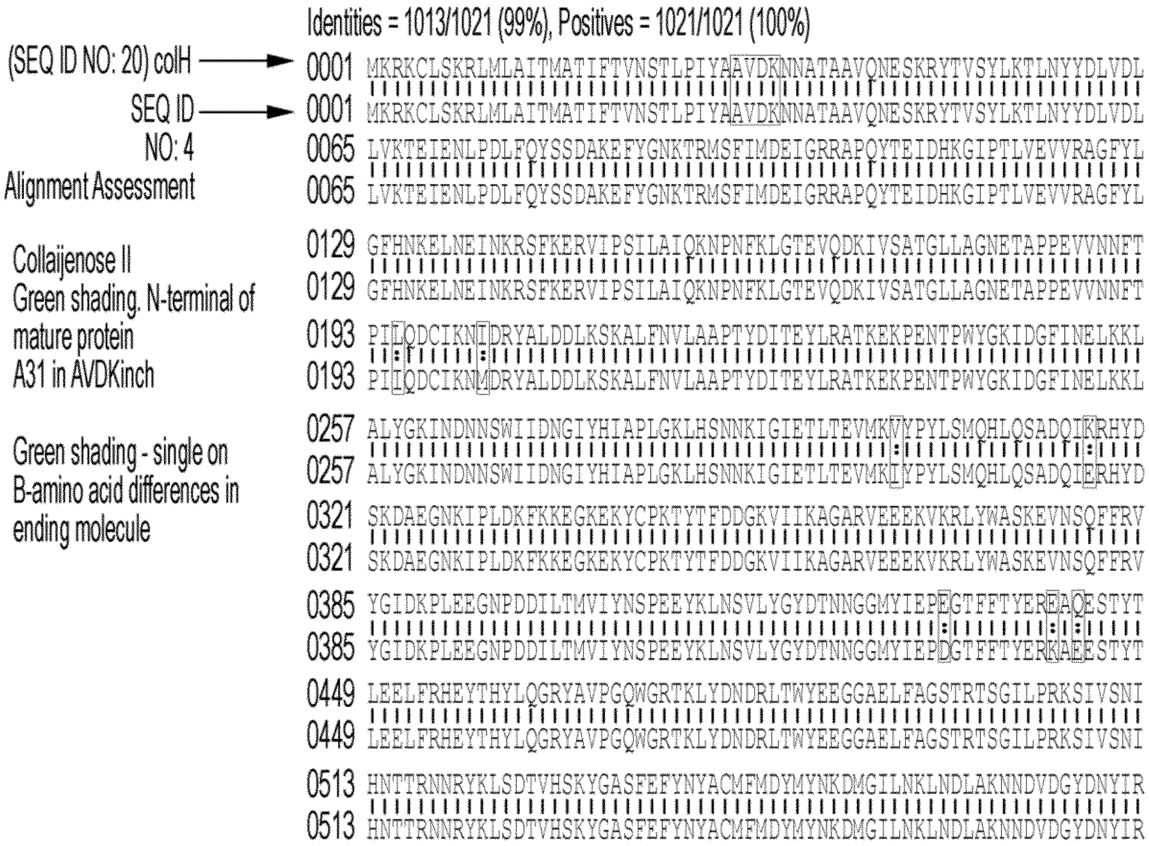

FIG. 10A

```
colH ─────▶ 0577 DLSSNYALNDKYQDHMQERIDNYENLTVPFVADDYLVRHAYKNPNEIYSEISEVAKLKDAKSEV
                 ||||| ||||||||||||||||||||||||||||||||||||||||||||||||||||||||||
SEQ ID NO: 4 ──▶ 0577 DLSSNHALNDKYQDHMQERIDNYENLTVPFVADDYLVRHAYKNPNEIYSEISEVAKLKDAKSEV
            0641 KKSQYFSTFTLRGSYTGGASKGKLEDQKAMNKFIDDSLKKLDTYSWSGYKTLTAYFTNYKVDSS
                 ||||||||||||||||||||||||||||||||||||||||||||||||||||||||||||||||
            0641 KKSQYFSTFTLRGSYTGGASKGKLEDQKAMNKFIDDSLKKLDTYSWSGYKTLTAYFTNYKVDSS
            0705 NRVTYDVVFHGYLPNEGDSKNSLPYGKINGTYKGTEKEKIKFSSEGSFDPDGKIVSYEWDFGDG
                 ||||||||||||||||||||||||||||||||||||||||||||||||||||||||||||||||
            0705 NRVTYDVVFHGYLPNEGDSKNSLPYGKINGTYKGTEKEKIKFSSEGSFDPDGKIVSYEWDFGDG
            0769 NKSNEENPEHSYDKVGTYTVKLKVTDDKGESSVSTTTAEIKDLSENKLPVIYMHVPKSGALNQK
                 ||||||||||||||||||||||||||||||||||||||||||||||||||||||||||||||||
            0769 NKSNEENPEHSYDKVGTYTVKLKVTDDKGESSVSTTTAEIKDLSENKLPVIYMHVPKSGALNQK
            0833 VVFYGKGTYDPDGSIAGYQWDFGDGSDFSSEQNPSHVYTKKGEYTVTLRVMDSSGQMSEKTMKI
                 ||||||||||||||||||||||||||||||||||||||||||||||||||||||||||||||||
            0833 VVFYGKGTYDPDGSIAGYQWDFGDGSDFSSEQNPSHVYTKKGEYTVTLRVMDSSGQMSEKTMKI
            0897 KITDPVYPIGTEKEPNNSKETASGPIVPGIPVSGTIENTSDQDYFYFDVITPGEVKIDINKLGY
                 ||||||||||||||||||||||||||||||||||||||||||||||||||||||||||||||||
            0897 KITDPVYPIGTEKEPNNSKETASGPIVPGIPVSGTIENTSDQDYFYFDVITPGEVKIDINKLGY
            0961 GGATWVVYDENNNAVSYATDDGQNLSGKFKADKPGRYYIHLYMFNGSYMPYRINIEGSVGR
                 ||||||||||||||||||||||||||||||||||||||||||||||||||||||||||||
            0961 GGATWVVYDENNNAVSYATDDGQNLSGKFKADKPGRYYIHLYMFNGSYMPYRINIEGSVGR
```

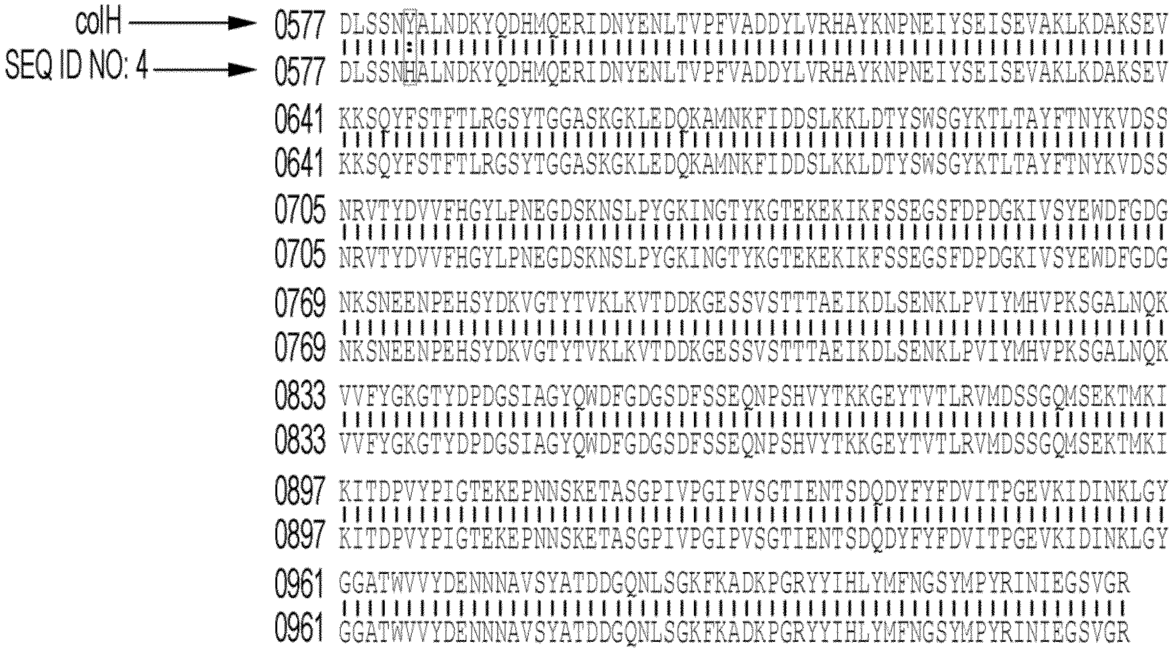

FIG. 10B

SEQUENCE LISTING

```
<160> NUMBER OF SEQ ID NOS: 32

<210> SEQ ID NO 1
<211> LENGTH: 3357
<212> TYPE: DNA
<213> ORGANISM: Clostridium histolyticum

<400> SEQUENCE: 1

atgaaaaaaa atattttaaa gattcttatg gatagttatt ctaaagaatc taaaattcaa      60

actgtacgta gggttacgag tgtatcactt ttagcggcat atcttactat gaatacttca     120

agtttagttt tagcaaaacc aatagaaaat actaatgata ctagtataaa aaatgtggag     180

aaattaagaa atgctccaaa tgaagagaat agtaaaaagg tagaagatag taaaaatgat     240

aaggtagaac atgtggaaaa tatagaagag gcaaaagttg agcaagttgc acccgaagta     300

aaatctaaat caactttaag aagtgcttct atagcgaata ctaattctga gaaatatgat     360

tttgagtatt taaatggttt gagctatact gaacttacaa atttaattaa aaatataaag     420

tggaatcaaa ttaatggttt atttaattat agtacaggtt ctcaaaagtt ctttggagat     480

aaaaatcgtg tacaagctat aattaatgct ttacaagaaa gtggaagaac ttacactgca     540

aatgatatga agggtataga aactttcact gaggttttaa gagctggttt ttatttaggg     600

tactataatg atggtttatc ttatttaaat gatagaaact tccaagataa atgtatacct     660

gcaatgattg caattcaaaa aaatcctaac tttaagctag gaactgcagt tcaagatgaa     720

gttataactt ctttaggaaa actaatagga aatgcttctg ctaatgctga agtagttaat     780

aattgtgtac cagttctaaa acaatttaga gaaaacttaa atcaatatgc tcctgattac     840

gttaaaggaa cagctgtaaa tgaattaatt aaaggtattg aattcgattt ttctggtgct     900

gcatatgaaa aagatgttaa gacaatgcct tggtatggaa aaattgatcc atttataaat     960

gaacttaagg ccttaggtct atatggaaat ataacaagtg caactgagtg ggcatctgat    1020

gttggaatat actatttaag taaattcggt ctttactcaa ctaaccgaaa tgacatagta    1080

cagtcacttg aaaaggctgt agatatgtat aagtatggta aaatagcctt tgtagcaatg    1140

gagagaataa cttgggatta tgatgggatt ggttctaatg gtaaaaaggt ggatcacgat    1200

aagttcttag atgatgctga aaaacattat ctgccaaaga catatacttt tgataatgga    1260

acctttatta taagagcagg ggagaaggta tccgaagaaa aaataaaaag gctatattgg    1320

gcatcaagag aagtgaagtc tcaattccat agagtagttg gcaatgataa agctttagag    1380
```

```
gtgggaaatg ccgatgatgt tttaactatg aaaatattta atagcccaga agaatataaa   1440
tttaatacca atataaatgg tgtaagcact gataatggtg gtctatatat agaaccaaga   1500
gggactttct acacttatga gagaacacct caacaaagta tatttagtct tgaagaattg   1560
tttagacatg aatatactca ctatttacaa gcgagatatc ttgtagatgg tttatgggga   1620
caaggtccat tttatgaaaa aaatagatta acttggtttg atgaaggtac agctgaattc   1680
tttgcaggat ctacccgtac atctggtgtt ttaccaagaa aatcaatatt aggatatttg   1740
gctaaggata aagtagatca tagatactca ttaaagaaga ctcttaattc agggtatgat   1800
gacagtgatt ggatgttcta taattatgga tttgcagttg cacattatct atatgaaaaa   1860
gatatgccta catttattaa gatgaataaa gctatattga atacagatgt gaaatcttat   1920
gatgaaataa taaaaaaatt aagtgatgat gcaaataaaa atacagaata tcaaaaccat   1980
attcaagagt tagcagataa atatcaagga gcaggcatac ctctagtatc agatgattac   2040
ttaaaagatc atggatataa gaaagcatct gaagtatatt ctgaaatttc aaaagctgct   2100
tctcttacaa acactagtgt aacagcagaa aaatctcaat attttaacac attcacttta   2160
agaggaactt atacaggtga aacttctaaa ggtgaattta aagattggga tgaaatgagt   2220
aaaaaattag atggaacttt ggagtccctt gctaaaaatt cttggagtgg atacaaaact   2280
ttaacagcat actttacgaa ttatagagtt acaagcgata ataaagttca atatgatgta   2340
gttttccatg ggttttaac agataatgcg gatattagta acaataaggc tccaatagca   2400
aaggtaactg gaccaagcac tggtgctgta ggaagaaata ttgaatttag tggaaaagat   2460
agtaaagatg aagatggtaa aatagtatca tatgattggg attttggcga tggtgcaact   2520
agtagaggca aaaattcagt acatgcttac aaaaaaacag gaacatataa tgttacatta   2580
aaagtaactg acgataaggg tgcaacagct acagaaagct ttactataga aataaagaac   2640
gaagatacaa caacacctat aactaaagaa atggaaccta atgatgatat aaaagaggct   2700
aatggtccaa tagttgaagg tgttactgta aaaggtgatt taaatggttc tgatgatgct   2760
gataccttct attttgatgt aaaagaagat ggtgatgtta caattgaact tccttattca   2820
gggtcatcta atttcacatg gttagtttat aaagagggag acgatcaaaa ccatattgca   2880
agtggtatag ataagaataa ctcaaaagtt ggaacattta aagctacaaa aggaagacat   2940
tatgtgttta tatataaaca cgattctgct tcaaatatat cctattcttt aaacataaaa   3000
ggattaggta acgagaaatt gaaggaaaaa gaaaataatg attcttctga taaagctaca   3060
gttataccaa atttcaatac cactatgcaa ggttcacttt taggtgatga ttcaagagat   3120
tattattctt ttgaggttaa ggaagaaggc gaagttaata tagaactaga taaaaaggat   3180
gaatttggtg taacatggac actacatcca gagtcaaata ttaatgacag aataacttac   3240
ggacaagttg atggtaataa ggtatctaat aaagttaaat taagaccagg aaaatattat   3300
ctacttgttt ataaatactc aggatcagga aactatgagt taagggtaaa taaataa      3357

<210> SEQ ID NO 2
<211> LENGTH: 3066
<212> TYPE: DNA
<213> ORGANISM: Clostridium histolyticum

<400> SEQUENCE: 2

atgaaaagga aatgtttatc taaaaggctt atgttagcta taacaatggc tacaatattt     60
acagtgaaca gtacattacc aatttatgca gctgtagata aaaataatgc aacagcagct    120
gtacaaaatg aaagtaagag gtatacagta tcatatttaa agactttaaa ttattatgac    180
```

-continued

```
ttagtagatt tgcttgttaa gactgaaatt gagaatttac cagacctttt tcagtatagt    240
tcagatgcaa aagagttcta tggaaataaa actcgtatga gctttatcat ggatgaaatt    300
ggtagaaggg caccacagta tacagagata gatcataaag gtattcctac tttagtagaa    360
gttgtaagag ctggatttta cttaggattc cataacaagg aattgaatga aataaataag    420
aggtctttta aagaaagggt aataccttct atattggcaa ttcaaaaaaa tcctaatttt    480
aaactaggta ctgaagttca agataaaata gtatctgcaa caggactttt agctggtaat    540
gaaacagcgc ctccagaagt tgtaaataat tttacaccaa taattcaaga ctgtatcaaa    600
aatatggaca gatatgctct tgatgattta aagtcaaaag cattatttaa tgttttagct    660
gcacctacct atgatataac tgagtattta agagctacta aagaaaaacc agaaaacact    720
ccttggtatg gtaaaataga tgggtttata aatgaactta aaaagttagc tctttatgga    780
aaaataaatg ataataactc ttggataata gataatggta tatatcatat agcaccttta    840
gggaagttac atagcaataa taaaatagga atagaaactt taacagaggt tatgaagata    900
tatccttatt taagtatgca acatttacaa tcagcagatc aaattgagcg tcattatgat    960
tcaaaagatg ctgaaggaaa taaaatacct ttagataagt ttaaaaagga aggaaaagag   1020
aaatactgtc caaaaactta tacatttgat gatggaaaag taataataaa agctggtgct   1080
agggtagaag aagaaaaagt taaaagacta tactgggcat caaaggaagt taactctcaa   1140
ttctttaggg tatatggaat agacaaacca ttagaagaag gtaatccaga tgatatatta   1200
acaatggtta tctacaacag tcctgaagaa tataaactta atagtgttct atacggatat   1260
gatactaata atggtggtat gtatatagag ccagatggaa ctttcttcac atatgaaaga   1320
aaagctgaag aaagcacata cacattagaa gaattattta gacatgaata tacacactat   1380
ttacaaggaa gatatgcagt tcctggtcaa tggggaagaa caaaacttta tgacaatgat   1440
agattaactt ggtatgaaga aggtggagca gaattatttg caggttctac tagaacttct   1500
ggaatattac caagaaagag tatagtatca aatattcata atacaacaag aaataataga   1560
tataagcttt cagacactgt acattctaaa tatggtgcta gttttgaatt ctataattat   1620
gcatgtatgt ttatggatta tatgtataat aaagatatgg gtatattaaa taaactaaat   1680
gatcttgcaa aaaataatga tgttgatgga tatgataatt atattagaga tttaagttct   1740
aatcatgctt taaatgataa atatcaagat catatgcagg agcgcataga taattatgaa   1800
aatttaacag tgccttttgt agctgatgat tatttagtaa gacatgctta taagaaccct   1860
aatgaaattt attctgaaat atctgaagta gcaaaattaa aggatgctaa gagtgaagtt   1920
aagaaatcac aatattttag tacctttact ttgagaggta gttacacagg tggagcatct   1980
aaggggaaat tagaagatca aaaagcaatg aataagttta tagatgattc acttaagaaa   2040
ttagatacgt attcttggag tgggtataaa actttaactg cttatttcac taattataaa   2100
gttgactctt caaatagagt tacttatgat gtagtattcc acggatattt accaaacgaa   2160
ggtgattcca aaaattcatt accttatggc aagatcaatg gaacttacaa gggaacagag   2220
aaagaaaaaa tcaaattctc tagtgaaggc tctttcgatc cagatggtaa aatagtttct   2280
tatgaatggg atttcggaga tggtaataag agtaatgagg aaaatccaga gcattcatat   2340
gacaaggtag gaacttatac agtgaaatta aaagttactg atgacaaggg agaatcttca   2400
gtatctacta ctactgcaga aataaaggat ctttcagaaa ataaacttcc agttatatat   2460
atgcatgtac ctaaatccgg agccttaaat caaaaagttg ttttctatgg aaaaggaaca   2520
```

tatgacccag atggatctat cgcaggatat caatgggact ttggtgatgg aagtgatttt 2580
agcagtgaac aaaacccaag ccatgtatat actaaaaaag gtgaatatac tgtaacatta 2640
agagtaatgg acagtagtgg acaaatgagt gaaaaaacta tgaagattaa gattacagat 2700
ccggtatatc caataggcac tgaaaaagaa ccaaataaca gtaaagaaac tgcaagtggt 2760
ccaatagtac caggtatacc tgttagtgga accatagaaa atacaagtga tcaagattat 2820
ttctattttg atgttataac accaggagaa gtaaaaatag atataaataa attagggtac 2880
ggaggagcta cttgggtagt atatgatgaa aataataatg cagtatctta tgccactgat 2940
gatgggcaaa atttaagtgg aaagtttaag gcagataaac caggtagata ttacatccat 3000
ctttacatgt ttaatggtag ttatatgcca tatagaatta atatagaagg ttcagtagga 3060
agataa 3066

<210> SEQ ID NO 3
<211> LENGTH: 1118
<212> TYPE: PRT
<213> ORGANISM: Clostridium histolyticum

<400> SEQUENCE: 3

Met Lys Lys Asn Ile Leu Lys Ile Leu Met Asp Ser Tyr Ser Lys Glu
1 5 10 15

Ser Lys Ile Gln Thr Val Arg Arg Val Thr Ser Val Ser Leu Leu Ala
20 25 30

Ala Tyr Leu Thr Met Asn Thr Ser Ser Leu Val Leu Ala Lys Pro Ile
35 40 45

Glu Asn Thr Asn Asp Thr Ser Ile Lys Asn Val Glu Lys Leu Arg Asn
50 55 60

Ala Pro Asn Glu Glu Asn Ser Lys Lys Val Glu Asp Ser Lys Asn Asp
65 70 75 80

Lys Val Glu His Val Glu Asn Ile Glu Glu Ala Lys Val Glu Gln Val
85 90 95

Ala Pro Glu Val Lys Ser Lys Ser Thr Leu Arg Ser Ala Ser Ile Ala
100 105 110

Asn Thr Asn Ser Glu Lys Tyr Asp Phe Glu Tyr Leu Asn Gly Leu Ser
115 120 125

Tyr Thr Glu Leu Thr Asn Leu Ile Lys Asn Ile Lys Trp Asn Gln Ile
130 135 140

Asn Gly Leu Phe Asn Tyr Ser Thr Gly Ser Gln Lys Phe Phe Gly Asp
145 150 155 160

Lys Asn Arg Val Gln Ala Ile Ile Asn Ala Leu Gln Glu Ser Gly Arg
165 170 175

Thr Tyr Thr Ala Asn Asp Met Lys Gly Ile Glu Thr Phe Thr Glu Val
180 185 190

Leu Arg Ala Gly Phe Tyr Leu Gly Tyr Tyr Asn Asp Gly Leu Ser Tyr
195 200 205

Leu Asn Asp Arg Asn Phe Gln Asp Lys Cys Ile Pro Ala Met Ile Ala
210 215 220

Ile Gln Lys Asn Pro Asn Phe Lys Leu Gly Thr Ala Val Gln Asp Glu
225 230 235 240

Val Ile Thr Ser Leu Gly Lys Leu Ile Gly Asn Ala Ser Ala Asn Ala
245 250 255

Glu Val Val Asn Asn Cys Val Pro Val Leu Lys Gln Phe Arg Glu Asn
260 265 270

-continued

```
Leu Asn Gln Tyr Ala Pro Asp Tyr Val Lys Gly Thr Ala Val Asn Glu
        275                 280                 285

Leu Ile Lys Gly Ile Glu Phe Asp Phe Ser Gly Ala Ala Tyr Glu Lys
    290                 295                 300

Asp Val Lys Thr Met Pro Trp Tyr Gly Lys Ile Asp Pro Phe Ile Asn
305                 310                 315                 320

Glu Leu Lys Ala Leu Gly Leu Tyr Gly Asn Ile Thr Ser Ala Thr Glu
                325                 330                 335

Trp Ala Ser Asp Val Gly Ile Tyr Tyr Leu Ser Lys Phe Gly Leu Tyr
            340                 345                 350

Ser Thr Asn Arg Asn Asp Ile Val Gln Ser Leu Glu Lys Ala Val Asp
        355                 360                 365

Met Tyr Lys Tyr Gly Lys Ile Ala Phe Val Ala Met Glu Arg Ile Thr
    370                 375                 380

Trp Asp Tyr Asp Gly Ile Gly Ser Asn Gly Lys Lys Val Asp His Asp
385                 390                 395                 400

Lys Phe Leu Asp Asp Ala Glu Lys His Tyr Leu Pro Lys Thr Tyr Thr
                405                 410                 415

Phe Asp Asn Gly Thr Phe Ile Ile Arg Ala Gly Glu Lys Val Ser Glu
            420                 425                 430

Glu Lys Ile Lys Arg Leu Tyr Trp Ala Ser Arg Glu Val Lys Ser Gln
        435                 440                 445

Phe His Arg Val Val Gly Asn Asp Lys Ala Leu Glu Val Gly Asn Ala
    450                 455                 460

Asp Asp Val Leu Thr Met Lys Ile Phe Asn Ser Pro Glu Glu Tyr Lys
465                 470                 475                 480

Phe Asn Thr Asn Ile Asn Gly Val Ser Thr Asp Asn Gly Gly Leu Tyr
                485                 490                 495

Ile Glu Pro Arg Gly Thr Phe Tyr Thr Tyr Glu Arg Thr Pro Gln Gln
            500                 505                 510

Ser Ile Phe Ser Leu Glu Glu Leu Phe Arg His Glu Tyr Thr His Tyr
        515                 520                 525

Leu Gln Ala Arg Tyr Leu Val Asp Gly Leu Trp Gly Gln Gly Pro Phe
    530                 535                 540

Tyr Glu Lys Asn Arg Leu Thr Trp Phe Asp Glu Gly Thr Ala Glu Phe
545                 550                 555                 560

Phe Ala Gly Ser Thr Arg Thr Ser Gly Val Leu Pro Arg Lys Ser Ile
                565                 570                 575

Leu Gly Tyr Leu Ala Lys Asp Lys Val Asp His Arg Tyr Ser Leu Lys
            580                 585                 590

Lys Thr Leu Asn Ser Gly Tyr Asp Asp Ser Asp Trp Met Phe Tyr Asn
        595                 600                 605

Tyr Gly Phe Ala Val Ala His Tyr Leu Tyr Glu Lys Asp Met Pro Thr
    610                 615                 620

Phe Ile Lys Met Asn Lys Ala Ile Leu Asn Thr Asp Val Lys Ser Tyr
625                 630                 635                 640

Asp Glu Ile Ile Lys Lys Leu Ser Asp Asp Ala Asn Lys Asn Thr Glu
                645                 650                 655

Tyr Gln Asn His Ile Gln Glu Leu Ala Asp Lys Tyr Gln Gly Ala Gly
            660                 665                 670

Ile Pro Leu Val Ser Asp Asp Tyr Leu Lys Asp His Gly Tyr Lys Lys
        675                 680                 685

Ala Ser Glu Val Tyr Ser Glu Ile Ser Lys Ala Ala Ser Leu Thr Asn
```

```
    690                 695                 700

Thr Ser Val Thr Ala Glu Lys Ser Gln Tyr Phe Asn Thr Phe Thr Leu
705                 710                 715                 720

Arg Gly Thr Tyr Thr Gly Glu Thr Ser Lys Gly Glu Phe Lys Asp Trp
                725                 730                 735

Asp Glu Met Ser Lys Lys Leu Asp Gly Thr Leu Glu Ser Leu Ala Lys
            740                 745                 750

Asn Ser Trp Ser Gly Tyr Lys Thr Leu Thr Ala Tyr Phe Thr Asn Tyr
        755                 760                 765

Arg Val Thr Ser Asp Asn Lys Val Gln Tyr Asp Val Val Phe His Gly
    770                 775                 780

Val Leu Thr Asp Asn Ala Asp Ile Ser Asn Asn Lys Ala Pro Ile Ala
785                 790                 795                 800

Lys Val Thr Gly Pro Ser Thr Gly Ala Val Gly Arg Asn Ile Glu Phe
                805                 810                 815

Ser Gly Lys Asp Ser Lys Asp Glu Asp Gly Lys Ile Val Ser Tyr Asp
            820                 825                 830

Trp Asp Phe Gly Asp Gly Ala Thr Ser Arg Gly Lys Asn Ser Val His
        835                 840                 845

Ala Tyr Lys Lys Thr Gly Thr Tyr Asn Val Thr Leu Lys Val Thr Asp
    850                 855                 860

Asp Lys Gly Ala Thr Ala Thr Glu Ser Phe Thr Ile Glu Ile Lys Asn
865                 870                 875                 880

Glu Asp Thr Thr Thr Pro Ile Thr Lys Glu Met Glu Pro Asn Asp Asp
                885                 890                 895

Ile Lys Glu Ala Asn Gly Pro Ile Val Glu Gly Val Thr Val Lys Gly
            900                 905                 910

Asp Leu Asn Gly Ser Asp Asp Ala Asp Thr Phe Tyr Phe Asp Val Lys
        915                 920                 925

Glu Asp Gly Asp Val Thr Ile Glu Leu Pro Tyr Ser Gly Ser Ser Asn
    930                 935                 940

Phe Thr Trp Leu Val Tyr Lys Glu Gly Asp Asp Gln Asn His Ile Ala
945                 950                 955                 960

Ser Gly Ile Asp Lys Asn Asn Ser Lys Val Gly Thr Phe Lys Ala Thr
                965                 970                 975

Lys Gly Arg His Tyr Val Phe Ile Tyr Lys His Asp Ser Ala Ser Asn
            980                 985                 990

Ile Ser Tyr Ser Leu Asn Ile Lys  Gly Leu Gly Asn Glu  Lys Leu Lys
        995                 1000                1005

Glu Lys  Glu Asn Asn Asp Ser  Ser Asp Lys Ala Thr  Val Ile Pro
    1010                1015                1020

Asn Phe  Asn Thr Thr Met Gln  Gly Ser Leu Leu Gly  Asp Asp Ser
    1025                1030                1035

Arg Asp  Tyr Tyr Ser Phe Glu  Val Lys Glu Glu Gly  Glu Val Asn
    1040                1045                1050

Ile Glu  Leu Asp Lys Lys Asp  Glu Phe Gly Val Thr  Trp Thr Leu
    1055                1060                1065

His Pro  Glu Ser Asn Ile Asn  Asp Arg Ile Thr Tyr  Gly Gln Val
    1070                1075                1080

Asp Gly  Asn Lys Val Ser Asn  Lys Val Lys Leu Arg  Pro Gly Lys
    1085                1090                1095

Tyr Tyr  Leu Leu Val Tyr Lys  Tyr Ser Gly Ser Gly  Asn Tyr Glu
    1100                1105                1110
```

Leu Arg Val Asn Lys
1115

<210> SEQ ID NO 4
<211> LENGTH: 1021
<212> TYPE: PRT
<213> ORGANISM: Clostridium histolyticum

<400> SEQUENCE: 4

Met Lys Arg Lys Cys Leu Ser Lys Arg Leu Met Leu Ala Ile Thr Met
1 5 10 15

Ala Thr Ile Phe Thr Val Asn Ser Thr Leu Pro Ile Tyr Ala Ala Val
20 25 30

Asp Lys Asn Asn Ala Thr Ala Ala Val Gln Asn Glu Ser Lys Arg Tyr
35 40 45

Thr Val Ser Tyr Leu Lys Thr Leu Asn Tyr Tyr Asp Leu Val Asp Leu
50 55 60

Leu Val Lys Thr Glu Ile Glu Asn Leu Pro Asp Leu Phe Gln Tyr Ser
65 70 75 80

Ser Asp Ala Lys Glu Phe Tyr Gly Asn Lys Thr Arg Met Ser Phe Ile
85 90 95

Met Asp Glu Ile Gly Arg Arg Ala Pro Gln Tyr Thr Glu Ile Asp His
100 105 110

Lys Gly Ile Pro Thr Leu Val Glu Val Val Arg Ala Gly Phe Tyr Leu
115 120 125

Gly Phe His Asn Lys Glu Leu Asn Glu Ile Asn Lys Arg Ser Phe Lys
130 135 140

Glu Arg Val Ile Pro Ser Ile Leu Ala Ile Gln Lys Asn Pro Asn Phe
145 150 155 160

Lys Leu Gly Thr Glu Val Gln Asp Lys Ile Val Ser Ala Thr Gly Leu
165 170 175

Leu Ala Gly Asn Glu Thr Ala Pro Pro Glu Val Val Asn Asn Phe Thr
180 185 190

Pro Ile Ile Gln Asp Cys Ile Lys Asn Met Asp Arg Tyr Ala Leu Asp
195 200 205

Asp Leu Lys Ser Lys Ala Leu Phe Asn Val Leu Ala Ala Pro Thr Tyr
210 215 220

Asp Ile Thr Glu Tyr Leu Arg Ala Thr Lys Glu Lys Pro Glu Asn Thr
225 230 235 240

Pro Trp Tyr Gly Lys Ile Asp Gly Phe Ile Asn Glu Leu Lys Lys Leu
245 250 255

Ala Leu Tyr Gly Lys Ile Asn Asp Asn Asn Ser Trp Ile Ile Asp Asn
260 265 270

Gly Ile Tyr His Ile Ala Pro Leu Gly Lys Leu His Ser Asn Asn Lys
275 280 285

Ile Gly Ile Glu Thr Leu Thr Glu Val Met Lys Ile Tyr Pro Tyr Leu
290 295 300

Ser Met Gln His Leu Gln Ser Ala Asp Gln Ile Glu Arg His Tyr Asp
305 310 315 320

Ser Lys Asp Ala Glu Gly Asn Lys Ile Pro Leu Asp Lys Phe Lys Lys
325 330 335

Glu Gly Lys Glu Lys Tyr Cys Pro Lys Thr Tyr Thr Phe Asp Asp Gly
340 345 350

Lys Val Ile Ile Lys Ala Gly Ala Arg Val Glu Glu Glu Lys Val Lys

```
        355                 360                 365

Arg Leu Tyr Trp Ala Ser Lys Glu Val Asn Ser Gln Phe Phe Arg Val
    370                 375                 380

Tyr Gly Ile Asp Lys Pro Leu Glu Glu Gly Asn Pro Asp Asp Ile Leu
385                 390                 395                 400

Thr Met Val Ile Tyr Asn Ser Pro Glu Glu Tyr Lys Leu Asn Ser Val
                405                 410                 415

Leu Tyr Gly Tyr Asp Thr Asn Asn Gly Gly Met Tyr Ile Glu Pro Asp
            420                 425                 430

Gly Thr Phe Phe Thr Tyr Glu Arg Lys Ala Glu Glu Ser Thr Tyr Thr
        435                 440                 445

Leu Glu Glu Leu Phe Arg His Glu Tyr Thr His Tyr Leu Gln Gly Arg
    450                 455                 460

Tyr Ala Val Pro Gly Gln Trp Gly Arg Thr Lys Leu Tyr Asp Asn Asp
465                 470                 475                 480

Arg Leu Thr Trp Tyr Glu Glu Gly Gly Ala Glu Leu Phe Ala Gly Ser
                485                 490                 495

Thr Arg Thr Ser Gly Ile Leu Pro Arg Lys Ser Ile Val Ser Asn Ile
            500                 505                 510

His Asn Thr Thr Arg Asn Asn Arg Tyr Lys Leu Ser Asp Thr Val His
        515                 520                 525

Ser Lys Tyr Gly Ala Ser Phe Glu Phe Tyr Asn Tyr Ala Cys Met Phe
    530                 535                 540

Met Asp Tyr Met Tyr Asn Lys Asp Met Gly Ile Leu Asn Lys Leu Asn
545                 550                 555                 560

Asp Leu Ala Lys Asn Asn Asp Val Asp Gly Tyr Asp Asn Tyr Ile Arg
                565                 570                 575

Asp Leu Ser Ser Asn His Ala Leu Asn Asp Lys Tyr Gln Asp His Met
            580                 585                 590

Gln Glu Arg Ile Asp Asn Tyr Glu Asn Leu Thr Val Pro Phe Val Ala
        595                 600                 605

Asp Asp Tyr Leu Val Arg His Ala Tyr Lys Asn Pro Asn Glu Ile Tyr
    610                 615                 620

Ser Glu Ile Ser Glu Val Ala Lys Leu Lys Asp Ala Lys Ser Glu Val
625                 630                 635                 640

Lys Lys Ser Gln Tyr Phe Ser Thr Phe Thr Leu Arg Gly Ser Tyr Thr
                645                 650                 655

Gly Gly Ala Ser Lys Gly Lys Leu Glu Asp Gln Lys Ala Met Asn Lys
            660                 665                 670

Phe Ile Asp Asp Ser Leu Lys Lys Leu Asp Thr Tyr Ser Trp Ser Gly
        675                 680                 685

Tyr Lys Thr Leu Thr Ala Tyr Phe Thr Asn Tyr Lys Val Asp Ser Ser
    690                 695                 700

Asn Arg Val Thr Tyr Asp Val Val Phe His Gly Tyr Leu Pro Asn Glu
705                 710                 715                 720

Gly Asp Ser Lys Asn Ser Leu Pro Tyr Gly Lys Ile Asn Gly Thr Tyr
                725                 730                 735

Lys Gly Thr Glu Lys Glu Lys Ile Lys Phe Ser Ser Glu Gly Ser Phe
            740                 745                 750

Asp Pro Asp Gly Lys Ile Val Ser Tyr Glu Trp Asp Phe Gly Asp Gly
        755                 760                 765

Asn Lys Ser Asn Glu Glu Asn Pro Glu His Ser Tyr Asp Lys Val Gly
    770                 775                 780
```

-continued

```
Thr Tyr Thr Val Lys Leu Lys Val Thr Asp Asp Lys Gly Glu Ser Ser
785                 790                 795                 800

Val Ser Thr Thr Thr Ala Glu Ile Lys Asp Leu Ser Glu Asn Lys Leu
                805                 810                 815

Pro Val Ile Tyr Met His Val Pro Lys Ser Gly Ala Leu Asn Gln Lys
            820                 825                 830

Val Val Phe Tyr Gly Lys Gly Thr Tyr Asp Pro Asp Gly Ser Ile Ala
        835                 840                 845

Gly Tyr Gln Trp Asp Phe Gly Asp Gly Ser Asp Phe Ser Ser Glu Gln
    850                 855                 860

Asn Pro Ser His Val Tyr Thr Lys Lys Gly Glu Tyr Thr Val Thr Leu
865                 870                 875                 880

Arg Val Met Asp Ser Ser Gly Gln Met Ser Glu Lys Thr Met Lys Ile
                885                 890                 895

Lys Ile Thr Asp Pro Val Tyr Pro Ile Gly Thr Glu Lys Glu Pro Asn
            900                 905                 910

Asn Ser Lys Glu Thr Ala Ser Gly Pro Ile Val Pro Gly Ile Pro Val
        915                 920                 925

Ser Gly Thr Ile Glu Asn Thr Ser Asp Gln Asp Tyr Phe Tyr Phe Asp
    930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
                965                 970                 975

Tyr Ala Thr Asp Asp Gly Gln Asn Leu Ser Gly Lys Phe Lys Ala Asp
            980                 985                 990

Lys Pro Gly Arg Tyr Tyr Ile His  Leu Tyr Met Phe Asn  Gly Ser Tyr
        995                 1000                1005

Met Pro  Tyr Arg Ile Asn Ile  Glu Gly Ser Val Gly  Arg
    1010                 1015                1020


<210> SEQ ID NO 5
<211> LENGTH: 1008
<212> TYPE: PRT
<213> ORGANISM: Clostridium histolyticum

<400> SEQUENCE: 5

Ile Ala Asn Thr Asn Ser Glu Lys Tyr Asp Phe Glu Tyr Leu Asn Gly
1               5                   10                  15

Leu Ser Tyr Thr Glu Leu Thr Asn Leu Ile Lys Asn Ile Lys Trp Asn
            20                  25                  30

Gln Ile Asn Gly Leu Phe Asn Tyr Ser Thr Gly Ser Gln Lys Phe Phe
        35                  40                  45

Gly Asp Lys Asn Arg Val Gln Ala Ile Ile Asn Ala Leu Gln Glu Ser
    50                  55                  60

Gly Arg Thr Tyr Thr Ala Asn Asp Met Lys Gly Ile Glu Thr Phe Thr
65                  70                  75                  80

Glu Val Leu Arg Ala Gly Phe Tyr Leu Gly Tyr Tyr Asn Asp Gly Leu
                85                  90                  95

Ser Tyr Leu Asn Asp Arg Asn Phe Gln Asp Lys Cys Ile Pro Ala Met
            100                 105                 110

Ile Ala Ile Gln Lys Asn Pro Asn Phe Lys Leu Gly Thr Ala Val Gln
        115                 120                 125

Asp Glu Val Ile Thr Ser Leu Gly Lys Leu Ile Gly Asn Ala Ser Ala
```

-continued

```
    130                 135                 140

Asn Ala Glu Val Val Asn Asn Cys Val Pro Val Leu Lys Gln Phe Arg
145                 150                 155                 160

Glu Asn Leu Asn Gln Tyr Ala Pro Asp Tyr Val Lys Gly Thr Ala Val
                165                 170                 175

Asn Glu Leu Ile Lys Gly Ile Glu Phe Asp Phe Ser Gly Ala Ala Tyr
            180                 185                 190

Glu Lys Asp Val Lys Thr Met Pro Trp Tyr Gly Lys Ile Asp Pro Phe
        195                 200                 205

Ile Asn Glu Leu Lys Ala Leu Gly Leu Tyr Gly Asn Ile Thr Ser Ala
    210                 215                 220

Thr Glu Trp Ala Ser Asp Val Gly Ile Tyr Tyr Leu Ser Lys Phe Gly
225                 230                 235                 240

Leu Tyr Ser Thr Asn Arg Asn Asp Ile Val Gln Ser Leu Glu Lys Ala
                245                 250                 255

Val Asp Met Tyr Lys Tyr Gly Lys Ile Ala Phe Val Ala Met Glu Arg
            260                 265                 270

Ile Thr Trp Asp Tyr Asp Gly Ile Gly Ser Asn Gly Lys Lys Val Asp
        275                 280                 285

His Asp Lys Phe Leu Asp Asp Ala Glu Lys His Tyr Leu Pro Lys Thr
    290                 295                 300

Tyr Thr Phe Asp Asn Gly Thr Phe Ile Ile Arg Ala Gly Glu Lys Val
305                 310                 315                 320

Ser Glu Glu Lys Ile Lys Arg Leu Tyr Trp Ala Ser Arg Glu Val Lys
                325                 330                 335

Ser Gln Phe His Arg Val Val Gly Asn Asp Lys Ala Leu Glu Val Gly
            340                 345                 350

Asn Ala Asp Asp Val Leu Thr Met Lys Ile Phe Asn Ser Pro Glu Glu
        355                 360                 365

Tyr Lys Phe Asn Thr Asn Ile Asn Gly Val Ser Thr Asp Asn Gly Gly
    370                 375                 380

Leu Tyr Ile Glu Pro Arg Gly Thr Phe Tyr Thr Tyr Glu Arg Thr Pro
385                 390                 395                 400

Gln Gln Ser Ile Phe Ser Leu Glu Glu Leu Phe Arg His Glu Tyr Thr
                405                 410                 415

His Tyr Leu Gln Ala Arg Tyr Leu Val Asp Gly Leu Trp Gly Gln Gly
            420                 425                 430

Pro Phe Tyr Glu Lys Asn Arg Leu Thr Trp Phe Asp Glu Gly Thr Ala
        435                 440                 445

Glu Phe Phe Ala Gly Ser Thr Arg Thr Ser Gly Val Leu Pro Arg Lys
    450                 455                 460

Ser Ile Leu Gly Tyr Leu Ala Lys Asp Lys Val Asp His Arg Tyr Ser
465                 470                 475                 480

Leu Lys Lys Thr Leu Asn Ser Gly Tyr Asp Asp Ser Asp Trp Met Phe
                485                 490                 495

Tyr Asn Tyr Gly Phe Ala Val Ala His Tyr Leu Tyr Glu Lys Asp Met
            500                 505                 510

Pro Thr Phe Ile Lys Met Asn Lys Ala Ile Leu Asn Thr Asp Val Lys
        515                 520                 525

Ser Tyr Asp Glu Ile Ile Lys Lys Leu Ser Asp Asp Ala Asn Lys Asn
    530                 535                 540

Thr Glu Tyr Gln Asn His Ile Gln Glu Leu Ala Asp Lys Tyr Gln Gly
545                 550                 555                 560
```

```
Ala Gly Ile Pro Leu Val Ser Asp Asp Tyr Leu Lys Asp His Gly Tyr
                565                 570                 575

Lys Lys Ala Ser Glu Val Tyr Ser Glu Ile Ser Lys Ala Ala Ser Leu
            580                 585                 590

Thr Asn Thr Ser Val Thr Ala Glu Lys Ser Gln Tyr Phe Asn Thr Phe
        595                 600                 605

Thr Leu Arg Gly Thr Tyr Thr Gly Glu Thr Ser Lys Gly Glu Phe Lys
    610                 615                 620

Asp Trp Asp Glu Met Ser Lys Lys Leu Asp Gly Thr Leu Glu Ser Leu
625                 630                 635                 640

Ala Lys Asn Ser Trp Ser Gly Tyr Lys Thr Leu Thr Ala Tyr Phe Thr
                645                 650                 655

Asn Tyr Arg Val Thr Ser Asp Asn Lys Val Gln Tyr Asp Val Val Phe
            660                 665                 670

His Gly Val Leu Thr Asp Asn Ala Asp Ile Ser Asn Asn Lys Ala Pro
        675                 680                 685

Ile Ala Lys Val Thr Gly Pro Ser Thr Gly Ala Val Gly Arg Asn Ile
    690                 695                 700

Glu Phe Ser Gly Lys Asp Ser Lys Asp Glu Asp Gly Lys Ile Val Ser
705                 710                 715                 720

Tyr Asp Trp Asp Phe Gly Asp Gly Ala Thr Ser Arg Gly Lys Asn Ser
                725                 730                 735

Val His Ala Tyr Lys Lys Thr Gly Thr Tyr Asn Val Thr Leu Lys Val
            740                 745                 750

Thr Asp Asp Lys Gly Ala Thr Ala Thr Glu Ser Phe Thr Ile Glu Ile
        755                 760                 765

Lys Asn Glu Asp Thr Thr Thr Pro Ile Thr Lys Glu Met Glu Pro Asn
    770                 775                 780

Asp Asp Ile Lys Glu Ala Asn Gly Pro Ile Val Glu Gly Val Thr Val
785                 790                 795                 800

Lys Gly Asp Leu Asn Gly Ser Asp Asp Ala Asp Thr Phe Tyr Phe Asp
                805                 810                 815

Val Lys Glu Asp Gly Asp Val Thr Ile Glu Leu Pro Tyr Ser Gly Ser
            820                 825                 830

Ser Asn Phe Thr Trp Leu Val Tyr Lys Glu Gly Asp Asp Gln Asn His
        835                 840                 845

Ile Ala Ser Gly Ile Asp Lys Asn Asn Ser Lys Val Gly Thr Phe Lys
    850                 855                 860

Ala Thr Lys Gly Arg His Tyr Val Phe Ile Tyr Lys His Asp Ser Ala
865                 870                 875                 880

Ser Asn Ile Ser Tyr Ser Leu Asn Ile Lys Gly Leu Gly Asn Glu Lys
                885                 890                 895

Leu Lys Glu Lys Glu Asn Asn Asp Ser Ser Asp Lys Ala Thr Val Ile
            900                 905                 910

Pro Asn Phe Asn Thr Thr Met Gln Gly Ser Leu Leu Gly Asp Asp Ser
        915                 920                 925

Arg Asp Tyr Tyr Ser Phe Glu Val Lys Glu Glu Gly Glu Val Asn Ile
    930                 935                 940

Glu Leu Asp Lys Lys Asp Glu Phe Gly Val Thr Trp Thr Leu His Pro
945                 950                 955                 960

Glu Ser Asn Ile Asn Asp Arg Ile Thr Tyr Gly Gln Val Asp Gly Asn
                965                 970                 975
```

```
Lys Val Ser Asn Lys Val Lys Leu Arg Pro Gly Lys Tyr Tyr Leu Leu
            980                 985                 990

Val Tyr Lys Tyr Ser Gly Ser Gly  Asn Tyr Glu Leu Arg  Val Asn Lys
        995                 1000                 1005


<210> SEQ ID NO 6
<211> LENGTH: 991
<212> TYPE: PRT
<213> ORGANISM: Clostridium histolyticum

<400> SEQUENCE: 6

Ala Val Asp Lys Asn Asn Ala Thr Ala Ala Val Gln Asn Glu Ser Lys
1               5                   10                  15

Arg Tyr Thr Val Ser Tyr Leu Lys Thr Leu Asn Tyr Tyr Asp Leu Val
            20                  25                  30

Asp Leu Leu Val Lys Thr Glu Ile Glu Asn Leu Pro Asp Leu Phe Gln
        35                  40                  45

Tyr Ser Ser Asp Ala Lys Glu Phe Tyr Gly Asn Lys Thr Arg Met Ser
    50                  55                  60

Phe Ile Met Asp Glu Ile Gly Arg Arg Ala Pro Gln Tyr Thr Glu Ile
65                  70                  75                  80

Asp His Lys Gly Ile Pro Thr Leu Val Glu Val Val Arg Ala Gly Phe
                85                  90                  95

Tyr Leu Gly Phe His Asn Lys Glu Leu Asn Glu Ile Asn Lys Arg Ser
            100                 105                 110

Phe Lys Glu Arg Val Ile Pro Ser Ile Leu Ala Ile Gln Lys Asn Pro
        115                 120                 125

Asn Phe Lys Leu Gly Thr Glu Val Gln Asp Lys Ile Val Ser Ala Thr
    130                 135                 140

Gly Leu Leu Ala Gly Asn Glu Thr Ala Pro Pro Glu Val Val Asn Asn
145                 150                 155                 160

Phe Thr Pro Ile Ile Gln Asp Cys Ile Lys Asn Met Asp Arg Tyr Ala
                165                 170                 175

Leu Asp Asp Leu Lys Ser Lys Ala Leu Phe Asn Val Leu Ala Ala Pro
            180                 185                 190

Thr Tyr Asp Ile Thr Glu Tyr Leu Arg Ala Thr Lys Glu Lys Pro Glu
        195                 200                 205

Asn Thr Pro Trp Tyr Gly Lys Ile Asp Gly Phe Ile Asn Glu Leu Lys
    210                 215                 220

Lys Leu Ala Leu Tyr Gly Lys Ile Asn Asp Asn Asn Ser Trp Ile Ile
225                 230                 235                 240

Asp Asn Gly Ile Tyr His Ile Ala Pro Leu Gly Lys Leu His Ser Asn
                245                 250                 255

Asn Lys Ile Gly Ile Glu Thr Leu Thr Glu Val Met Lys Ile Tyr Pro
            260                 265                 270

Tyr Leu Ser Met Gln His Leu Gln Ser Ala Asp Gln Ile Glu Arg His
        275                 280                 285

Tyr Asp Ser Lys Asp Ala Glu Gly Asn Lys Ile Pro Leu Asp Lys Phe
    290                 295                 300

Lys Lys Glu Gly Lys Glu Lys Tyr Cys Pro Lys Thr Tyr Thr Phe Asp
305                 310                 315                 320

Asp Gly Lys Val Ile Ile Lys Ala Gly Ala Arg Val Glu Glu Glu Lys
                325                 330                 335

Val Lys Arg Leu Tyr Trp Ala Ser Lys Glu Val Asn Ser Gln Phe Phe
            340                 345                 350
```

```
Arg Val Tyr Gly Ile Asp Lys Pro Leu Glu Glu Gly Asn Pro Asp Asp
        355                 360                 365

Ile Leu Thr Met Val Ile Tyr Asn Ser Pro Glu Glu Tyr Lys Leu Asn
    370                 375                 380

Ser Val Leu Tyr Gly Tyr Asp Thr Asn Asn Gly Gly Met Tyr Ile Glu
385                 390                 395                 400

Pro Asp Gly Thr Phe Phe Thr Tyr Glu Arg Lys Ala Glu Glu Ser Thr
                405                 410                 415

Tyr Thr Leu Glu Glu Leu Phe Arg His Glu Tyr Thr His Tyr Leu Gln
            420                 425                 430

Gly Arg Tyr Ala Val Pro Gly Gln Trp Gly Arg Thr Lys Leu Tyr Asp
        435                 440                 445

Asn Asp Arg Leu Thr Trp Tyr Glu Glu Gly Gly Ala Glu Leu Phe Ala
    450                 455                 460

Gly Ser Thr Arg Thr Ser Gly Ile Leu Pro Arg Lys Ser Ile Val Ser
465                 470                 475                 480

Asn Ile His Asn Thr Thr Arg Asn Asn Arg Tyr Lys Leu Ser Asp Thr
                485                 490                 495

Val His Ser Lys Tyr Gly Ala Ser Phe Glu Phe Tyr Asn Tyr Ala Cys
            500                 505                 510

Met Phe Met Asp Tyr Met Tyr Asn Lys Asp Met Gly Ile Leu Asn Lys
        515                 520                 525

Leu Asn Asp Leu Ala Lys Asn Asn Asp Val Asp Gly Tyr Asp Asn Tyr
    530                 535                 540

Ile Arg Asp Leu Ser Ser Asn His Ala Leu Asn Asp Lys Tyr Gln Asp
545                 550                 555                 560

His Met Gln Glu Arg Ile Asp Asn Tyr Glu Asn Leu Thr Val Pro Phe
                565                 570                 575

Val Ala Asp Asp Tyr Leu Val Arg His Ala Tyr Lys Asn Pro Asn Glu
            580                 585                 590

Ile Tyr Ser Glu Ile Ser Glu Val Ala Lys Leu Lys Asp Ala Lys Ser
        595                 600                 605

Glu Val Lys Lys Ser Gln Tyr Phe Ser Thr Phe Thr Leu Arg Gly Ser
    610                 615                 620

Tyr Thr Gly Gly Ala Ser Lys Gly Lys Leu Glu Asp Gln Lys Ala Met
625                 630                 635                 640

Asn Lys Phe Ile Asp Asp Ser Leu Lys Lys Leu Asp Thr Tyr Ser Trp
                645                 650                 655

Ser Gly Tyr Lys Thr Leu Thr Ala Tyr Phe Thr Asn Tyr Lys Val Asp
            660                 665                 670

Ser Ser Asn Arg Val Thr Tyr Asp Val Val Phe His Gly Tyr Leu Pro
        675                 680                 685

Asn Glu Gly Asp Ser Lys Asn Ser Leu Pro Tyr Gly Lys Ile Asn Gly
    690                 695                 700

Thr Tyr Lys Gly Thr Glu Lys Glu Lys Ile Lys Phe Ser Ser Glu Gly
705                 710                 715                 720

Ser Phe Asp Pro Asp Gly Lys Ile Val Ser Tyr Glu Trp Asp Phe Gly
                725                 730                 735

Asp Gly Asn Lys Ser Asn Glu Glu Asn Pro Glu His Ser Tyr Asp Lys
            740                 745                 750

Val Gly Thr Tyr Thr Val Lys Leu Lys Val Thr Asp Asp Lys Gly Glu
        755                 760                 765
```

```
Ser Ser Val Ser Thr Thr Thr Ala Glu Ile Lys Asp Leu Ser Glu Asn
    770                 775                 780

Lys Leu Pro Val Ile Tyr Met His Val Pro Lys Ser Gly Ala Leu Asn
785                 790                 795                 800

Gln Lys Val Val Phe Tyr Gly Lys Gly Thr Tyr Asp Pro Asp Gly Ser
                805                 810                 815

Ile Ala Gly Tyr Gln Trp Asp Phe Gly Asp Gly Ser Asp Phe Ser Ser
            820                 825                 830

Glu Gln Asn Pro Ser His Val Tyr Thr Lys Lys Gly Glu Tyr Thr Val
        835                 840                 845

Thr Leu Arg Val Met Asp Ser Ser Gly Gln Met Ser Glu Lys Thr Met
    850                 855                 860

Lys Ile Lys Ile Thr Asp Pro Val Tyr Pro Ile Gly Thr Glu Lys Glu
865                 870                 875                 880

Pro Asn Asn Ser Lys Glu Thr Ala Ser Gly Pro Ile Val Pro Gly Ile
                885                 890                 895

Pro Val Ser Gly Thr Ile Glu Asn Thr Ser Asp Gln Asp Tyr Phe Tyr
            900                 905                 910

Phe Asp Val Ile Thr Pro Gly Glu Val Lys Ile Asp Ile Asn Lys Leu
        915                 920                 925

Gly Tyr Gly Gly Ala Thr Trp Val Val Tyr Asp Glu Asn Asn Asn Ala
    930                 935                 940

Val Ser Tyr Ala Thr Asp Asp Gly Gln Asn Leu Ser Gly Lys Phe Lys
945                 950                 955                 960

Ala Asp Lys Pro Gly Arg Tyr Tyr Ile His Leu Tyr Met Phe Asn Gly
                965                 970                 975

Ser Tyr Met Pro Tyr Arg Ile Asn Ile Glu Gly Ser Val Gly Arg
            980                 985                 990


<210> SEQ ID NO 7
<211> LENGTH: 443
<212> TYPE: PRT
<213> ORGANISM: Clostridium septicum

<400> SEQUENCE: 7

Met Ser Lys Lys Ser Phe Ala Lys Lys Val Ile Cys Thr Ser Met Ile
1               5                   10                  15

Ala Ile Gln Cys Ala Ala Val Val Pro His Val Gln Ala Tyr Ala Leu
            20                  25                  30

Thr Asn Leu Glu Glu Gly Gly Tyr Ala Asn His Asn Asn Ala Ser Ser
        35                  40                  45

Ile Lys Ile Phe Gly Tyr Glu Asp Asn Glu Asp Leu Lys Ala Lys Ile
    50                  55                  60

Ile Gln Asp Pro Glu Phe Ile Arg Asn Trp Ala Asn Val Ala His Ser
65                  70                  75                  80

Leu Gly Phe Gly Trp Cys Gly Gly Thr Ala Asn Pro Asn Val Gly Gln
                85                  90                  95

Gly Phe Glu Phe Lys Arg Glu Val Gly Ala Gly Gly Lys Val Ser Tyr
            100                 105                 110

Leu Leu Ser Ala Arg Tyr Asn Pro Asn Asp Pro Tyr Ala Ser Gly Tyr
        115                 120                 125

Arg Ala Lys Asp Arg Leu Ser Met Lys Ile Ser Asn Val Arg Phe Val
    130                 135                 140

Ile Asp Asn Asp Ser Ile Lys Leu Gly Thr Pro Lys Val Lys Lys Leu
145                 150                 155                 160
```

```
Ala Pro Leu Asn Ser Ala Ser Phe Asp Leu Ile Asn Glu Ser Lys Thr
                165                 170                 175

Glu Ser Lys Leu Ser Lys Thr Phe Asn Tyr Thr Thr Ser Lys Thr Val
            180                 185                 190

Ser Lys Thr Asp Asn Phe Lys Phe Gly Glu Lys Ile Gly Val Lys Thr
        195                 200                 205

Ser Phe Lys Val Gly Leu Glu Ala Ile Ala Asp Ser Lys Val Glu Thr
    210                 215                 220

Ser Phe Glu Phe Asn Ala Glu Gln Gly Trp Ser Asn Thr Asn Ser Thr
225                 230                 235                 240

Thr Glu Thr Lys Gln Glu Ser Thr Thr Tyr Thr Ala Thr Val Ser Pro
                245                 250                 255

Gln Thr Lys Lys Arg Leu Phe Leu Asp Val Leu Gly Ser Gln Ile Asp
            260                 265                 270

Ile Pro Tyr Glu Gly Lys Ile Tyr Met Glu Tyr Asp Ile Glu Leu Met
        275                 280                 285

Gly Phe Leu Arg Tyr Thr Gly Asn Ala Arg Glu Asp His Thr Glu Asp
    290                 295                 300

Arg Pro Thr Val Lys Leu Lys Phe Gly Lys Asn Gly Met Ser Ala Glu
305                 310                 315                 320

Glu His Leu Lys Asp Leu Tyr Ser His Lys Asn Ile Asn Gly Tyr Ser
                325                 330                 335

Glu Trp Asp Trp Lys Trp Val Asp Glu Lys Phe Gly Tyr Leu Phe Lys
            340                 345                 350

Asn Ser Tyr Asp Ala Leu Thr Ser Arg Lys Leu Gly Gly Ile Ile Lys
        355                 360                 365

Gly Ser Phe Thr Asn Ile Asn Gly Thr Lys Ile Val Ile Arg Glu Gly
    370                 375                 380

Lys Glu Ile Pro Leu Pro Asp Lys Lys Arg Arg Gly Lys Arg Ser Val
385                 390                 395                 400

Asp Ser Leu Asp Ala Arg Leu Gln Asn Glu Gly Ile Arg Ile Glu Asn
                405                 410                 415

Ile Glu Thr Gln Asp Val Pro Gly Phe Arg Leu Asn Ser Ile Thr Tyr
            420                 425                 430

Asn Asp Lys Lys Leu Ile Leu Ile Asn Asn Ile
        435                 440


<210> SEQ ID NO 8
<211> LENGTH: 419
<212> TYPE: PRT
<213> ORGANISM: Clostridium histolyticum

<400> SEQUENCE: 8

Met Leu Lys Lys Ser Phe Phe Lys Lys Ala Ile Cys Ala Ser Leu Val
1               5                   10                  15

Val Leu Gln Cys Leu Ile Leu Val Ser Pro Ala Gln Thr Leu Ala Ser
            20                  25                  30

Thr Asp Leu Pro Thr Lys Gly Lys Thr Ser Ile Glu Leu Phe Asn Tyr
        35                  40                  45

Glu Asp His Met Ala His Cys Leu Gly Phe Gly Trp Cys Phe Gly Thr
    50                  55                  60

Ala Ser Lys Glu Ile Gly Glu Asp Phe Glu Phe Lys Arg Ala Glu Glu
65                  70                  75                  80

Glu Gly Lys Thr Val Tyr Tyr Leu Ser Ala Arg Tyr Asn Gln Asn Asp
```

-continued

```
                85                  90                  95

Pro Tyr Ala Lys Gly Tyr Tyr Arg Ala His Asp Arg Leu Val Met Lys
            100                 105                 110

Val Ser Asn Ala Arg Phe Phe Ile Asp His Asp Ser Leu Thr Leu Gly
        115                 120                 125

Lys Ala Lys Val Ile Ser Leu Asp Pro Leu Ala Ser Ser Thr Leu Gln
    130                 135                 140

Val Val Asn Lys Ser Asn Ser Glu Ala Lys Thr Ser Leu Ser Phe Gly
145                 150                 155                 160

Tyr Glu Thr Thr Glu Ser Thr Ser Lys Thr Asp His Val Lys Phe Gly
                165                 170                 175

Glu Lys Ile Gly Ile Lys Ser Ser Phe Asn Val Lys Val Pro Phe Ile
            180                 185                 190

Gly Glu Lys Ser Ile Glu Thr Asn Leu Glu Phe Asn Ser Glu Gln Gly
        195                 200                 205

Trp Ser Asn Thr Lys Thr Asn Ser Val Thr Thr Lys His Thr Ile Ser
    210                 215                 220

His Thr Thr Thr Thr Pro Ala Lys Ser Arg Lys Lys Val Arg Leu Asn
225                 230                 235                 240

Val Leu Asn Lys Lys Ser Asp Ile Pro Tyr Glu Gly Lys Ile Tyr Met
                245                 250                 255

Glu Tyr Asp Ile Glu Phe Phe Gly Phe Leu Arg Tyr Thr Gly Asn Ala
            260                 265                 270

Arg Lys Asp His Pro Thr Asp Arg Pro Ser Val Ser Val Lys Phe Gly
        275                 280                 285

Gly Lys Asn Asn Met Ser Ala Val Asp His Ile Ile Asp Leu Tyr Lys
    290                 295                 300

His Lys Asp Ile Asn Gly Tyr Ser Glu Trp Asp Trp Asn Trp Ile Glu
305                 310                 315                 320

Glu Asn Phe Tyr Asp Arg Phe Ser Glu Tyr Ser Ser Asn Val Ala Ser
                325                 330                 335

Gln Tyr Phe Gly Gly Ile Ile Ser Gly Val Phe Thr Asn Val Gly Gly
            340                 345                 350

Thr Asp Val Lys Val Glu Glu Gly Arg Glu Arg Pro Leu Lys Asn Thr
        355                 360                 365

Ser Ser Thr Glu Gln Asn Val Glu Val Gln Asn Phe Lys Ser Ser Lys
    370                 375                 380

Ser Lys Glu Phe Arg Val Gly Ser Leu Thr Tyr Thr Thr Pro Asn Gly
385                 390                 395                 400

Glu Gln Thr Ile Tyr Pro Glu Asp Val Ser Ser Leu Asn Ala Asn Asn
                405                 410                 415

Asn Glu Asn


<210> SEQ ID NO 9
<211> LENGTH: 548
<212> TYPE: PRT
<213> ORGANISM: Bacillus proteolyticus

<400> SEQUENCE: 9

Met Lys Met Lys Met Lys Leu Ala Ser Phe Gly Leu Ala Ala Gly Leu
1               5                   10                  15

Ala Ala Gln Val Phe Leu Pro Tyr Asn Ala Leu Ala Ser Thr Glu His
            20                  25                  30

Val Thr Trp Asn Gln Gln Phe Gln Thr Pro Gln Phe Ile Ser Gly Asp
```

-continued

```
        35                  40                  45

Leu Leu Lys Val Asn Gly Thr Ser Pro Glu Glu Leu Val Tyr Gln Tyr
    50                  55                  60

Val Glu Lys Asn Glu Asn Lys Phe Lys Phe His Glu Asn Ala Lys Asp
65                  70                  75                  80

Thr Leu Gln Leu Lys Glu Lys Lys Asn Asp Asn Leu Gly Phe Thr Phe
                85                  90                  95

Met Arg Phe Gln Gln Thr Tyr Lys Gly Ile Pro Val Phe Gly Ala Val
            100                 105                 110

Val Thr Ser His Val Lys Asp Gly Thr Leu Thr Ala Leu Ser Gly Thr
        115                 120                 125

Leu Ile Pro Asn Leu Asp Thr Lys Gly Ser Leu Lys Ser Gly Lys Lys
    130                 135                 140

Leu Ser Glu Lys Gln Ala Arg Asp Ile Ala Glu Lys Asp Leu Val Ala
145                 150                 155                 160

Asn Val Thr Lys Glu Val Pro Glu Tyr Glu Gln Gly Lys Asp Thr Glu
                165                 170                 175

Phe Val Val Tyr Val Asn Gly Asp Glu Ala Ser Leu Ala Tyr Val Val
            180                 185                 190

Asn Leu Asn Phe Leu Thr Pro Glu Pro Gly Asn Trp Leu Tyr Ile Ile
        195                 200                 205

Asp Ala Val Asp Gly Lys Ile Leu Asn Lys Phe Asn Gln Leu Asp Ala
    210                 215                 220

Ala Lys Pro Gly Asp Val Lys Ser Ile Thr Gly Thr Ser Thr Val Gly
225                 230                 235                 240

Val Gly Arg Gly Val Leu Gly Asp Gln Lys Asn Ile Asn Thr Thr Tyr
                245                 250                 255

Ser Thr Tyr Tyr Tyr Leu Gln Asp Asn Thr Arg Gly Asn Gly Ile Phe
            260                 265                 270

Thr Tyr Asp Ala Lys Tyr Arg Thr Thr Leu Pro Gly Ser Leu Trp Ala
        275                 280                 285

Asp Ala Asp Asn Gln Phe Phe Ala Ser Tyr Asp Ala Pro Ala Val Asp
    290                 295                 300

Ala His Tyr Tyr Ala Gly Val Thr Tyr Asp Tyr Tyr Lys Asn Val His
305                 310                 315                 320

Asn Arg Leu Ser Tyr Asp Gly Asn Asn Ala Ala Ile Arg Ser Ser Val
                325                 330                 335

His Tyr Ser Gln Gly Tyr Asn Asn Ala Phe Trp Asn Gly Ser Gln Met
            340                 345                 350

Val Tyr Gly Asp Gly Asp Gly Gln Thr Phe Ile Pro Leu Ser Gly Gly
        355                 360                 365

Ile Asp Val Val Ala His Glu Leu Thr His Ala Val Thr Asp Tyr Thr
    370                 375                 380

Ala Gly Leu Ile Tyr Gln Asn Glu Ser Gly Ala Ile Asn Glu Ala Ile
385                 390                 395                 400

Ser Asp Ile Phe Gly Thr Leu Val Glu Phe Tyr Ala Asn Lys Asn Pro
                405                 410                 415

Asp Trp Glu Ile Gly Glu Asp Val Tyr Thr Pro Gly Ile Ser Gly Asp
            420                 425                 430

Ser Leu Arg Ser Met Ser Asp Pro Ala Lys Tyr Gly Asp Pro Asp His
        435                 440                 445

Tyr Ser Lys Arg Tyr Thr Gly Thr Gln Asp Asn Gly Gly Val His Ile
    450                 455                 460
```

```
Asn Ser Gly Ile Ile Asn Lys Ala Ala Tyr Leu Ile Ser Gln Gly Gly
465                 470                 475                 480

Thr His Tyr Gly Val Ser Val Val Gly Ile Gly Arg Asp Lys Leu Gly
                485                 490                 495

Lys Ile Phe Tyr Arg Ala Leu Thr Gln Tyr Leu Thr Pro Thr Ser Asn
            500                 505                 510

Phe Ser Gln Leu Arg Ala Ala Ala Val Gln Ser Ala Thr Asp Leu Tyr
        515                 520                 525

Gly Ser Thr Ser Gln Glu Val Ala Ser Val Lys Gln Ala Phe Asp Ala
    530                 535                 540

Val Gly Val Lys
545


<210> SEQ ID NO 10
<211> LENGTH: 532
<212> TYPE: PRT
<213> ORGANISM: Clostridium histolyticum

<400> SEQUENCE: 10

Met Lys Lys Lys Phe Leu Ser Phe Ile Ile Ile Ser Ala Ile Ser Leu
1               5                   10                  15

Asn Ile Ser Ser Met Thr Val Gly Ala Lys Gln Val Lys Glu Ile Lys
            20                  25                  30

Pro Pro Lys Asp Lys Glu Ser Ile Ser Val Leu Lys Thr Asp Leu Glu
        35                  40                  45

Lys Thr Lys Asn Ile Lys Ser Asn Asn Lys Glu Gly Asp Asp Val Thr
    50                  55                  60

Lys Val Val Lys Ser Ala Leu Lys Glu Glu Gly Asn Leu Gly Asp Phe
65                  70                  75                  80

Lys Val Asp Asn Lys Glu Thr Asp Val Lys Gly Lys Lys His Leu Arg
                85                  90                  95

Ser Gln Met Phe Ile Asp Gly Ile Pro Val Tyr Gly Ser Gln Val Ile
            100                 105                 110

Ile His Thr Asn Lys Asp Gly Gln Val Tyr Ser Val Asn Gly Lys Val
        115                 120                 125

Asp Lys Gln Pro Lys Ala Gln Ser Phe Lys Asn Arg Val Arg Ile Lys
    130                 135                 140

Asp Asp Lys Ala Ile Lys Ile Ala Glu Asp Ser Leu Gly Lys Glu Ile
145                 150                 155                 160

Lys Lys Asn Lys Asn Tyr His Ser Glu Ser Lys Leu Tyr Leu Tyr Lys
                165                 170                 175

Val Asn Gly Asp Leu Gln Pro Val Tyr Leu Val Lys Ile Ser Ser Thr
            180                 185                 190

Glu Pro Glu Ala Ser Phe Trp His Met Phe Val Ser Ala Glu Asn Gly
        195                 200                 205

Lys Ile Val Asp Lys Tyr Asn Ala Leu Ser Cys Gln Ala Thr His Ala
    210                 215                 220

Gln Val Arg Gly Val Asn Ser Ser Gly Glu His Lys Ile Leu Asn Gly
225                 230                 235                 240

Met Phe Glu Asn Gly Arg Tyr Phe Leu Ala Asp Ser Thr Arg Pro Ser
                245                 250                 255

Asn Gly Tyr Ile Leu Thr Tyr Asp Ala Asn Asn Gln Glu Tyr Gly Phe
            260                 265                 270

Pro Gly Ser Leu Phe Ser Asn Leu Thr Gly Ile Phe Asp Ser Asp Arg
```

-continued

```
        275                 280                 285

Gln Lys Ala Gly Val Asp Ala His His Asn Leu Thr Gln Val Tyr Asp
    290                 295                 300

Tyr Tyr Lys Asn Val Leu Asn Arg Asp Ser Phe Asp Gly Lys Gly Ala
305                 310                 315                 320

Ser Ile Ile Ser Ser Val His Val Gly Asn Asn Leu Asn Asn Ala Phe
                325                 330                 335

Trp Asn Gly Arg Gln Ile Leu Phe Gly Asp Gly Asp Gly Val Thr Phe
            340                 345                 350

Ser Asn Leu Ala Lys Cys Leu Glu Val Thr Ala His Glu Phe Thr His
        355                 360                 365

Ala Val Thr Gln Ser Thr Ala Gly Leu Glu Tyr Arg Phe Gln Ser Gly
    370                 375                 380

Ala Leu Asn Glu Ala Phe Ser Asp Ile Leu Gly Ile Ala Val His Ser
385                 390                 395                 400

Asp Pro Asn Asp Trp Glu Ile Gly Glu Asp Ile Tyr Thr Pro Asn Val
                405                 410                 415

Ala Gly Asp Ala Leu Arg Ser Met Ser Asn Pro Arg Leu Tyr Arg Gln
            420                 425                 430

Pro Asp His Met Lys Asp Tyr Leu Tyr Trp Asp Tyr Ser Met Asp Lys
        435                 440                 445

Gly Gly Val His Tyr Asn Ser Gly Ile Pro Asn Lys Ala Ala Tyr Leu
    450                 455                 460

Met Gly Lys Glu Val Gly Lys Asp Ser Met Ala Lys Ile Tyr Tyr His
465                 470                 475                 480

Ala Leu Val Asn Tyr Leu Thr Pro Gln Ser Thr Phe Glu Asp Ala Arg
                485                 490                 495

Asn Ala Val Val Ser Ser Ala Ile Asp Leu His Gly Glu Asn Ser Lys
            500                 505                 510

Glu His Lys Leu Ala Ile Lys Ser Trp Ala Asp Val Gly Val Gly Glu
        515                 520                 525

Glu Ala Val Arg
    530


<210> SEQ ID NO 11
<211> LENGTH: 204
<212> TYPE: PRT
<213> ORGANISM: Bacillus proteolyticus

<400> SEQUENCE: 11

Ser Thr Glu His Val Thr Trp Asn Gln Gln Phe Gln Thr Pro Gln Phe
1               5                   10                  15

Ile Ser Gly Asp Leu Leu Lys Val Asn Gly Thr Ser Pro Glu Glu Leu
            20                  25                  30

Val Tyr Gln Tyr Val Glu Lys Asn Glu Asn Lys Phe Lys Phe His Glu
        35                  40                  45

Asn Ala Lys Asp Thr Leu Gln Leu Lys Glu Lys Lys Asn Asp Asn Leu
    50                  55                  60

Gly Phe Thr Phe Met Arg Phe Gln Gln Thr Tyr Lys Gly Ile Pro Val
65                  70                  75                  80

Phe Gly Ala Val Val Thr Ser His Val Lys Asp Gly Thr Leu Thr Ala
                85                  90                  95

Leu Ser Gly Thr Leu Ile Pro Asn Leu Asp Thr Lys Gly Ser Leu Lys
            100                 105                 110
```

```
Ser Gly Lys Lys Leu Ser Glu Lys Gln Ala Arg Asp Ile Ala Glu Lys
        115                 120                 125

Asp Leu Val Ala Asn Val Thr Lys Glu Val Pro Glu Tyr Glu Gln Gly
    130                 135                 140

Lys Asp Thr Glu Phe Val Val Tyr Val Asn Gly Asp Glu Ala Ser Leu
145                 150                 155                 160

Ala Tyr Val Val Asn Leu Asn Phe Leu Thr Pro Glu Pro Gly Asn Trp
                165                 170                 175

Leu Tyr Ile Ile Asp Ala Val Asp Gly Lys Ile Leu Asn Lys Phe Asn
            180                 185                 190

Gln Leu Asp Ala Ala Lys Pro Gly Asp Val Lys Ser
        195                 200


<210> SEQ ID NO 12
<211> LENGTH: 194
<212> TYPE: PRT
<213> ORGANISM: Clostridium histolyticum

<400> SEQUENCE: 12

Lys Pro Pro Lys Asp Lys Glu Ser Ile Ser Val Leu Lys Thr Asp Leu
1               5                   10                  15

Glu Lys Thr Lys Asn Ile Lys Ser Asn Asn Lys Glu Gly Asp Asp Val
            20                  25                  30

Thr Lys Val Val Lys Ser Ala Leu Lys Glu Glu Gly Asn Leu Gly Asp
        35                  40                  45

Phe Lys Val Asp Asn Lys Glu Thr Asp Val Lys Gly Lys Lys His Leu
    50                  55                  60

Arg Ser Gln Met Phe Ile Asp Gly Ile Pro Val Tyr Gly Ser Gln Val
65                  70                  75                  80

Ile Ile His Thr Asn Lys Asp Gly Gln Val Tyr Ser Val Asn Gly Lys
                85                  90                  95

Val Asp Lys Gln Pro Lys Ala Gln Ser Phe Lys Asn Arg Val Arg Ile
            100                 105                 110

Lys Asp Asp Lys Ala Ile Lys Ile Ala Glu Asp Ser Leu Gly Lys Glu
        115                 120                 125

Ile Lys Lys Asn Lys Asn Tyr His Ser Glu Ser Lys Leu Tyr Leu Tyr
    130                 135                 140

Lys Val Asn Gly Asp Leu Gln Pro Val Tyr Leu Val Lys Ile Ser Ser
145                 150                 155                 160

Thr Glu Pro Glu Ala Ser Phe Trp His Met Phe Val Ser Ala Glu Asn
                165                 170                 175

Gly Lys Ile Val Asp Lys Tyr Asn Ala Leu Ser Cys Gln Ala Thr His
            180                 185                 190

Ala Gln


<210> SEQ ID NO 13
<211> LENGTH: 316
<212> TYPE: PRT
<213> ORGANISM: Bacillus proteolyticus

<400> SEQUENCE: 13

Ile Thr Gly Thr Ser Thr Val Gly Val Gly Arg Gly Val Leu Gly Asp
1               5                   10                  15

Gln Lys Asn Ile Asn Thr Thr Tyr Ser Thr Tyr Tyr Tyr Leu Gln Asp
            20                  25                  30

Asn Thr Arg Gly Asn Gly Ile Phe Thr Tyr Asp Ala Lys Tyr Arg Thr
```

```
        35                  40                  45

Thr Leu Pro Gly Ser Leu Trp Ala Asp Ala Asp Asn Gln Phe Phe Ala
    50                  55                  60

Ser Tyr Asp Ala Pro Ala Val Asp Ala His Tyr Tyr Ala Gly Val Thr
65                  70                  75                  80

Tyr Asp Tyr Tyr Lys Asn Val His Asn Arg Leu Ser Tyr Asp Gly Asn
                85                  90                  95

Asn Ala Ala Ile Arg Ser Ser Val His Tyr Ser Gln Gly Tyr Asn Asn
            100                 105                 110

Ala Phe Trp Asn Gly Ser Gln Met Val Tyr Gly Asp Gly Asp Gly Gln
        115                 120                 125

Thr Phe Ile Pro Leu Ser Gly Gly Ile Asp Val Val Ala His Glu Leu
    130                 135                 140

Thr His Ala Val Thr Asp Tyr Thr Ala Gly Leu Ile Tyr Gln Asn Glu
145                 150                 155                 160

Ser Gly Ala Ile Asn Glu Ala Ile Ser Asp Ile Phe Gly Thr Leu Val
                165                 170                 175

Glu Phe Tyr Ala Asn Lys Asn Pro Asp Trp Glu Ile Gly Glu Asp Val
            180                 185                 190

Tyr Thr Pro Gly Ile Ser Gly Asp Ser Leu Arg Ser Met Ser Asp Pro
        195                 200                 205

Ala Lys Tyr Gly Asp Pro Asp His Tyr Ser Lys Arg Tyr Thr Gly Thr
    210                 215                 220

Gln Asp Asn Gly Gly Val His Ile Asn Ser Gly Ile Ile Asn Lys Ala
225                 230                 235                 240

Ala Tyr Leu Ile Ser Gln Gly Gly Thr His Tyr Gly Val Ser Val Val
                245                 250                 255

Gly Ile Gly Arg Asp Lys Leu Gly Lys Ile Phe Tyr Arg Ala Leu Thr
            260                 265                 270

Gln Tyr Leu Thr Pro Thr Ser Asn Phe Ser Gln Leu Arg Ala Ala Ala
        275                 280                 285

Val Gln Ser Ala Thr Asp Leu Tyr Gly Ser Thr Ser Gln Glu Val Ala
    290                 295                 300

Ser Val Lys Gln Ala Phe Asp Ala Val Gly Val Lys
305                 310                 315


<210> SEQ ID NO 14
<211> LENGTH: 307
<212> TYPE: PRT
<213> ORGANISM: Clostridium histolyticum

<400> SEQUENCE: 14

Val Arg Gly Val Asn Ser Ser Gly Glu His Lys Ile Leu Asn Gly Met
1               5                   10                  15

Phe Glu Asn Gly Arg Tyr Phe Leu Ala Asp Ser Thr Arg Pro Ser Asn
            20                  25                  30

Gly Tyr Ile Leu Thr Tyr Asp Ala Asn Asn Gln Glu Tyr Gly Phe Pro
        35                  40                  45

Gly Ser Leu Phe Ser Asn Leu Thr Gly Ile Phe Asp Ser Asp Arg Gln
    50                  55                  60

Lys Ala Gly Val Asp Ala His His Asn Leu Thr Gln Val Tyr Asp Tyr
65                  70                  75                  80

Tyr Lys Asn Val Leu Asn Arg Asp Ser Phe Asp Gly Lys Gly Ala Ser
                85                  90                  95
```

-continued

```
Ile Ile Ser Ser Val His Val Gly Asn Asn Leu Asn Asn Ala Phe Trp
            100                 105                 110

Asn Gly Arg Gln Ile Leu Phe Gly Asp Gly Asp Gly Val Thr Phe Ser
        115                 120                 125

Asn Leu Ala Lys Cys Leu Glu Val Thr Ala His Glu Phe Thr His Ala
    130                 135                 140

Val Thr Gln Ser Thr Ala Gly Leu Glu Tyr Arg Phe Gln Ser Gly Ala
145                 150                 155                 160

Leu Asn Glu Ala Phe Ser Asp Ile Leu Gly Ile Ala Val His Ser Asp
                165                 170                 175

Pro Asn Asp Trp Glu Ile Gly Glu Asp Ile Tyr Thr Pro Asn Val Ala
            180                 185                 190

Gly Asp Ala Leu Arg Ser Met Ser Asn Pro Arg Leu Tyr Arg Gln Pro
        195                 200                 205

Asp His Met Lys Asp Tyr Leu Tyr Trp Asp Tyr Ser Met Asp Lys Gly
    210                 215                 220

Gly Val His Tyr Asn Ser Gly Ile Pro Asn Lys Ala Ala Tyr Leu Met
225                 230                 235                 240

Gly Lys Glu Val Gly Lys Asp Ser Met Ala Lys Ile Tyr Tyr His Ala
                245                 250                 255

Leu Val Asn Tyr Leu Thr Pro Gln Ser Thr Phe Glu Asp Ala Arg Asn
            260                 265                 270

Ala Val Val Ser Ser Ala Ile Asp Leu His Gly Glu Asn Ser Lys Glu
        275                 280                 285

His Lys Leu Ala Ile Lys Ser Trp Ala Asp Val Gly Val Gly Glu Glu
    290                 295                 300

Ala Val Arg
305


<210> SEQ ID NO 15
<211> LENGTH: 500
<212> TYPE: PRT
<213> ORGANISM: Clostridium perfringens

<400> SEQUENCE: 15

Met Ile Arg Phe Lys Lys Thr Lys Leu Ile Ala Ser Ile Ala Met Ala
1               5                   10                  15

Leu Cys Leu Phe Ser Gln Pro Val Ile Ser Phe Ser Lys Asp Ile Thr
            20                  25                  30

Asp Lys Asn Gln Ser Ile Asp Ser Gly Ile Ser Ser Leu Ser Tyr Asn
        35                  40                  45

Arg Asn Glu Val Leu Ala Ser Asn Gly Asp Lys Ile Glu Ser Phe Val
    50                  55                  60

Pro Lys Glu Gly Lys Lys Thr Gly Asn Lys Phe Ile Val Val Glu Arg
65                  70                  75                  80

Gln Lys Arg Ser Leu Thr Thr Ser Pro Val Asp Ile Ser Ile Ile Asp
                85                  90                  95

Ser Val Asn Asp Arg Thr Tyr Pro Gly Ala Leu Gln Leu Ala Asp Lys
            100                 105                 110

Ala Phe Val Glu Asn Arg Pro Thr Ile Leu Met Val Lys Arg Lys Pro
        115                 120                 125

Ile Asn Ile Asn Ile Asp Leu Pro Gly Leu Lys Gly Glu Asn Ser Ile
    130                 135                 140

Lys Val Asp Asp Pro Thr Tyr Gly Lys Val Ser Gly Ala Ile Asp Glu
145                 150                 155                 160
```

```
Leu Val Ser Lys Trp Asn Glu Lys Tyr Ser Ser Thr His Thr Leu Pro
                165                 170                 175

Ala Arg Thr Gln Tyr Ser Glu Ser Met Val Tyr Ser Lys Ser Gln Ile
            180                 185                 190

Ser Ser Ala Leu Asn Val Asn Ala Lys Val Leu Glu Asn Ser Leu Gly
        195                 200                 205

Val Asp Phe Asn Ala Val Ala Asn Asn Glu Lys Lys Val Met Ile Leu
    210                 215                 220

Ala Tyr Lys Gln Ile Phe Tyr Thr Val Ser Ala Asp Leu Pro Lys Asn
225                 230                 235                 240

Pro Ser Asp Leu Phe Asp Asp Ser Val Thr Phe Asn Asp Leu Lys Gln
                245                 250                 255

Lys Gly Val Ser Asn Glu Ala Pro Pro Leu Met Val Ser Asn Val Ala
            260                 265                 270

Tyr Gly Arg Thr Ile Tyr Val Lys Leu Glu Thr Thr Ser Ser Ser Lys
        275                 280                 285

Asp Val Gln Ala Ala Phe Lys Ala Leu Ile Lys Asn Thr Asp Ile Lys
    290                 295                 300

Asn Ser Gln Gln Tyr Lys Asp Ile Tyr Glu Asn Ser Ser Phe Thr Ala
305                 310                 315                 320

Val Val Leu Gly Gly Asp Ala Gln Glu His Asn Lys Val Val Thr Lys
                325                 330                 335

Asp Phe Asp Glu Ile Arg Lys Val Ile Lys Asp Asn Ala Thr Phe Ser
            340                 345                 350

Thr Lys Asn Pro Ala Tyr Pro Ile Ser Tyr Thr Ser Val Phe Leu Lys
        355                 360                 365

Asp Asn Ser Val Ala Ala Val His Asn Lys Thr Asp Tyr Ile Glu Thr
    370                 375                 380

Thr Ser Thr Glu Tyr Ser Lys Gly Lys Ile Asn Leu Asp His Ser Gly
385                 390                 395                 400

Ala Tyr Val Ala Gln Phe Glu Val Ala Trp Asp Glu Val Ser Tyr Asp
                405                 410                 415

Lys Glu Gly Asn Glu Val Leu Thr His Lys Thr Trp Asp Gly Asn Tyr
            420                 425                 430

Gln Asp Lys Thr Ala His Tyr Ser Thr Val Ile Pro Leu Glu Ala Asn
        435                 440                 445

Ala Arg Asn Ile Arg Ile Lys Ala Arg Glu Cys Thr Gly Leu Ala Trp
    450                 455                 460

Glu Trp Trp Arg Asp Val Ile Ser Glu Tyr Asp Val Pro Leu Thr Asn
465                 470                 475                 480

Asn Ile Asn Val Ser Ile Trp Gly Thr Thr Leu Tyr Pro Gly Ser Ser
                485                 490                 495

Ile Thr Tyr Asn
            500
```

<210> SEQ ID NO 16
<211> LENGTH: 520
<212> TYPE: PRT
<213> ORGANISM: Clostridium histolyticum

<400> SEQUENCE: 16

```
Met Lys Ile Thr Lys Lys Gly Leu Arg Ser Leu Ser Arg Leu Met Leu
1               5                   10                  15

Ile Thr Met Ile Thr Gly Leu Thr Tyr Asn Tyr His Leu Gly Ser Ser
```

-continued

```
            20                  25                  30

Phe Asn Gly Asn Arg Val Val Leu Ala Asn Pro Asn Thr Lys Thr Asp
        35                  40                  45

Asn Leu Ile Lys Asn Asn Ser Asp Glu Ile Asp Glu Lys Ile Tyr Gly
    50                  55                  60

Leu Ser Tyr Asp Pro Tyr Lys Ile Leu Ser Tyr Asn Gly Glu Lys Val
65                  70                  75                  80

Glu Asn Phe Val Pro Ala Glu Cys Ser Glu Asn Ser Gly Lys Phe Thr
                85                  90                  95

Val Ile Lys Arg Glu Lys Lys Asn Ile Ser Asp Ser Thr Thr Asp Ile
            100                 105                 110

Ser Ile Met Asp Ser Ile Asn Asp Arg Thr Tyr Pro Gly Ala Ile Gln
        115                 120                 125

Leu Ala Asn Arg Asp Leu Ile Glu Asn Lys Pro Asn Leu Ile Ser Cys
    130                 135                 140

Glu Arg Lys Pro Ile Thr Ile Ser Val Asp Leu Pro Gly Met Gly Glu
145                 150                 155                 160

Asp Gly Lys Lys Val Val Asn Ser Pro Thr Tyr Ser Ser Val Asn Ser
                165                 170                 175

Ala Ile Asn Tyr Leu Leu Asp Thr Trp Asn Ser Lys Tyr Ser Ser Lys
            180                 185                 190

Tyr Thr Ile Pro Thr Arg Met Asn Tyr Ser Asp Thr Met Val Tyr Ser
        195                 200                 205

Lys Ser Gln Leu Ser Thr Met Phe Gly Cys Asn Phe Lys Thr Leu Ser
    210                 215                 220

Lys Ser Leu Asn Ile Asp Phe Asp Ser Ile Phe Lys Gly Glu Lys Lys
225                 230                 235                 240

Ala Met Ile Leu Ser Tyr Lys Gln Ile Phe Tyr Thr Val Ser Val Asp
                245                 250                 255

Gly Pro Asn Arg Pro Ser Asp Leu Phe Gly Tyr Ser Val Thr Ser Lys
            260                 265                 270

Ser Leu Ala Leu Lys Gly Val Asn Asn Asp Asn Pro Pro Ala Tyr Val
        275                 280                 285

Ser Asn Val Ala Tyr Gly Arg Thr Val Tyr Val Lys Leu Glu Thr Thr
    290                 295                 300

Ser Lys Ser Ser Lys Val Lys Ala Ala Phe Lys Ala Leu Val Glu Asn
305                 310                 315                 320

Gln Asp Ile Ser Ser Asn Ala Glu Tyr Lys Asp Ile Ile Asn Gln Ser
                325                 330                 335

Ser Phe Thr Ala Thr Val Leu Gly Gly Gly Ala Gln Lys His Asn Lys
            340                 345                 350

Val Val Thr Lys Asp Phe Asp Val Ile Arg Asn Ile Ile Lys Asn Asn
        355                 360                 365

Ser Val Tyr Ser Pro Gln Asn Pro Gly Tyr Pro Ile Ser Tyr Thr Ser
    370                 375                 380

Thr Phe Leu Lys Asp Asn Lys Ile Ala Thr Val Asn Asn Arg Thr Glu
385                 390                 395                 400

Tyr Ile Glu Thr Thr Ala Thr Glu Tyr Asp Ser Gly Lys Ile Met Leu
                405                 410                 415

Asp His Ser Gly Val Tyr Val Ala Gln Phe Glu Val Thr Trp Asp Glu
            420                 425                 430

Val Ser Tyr Asp Lys Gln Gly Asn Glu Ile Ile Glu His Lys Ser Trp
        435                 440                 445
```

```
Ser Gly Asn Asn Ser Asp Arg Thr Ala His Phe Asn Thr Glu Leu Tyr
    450                 455                 460

Leu Lys Gly Asn Ala Arg Asn Ile Ser Ile Lys Ala Lys Glu Cys Thr
465                 470                 475                 480

Gly Leu Ala Trp Glu Trp Trp Arg Thr Val Val Asp Ala Lys Asn Leu
                485                 490                 495

Pro Leu Val Lys Glu Arg Lys Leu Ser Ile Trp Gly Thr Thr Leu Tyr
            500                 505                 510

Pro Arg Tyr Ser Met Glu Glu Lys
        515                 520
```

<210> SEQ ID NO 17
<211> LENGTH: 526
<212> TYPE: PRT
<213> ORGANISM: Clostridium histolyticum

<400> SEQUENCE: 17

```
Met Leu Arg Arg Lys Val Ser Thr Leu Leu Met Thr Ala Leu Ile Thr
1               5                   10                  15

Thr Ser Phe Leu Asn Ser Lys Pro Val Tyr Ala Asn Pro Val Thr Lys
            20                  25                  30

Ser Lys Asp Asn Asn Leu Lys Glu Val Gln Gln Val Thr Ser Lys Ser
        35                  40                  45

Asn Lys Asn Lys Asn Gln Lys Val Thr Ile Met Tyr Tyr Cys Asp Ala
    50                  55                  60

Asp Asn Asn Leu Glu Gly Ser Leu Leu Asn Asp Ile Glu Glu Met Lys
65                  70                  75                  80

Thr Gly Tyr Lys Asp Ser Pro Asn Leu Asn Leu Ile Ala Leu Val Asp
                85                  90                  95

Arg Ser Pro Arg Tyr Ser Ser Asp Glu Lys Val Leu Gly Glu Asp Phe
            100                 105                 110

Ser Asp Thr Arg Leu Tyr Lys Ile Glu His Asn Lys Ala Asn Arg Leu
        115                 120                 125

Asp Gly Lys Asn Glu Phe Pro Glu Ile Ser Thr Thr Ser Lys Tyr Glu
    130                 135                 140

Ala Asn Met Gly Asp Pro Glu Val Leu Lys Lys Phe Ile Asp Tyr Cys
145                 150                 155                 160

Lys Ser Asn Tyr Glu Ala Asp Lys Tyr Val Leu Ile Met Ala Asn His
                165                 170                 175

Gly Gly Gly Ala Arg Glu Lys Ser Asn Pro Arg Leu Asn Arg Ala Ile
            180                 185                 190

Cys Trp Asp Asp Ser Asn Leu Asp Lys Asn Gly Glu Ala Asp Cys Leu
        195                 200                 205

Tyr Met Gly Glu Ile Ser Asp His Leu Thr Glu Lys Gln Ser Val Asp
    210                 215                 220

Leu Leu Ala Phe Asp Ala Cys Leu Met Gly Thr Ala Glu Val Ala Tyr
225                 230                 235                 240

Gln Tyr Arg Pro Gly Asn Gly Gly Phe Ser Ala Asp Thr Leu Val Ala
                245                 250                 255

Ser Ser Pro Val Val Trp Gly Pro Gly Phe Lys Tyr Asp Lys Ile Phe
            260                 265                 270

Asp Arg Ile Lys Ala Gly Gly Gly Thr Asn Asn Glu Asp Asp Leu Thr
        275                 280                 285

Leu Gly Gly Lys Glu Gln Asn Phe Asp Pro Ala Thr Ile Thr Asn Glu
```

```
    290                 295                 300

Gln Leu Gly Ala Leu Phe Val Glu Glu Gln Arg Asp Ser Thr His Ala
305                 310                 315                 320

Asn Gly Arg Tyr Asp Gln His Leu Ser Phe Tyr Asp Leu Lys Lys Ala
                325                 330                 335

Glu Ser Val Lys Arg Ala Ile Asp Asn Leu Ala Val Asn Leu Ser Asn
            340                 345                 350

Glu Asn Lys Lys Ser Glu Ile Glu Lys Leu Arg Gly Ser Gly Ile His
        355                 360                 365

Thr Asp Leu Met His Tyr Phe Asp Glu Tyr Ser Glu Gly Glu Trp Val
    370                 375                 380

Glu Tyr Pro Tyr Phe Asp Val Tyr Asp Leu Cys Glu Lys Ile Asn Lys
385                 390                 395                 400

Ser Glu Asn Phe Ser Ser Lys Thr Lys Asp Leu Ala Ser Asn Ala Met
                405                 410                 415

Asn Lys Leu Asn Glu Met Ile Val Tyr Ser Phe Gly Asp Pro Ser Asn
            420                 425                 430

Asn Phe Lys Glu Gly Lys Asn Gly Leu Ser Ile Phe Leu Pro Asn Gly
        435                 440                 445

Asp Lys Lys Tyr Ser Thr Tyr Tyr Thr Ser Thr Lys Ile Pro His Trp
    450                 455                 460

Thr Met Gln Ser Trp Tyr Asn Ser Ile Asp Thr Val Lys Tyr Gly Leu
465                 470                 475                 480

Asn Pro Tyr Gly Lys Leu Ser Trp Cys Lys Asp Gly Gln Asp Pro Glu
                485                 490                 495

Ile Asn Lys Val Gly Asn Trp Phe Glu Leu Leu Asp Ser Trp Phe Asp
            500                 505                 510

Lys Thr Asn Asp Val Thr Gly Gly Val Asn His Tyr Gln Trp
        515                 520                 525


<210> SEQ ID NO 18
<211> LENGTH: 526
<212> TYPE: PRT
<213> ORGANISM: Clostridium histolyticum

<400> SEQUENCE: 18

Met Leu Arg Arg Lys Val Ser Thr Leu Leu Met Thr Ala Leu Ile Thr
1               5                   10                  15

Thr Ser Phe Leu Asn Ser Lys Pro Val Tyr Ala Asn Pro Val Thr Lys
            20                  25                  30

Ser Lys Asp Asn Asn Leu Lys Glu Val Gln Gln Val Ile Ser Lys Ser
        35                  40                  45

Asn Lys Asn Lys Asn Gln Lys Val Thr Ile Met Tyr Tyr Cys Asp Ala
    50                  55                  60

Asp Asn Asn Leu Glu Gly Ser Leu Leu Asn Asp Ile Glu Glu Met Lys
65                  70                  75                  80

Thr Gly Tyr Lys Asp Ser Pro Asn Leu Asn Leu Ile Ala Leu Val Asp
                85                  90                  95

Arg Ser Pro Arg Tyr Ser Ser Asp Glu Lys Val Leu Gly Glu Asp Phe
            100                 105                 110

Ser Asp Thr Arg Leu Tyr Lys Ile Glu Leu Asn Lys Ala Asn Arg Leu
        115                 120                 125

Asp Gly Lys Asn Glu Phe Pro Glu Ile Ser Thr Thr Ser Lys Tyr Glu
    130                 135                 140
```

-continued

```
Ala Asn Met Gly Asp Pro Glu Val Leu Lys Lys Phe Ile Asp Tyr Cys
145                 150                 155                 160

Lys Ser Asn Tyr Glu Ala Asp Lys Tyr Val Leu Ile Met Ala Asn His
                165                 170                 175

Gly Gly Gly Ala Arg Glu Lys Ser Asn Pro Arg Leu Asn Arg Ala Ile
            180                 185                 190

Cys Trp Asp Asp Ser Asn Leu Asp Lys Asn Gly Glu Ala Asp Cys Leu
        195                 200                 205

Tyr Met Gly Glu Ile Ser Asp His Leu Thr Glu Lys Gln Ser Val Asp
    210                 215                 220

Leu Leu Ala Phe Asp Ala Cys Leu Met Gly Thr Ala Glu Val Ala Tyr
225                 230                 235                 240

Gln Tyr Arg Pro Gly Asn Gly Gly Phe Ser Ala Asp Thr Leu Val Ala
                245                 250                 255

Ser Ser Pro Val Val Trp Gly Pro Gly Phe Lys Tyr Asp Lys Ile Phe
            260                 265                 270

Asp Arg Ile Lys Ala Gly Gly Gly Thr Asn Asn Glu Asp Asp Leu Thr
        275                 280                 285

Leu Gly Gly Lys Glu Gln Asn Phe Asp Pro Ala Thr Ile Thr Asn Glu
    290                 295                 300

Gln Leu Gly Ala Leu Phe Val Glu Glu Gln Arg Asp Ser Thr His Ala
305                 310                 315                 320

Asn Gly Arg Tyr Asp Gln His Leu Ser Phe Tyr Asp Leu Lys Lys Ala
                325                 330                 335

Glu Ser Val Lys Arg Ala Ile Asp Asn Leu Ala Val Asn Leu Ser Asn
            340                 345                 350

Glu Asn Lys Lys Ser Glu Ile Glu Lys Leu Arg Gly Ser Gly Ile His
        355                 360                 365

Thr Asp Leu Met His Tyr Phe Asp Glu Tyr Ser Glu Gly Glu Trp Val
    370                 375                 380

Glu Tyr Pro Tyr Phe Asp Val Tyr Asp Leu Cys Glu Lys Ile Asn Lys
385                 390                 395                 400

Ser Glu Asn Phe Ser Ser Lys Thr Lys Asp Leu Ala Ser Asn Ala Met
                405                 410                 415

Asn Lys Leu Asn Glu Met Ile Val Tyr Ser Phe Gly Asp Pro Ser Asn
            420                 425                 430

Asn Phe Lys Glu Gly Lys Asn Gly Leu Ser Thr Phe Leu Pro Asn Gly
        435                 440                 445

Asp Lys Lys Tyr Ser Thr Tyr Tyr Thr Ser Thr Lys Ile Pro His Trp
    450                 455                 460

Thr Met Gln Ser Trp Tyr Asn Ser Ile Asp Thr Val Lys Tyr Gly Leu
465                 470                 475                 480

Asn Pro Tyr Gly Lys Leu Ser Trp Cys Lys Asp Gly Gln Asp Pro Glu
                485                 490                 495

Ile Asn Lys Val Gly Asn Trp Phe Glu Leu Leu Asp Ser Trp Phe Asp
            500                 505                 510

Lys Thr Asn Asp Val Thr Gly Gly Val Asn His Tyr Gln Trp
        515                 520                 525


<210> SEQ ID NO 19
<211> LENGTH: 1118
<212> TYPE: PRT
<213> ORGANISM: Clostridium histolyticum

<400> SEQUENCE: 19
```

-continued

```
Met Lys Lys Asn Ile Leu Lys Ile Leu Met Asp Ser Tyr Ser Lys Glu
1               5                   10                  15

Ser Lys Ile Gln Thr Val Arg Arg Val Thr Ser Val Ser Leu Leu Ala
            20                  25                  30

Val Tyr Leu Thr Met Asn Thr Ser Ser Leu Val Leu Ala Lys Pro Ile
        35                  40                  45

Glu Asn Thr Asn Asp Thr Ser Ile Lys Asn Val Glu Lys Leu Arg Asn
    50                  55                  60

Ala Pro Asn Glu Glu Asn Ser Lys Lys Val Glu Asp Ser Lys Asn Asp
65                  70                  75                  80

Lys Val Glu His Val Lys Asn Ile Glu Glu Ala Lys Val Glu Gln Val
                85                  90                  95

Ala Pro Glu Val Lys Ser Lys Ser Thr Leu Arg Ser Ala Ser Ile Ala
            100                 105                 110

Asn Thr Asn Ser Glu Lys Tyr Asp Phe Glu Tyr Leu Asn Gly Leu Ser
        115                 120                 125

Tyr Thr Glu Leu Thr Asn Leu Ile Lys Asn Ile Lys Trp Asn Gln Ile
    130                 135                 140

Asn Gly Leu Phe Asn Tyr Ser Thr Gly Ser Gln Lys Phe Phe Gly Asp
145                 150                 155                 160

Lys Asn Arg Val Gln Ala Ile Ile Asn Ala Leu Gln Glu Ser Gly Arg
                165                 170                 175

Thr Tyr Thr Ala Asn Asp Met Lys Gly Ile Glu Thr Phe Thr Glu Val
            180                 185                 190

Leu Arg Ala Gly Phe Tyr Leu Gly Tyr Tyr Asn Asp Gly Leu Ser Tyr
        195                 200                 205

Leu Asn Asp Arg Asn Phe Gln Asp Lys Cys Ile Pro Ala Met Ile Ala
    210                 215                 220

Ile Gln Lys Asn Pro Asn Phe Lys Leu Gly Thr Ala Val Gln Asp Glu
225                 230                 235                 240

Val Ile Thr Ser Leu Gly Lys Leu Ile Gly Asn Ala Ser Ala Asn Ala
                245                 250                 255

Glu Val Val Asn Asn Cys Val Pro Val Leu Lys Gln Phe Arg Glu Asn
            260                 265                 270

Leu Asn Gln Tyr Ala Pro Asp Tyr Val Lys Gly Thr Ala Val Asn Glu
        275                 280                 285

Leu Ile Lys Gly Ile Glu Phe Asp Phe Ser Gly Ala Ala Tyr Glu Lys
    290                 295                 300

Asp Val Lys Thr Met Pro Trp Tyr Gly Lys Ile Asp Pro Phe Ile Asn
305                 310                 315                 320

Glu Leu Lys Ala Leu Gly Leu Tyr Gly Asn Ile Thr Ser Ala Thr Glu
                325                 330                 335

Trp Ala Ser Asp Val Gly Ile Tyr Tyr Leu Ser Lys Phe Gly Leu Tyr
            340                 345                 350

Ser Thr Asn Arg Asn Asp Ile Val Gln Ser Leu Glu Lys Ala Val Asp
        355                 360                 365

Met Tyr Lys Tyr Gly Lys Ile Ala Phe Val Ala Met Glu Arg Ile Thr
    370                 375                 380

Trp Asp Tyr Asp Gly Ile Gly Ser Asn Gly Lys Lys Val Asp His Asp
385                 390                 395                 400

Lys Phe Leu Asp Asp Ala Glu Lys His Tyr Leu Pro Lys Thr Tyr Thr
                405                 410                 415
```

```
Phe Asp Asn Gly Thr Phe Ile Ile Arg Ala Gly Asp Lys Val Ser Glu
            420                 425                 430

Glu Lys Ile Lys Arg Leu Tyr Trp Ala Ser Arg Glu Val Lys Ser Gln
        435                 440                 445

Phe His Arg Val Val Gly Asn Asp Lys Ala Leu Glu Val Gly Asn Ala
    450                 455                 460

Asp Asp Val Leu Thr Met Lys Ile Phe Asn Ser Pro Glu Glu Tyr Lys
465                 470                 475                 480

Phe Asn Thr Asn Ile Asn Gly Val Ser Thr Asp Asn Gly Gly Leu Tyr
                485                 490                 495

Ile Glu Pro Arg Gly Thr Phe Tyr Thr Tyr Glu Arg Thr Pro Gln Gln
            500                 505                 510

Ser Ile Phe Ser Leu Glu Glu Leu Phe Arg His Glu Tyr Thr His Tyr
        515                 520                 525

Leu Gln Ala Arg Tyr Leu Val Asp Gly Leu Trp Gly Gln Gly Pro Phe
    530                 535                 540

Tyr Glu Lys Asn Arg Leu Thr Trp Phe Asp Glu Gly Thr Ala Glu Phe
545                 550                 555                 560

Phe Ala Gly Ser Thr Arg Thr Ser Gly Val Leu Pro Arg Lys Ser Ile
                565                 570                 575

Leu Gly Tyr Leu Ala Lys Asp Lys Val Asp His Arg Tyr Ser Leu Lys
            580                 585                 590

Lys Thr Leu Asn Ser Gly Tyr Asp Asp Ser Asp Trp Met Phe Tyr Asn
        595                 600                 605

Tyr Gly Phe Ala Val Ala His Tyr Leu Tyr Glu Lys Asp Met Pro Thr
    610                 615                 620

Phe Ile Lys Met Asn Lys Ala Ile Leu Asn Thr Asp Val Lys Ser Tyr
625                 630                 635                 640

Asp Glu Ile Ile Lys Lys Leu Ser Asp Asp Ala Asn Lys Asn Thr Glu
                645                 650                 655

Tyr Gln Asn His Ile Gln Glu Leu Ala Asp Lys Tyr Gln Gly Ala Gly
            660                 665                 670

Ile Pro Leu Val Ser Asp Asp Tyr Leu Lys Asp His Gly Tyr Lys Lys
        675                 680                 685

Ala Ser Glu Val Tyr Ser Glu Ile Ser Lys Ala Ala Ser Leu Thr Asn
    690                 695                 700

Thr Ser Val Thr Ala Glu Lys Ser Gln Tyr Phe Asn Thr Phe Thr Leu
705                 710                 715                 720

Arg Gly Thr Tyr Thr Gly Glu Thr Ser Lys Gly Glu Phe Lys Asp Trp
                725                 730                 735

Asp Glu Met Ser Lys Lys Leu Asp Gly Thr Leu Glu Ser Leu Ala Lys
            740                 745                 750

Asn Ser Trp Ser Gly Tyr Lys Thr Leu Thr Ala Tyr Phe Thr Asn Tyr
        755                 760                 765

Arg Val Thr Ser Asp Asn Lys Val Gln Tyr Asp Val Val Phe His Gly
    770                 775                 780

Val Leu Thr Asp Asn Ala Asp Ile Ser Asn Asn Lys Ala Pro Ile Ala
785                 790                 795                 800

Lys Val Thr Gly Pro Ser Thr Gly Ala Val Gly Arg Asn Ile Glu Phe
                805                 810                 815

Ser Gly Lys Asp Ser Lys Asp Glu Asp Gly Lys Ile Val Ser Tyr Asp
            820                 825                 830

Trp Asp Phe Gly Asp Gly Ala Thr Ser Arg Gly Lys Asn Ser Val His
```

```
        835                 840                 845

Ala Tyr Lys Lys Ala Gly Thr Tyr Asn Val Thr Leu Lys Val Thr Asp
    850                 855                 860

Asp Lys Gly Ala Thr Ala Thr Glu Ser Phe Thr Ile Glu Ile Lys Asn
865                 870                 875                 880

Glu Asp Thr Thr Thr Pro Ile Thr Lys Glu Met Glu Pro Asn Asp Asp
                885                 890                 895

Ile Lys Glu Ala Asn Gly Pro Ile Val Glu Gly Val Thr Val Lys Gly
            900                 905                 910

Asp Leu Asn Gly Ser Asp Asp Ala Asp Thr Phe Tyr Phe Asp Val Lys
        915                 920                 925

Glu Asp Gly Asp Val Thr Ile Glu Leu Pro Tyr Ser Gly Ser Ser Asn
    930                 935                 940

Phe Thr Trp Leu Val Tyr Lys Glu Gly Asp Asp Gln Asn His Ile Ala
945                 950                 955                 960

Ser Gly Ile Asp Lys Asn Asn Ser Lys Val Gly Thr Phe Lys Ser Thr
                965                 970                 975

Lys Gly Arg His Tyr Val Phe Ile Tyr Lys His Asp Ser Ala Ser Asn
            980                 985                 990

Ile Ser Tyr Ser Leu Asn Ile Lys  Gly Leu Gly Asn Glu  Lys Leu Lys
        995                 1000                1005

Glu Lys  Glu Asn Asn Asp Ser  Ser Asp Lys Ala Thr  Val Ile Pro
    1010                1015                1020

Asn Phe  Asn Thr Thr Met Gln  Gly Ser Leu Leu Gly  Asp Asp Ser
    1025                1030                1035

Arg Asp  Tyr Tyr Ser Phe Glu  Val Lys Glu Glu Gly  Glu Val Asn
    1040                1045                1050

Ile Glu  Leu Asp Lys Lys Asp  Glu Phe Gly Val Thr  Trp Thr Leu
    1055                1060                1065

His Pro  Glu Ser Asn Ile Asn  Asp Arg Ile Thr Tyr  Gly Gln Val
    1070                1075                1080

Asp Gly  Asn Lys Val Ser Asn  Lys Val Lys Leu Arg  Pro Gly Lys
    1085                1090                1095

Tyr Tyr  Leu Leu Val Tyr Lys  Tyr Ser Gly Ser Gly  Asn Tyr Glu
    1100                1105                1110

Leu Arg  Val Asn Lys
    1115


<210> SEQ ID NO 20
<211> LENGTH: 1021
<212> TYPE: PRT
<213> ORGANISM: Clostridium histolyticum

<400> SEQUENCE: 20

Met Lys Arg Lys Cys Leu Ser Lys Arg Leu Met Leu Ala Ile Thr Met
1               5                   10                  15

Ala Thr Ile Phe Thr Val Asn Ser Thr Leu Pro Ile Tyr Ala Ala Val
            20                  25                  30

Asp Lys Asn Asn Ala Thr Ala Ala Val Gln Asn Glu Ser Lys Arg Tyr
        35                  40                  45

Thr Val Ser Tyr Leu Lys Thr Leu Asn Tyr Tyr Asp Leu Val Asp Leu
    50                  55                  60

Leu Val Lys Thr Glu Ile Glu Asn Leu Pro Asp Leu Phe Gln Tyr Ser
65                  70                  75                  80
```

-continued

```
Ser Asp Ala Lys Glu Phe Tyr Gly Asn Lys Thr Arg Met Ser Phe Ile
                85                  90                  95

Met Asp Glu Ile Gly Arg Arg Ala Pro Gln Tyr Thr Glu Ile Asp His
            100                 105                 110

Lys Gly Ile Pro Thr Leu Val Glu Val Val Arg Ala Gly Phe Tyr Leu
        115                 120                 125

Gly Phe His Asn Lys Glu Leu Asn Glu Ile Asn Lys Arg Ser Phe Lys
    130                 135                 140

Glu Arg Val Ile Pro Ser Ile Leu Ala Ile Gln Lys Asn Pro Asn Phe
145                 150                 155                 160

Lys Leu Gly Thr Glu Val Gln Asp Lys Ile Val Ser Ala Thr Gly Leu
                165                 170                 175

Leu Ala Gly Asn Glu Thr Ala Pro Pro Glu Val Val Asn Asn Phe Thr
            180                 185                 190

Pro Ile Leu Gln Asp Cys Ile Lys Asn Ile Asp Arg Tyr Ala Leu Asp
        195                 200                 205

Asp Leu Lys Ser Lys Ala Leu Phe Asn Val Leu Ala Ala Pro Thr Tyr
    210                 215                 220

Asp Ile Thr Glu Tyr Leu Arg Ala Thr Lys Glu Lys Pro Glu Asn Thr
225                 230                 235                 240

Pro Trp Tyr Gly Lys Ile Asp Gly Phe Ile Asn Glu Leu Lys Lys Leu
                245                 250                 255

Ala Leu Tyr Gly Lys Ile Asn Asp Asn Asn Ser Trp Ile Ile Asp Asn
            260                 265                 270

Gly Ile Tyr His Ile Ala Pro Leu Gly Lys Leu His Ser Asn Asn Lys
        275                 280                 285

Ile Gly Ile Glu Thr Leu Thr Glu Val Met Lys Val Tyr Pro Tyr Leu
    290                 295                 300

Ser Met Gln His Leu Gln Ser Ala Asp Gln Ile Lys Arg His Tyr Asp
305                 310                 315                 320

Ser Lys Asp Ala Glu Gly Asn Lys Ile Pro Leu Asp Lys Phe Lys Lys
                325                 330                 335

Glu Gly Lys Glu Lys Tyr Cys Pro Lys Thr Tyr Thr Phe Asp Asp Gly
            340                 345                 350

Lys Val Ile Ile Lys Ala Gly Ala Arg Val Glu Glu Glu Lys Val Lys
        355                 360                 365

Arg Leu Tyr Trp Ala Ser Lys Glu Val Asn Ser Gln Phe Phe Arg Val
    370                 375                 380

Tyr Gly Ile Asp Lys Pro Leu Glu Glu Gly Asn Pro Asp Asp Ile Leu
385                 390                 395                 400

Thr Met Val Ile Tyr Asn Ser Pro Glu Glu Tyr Lys Leu Asn Ser Val
                405                 410                 415

Leu Tyr Gly Tyr Asp Thr Asn Asn Gly Gly Met Tyr Ile Glu Pro Glu
            420                 425                 430

Gly Thr Phe Phe Thr Tyr Glu Arg Glu Ala Gln Glu Ser Thr Tyr Thr
        435                 440                 445

Leu Glu Glu Leu Phe Arg His Glu Tyr Thr His Tyr Leu Gln Gly Arg
    450                 455                 460

Tyr Ala Val Pro Gly Gln Trp Gly Arg Thr Lys Leu Tyr Asp Asn Asp
465                 470                 475                 480

Arg Leu Thr Trp Tyr Glu Glu Gly Gly Ala Glu Leu Phe Ala Gly Ser
                485                 490                 495

Thr Arg Thr Ser Gly Ile Leu Pro Arg Lys Ser Ile Val Ser Asn Ile
```

-continued

```
            500                 505                 510

His Asn Thr Thr Arg Asn Asn Arg Tyr Lys Leu Ser Asp Thr Val His
        515                 520                 525

Ser Lys Tyr Gly Ala Ser Phe Glu Phe Tyr Asn Tyr Ala Cys Met Phe
    530                 535                 540

Met Asp Tyr Met Tyr Asn Lys Asp Met Gly Ile Leu Asn Lys Leu Asn
545                 550                 555                 560

Asp Leu Ala Lys Asn Asn Asp Val Asp Gly Tyr Asp Asn Tyr Ile Arg
                565                 570                 575

Asp Leu Ser Ser Asn Tyr Ala Leu Asn Asp Lys Tyr Gln Asp His Met
            580                 585                 590

Gln Glu Arg Ile Asp Asn Tyr Glu Asn Leu Thr Val Pro Phe Val Ala
        595                 600                 605

Asp Asp Tyr Leu Val Arg His Ala Tyr Lys Asn Pro Asn Glu Ile Tyr
    610                 615                 620

Ser Glu Ile Ser Glu Val Ala Lys Leu Lys Asp Ala Lys Ser Glu Val
625                 630                 635                 640

Lys Lys Ser Gln Tyr Phe Ser Thr Phe Thr Leu Arg Gly Ser Tyr Thr
                645                 650                 655

Gly Gly Ala Ser Lys Gly Lys Leu Glu Asp Gln Lys Ala Met Asn Lys
            660                 665                 670

Phe Ile Asp Asp Ser Leu Lys Lys Leu Asp Thr Tyr Ser Trp Ser Gly
        675                 680                 685

Tyr Lys Thr Leu Thr Ala Tyr Phe Thr Asn Tyr Lys Val Asp Ser Ser
    690                 695                 700

Asn Arg Val Thr Tyr Asp Val Val Phe His Gly Tyr Leu Pro Asn Glu
705                 710                 715                 720

Gly Asp Ser Lys Asn Ser Leu Pro Tyr Gly Lys Ile Asn Gly Thr Tyr
                725                 730                 735

Lys Gly Thr Glu Lys Glu Lys Ile Lys Phe Ser Ser Glu Gly Ser Phe
            740                 745                 750

Asp Pro Asp Gly Lys Ile Val Ser Tyr Glu Trp Asp Phe Gly Asp Gly
        755                 760                 765

Asn Lys Ser Asn Glu Glu Asn Pro Glu His Ser Tyr Asp Lys Val Gly
    770                 775                 780

Thr Tyr Thr Val Lys Leu Lys Val Thr Asp Asp Lys Gly Glu Ser Ser
785                 790                 795                 800

Val Ser Thr Thr Thr Ala Glu Ile Lys Asp Leu Ser Glu Asn Lys Leu
                805                 810                 815

Pro Val Ile Tyr Met His Val Pro Lys Ser Gly Ala Leu Asn Gln Lys
            820                 825                 830

Val Val Phe Tyr Gly Lys Gly Thr Tyr Asp Pro Asp Gly Ser Ile Ala
        835                 840                 845

Gly Tyr Gln Trp Asp Phe Gly Asp Gly Ser Asp Phe Ser Ser Glu Gln
    850                 855                 860

Asn Pro Ser His Val Tyr Thr Lys Lys Gly Glu Tyr Thr Val Thr Leu
865                 870                 875                 880

Arg Val Met Asp Ser Ser Gly Gln Met Ser Glu Lys Thr Met Lys Ile
                885                 890                 895

Lys Ile Thr Asp Pro Val Tyr Pro Ile Gly Thr Glu Lys Glu Pro Asn
            900                 905                 910

Asn Ser Lys Glu Thr Ala Ser Gly Pro Ile Val Pro Gly Ile Pro Val
        915                 920                 925
```

```
Ser Gly Thr Ile Glu Asn Thr Ser Asp Gln Asp Tyr Phe Tyr Phe Asp
    930                 935                 940

Val Ile Thr Pro Gly Glu Val Lys Ile Asp Ile Asn Lys Leu Gly Tyr
945                 950                 955                 960

Gly Gly Ala Thr Trp Val Val Tyr Asp Glu Asn Asn Asn Ala Val Ser
                965                 970                 975

Tyr Ala Thr Asp Asp Gly Gln Asn Leu Ser Gly Lys Phe Lys Ala Asp
            980                 985                 990

Lys Pro Gly Arg Tyr Tyr Ile His  Leu Tyr Met Phe Asn  Gly Ser Tyr
        995                 1000                 1005

Met Pro  Tyr Arg Ile Asn Ile  Glu Gly Ser Val Gly  Arg
    1010                 1015                 1020
```

```
<210> SEQ ID NO 21
<211> LENGTH: 1263
<212> TYPE: DNA
<213> ORGANISM: Clostridium histolyticum

<400> SEQUENCE: 21

atgttaaaaa aatctttttt taaaaaggca atttgcgcat ctttggtggt gctacaatgt     60

ttgatattag tgtcaccagc tcaaacattg gcatcaacag atttgccgac aaaaggaaaa    120

acttcaattg aactatttaa ctatgaagat cattaaatgg ctcattgttt gggatttgga    180

tggtgcttcg gtacagcatc aaaagaaata ggggaagatt ttgaatttaa aagagcagaa    240

gaagaaggaa aaacagtata ttatttatca gctagataca atcaaaatga tccttacgct    300

aaaggctatt atcgcgcgca tgataggctt gttatgaagg ttagtaatgc taggtttttt    360

atcgatcatg attcattaac tttaggaaaa gctaaagtta taagtctaga tccactggca    420

tcatcaactc ttcaagtagt aaataaaagt aattctgaag ctaaaacatc attatctttt    480

ggatatgaaa ctactgaaag tacttccaaa acggatcacg ttaaattcgg agaaaaaatt    540

ggaattaagt catcatttaa tgttaaagtt ccatttatag gagaaaaatc aattgaaaca    600

aatcttgaat tcaattcaga gcagggttgg tccaatacga aaactaactc tgtaactact    660

aaacatacaa tttctcatac aacaacaaca cctgcaaaga gcaggaaaaa ggtacgatta    720

aatgttctta ataaaaagtc cgacatacca tatgagggta agatatatat ggaatatgat    780

atagagtttt ttggtttttt aagatatact ggaaatgcgc gtaaagatca tcctacagat    840

agacctagtg tatcagtaaa atttggggga aaaaataata tgagtgcggt agatcatatt    900

atagatttgt acaagcataa agatattaat ggctattcag aatgggattg gaattggatt    960

gaagaaaatt tttatgatag atttagtgaa tattcatcta atgttgctag tcaatatttt   1020

gggggcatta tttctggtgt atttactaat gtgggtggaa cagatgtaaa agttgaagaa   1080

ggtagagaaa ggccacttaa aaatacaagt tctacagaac aaaatgtcga agtacagaat   1140

tttaaaagct ctaaatctaa agagtttaga gtgggtagtt taacatatac tactcctaat   1200

ggagaacaga ccatatatcc tgaagacgta tcatctctta acgctaacaa caatgagaat   1260

taa                                                                 1263
```

```
<210> SEQ ID NO 22
<211> LENGTH: 1599
<212> TYPE: DNA
<213> ORGANISM: Clostridium histolyticum

<400> SEQUENCE: 22
```

-continued

```
atgaaaaaaa aatttttaag ttttattatt atttctgcca tatcacttaa catttcttct     60

atgactgtgg gggcaaagca agtgaaagaa atcaaacctc caaaagataa agaatctatt    120

tctgtattaa aaacagattt agaaaaaacc aagaatataa aatctaataa taaggagggg    180

gatgatgtaa caaaagtagt taagagtgct ttaaaagaag aaggcaattt aggagatttt    240

aaggttgata ataaagaaac tgatgtaaaa ggtaaaaagc acttgcgttc acaaatgttt    300

atagatggta ttcctgtata tggtagtcaa gttataattc atactaataa agatggacaa    360

gtatatagcg taaatggaaa agtagataaa cagcctaaag ctcaatcttt taagaaccgt    420

gtaaggatta aggacgataa agctattaaa atagcagaag acagtttagg taaggaaata    480

aagaaaaaca aaaattatca ttctgaaagt aagttgtacc tatacaaggt taatggagat    540

ttacaacctg tgtatttggt aaagatatca tctacagaac cagaagcttc attttggcat    600

atgtttgtaa gtgctgaaaa tggaaagata gttgataagt ataatgcttt atcatgccaa    660

gctacacatg ctcaagtaag aggagttaat agcagtggag agcataaaat cttaaatggt    720

atgtttgaaa atggaagata ttttttagca gattcaacaa gaccttcaaa tggatatata    780

ttaacatatg atgctaataa ccaagagtat ggtttcccag gtagcttatt tagtaattta    840

acaggcattt ttgatagtga tagacaaaag gcaggagtag atgctcacca taatctaact    900

caagtatatg attattataa aaatgtttta aatagagata gttttgatgg aaaaggtgct    960

agtataatat cttctgtgca tgtaggaaat aatttaaata atgctttctg gaatggtaga   1020

caaatacttt ttggtgatgg agacggagtt acatttagta acctagcaaa atgtttagaa   1080

gttactgccc atgaatttac acatgcagtt actcaaagta ctgcaggtct agaatataga   1140

tttcaatctg gtgctctaaa tgaagctttt tctgatattt taggtatagc tgttcacagt   1200

gatccaaatg attgggaaat tggagaagat atatacactc ctaatgtagc aggagatgct   1260

ttaagaagta tgtcaaatcc tagattatat agacaaccag accatatgaa ggactattta   1320

tattgggatt attcaatgga taaaggtgga gttcattata attcaggtat tccaaataaa   1380

gcagcttatt tgatgggaaa agaagttgga aaagattcaa tggctaaaat ttattatcat   1440

gctttagtga attatttaac tcctcaaagt acatttgaag atgctagaaa tgcagtagta   1500

tcatctgcaa tagatttaca tggtgagaat agtaaagaac ataaacttgc tataaaatct   1560

tgggcagatg taggcgttgg agaagaggca gtaagataa                           1599
```

<210> SEQ ID NO 23
<211> LENGTH: 1563
<212> TYPE: DNA
<213> ORGANISM: Clostridium histolyticum

<400> SEQUENCE: 23

```
atgaagatta caaagaaagg cttaagatca ttatcacgct taatgttaat tactatgata     60

acaggattaa catacaatta tcacctaggt agtagcttta atgggaatcg agtagtactt    120

gcaaatccaa atacaaaaac agataattta attaagaata atagtgatga aatagacgaa    180

aagatttatg gattgtctta tgatccatat aaaatattat cttataatgg agaaaaggtt    240

gaaaactttg ttccagctga atgttccgag aattccggaa aatttactgt aataaaacgt    300

gaaaagaaaa atatttcaga ttcaactaca gatatttcaa taatggattc aataaatgat    360

agaacttatc ctggtgctat acaactagca aatagggatc ttatagaaaa taagcctaat    420

ttaatttcat gcgagagaaa acctattact ataagtgttg atttacctgg tatgggtgag    480

gatgggaaaa aggttgttaa ttctccaaca tactcttcag ttaattcagc aataaattat    540
```

```
ttgctagata catggaattc aaaatattca tctaaatata ctatacctac aaggatgaat    600

tattctgata ctatggtgta tagtaaatca cagttatcta caatgtttgg atgtaacttt    660

aaaactttaa gtaaatcctt aaatatagat tttgattcta tatttaaagg cgaaaaaaag    720

gctatgattc tatcatataa acaaattttc tacacagtga gtgtagatgg acctaatcgc    780

ccatcagatt tatttggtta cagtgtaact tctaagagct tagctttaaa aggagtaaat    840

aatgataatc ctccagcata cgtttccaat gttgcatatg gtagaactgt ttatgtaaaa    900

ctagagacaa catctaagag ttcaaaggtt aaagcagcat ttaaggcatt agtagagaat    960

caagatataa gtagtaatgc agaatataaa gacataataa atcaaagttc atttacagct   1020

actgttctag gtggaggagc acaaaaacac aataaagtag ttactaaaga tttcgatgta   1080

ataagaaata ttattaaaaa taattcagta tatagcccac aaaatcctgg atatcctatt   1140

tcatatacaa gtacattttt aaaagacaat aaaatagcaa ctgtaaacaa tagaacagaa   1200

tatatagaaa caactgcaac agaatacgat agcggcaaaa taatgcttga ccatagtgga   1260

gtttatgttg ctcaatttga agtaacctgg gatgaagtta gttatgacaa acaaggaaat   1320

gaaataattg agcataaatc ttggtctgga aacaatagtg atagaacagc tcactttaat   1380

acagaactat atttaaaagg aaatgcaaga aacatttcta taaaagcaaa agaatgtaca   1440

ggccttgctt gggaatggtg gagaactgtt gtagatgcta aaaatttacc acttgtaaaa   1500

gaaagaaagt tatcaatatg gggtacaaca ttatatccta gatattctat ggaagagaaa   1560

taa                                                                 1563
```

<210> SEQ ID NO 24
<211> LENGTH: 1581
<212> TYPE: DNA
<213> ORGANISM: Clostridium histolyticum

<400> SEQUENCE: 24

```
atgttaagaa gaaaagtatc aacactatta atgacagctt tgataactac ttcattttta     60

aattccaaac ccgtatatgc aaatccagta actaaatcca aggataataa cttaaaagaa    120

gtacaacaag ttataagcaa gagtaataaa aacaaaaatc aaaaagtaac tattatgtac    180

tattgcgacg cagataataa cttggaagga agtctattaa atgatatcga ggaaatgaaa    240

acaggatata aggatagtcc taatttaaat ttaattgctc ttgtagacag atccccaaga    300

tatagcagtg acgaaaaagt tttaggtgaa gattttagtg atacacgtct ttataagatt    360

gaactcaata aggcaaatag attagacggt aaaaatgaat ttccagaaat aagtactact    420

agtaaatatg aagctaacat gggggatcct gaagttctta aaaaatttat tgattattgt    480

aaatctaatt atgaggctga taaatatgtg cttataatgg ctaatcatgg tggtggtgca    540

agggaaaaat caaatccaag attaaataga gcaatttgct gggatgatag taaccttgat    600

aaaaatggtg aagcagactg cctttatatg ggtgaaattt cagatcattt aacagaaaaa    660

caatcagttg atttacttgc ctttgatgca tgccttatgg gaactgcaga agtagcgtat    720

cagtatagac caggtaatgg aggattttct gccgatactt tagttgcttc aagcccagta    780

gtttggggtc ctggattcaa atatgataag attttcgata ggataaaagc tggtggagga    840

actaataatg aggatgattt aactttaggt ggtaaagaac aaaactttga tcctgcaacc    900

attaccaatg agcaattagg tgcattattt gtagaagagc aaagagactc aacacatgcc    960

aatggtcgct atgatcaaca cttaagcttt tatgatttaa agaaagctga atcagtaaaa   1020
```

```
agagccatag ataatttagc tgttaatcta agtaatgaaa acaaaaaatc tgaaattgaa   1080

aaattaagag gaagtggaat tcatacagat ttaatgcatt acttcgatga atattctgaa   1140

ggagaatggg ttgaatatcc ttattttgac gtgtatgatt tatgtgaaaa aataaataaa   1200

agtgaaaatt ttagtagtaa aactaaagat ttagcttcaa atgctatgaa taaattaaat   1260

gaaatgatag tttattcttt tggagaccct agtaataatt ttaaagaagg aaaaaatgga   1320

ttgagtacat tcttacctaa tggagataaa aaatattcaa cttattatac atcaaccaag   1380

atacctcatt ggactatgca aagttggtat aattcaatag atacagttaa atatggattg   1440

aatccttacg gaaaattaag ttggtgtaaa gatggacaag atcctgaaat aaataaagtt   1500

ggaaattggt ttgaacttct agattcttgg tttgataaaa ctaatgatgt aactggagga   1560

gttaatcatt accaatggta a                                             1581
```

<210> SEQ ID NO 25
<211> LENGTH: 6
<212> TYPE: PRT
<213> ORGANISM: Artificial Sequence
<220> FEATURE:
<223> OTHER INFORMATION: Description of Artificial Sequence: Synthetic 6xHis tag

<400> SEQUENCE: 25

```
His His His His His His
1               5
```

<210> SEQ ID NO 26
<211> LENGTH: 12
<212> TYPE: PRT
<213> ORGANISM: Clostridium septicum

<400> SEQUENCE: 26

```
Asp Lys Lys Arg Arg Gly Lys Arg Ser Val Asp Ser
1               5                   10
```

<210> SEQ ID NO 27
<211> LENGTH: 11
<212> TYPE: PRT
<213> ORGANISM: Clostridium histolyticum

<400> SEQUENCE: 27

```
Asn Thr Ser Ser Thr Glu Gln Asn Val Glu Val
1               5                   10
```

<210> SEQ ID NO 28
<211> LENGTH: 10
<212> TYPE: PRT
<213> ORGANISM: Bacillus proteolyticus

<400> SEQUENCE: 28

```
Ala His Glu Leu Thr His Ala Val Thr Asp
1               5                   10
```

<210> SEQ ID NO 29
<211> LENGTH: 11
<212> TYPE: PRT
<213> ORGANISM: Clostridium perfringens

<400> SEQUENCE: 29

```
Glu Cys Thr Gly Leu Ala Trp Glu Trp Trp Arg
1               5                   10
```

-continued

```
<210> SEQ ID NO 30
<211> LENGTH: 4
<212> TYPE: PRT
<213> ORGANISM: Clostridium histolyticum

<400> SEQUENCE: 30

Ala Val Asp Lys
1


<210> SEQ ID NO 31
<211> LENGTH: 4
<212> TYPE: PRT
<213> ORGANISM: Clostridium septicum
<220> FEATURE:
<221> NAME/KEY: misc_feature
<222> LOCATION: (2)..(2)
<223> OTHER INFORMATION: Xaa can be any naturally occurring amino acid
<220> FEATURE:
<221> NAME/KEY: misc_feature
<222> LOCATION: (3)..(3)
<223> OTHER INFORMATION: XAA is either ARG or LYS

<400> SEQUENCE: 31

Arg Xaa Xaa Arg
1


<210> SEQ ID NO 32
<211> LENGTH: 4
<212> TYPE: PRT
<213> ORGANISM: Clostridium septicum
<220> FEATURE:
<221> NAME/KEY: misc_feature
<222> LOCATION: (2)..(3)
<223> OTHER INFORMATION: Xaa can be any naturally occurring amino acid

<400> SEQUENCE: 32

Arg Xaa Xaa Arg
1
```